(12) United States Patent
Nyuli et al.

(10) Patent No.: US 11,617,650 B2
(45) Date of Patent: Apr. 4, 2023

(54) METHODS AND APPARATUS FOR LOADING A PROSTHESIS ONTO A DELIVERY SYSTEM

(71) Applicant: Neovasc Tiara Inc., Richmond (CA)

(72) Inventors: Colin A. Nyuli, Vancouver (CA); Randy Matthew Lane, Langley (CA)

(73) Assignee: Neovasc Tiara Inc., Richmond (CA)

( * ) Notice: Subject to any disclaimer, the term of this patent is extended or adjusted under 35 U.S.C. 154(b) by 0 days.

(21) Appl. No.: 17/842,291

(22) Filed: Jun. 16, 2022

(65) Prior Publication Data

US 2022/0313436 A1  Oct. 6, 2022

Related U.S. Application Data

(60) Continuation of application No. 17/168,818, filed on Feb. 5, 2021, now Pat. No. 11,389,294, which is a
(Continued)

(51) Int. Cl.
*A61F 2/24* (2006.01)
*A61F 2/962* (2013.01)
*A61F 2/95* (2013.01)

(52) U.S. Cl.
CPC ............ *A61F 2/2436* (2013.01); *A61F 2/243* (2013.01); *A61F 2/2412* (2013.01); *A61F 2/2418* (2013.01); *A61F 2/962* (2013.01); *A61F 2/9522* (2020.05); *A61F 2220/005* (2013.01); *A61F 2220/0016* (2013.01); *A61F 2220/0058* (2013.01); *A61F 2230/005* (2013.01); *A61F 2230/0013* (2013.01);
(Continued)

(58) Field of Classification Search
CPC .... A61F 2/2436; A61F 2/2412; A61F 2/2418; A61F 2/243; A61F 2/962; A61F 2/9522; A61F 2220/0016; A61F 2220/005; A61F 2220/0058; A61F 2230/0013; A61F 2230/005; A61F 2230/0054; A61F 2250/006; Y10T 29/49908; Y10T 29/49913; Y10T 29/49925
See application file for complete search history.

(56) References Cited

U.S. PATENT DOCUMENTS

| 2,967,856 A | 1/1961 | Coover, Jr. et al. |
| 3,657,744 A | 4/1972 | Ersek |

(Continued)

FOREIGN PATENT DOCUMENTS

| AU | 2013270351 A1 | 11/2014 |
| CA | 2263006 A1 | 8/1999 |

(Continued)

OTHER PUBLICATIONS

US 8,062,357 B2, 11/2011, Salahieh et al. (withdrawn)
(Continued)

*Primary Examiner* — Bayan Salone
(74) *Attorney, Agent, or Firm* — Schwegman Lundberg & Woessner, P.A.

(57) ABSTRACT

A device for loading a prosthesis onto a delivery system includes a first housing having a central bore. One or more actuators on the first housing may be actuated radially inward to selectively compress a discrete portion of the prosthesis disposed in the central bore.

11 Claims, 60 Drawing Sheets

Related U.S. Application Data continuation of application No. 16/295,913, filed on Mar. 7, 2019, now Pat. No. 10,940,001, which is a continuation of application No. 15/890,119, filed on Feb. 6, 2018, now Pat. No. 10,314,705, which is a continuation of application No. 15/134,164, filed on Apr. 20, 2016, now Pat. No. 10,016,275, which is a division of application No. 13/904,827, filed on May 29, 2013, now Pat. No. 9,345,573.

(60) Provisional application No. 61/653,273, filed on May 30, 2012.

(52) U.S. Cl.
CPC . *A61F 2230/0054* (2013.01); *A61F 2250/006* (2013.01); *Y10T 29/49908* (2015.01); *Y10T 29/49913* (2015.01); *Y10T 29/49925* (2015.01)

(56) References Cited

U.S. PATENT DOCUMENTS

| | | |
|---|---|---|
| 3,671,979 A | 6/1972 | Moulopoulos |
| 3,739,402 A | 6/1973 | Cooley et al. |
| 4,056,854 A | 11/1977 | Boretos et al. |
| 4,079,468 A | 3/1978 | Liotta et al. |
| 4,204,283 A | 5/1980 | Bellhouse et al. |
| 4,222,126 A | 9/1980 | Boretos et al. |
| 4,265,694 A | 5/1981 | Boretos et al. |
| 4,339,831 A | 7/1982 | Johnson |
| 4,340,977 A | 7/1982 | Brownlee et al. |
| 4,470,157 A | 9/1984 | Love |
| 4,477,930 A | 10/1984 | Totten et al. |
| 4,490,859 A | 1/1985 | Black et al. |
| 4,553,545 A | 11/1985 | Maass et al. |
| 4,655,771 A | 4/1987 | Wallsten |
| 4,733,665 A | 3/1988 | Palmar |
| 4,776,337 A | 10/1988 | Palmaz |
| 4,777,951 A | 10/1988 | Cribier et al. |
| 4,865,600 A | 9/1989 | Carpentier et al. |
| 4,950,227 A | 8/1990 | Savin et al. |
| 4,994,077 A | 2/1991 | Dobben |
| 5,067,957 A | 11/1991 | Jervis |
| 5,197,978 A | 3/1993 | Hess |
| 5,326,371 A | 7/1994 | Love et al. |
| 5,332,402 A | 7/1994 | Teitelbaum |
| 5,344,427 A | 9/1994 | Cottenceau et al. |
| 5,370,685 A | 12/1994 | Stevens |
| 5,397,355 A | 3/1995 | Marin et al. |
| 5,411,552 A | 5/1995 | Andersen et al. |
| 5,415,667 A | 5/1995 | Frater |
| 5,439,446 A | 8/1995 | Barry |
| 5,474,563 A | 12/1995 | Myler et al. |
| 5,509,930 A | 4/1996 | Love |
| 5,545,214 A | 8/1996 | Stevens |
| 5,554,185 A | 9/1996 | Block et al. |
| 5,575,818 A | 11/1996 | Pinchuk |
| 5,607,444 A | 3/1997 | Lam |
| 5,607,469 A | 3/1997 | Frey |
| 5,669,919 A | 9/1997 | Sanders et al. |
| 5,672,169 A | 9/1997 | Verbeek |
| 5,697,382 A | 12/1997 | Love et al. |
| D390,957 S | 2/1998 | Fontaine |
| 5,713,952 A | 2/1998 | Vanney et al. |
| 5,725,519 A | 3/1998 | Penner et al. |
| 5,769,812 A | 6/1998 | Stevens et al. |
| 5,807,398 A | 9/1998 | Shaknovich |
| 5,810,873 A | 9/1998 | Morales |
| 5,840,081 A | 11/1998 | Andersen et al. |
| 5,855,601 A | 1/1999 | Bessler et al. |
| 5,868,777 A | 2/1999 | Lam |
| 5,868,782 A | 2/1999 | Frantzen |
| 5,876,437 A | 3/1999 | Vanney et al. |
| 5,879,381 A | 3/1999 | Moriuchi et al. |
| 5,893,867 A | 4/1999 | Bagaoisan et al. |
| 5,902,334 A | 5/1999 | Dwyer et al. |
| 5,928,281 A | 7/1999 | Huynh et al. |
| 5,935,108 A | 8/1999 | Katoh |
| 5,954,764 A | 9/1999 | Parodi |
| 5,957,949 A | 9/1999 | Leonhardt et al. |
| 5,992,000 A | 11/1999 | Humphrey et al. |
| 6,004,328 A | 12/1999 | Solar et al. |
| 6,015,431 A | 1/2000 | Thornton et al. |
| 6,042,606 A | 3/2000 | Frantzen |
| 6,053,940 A | 4/2000 | Wijay |
| 6,074,417 A | 6/2000 | Peredo |
| 6,082,990 A * | 7/2000 | Jackson .................. A61F 2/958 264/249 |
| 6,086,612 A | 7/2000 | Jansen |
| 6,113,612 A | 9/2000 | Swanson et al. |
| 6,113,631 A | 9/2000 | Jansen |
| 6,132,458 A | 10/2000 | Staehle et al. |
| 6,152,937 A | 11/2000 | Peterson et al. |
| 6,159,237 A | 12/2000 | Alt et al. |
| 6,168,614 B1 | 1/2001 | Andersen |
| 6,168,616 B1 | 1/2001 | Brown, III |
| 6,251,093 B1 | 6/2001 | Valley et al. |
| 6,280,466 B1 | 8/2001 | Kugler et al. |
| 6,306,141 B1 | 10/2001 | Jervis |
| 6,312,465 B1 | 11/2001 | Griffin et al. |
| 6,336,938 B1 | 1/2002 | Kavteladze et al. |
| 6,352,543 B1 | 3/2002 | Cole |
| 6,358,277 B1 | 3/2002 | Duran |
| 6,425,916 B1 | 7/2002 | Garrison et al. |
| 6,440,164 B1 | 8/2002 | Dimatteo et al. |
| 6,458,153 B1 | 10/2002 | Bailey et al. |
| 6,475,237 B2 | 11/2002 | Drasler et al. |
| 6,482,228 B1 | 11/2002 | Norred |
| 6,511,491 B2 | 1/2003 | Grudem et al. |
| 6,517,573 B1 | 2/2003 | Pollock et al. |
| 6,527,800 B1 | 3/2003 | McGuckin, Jr. et al. |
| 6,551,303 B1 | 4/2003 | Van Tassel et al. |
| 6,582,462 B1 | 6/2003 | Andersen et al. |
| 6,602,281 B1 | 8/2003 | Klein |
| 6,610,088 B1 | 8/2003 | Gabbay |
| 6,629,534 B1 | 10/2003 | Goar et al. |
| 6,641,606 B2 | 11/2003 | Ouriel et al. |
| 6,652,578 B2 | 11/2003 | Bailey et al. |
| D484,979 S | 1/2004 | Fontaine |
| 6,676,698 B2 | 1/2004 | McGuckin, Jr. et al. |
| 6,682,537 B2 | 1/2004 | Ouriel et al. |
| 6,695,878 B2 | 2/2004 | Mcguckin, Jr. et al. |
| 6,712,836 B1 | 3/2004 | Berg et al. |
| 6,723,123 B1 | 4/2004 | Kazatchkov et al. |
| 6,730,118 B2 | 5/2004 | Spenser et al. |
| 6,733,523 B2 | 5/2004 | Shaolian et al. |
| 6,764,505 B1 | 7/2004 | Hossainy et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,814,746 B2 | 11/2004 | Thompson et al. |
| 6,858,034 B1 | 2/2005 | Hijlkema et al. |
| 6,875,231 B2 | 4/2005 | Anduiza et al. |
| 6,893,460 B2 | 5/2005 | Spenser et al. |
| 6,908,477 B2 | 6/2005 | Mcguckin, Jr. et al. |
| 6,908,481 B2 | 6/2005 | Cribier |
| 6,920,674 B2 | 7/2005 | Thornton |
| 6,926,732 B2 | 8/2005 | Derus et al. |
| 6,929,660 B1 | 8/2005 | Ainsworth et al. |
| 6,936,058 B2 | 8/2005 | Forde et al. |
| 6,979,350 B2 | 12/2005 | Moll et al. |
| 7,014,653 B2 | 3/2006 | Ouriel et al. |
| 7,018,401 B1 | 3/2006 | Hyodoh et al. |
| 7,018,406 B2 | 3/2006 | Seguin et al. |
| 7,025,780 B2 | 4/2006 | Gabbay |
| 7,044,962 B2 | 5/2006 | Elliott |
| 7,044,966 B2 | 5/2006 | Svanidze et al. |
| 7,087,088 B2 | 8/2006 | Berg et al. |
| 7,147,660 B2 | 12/2006 | Chobotov et al. |
| 7,147,661 B2 | 12/2006 | Chobotov et al. |
| 7,147,663 B1 | 12/2006 | Berg et al. |
| 7,153,322 B2 | 12/2006 | Alt |
| 7,186,265 B2 | 3/2007 | Sharkawy et al. |

(56) References Cited

U.S. PATENT DOCUMENTS

| | | |
|---|---|---|
| 7,198,646 B2 | 4/2007 | Figulla et al. |
| 7,201,772 B2 | 4/2007 | Schwammenthal |
| 7,252,682 B2 | 8/2007 | Seguin |
| D553,747 S | 10/2007 | Fliedner |
| 7,276,078 B2 | 10/2007 | Spenser et al. |
| 7,276,084 B2 | 10/2007 | Yang et al. |
| 7,311,730 B2 | 12/2007 | Gabbay |
| 7,329,278 B2 | 2/2008 | Seguin et al. |
| 7,377,938 B2 | 5/2008 | Sarac et al. |
| 7,381,210 B2 | 6/2008 | Zarbatany et al. |
| 7,381,219 B2 | 6/2008 | Salahieh et al. |
| 7,393,360 B2 | 7/2008 | Spenser et al. |
| 7,422,603 B2 | 9/2008 | Lane |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,455,689 B2 | 11/2008 | Johnson |
| 7,462,191 B2 | 12/2008 | Spenser et al. |
| 7,510,572 B2 | 3/2009 | Gabbay |
| 7,510,575 B2 | 3/2009 | Spenser et al. |
| 7,524,330 B2 | 4/2009 | Berreklouw |
| 7,527,646 B2 | 5/2009 | Rahdert et al. |
| 7,534,259 B2 | 5/2009 | Lashinski et al. |
| 7,534,261 B2 | 5/2009 | Friedman |
| 7,585,321 B2 | 9/2009 | Cribier |
| 7,608,114 B2 | 10/2009 | Levine et al. |
| 7,615,072 B2 | 11/2009 | Rust et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,628,805 B2 | 12/2009 | Spenser et al. |
| 7,632,298 B2 | 12/2009 | Hijlkema |
| 7,637,945 B2 | 12/2009 | Solem et al. |
| 7,637,946 B2 | 12/2009 | Solem et al. |
| 7,682,390 B2 | 3/2010 | Seguin |
| 7,708,775 B2 | 5/2010 | Rowe et al. |
| 7,712,606 B2 | 5/2010 | Salahieh et al. |
| 7,748,389 B2 | 7/2010 | Salahieh et al. |
| 7,753,949 B2 | 7/2010 | Lamphere et al. |
| D622,387 S | 8/2010 | Igaki |
| D622,388 S | 8/2010 | Igaki |
| 7,771,463 B2 | 8/2010 | Ton et al. |
| 7,771,472 B2 | 8/2010 | Hendricksen et al. |
| 7,780,725 B2 | 8/2010 | Haug et al. |
| 7,785,360 B2 | 8/2010 | Freitag |
| 7,803,185 B2 | 9/2010 | Gabbay et al. |
| 7,806,917 B2 | 10/2010 | Xiao |
| 7,806,919 B2 | 10/2010 | Bloom et al. |
| 7,815,589 B2 | 10/2010 | Meade et al. |
| 7,815,673 B2 | 10/2010 | Bloom et al. |
| 7,824,443 B2 | 11/2010 | Salahieh et al. |
| 7,837,727 B2 | 11/2010 | Goetz et al. |
| 7,846,203 B2 | 12/2010 | Cribier |
| 7,871,435 B2 | 1/2011 | Carpentier et al. |
| 7,892,281 B2 | 2/2011 | Seguin et al. |
| D635,261 S | 3/2011 | Rossi |
| D635,262 S | 3/2011 | Rossi |
| 7,896,915 B2 | 3/2011 | Guyenot et al. |
| 7,914,569 B2 | 3/2011 | Nguyen et al. |
| 7,919,112 B2 | 4/2011 | Pathak et al. |
| 7,947,075 B2 | 5/2011 | Goetz et al. |
| 7,959,672 B2 | 6/2011 | Salahieh et al. |
| 7,967,853 B2 | 6/2011 | Eidenschink et al. |
| 7,972,377 B2 | 7/2011 | Lane |
| 7,972,378 B2 | 7/2011 | Tabor et al. |
| 7,981,151 B2 | 7/2011 | Rowe |
| 7,993,392 B2 | 8/2011 | Righini et al. |
| 7,993,394 B2 | 8/2011 | Hariton et al. |
| 7,993,395 B2 | 8/2011 | Vanermen et al. |
| 7,998,196 B2 | 8/2011 | Mathison |
| 8,006,535 B2 | 8/2011 | Righini et al. |
| 8,009,887 B2 | 8/2011 | Ionasec et al. |
| 8,016,870 B2 | 9/2011 | Chew et al. |
| 8,016,877 B2 | 9/2011 | Seguin et al. |
| 8,029,564 B2 | 10/2011 | Johnson et al. |
| 8,034,104 B2 | 10/2011 | Carpentier et al. |
| 8,048,153 B2 | 11/2011 | Salahieh et al. |
| 8,052,747 B2 | 11/2011 | Melnikov et al. |
| 8,052,749 B2 | 11/2011 | Salahieh et al. |
| 8,052,750 B2 | 11/2011 | Tuval et al. |
| 8,057,538 B2 | 11/2011 | Bergin et al. |
| 8,057,539 B2 | 11/2011 | Ghione et al. |
| 8,057,540 B2 | 11/2011 | Letac et al. |
| 8,062,350 B2 | 11/2011 | Gale et al. |
| 8,062,355 B2 | 11/2011 | Figulla et al. |
| 8,062,359 B2 | 11/2011 | Marquez et al. |
| 8,066,755 B2 | 11/2011 | Zacharias et al. |
| 8,066,763 B2 | 11/2011 | Alt |
| 8,070,743 B2 | 12/2011 | Kagan et al. |
| 8,070,799 B2 | 12/2011 | Righini et al. |
| 8,070,800 B2 | 12/2011 | Lock et al. |
| 8,070,801 B2 | 12/2011 | Cohn |
| 8,070,802 B2 | 12/2011 | Lamphere et al. |
| 8,075,609 B2 | 12/2011 | Penn et al. |
| 8,075,611 B2 | 12/2011 | Millwee et al. |
| 8,075,615 B2 | 12/2011 | Eberhardt et al. |
| 8,078,279 B2 | 12/2011 | Dennis et al. |
| 8,080,054 B2 | 12/2011 | Rowe |
| 8,083,793 B2 | 12/2011 | Lane et al. |
| 8,088,158 B2 | 1/2012 | Brodeur |
| 8,088,404 B2 | 1/2012 | Udipi et al. |
| 8,092,520 B2 | 1/2012 | Quadri |
| 8,100,964 B2 | 1/2012 | Spence |
| 8,105,375 B2 | 1/2012 | Navia et al. |
| 8,105,377 B2 | 1/2012 | Liddicoat |
| 8,109,995 B2 | 2/2012 | Paniagua et al. |
| 8,109,996 B2 | 2/2012 | Stacchino et al. |
| 8,114,154 B2 | 2/2012 | Righini et al. |
| 8,118,866 B2 | 2/2012 | Herrmann et al. |
| 8,119,704 B2 | 2/2012 | Wang et al. |
| 8,123,801 B2 | 2/2012 | Milo |
| 8,128,681 B2 | 3/2012 | Shoemaker et al. |
| 8,128,688 B2 | 3/2012 | Ding et al. |
| 8,136,218 B2 | 3/2012 | Millwee et al. |
| 8,137,398 B2 | 3/2012 | Tuval et al. |
| 8,137,687 B2 | 3/2012 | Chen et al. |
| 8,142,492 B2 | 3/2012 | Forster et al. |
| 8,142,494 B2 | 3/2012 | Rahdert et al. |
| 8,147,504 B2 | 4/2012 | Ino et al. |
| 8,155,754 B2 | 4/2012 | Nygren et al. |
| 8,157,852 B2 | 4/2012 | Bloom et al. |
| 8,157,853 B2 | 4/2012 | Laske et al. |
| 8,158,187 B2 | 4/2012 | Chen et al. |
| 8,163,014 B2 | 4/2012 | Lane et al. |
| 8,167,926 B2 | 5/2012 | Hartley et al. |
| 8,167,932 B2 | 5/2012 | Bourang et al. |
| 8,167,934 B2 | 5/2012 | Styrc et al. |
| 8,168,275 B2 | 5/2012 | Lee et al. |
| 8,170,645 B2 | 5/2012 | Solar et al. |
| 8,177,799 B2 | 5/2012 | Orban, III |
| 8,177,836 B2 | 5/2012 | Lee et al. |
| 8,180,428 B2 | 5/2012 | Kaiser et al. |
| 8,182,528 B2 | 5/2012 | Salahieh et al. |
| 8,182,530 B2 | 5/2012 | Huber |
| 8,182,829 B2 | 5/2012 | Kleiner et al. |
| 8,187,851 B2 | 5/2012 | Shah et al. |
| 8,195,293 B2 | 6/2012 | Limousin et al. |
| 8,202,529 B2 | 6/2012 | Hossainy et al. |
| 8,211,169 B2 | 7/2012 | Lane et al. |
| 8,216,261 B2 | 7/2012 | Solem |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,221,482 B2 | 7/2012 | Cottone et al. |
| 8,221,493 B2 | 7/2012 | Boyle et al. |
| 8,226,666 B2 | 7/2012 | Zarbatany et al. |
| 8,226,710 B2 | 7/2012 | Nguyen et al. |
| 8,231,930 B2 | 7/2012 | Castro et al. |
| D665,079 S | 8/2012 | Zago |
| D665,080 S | 8/2012 | Zago |
| 8,236,045 B2 | 8/2012 | Benichou et al. |
| 8,236,241 B2 | 8/2012 | Carpentier et al. |
| 8,241,274 B2 | 8/2012 | Keogh et al. |
| 8,246,675 B2 | 8/2012 | Zegdi |

(56) References Cited

U.S. PATENT DOCUMENTS

| | | |
|---|---|---|
| 8,246,677 B2 | 8/2012 | Ryan |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,257,724 B2 | 9/2012 | Cromack et al. |
| 8,257,725 B2 | 9/2012 | Cromack et al. |
| 8,262,724 B2 | 9/2012 | Seguin et al. |
| 8,273,118 B2 | 9/2012 | Bergin |
| 8,273,120 B2 | 9/2012 | Dolan |
| 8,276,533 B2 | 10/2012 | Chambers et al. |
| 8,287,584 B2 | 10/2012 | Salahieh et al. |
| 8,287,591 B2 | 10/2012 | Keidar et al. |
| 8,303,653 B2 | 11/2012 | Bonhoeffer et al. |
| 8,308,798 B2 | 11/2012 | Pintor et al. |
| 8,313,520 B2 | 11/2012 | Barbut et al. |
| 8,313,525 B2 | 11/2012 | Tuval et al. |
| 8,317,854 B1 | 11/2012 | Ryan et al. |
| 8,323,335 B2 | 12/2012 | Rowe et al. |
| 8,323,336 B2 | 12/2012 | Hill et al. |
| 8,337,541 B2 | 12/2012 | Quadri et al. |
| 8,348,995 B2 | 1/2013 | Tuval et al. |
| 8,349,001 B2 | 1/2013 | Mensah et al. |
| 8,349,003 B2 | 1/2013 | Shu et al. |
| 8,353,921 B2 | 1/2013 | Schaller et al. |
| 8,353,948 B2 | 1/2013 | Besselink et al. |
| 8,353,953 B2 | 1/2013 | Giannetti et al. |
| 8,353,954 B2 | 1/2013 | Cai et al. |
| 8,357,387 B2 | 1/2013 | Dove et al. |
| 8,361,137 B2 | 1/2013 | Perouse |
| 8,361,537 B2 | 1/2013 | Shanley |
| 8,366,769 B2 | 2/2013 | Huynh et al. |
| 8,377,116 B2 | 2/2013 | Hsu et al. |
| 8,377,499 B2 | 2/2013 | Kleiner et al. |
| 8,382,816 B2 | 2/2013 | Pollock et al. |
| RE44,075 E | 3/2013 | Williamson et al. |
| 8,398,707 B2 | 3/2013 | Bergin |
| 8,398,708 B2 | 3/2013 | Meiri et al. |
| 8,403,983 B2 | 3/2013 | Quadri et al. |
| 8,408,214 B2 | 4/2013 | Spenser |
| 8,409,274 B2 | 4/2013 | Li et al. |
| 8,414,635 B2 | 4/2013 | Hyodoh et al. |
| 8,414,643 B2 | 4/2013 | Tuval et al. |
| 8,414,644 B2 * | 4/2013 | Quadri .................. A61F 2/243 623/2.11 |
| 8,414,645 B2 | 4/2013 | Dwork et al. |
| 8,430,902 B2 | 4/2013 | Bergheim |
| 8,430,927 B2 | 4/2013 | Bonhoeffer |
| 8,444,689 B2 | 5/2013 | Zhang |
| 8,449,466 B2 | 5/2013 | Duhay et al. |
| 8,449,599 B2 | 5/2013 | Chau et al. |
| 8,449,625 B2 | 5/2013 | Campbell et al. |
| 8,454,684 B2 | 6/2013 | Bergin et al. |
| 8,454,685 B2 | 6/2013 | Hariton et al. |
| 8,460,335 B2 | 6/2013 | Carpenter |
| 8,460,365 B2 | 6/2013 | Haverkost et al. |
| 8,460,366 B2 | 6/2013 | Rowe |
| 8,460,370 B2 | 6/2013 | Zakay et al. |
| 8,460,373 B2 | 6/2013 | Fogarty et al. |
| 8,468,667 B2 * | 6/2013 | Straubinger .......... A61F 2/2427 29/280 |
| 8,470,023 B2 | 6/2013 | Eidenschink et al. |
| 8,470,024 B2 | 6/2013 | Ghione et al. |
| 8,475,521 B2 | 7/2013 | Suri et al. |
| 8,475,522 B2 | 7/2013 | Jimenez et al. |
| 8,475,523 B2 | 7/2013 | Duffy |
| 8,479,380 B2 | 7/2013 | Malewicz et al. |
| 8,480,730 B2 | 7/2013 | Maurer et al. |
| 8,480,731 B2 | 7/2013 | Elizondo et al. |
| 8,486,137 B2 | 7/2013 | Suri et al. |
| 8,491,650 B2 | 7/2013 | Wiemeyer et al. |
| 8,500,688 B2 | 8/2013 | Engel et al. |
| 8,500,755 B2 | 8/2013 | Ino et al. |
| 8,500,798 B2 | 8/2013 | Rowe et al. |
| 8,500,801 B2 | 8/2013 | Eberhardt et al. |
| 8,500,802 B2 | 8/2013 | Lane et al. |
| 8,506,620 B2 | 8/2013 | Ryan |
| 8,506,625 B2 | 8/2013 | Johnson |
| 8,511,244 B2 | 8/2013 | Holecek et al. |
| 8,512,397 B2 | 8/2013 | Rolando et al. |
| 8,512,398 B2 | 8/2013 | Alkhatib |
| 8,512,399 B2 | 8/2013 | Lafontaine |
| 8,512,400 B2 | 8/2013 | Tran et al. |
| 8,512,401 B2 | 8/2013 | Murray, III et al. |
| 8,512,403 B2 | 8/2013 | Navia et al. |
| 8,518,106 B2 | 8/2013 | Duffy et al. |
| 8,518,108 B2 | 8/2013 | Huynh et al. |
| 8,529,621 B2 | 9/2013 | Alfieri et al. |
| 8,535,368 B2 | 9/2013 | Headley, Jr. et al. |
| 8,539,662 B2 | 9/2013 | Stacchino et al. |
| 8,545,742 B2 | 10/2013 | Gada et al. |
| 8,551,162 B2 | 10/2013 | Fogarty et al. |
| 8,562,663 B2 | 10/2013 | Mearns et al. |
| 8,562,672 B2 | 10/2013 | Bonhoeffer et al. |
| 8,562,673 B2 | 10/2013 | Yeung et al. |
| 8,565,872 B2 | 10/2013 | Pederson |
| 8,568,472 B2 | 10/2013 | Marchand et al. |
| 8,579,964 B2 | 11/2013 | Lane et al. |
| 8,579,965 B2 | 11/2013 | Bonhoeffer et al. |
| 8,584,849 B2 | 11/2013 | Mccaffrey |
| 8,585,749 B2 | 11/2013 | Shelso |
| 8,585,755 B2 | 11/2013 | Chau et al. |
| 8,585,756 B2 | 11/2013 | Bonhoeffer et al. |
| 8,591,570 B2 | 11/2013 | Revuelta et al. |
| 8,591,574 B2 | 11/2013 | Lambrecht et al. |
| 8,597,348 B2 | 12/2013 | Rowe et al. |
| 8,603,154 B2 | 12/2013 | Strauss et al. |
| 8,603,160 B2 | 12/2013 | Salahieh et al. |
| 8,603,161 B2 | 12/2013 | Drews et al. |
| 8,608,648 B2 | 12/2013 | Banik et al. |
| 8,608,797 B2 | 12/2013 | Gross et al. |
| 8,617,236 B2 | 12/2013 | Paul et al. |
| 8,623,074 B2 | 1/2014 | Ryan |
| 8,623,079 B2 | 1/2014 | Savage et al. |
| 8,623,080 B2 | 1/2014 | Fogarty et al. |
| 8,628,566 B2 | 1/2014 | Eberhardt et al. |
| 8,632,586 B2 | 1/2014 | Spenser et al. |
| 8,632,608 B2 | 1/2014 | Carpentier et al. |
| 8,640,521 B2 | 2/2014 | Righini et al. |
| 8,641,639 B2 | 2/2014 | Manstrom et al. |
| 8,647,381 B2 | 2/2014 | Essinger et al. |
| 8,652,145 B2 | 2/2014 | Maimon et al. |
| 8,652,201 B2 | 2/2014 | Oberti et al. |
| 8,652,202 B2 | 2/2014 | Alon et al. |
| 8,652,203 B2 | 2/2014 | Quadri et al. |
| 8,653,632 B2 | 2/2014 | Pederson et al. |
| 8,663,318 B2 | 3/2014 | Ho |
| 8,663,319 B2 | 3/2014 | Ho |
| 8,668,730 B2 | 3/2014 | Mcguckin, Jr. et al. |
| 8,668,733 B2 | 3/2014 | Haug |
| 8,672,992 B2 | 3/2014 | Orr |
| 8,672,997 B2 | 3/2014 | Drasler et al. |
| 8,672,998 B2 | 3/2014 | Lichtenstein et al. |
| 8,672,999 B2 | 3/2014 | Cali et al. |
| 8,673,000 B2 | 3/2014 | Tabor et al. |
| 8,679,174 B2 | 3/2014 | Ottma et al. |
| 8,679,404 B2 | 3/2014 | Liburd et al. |
| 8,685,083 B2 | 4/2014 | Perier et al. |
| 8,685,086 B2 | 4/2014 | Navia et al. |
| 8,690,787 B2 | 4/2014 | Blomqvist et al. |
| 8,690,936 B2 | 4/2014 | Nguyen et al. |
| 8,696,742 B2 | 4/2014 | Pintor et al. |
| 8,707,957 B2 | 4/2014 | Callister et al. |
| 8,715,207 B2 | 5/2014 | Righini et al. |
| 8,715,337 B2 | 5/2014 | Chuter |
| 8,715,343 B2 | 5/2014 | Navia et al. |
| 8,721,707 B2 | 5/2014 | Boucher et al. |
| 8,721,708 B2 | 5/2014 | Seguin et al. |
| 8,721,713 B2 | 5/2014 | Tower et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,731,658 B2 | 5/2014 | Hampton et al. |
| 8,734,484 B2 | 5/2014 | Ahlberg et al. |
| 8,740,930 B2 | 6/2014 | Goodwin |

(56) References Cited

U.S. PATENT DOCUMENTS

| | | | |
|---|---|---|---|
| 8,740,974 B2 | 6/2014 | Lambrecht et al. |
| 8,740,975 B2 | 6/2014 | Yang et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,747,460 B2 | 6/2014 | Tuval et al. |
| 8,753,384 B2 | 6/2014 | Leanna |
| 8,758,432 B2 | 6/2014 | Solem |
| 8,764,814 B2 | 7/2014 | Solem |
| 8,764,820 B2 | 7/2014 | Dehdashtian et al. |
| 8,771,302 B2 | 7/2014 | Woolfson et al. |
| 8,771,344 B2 | 7/2014 | Tran et al. |
| 8,771,345 B2 | 7/2014 | Tuval et al. |
| 8,771,346 B2 | 7/2014 | Tuval et al. |
| 8,777,975 B2 | 7/2014 | Kashkarov et al. |
| 8,778,018 B2 | 7/2014 | Iobbi |
| 8,784,478 B2 | 7/2014 | Tuval et al. |
| 8,784,480 B2 | 7/2014 | Taylor et al. |
| 8,784,481 B2 | 7/2014 | Alkhatib et al. |
| 8,790,387 B2 | 7/2014 | Nguyen et al. |
| 8,790,395 B2 | 7/2014 | Straubinger et al. |
| 8,790,396 B2 | 7/2014 | Bergheim et al. |
| 8,791,171 B2 | 7/2014 | Pacetti |
| 8,795,356 B2 | 8/2014 | Quadri et al. |
| 8,801,776 B2 | 8/2014 | House et al. |
| 8,808,366 B2 | 8/2014 | Braido et al. |
| 8,808,370 B2 | 8/2014 | Nitzan et al. |
| 8,821,569 B2 | 9/2014 | Gurskis et al. |
| 8,821,570 B2 | 9/2014 | Dumontelle et al. |
| 8,828,078 B2 | 9/2014 | Salahieh et al. |
| 8,828,079 B2 | 9/2014 | Thielen et al. |
| 8,834,561 B2 | 9/2014 | Figulla et al. |
| 8,834,564 B2 | 9/2014 | Tuval et al. |
| 8,840,661 B2 | 9/2014 | Manasse |
| 8,845,718 B2 | 9/2014 | Tuval et al. |
| 8,845,720 B2 | 9/2014 | Conklin |
| 8,852,267 B2 | 10/2014 | Cattaneo |
| 8,858,620 B2 | 10/2014 | Salahieh et al. |
| 8,858,621 B2 | 10/2014 | Oba et al. |
| 8,870,936 B2 | 10/2014 | Rowe |
| 8,870,947 B2 | 10/2014 | Shaw |
| 8,870,948 B1 | 10/2014 | Erzberger et al. |
| 8,876,712 B2 | 11/2014 | Yee et al. |
| 8,876,883 B2 | 11/2014 | Rust |
| 8,876,893 B2 | 11/2014 | Dwork et al. |
| 8,876,894 B2 | 11/2014 | Tuval et al. |
| 8,876,895 B2 | 11/2014 | Tuval et al. |
| 8,882,831 B2 | 11/2014 | Alkhatib |
| 8,893,370 B2 | 11/2014 | Hillukka et al. |
| 8,894,702 B2 | 11/2014 | Quadri et al. |
| 8,894,703 B2 | 11/2014 | Salahieh et al. |
| 8,906,081 B2 | 12/2014 | Cully et al. |
| 8,911,455 B2 | 12/2014 | Quadri et al. |
| 8,911,844 B2 | 12/2014 | Ford |
| 8,926,688 B2 | 1/2015 | Burkart et al. |
| 8,926,693 B2 | 1/2015 | Duffy et al. |
| 8,932,349 B2 | 1/2015 | Jenson et al. |
| 8,940,887 B2 | 1/2015 | Chatterton et al. |
| 8,945,208 B2 | 2/2015 | Jimenez et al. |
| 8,945,209 B2 | 2/2015 | Bonyuet et al. |
| 8,945,210 B2 | 2/2015 | Cartledge et al. |
| 8,951,280 B2 | 2/2015 | Cohn et al. |
| 8,951,299 B2 | 2/2015 | Paul et al. |
| 8,961,583 B2 | 2/2015 | Hojeibane et al. |
| 8,961,589 B2 | 2/2015 | Kleiner et al. |
| 8,961,593 B2 | 2/2015 | Bonhoeffer et al. |
| 8,961,595 B2 | 2/2015 | Alkhatib |
| 8,968,393 B2 | 3/2015 | Rothstein |
| 8,968,395 B2 | 3/2015 | Hauser et al. |
| 8,974,524 B2 | 3/2015 | Yeung et al. |
| 8,979,922 B2 | 3/2015 | Jayasinghe et al. |
| 8,986,372 B2 | 3/2015 | Murry, III et al. |
| 8,986,713 B2 | 3/2015 | Cleek et al. |
| 8,992,608 B2 | 3/2015 | Haug et al. |
| 8,998,978 B2 | 4/2015 | Wang |
| 8,998,979 B2 | 4/2015 | Seguin et al. |
| 8,998,980 B2 | 4/2015 | Shipley et al. |
| 8,998,981 B2 | 4/2015 | Tuval et al. |
| 8,999,369 B2 | 4/2015 | Gale et al. |
| 9,005,273 B2 | 4/2015 | Salahieh et al. |
| 9,005,277 B2 | 4/2015 | Pintor et al. |
| 9,011,521 B2 | 4/2015 | Haug et al. |
| 9,011,523 B2 | 4/2015 | Seguin |
| 9,011,524 B2 | 4/2015 | Eberhardt |
| 9,011,528 B2 | 4/2015 | Ryan et al. |
| 9,021,674 B2 | 5/2015 | Hillukka et al. |
| 9,023,100 B2 | 5/2015 | Quadri et al. |
| 9,028,545 B2 | 5/2015 | Taylor |
| 9,029,418 B2 | 5/2015 | Dove et al. |
| 9,034,032 B2 | 5/2015 | Mclean et al. |
| 9,034,033 B2 | 5/2015 | Mclean et al. |
| 9,055,937 B2 | 6/2015 | Rowe et al. |
| 9,072,603 B2 | 7/2015 | Tuval et al. |
| 9,078,749 B2 | 7/2015 | Lutter et al. |
| 9,078,751 B2 | 7/2015 | Naor |
| 9,084,676 B2 | 7/2015 | Chau et al. |
| 9,125,738 B2 | 9/2015 | Figulla et al. |
| 9,138,312 B2 | 9/2015 | Tuval et al. |
| 9,161,834 B2 | 10/2015 | Taylor et al. |
| 9,320,597 B2 | 4/2016 | Savage et al. |
| D755,384 S | 5/2016 | Pesce et al. |
| 9,333,074 B2 | 5/2016 | Quadri et al. |
| 9,333,077 B2 | 5/2016 | Peter |
| 9,345,573 B2 * | 5/2016 | Nyuli ................... A61F 2/2412 |
| 9,554,897 B2 | 1/2017 | Lane et al. |
| 9,770,329 B2 | 9/2017 | Lane et al. |
| 10,016,275 B2 * | 7/2018 | Nyuli ...................... A61F 2/243 |
| 10,123,892 B2 | 11/2018 | Hacker et al. |
| 10,188,515 B2 | 1/2019 | Duffy et al. |
| 10,245,145 B2 | 4/2019 | Mantanus et al. |
| 10,314,705 B2 | 6/2019 | Nyuli et al. |
| 10,350,047 B2 | 7/2019 | Rajpara et al. |
| 10,583,002 B2 | 3/2020 | Lane et al. |
| 10,639,147 B2 | 5/2020 | Landon et al. |
| 10,682,228 B2 | 6/2020 | Mantanus et al. |
| 10,940,001 B2 | 3/2021 | Nyuli et al. |
| 10,973,635 B2 | 4/2021 | Duffy et al. |
| 11,020,221 B2 | 6/2021 | Arcaro et al. |
| 11,389,294 B2 | 7/2022 | Nyuli et al. |
| 2001/0007956 A1 | 7/2001 | Letac et al. |
| 2001/0021872 A1 | 9/2001 | Bailey et al. |
| 2001/0045539 A1 * | 11/2001 | Doyle ................... A61M 39/26 |
| | | 604/249 |
| 2001/0047180 A1 | 11/2001 | Grudem et al. |
| 2001/0047200 A1 | 11/2001 | White et al. |
| 2002/0016623 A1 | 2/2002 | Kula et al. |
| 2002/0022853 A1 | 2/2002 | Swanson et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2002/0055772 A1 | 5/2002 | Mcguckin et al. |
| 2002/0111619 A1 | 8/2002 | Keast et al. |
| 2002/0177899 A1 * | 11/2002 | Eum ........................ A61F 2/95 |
| | | 623/1.19 |
| 2002/0183827 A1 | 12/2002 | Derus et al. |
| 2002/0198584 A1 * | 12/2002 | Unsworth ............... A61F 2/954 |
| | | 623/1.11 |
| 2003/0040792 A1 | 2/2003 | Gabbay |
| 2003/0105517 A1 | 6/2003 | White et al. |
| 2003/0114913 A1 | 6/2003 | Spenser et al. |
| 2003/0120263 A1 | 6/2003 | Ouriel et al. |
| 2003/0120330 A1 | 6/2003 | Ouriel et al. |
| 2003/0120333 A1 | 6/2003 | Ouriel et al. |
| 2003/0125797 A1 | 7/2003 | Chobotov et al. |
| 2003/0130729 A1 | 7/2003 | Paniagua et al. |
| 2003/0135970 A1 | 7/2003 | Thornton |
| 2003/0176914 A1 | 9/2003 | Rabkin et al. |
| 2003/0199971 A1 | 10/2003 | Tower et al. |
| 2003/0220683 A1 | 11/2003 | Minasian et al. |
| 2004/0039436 A1 | 2/2004 | Spenser et al. |
| 2004/0087900 A1 | 5/2004 | Thompson et al. |
| 2004/0093058 A1 | 5/2004 | Cottone et al. |
| 2004/0093060 A1 | 5/2004 | Seguin et al. |
| 2004/0102842 A1 | 5/2004 | Jansen |

(56) References Cited

U.S. PATENT DOCUMENTS

| | | |
|---|---|---|
| 2004/0117009 A1 | 6/2004 | Cali et al. |
| 2004/0133273 A1 | 7/2004 | Cox |
| 2004/0181238 A1 | 9/2004 | Zarbatany et al. |
| 2004/0186561 A1 | 9/2004 | Mcguckin et al. |
| 2004/0193261 A1 | 9/2004 | Berreklouw |
| 2004/0210304 A1 | 10/2004 | Seguin et al. |
| 2004/0210307 A1 | 10/2004 | Khairkhahan |
| 2004/0215325 A1 | 10/2004 | Penn et al. |
| 2004/0225353 A1 | 11/2004 | James, Jr. et al. |
| 2004/0236411 A1 | 11/2004 | Sarac et al. |
| 2004/0243230 A1 | 12/2004 | Navia et al. |
| 2004/0249433 A1 | 12/2004 | Freitag |
| 2004/0260390 A1 | 12/2004 | Sarac et al. |
| 2005/0033398 A1 | 2/2005 | Seguin |
| 2005/0038470 A1 | 2/2005 | Van Der Burg et al. |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0125020 A1 | 6/2005 | Meade et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137690 A1 | 6/2005 | Salahieh et al. |
| 2005/0137691 A1 | 6/2005 | Salahieh et al. |
| 2005/0137693 A1 | 6/2005 | Haug |
| 2005/0137695 A1 | 6/2005 | Salahieh et al. |
| 2005/0137701 A1 | 6/2005 | Salahieh et al. |
| 2005/0154444 A1 | 7/2005 | Quadri |
| 2005/0159811 A1 | 7/2005 | Lane |
| 2005/0182483 A1 | 8/2005 | Osborne et al. |
| 2005/0182486 A1 | 8/2005 | Gabbay |
| 2005/0203616 A1 | 9/2005 | Cribier |
| 2005/0216079 A1 | 9/2005 | Macoviak |
| 2005/0234546 A1 | 10/2005 | Nugent et al. |
| 2005/0283231 A1 | 12/2005 | Haug et al. |
| 2006/0020247 A1 | 1/2006 | Kagan et al. |
| 2006/0020327 A1 | 1/2006 | Lashinski et al. |
| 2006/0020334 A1 | 1/2006 | Lashinski et al. |
| 2006/0052802 A1 | 3/2006 | Sterman et al. |
| 2006/0052867 A1 | 3/2006 | Revuelta et al. |
| 2006/0058872 A1 | 3/2006 | Salahieh et al. |
| 2006/0064120 A1 | 3/2006 | Levine et al. |
| 2006/0095115 A1 | 5/2006 | Bladillah et al. |
| 2006/0106454 A1 | 5/2006 | Osborne et al. |
| 2006/0116625 A1 | 6/2006 | Renati et al. |
| 2006/0129235 A1 | 6/2006 | Seguin et al. |
| 2006/0149360 A1 | 7/2006 | Schwammenthal et al. |
| 2006/0161265 A1 | 7/2006 | Levine et al. |
| 2006/0173537 A1 | 8/2006 | Yang et al. |
| 2006/0195183 A1 | 8/2006 | Navia et al. |
| 2006/0212110 A1 | 9/2006 | Osborne et al. |
| 2006/0224232 A1 | 10/2006 | Chobotov |
| 2006/0241745 A1 | 10/2006 | Solem |
| 2006/0253191 A1 | 11/2006 | Salahieh et al. |
| 2006/0259135 A1 | 11/2006 | Navia et al. |
| 2006/0259136 A1 | 11/2006 | Nguyen et al. |
| 2006/0265056 A1 | 11/2006 | Nguyen et al. |
| 2006/0287717 A1 | 12/2006 | Rowe et al. |
| 2006/0287719 A1 | 12/2006 | Rowe et al. |
| 2006/0293698 A1 | 12/2006 | Douk |
| 2006/0293745 A1 | 12/2006 | Carpentier et al. |
| 2007/0010876 A1 | 1/2007 | Salahieh |
| 2007/0016286 A1 | 1/2007 | Herrmann et al. |
| 2007/0043435 A1 | 2/2007 | Seguin et al. |
| 2007/0050020 A1 | 3/2007 | Spence |
| 2007/0050021 A1 | 3/2007 | Johnson |
| 2007/0067016 A1 | 3/2007 | Jung |
| 2007/0100432 A1 | 5/2007 | Case et al. |
| 2007/0118206 A1 | 5/2007 | Colgan et al. |
| 2007/0118207 A1 | 5/2007 | Amplatz et al. |
| 2007/0129794 A1 | 6/2007 | Realyvasquez |
| 2007/0142906 A1 | 6/2007 | Figulla et al. |
| 2007/0162107 A1 | 7/2007 | Haug et al. |
| 2007/0185559 A1 | 8/2007 | Shelso |
| 2007/0213813 A1 | 9/2007 | Von Segesser et al. |
| 2007/0219620 A1 | 9/2007 | Eells et al. |
| 2007/0233228 A1 | 10/2007 | Eberhardt et al. |
| 2007/0250151 A1 | 10/2007 | Pereira |
| 2007/0255391 A1 | 11/2007 | Hojeibane et al. |
| 2007/0255394 A1 | 11/2007 | Ryan |
| 2007/0265656 A1 | 11/2007 | Amplatz et al. |
| 2007/0270932 A1 | 11/2007 | Headley et al. |
| 2007/0270937 A1 | 11/2007 | Leanna |
| 2007/0293940 A1 | 12/2007 | Schaeffer et al. |
| 2008/0009934 A1 | 1/2008 | Schneider et al. |
| 2008/0021546 A1 | 1/2008 | Patz et al. |
| 2008/0022504 A1 | 1/2008 | Melsheimer |
| 2008/0053577 A1 | 3/2008 | Syed et al. |
| 2008/0071361 A1 | 3/2008 | Tuval et al. |
| 2008/0071363 A1 | 3/2008 | Tuval et al. |
| 2008/0071366 A1 | 3/2008 | Tuval et al. |
| 2008/0071369 A1 | 3/2008 | Tuval et al. |
| 2008/0082164 A1 | 4/2008 | Friedman |
| 2008/0082165 A1 | 4/2008 | Wilson et al. |
| 2008/0082166 A1 | 4/2008 | Styrc et al. |
| 2008/0087581 A1 | 4/2008 | Eisenhut et al. |
| 2008/0097571 A1 | 4/2008 | Denison et al. |
| 2008/0114441 A1 | 5/2008 | Rust et al. |
| 2008/0125853 A1 | 5/2008 | Bailey et al. |
| 2008/0125859 A1 | 5/2008 | Salahieh et al. |
| 2008/0127707 A1 | 6/2008 | Kokish et al. |
| 2008/0133003 A1 | 6/2008 | Seguin et al. |
| 2008/0140189 A1 | 6/2008 | Nguyen et al. |
| 2008/0147179 A1 | 6/2008 | Cai et al. |
| 2008/0147183 A1 | 6/2008 | Styrc |
| 2008/0154358 A1 | 6/2008 | Tansley et al. |
| 2008/0161911 A1 | 7/2008 | Revuelta et al. |
| 2008/0177381 A1 | 7/2008 | Navia et al. |
| 2008/0183273 A1 | 7/2008 | Mesana et al. |
| 2008/0208307 A1 | 8/2008 | Ben-muvhar et al. |
| 2008/0208328 A1 | 8/2008 | Antocci et al. |
| 2008/0208332 A1 | 8/2008 | Lamphere et al. |
| 2008/0221672 A1 | 9/2008 | Lamphere |
| 2008/0228201 A1 | 9/2008 | Zarbatany et al. |
| 2008/0228254 A1 | 9/2008 | Ryan |
| 2008/0243233 A1 | 10/2008 | Ben-muvhar et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0262596 A1 | 10/2008 | Xiao |
| 2008/0262603 A1 | 10/2008 | Giaquinta et al. |
| 2008/0269878 A1 | 10/2008 | Lobbi |
| 2008/0275549 A1 | 11/2008 | Rowe |
| 2008/0288062 A1 | 11/2008 | Andrieu et al. |
| 2008/0319526 A1 | 12/2008 | Hill et al. |
| 2009/0005863 A1 | 1/2009 | Goetz et al. |
| 2009/0012602 A1 | 1/2009 | Quadri |
| 2009/0054976 A1 | 2/2009 | Tuval et al. |
| 2009/0062908 A1 | 3/2009 | Bonhoeffer et al. |
| 2009/0076531 A1 | 3/2009 | Richardson et al. |
| 2009/0076585 A1 | 3/2009 | Hendriksen et al. |
| 2009/0076598 A1 | 3/2009 | Salahieh et al. |
| 2009/0082844 A1 | 3/2009 | Zacharias et al. |
| 2009/0082847 A1 | 3/2009 | Zacharias et al. |
| 2009/0088832 A1 | 4/2009 | Chew et al. |
| 2009/0093876 A1 | 4/2009 | Nitzan et al. |
| 2009/0112309 A1 | 4/2009 | Jaramillo et al. |
| 2009/0118744 A1 | 5/2009 | Wells et al. |
| 2009/0118824 A1 | 5/2009 | Samkov |
| 2009/0118826 A1 | 5/2009 | Khaghani |
| 2009/0125096 A1 | 5/2009 | Chu et al. |
| 2009/0132035 A1 | 5/2009 | Roth et al. |
| 2009/0138079 A1 | 5/2009 | Tuval et al. |
| 2009/0149946 A1 | 6/2009 | Dixon |
| 2009/0157175 A1 | 6/2009 | Benichou |
| 2009/0163934 A1 | 6/2009 | Raschdorf, Jr. et al. |
| 2009/0171438 A1 | 7/2009 | Chuter et al. |
| 2009/0171456 A1 | 7/2009 | Kveen |
| 2009/0177262 A1 | 7/2009 | Oberti et al. |
| 2009/0182407 A1 | 7/2009 | Leanna et al. |
| 2009/0182413 A1 | 7/2009 | Burkart et al. |
| 2009/0188964 A1 | 7/2009 | Orlov |
| 2009/0192601 A1 | 7/2009 | Rafiee et al. |

(56) References Cited

U.S. PATENT DOCUMENTS

| | | |
|---|---|---|
| 2009/0216314 A1 | 8/2009 | Quadri |
| 2009/0216317 A1 | 8/2009 | Cromack et al. |
| 2009/0222076 A1 | 9/2009 | Figulla et al. |
| 2009/0227992 A1 | 9/2009 | Nir et al. |
| 2009/0234443 A1 | 9/2009 | Ottma et al. |
| 2009/0248132 A1 | 10/2009 | Bloom et al. |
| 2009/0248133 A1 | 10/2009 | Bloom et al. |
| 2009/0258958 A1 | 10/2009 | Ford |
| 2009/0264989 A1 | 10/2009 | Bonhoeffer et al. |
| 2009/0264997 A1 | 10/2009 | Salahieh |
| 2009/0270972 A1 | 10/2009 | Lane |
| 2009/0276040 A1 | 11/2009 | Rowe et al. |
| 2009/0281618 A1 | 11/2009 | Hill et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0292350 A1 | 11/2009 | Eberhardt et al. |
| 2009/0306768 A1 | 12/2009 | Quadri |
| 2009/0318871 A1 | 12/2009 | Zarbatany et al. |
| 2010/0004740 A1 | 1/2010 | Seguin et al. |
| 2010/0036479 A1 | 2/2010 | Hill et al. |
| 2010/0049306 A1 | 2/2010 | House et al. |
| 2010/0082089 A1 | 4/2010 | Quadri et al. |
| 2010/0082094 A1 | 4/2010 | Quadri et al. |
| 2010/0094411 A1 | 4/2010 | Tuval et al. |
| 2010/0114299 A1 | 5/2010 | Ben Muvhar et al. |
| 2010/0114305 A1 | 5/2010 | Kang et al. |
| 2010/0121424 A1 | 5/2010 | Kubena et al. |
| 2010/0121461 A1 | 5/2010 | Sobrino-Serrano et al. |
| 2010/0161027 A1 | 6/2010 | Orr |
| 2010/0179633 A1 | 7/2010 | Solem |
| 2010/0179647 A1 | 7/2010 | Carpenter et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0249908 A1 | 9/2010 | Chau et al. |
| 2010/0256723 A1 | 10/2010 | Murray |
| 2010/0262157 A1 | 10/2010 | Silver et al. |
| 2010/0274345 A1 | 10/2010 | Rust |
| 2010/0280606 A1 | 11/2010 | Naor |
| 2010/0286768 A1 | 11/2010 | Alkhatib |
| 2010/0292779 A1 | 11/2010 | Straubinger et al. |
| 2010/0292780 A1* | 11/2010 | Straubinger .......... A61F 2/95 623/1.23 |
| 2010/0298931 A1* | 11/2010 | Quadri .................. A61F 2/2418 623/2.11 |
| 2010/0305685 A1 | 12/2010 | Millwee et al. |
| 2010/0312333 A1 | 12/2010 | Navia et al. |
| 2011/0004296 A1 | 1/2011 | Lutter et al. |
| 2011/0015731 A1 | 1/2011 | Carpentier et al. |
| 2011/0022157 A1 | 1/2011 | Essinger et al. |
| 2011/0022165 A1 | 1/2011 | Oba et al. |
| 2011/0029067 A1 | 2/2011 | Mcguckin, Jr. et al. |
| 2011/0114230 A1 | 5/2011 | Syed et al. |
| 2011/0137397 A1 | 6/2011 | Chau et al. |
| 2011/0166644 A1 | 7/2011 | Keeble et al. |
| 2011/0178597 A9 | 7/2011 | Navia et al. |
| 2011/0208297 A1 | 8/2011 | Tuval et al. |
| 2011/0208298 A1 | 8/2011 | Tuval et al. |
| 2011/0218619 A1 | 9/2011 | Benichou et al. |
| 2011/0224678 A1 | 9/2011 | Gabbay |
| 2011/0224785 A1 | 9/2011 | Hacohen |
| 2011/0251680 A1 | 10/2011 | Tran et al. |
| 2011/0264196 A1 | 10/2011 | Savage et al. |
| 2011/0282438 A1 | 11/2011 | Drews et al. |
| 2011/0301704 A1 | 12/2011 | Alfieri et al. |
| 2011/0313515 A1 | 12/2011 | Quadri et al. |
| 2011/0319981 A1 | 12/2011 | Hill et al. |
| 2011/0319989 A1 | 12/2011 | Lane et al. |
| 2012/0012487 A1 | 1/2012 | Tian et al. |
| 2012/0016342 A1 | 1/2012 | Brecker |
| 2012/0016411 A1 | 1/2012 | Tuval |
| 2012/0022605 A1 | 1/2012 | Jahns et al. |
| 2012/0022639 A1 | 1/2012 | Hacohen et al. |
| 2012/0022642 A1 | 1/2012 | Haug et al. |
| 2012/0029627 A1 | 2/2012 | Salahieh et al. |
| 2012/0035703 A1 | 2/2012 | Lutter et al. |
| 2012/0035713 A1 | 2/2012 | Lutter et al. |
| 2012/0041550 A1 | 2/2012 | Salahieh et al. |
| 2012/0041551 A1 | 2/2012 | Spenser et al. |
| 2012/0059452 A1 | 3/2012 | Boucher et al. |
| 2012/0059454 A1 | 3/2012 | Millwee et al. |
| 2012/0078353 A1 | 3/2012 | Quadri et al. |
| 2012/0078360 A1 | 3/2012 | Rafiee |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0179051 A1 | 7/2012 | Pfeiffer et al. |
| 2012/0179239 A1 | 7/2012 | Quadri |
| 2012/0179243 A1 | 7/2012 | Yang et al. |
| 2012/0185033 A1 | 7/2012 | Ryan |
| 2012/0215303 A1 | 8/2012 | Quadri et al. |
| 2012/0259405 A1 | 10/2012 | Weber et al. |
| 2012/0259409 A1 | 10/2012 | Nguyen et al. |
| 2012/0271398 A1 | 10/2012 | Essinger et al. |
| 2012/0283820 A1 | 11/2012 | Tseng et al. |
| 2012/0283824 A1 | 11/2012 | Lutter et al. |
| 2012/0290062 A1 | 11/2012 | Mcnamara et al. |
| 2012/0296418 A1 | 11/2012 | Bonyuet et al. |
| 2012/0303116 A1 | 11/2012 | Gorman, III et al. |
| 2012/0310328 A1 | 12/2012 | Olson et al. |
| 2012/0323316 A1 | 12/2012 | Chau et al. |
| 2012/0330408 A1 | 12/2012 | Hillukka et al. |
| 2012/0330409 A1 | 12/2012 | Haug et al. |
| 2013/0006294 A1 | 1/2013 | Kashkarov et al. |
| 2013/0018458 A1 | 1/2013 | Yohanan et al. |
| 2013/0030418 A1 | 1/2013 | Taft et al. |
| 2013/0030523 A1 | 1/2013 | Padala et al. |
| 2013/0046378 A1 | 2/2013 | Millwee et al. |
| 2013/0053949 A1 | 2/2013 | Pintor et al. |
| 2013/0053950 A1 | 2/2013 | Rowe et al. |
| 2013/0095264 A1 | 4/2013 | Sowinski et al. |
| 2013/0096671 A1 | 4/2013 | Iobbi |
| 2013/0110226 A1 | 5/2013 | Gurskis |
| 2013/0110227 A1 | 5/2013 | Quadri et al. |
| 2013/0110230 A1 | 5/2013 | Solem |
| 2013/0116777 A1 | 5/2013 | Pintor et al. |
| 2013/0131788 A1 | 5/2013 | Quadri et al. |
| 2013/0131793 A1 | 5/2013 | Quadri et al. |
| 2013/0138203 A1 | 5/2013 | Quadri |
| 2013/0138207 A1 | 5/2013 | Quadri et al. |
| 2013/0144375 A1 | 6/2013 | Giasolli et al. |
| 2013/0144378 A1 | 6/2013 | Quadri et al. |
| 2013/0144380 A1 | 6/2013 | Quadri et al. |
| 2013/0144381 A1 | 6/2013 | Quadri et al. |
| 2013/0150956 A1 | 6/2013 | Yohanan et al. |
| 2013/0166020 A1 | 6/2013 | Hillukka et al. |
| 2013/0166024 A1 | 6/2013 | Drews et al. |
| 2013/0172983 A1 | 7/2013 | Clerc et al. |
| 2013/0184813 A1 | 7/2013 | Quadri et al. |
| 2013/0184814 A1 | 7/2013 | Huynh et al. |
| 2013/0211508 A1 | 8/2013 | Lane et al. |
| 2013/0236889 A1 | 9/2013 | Kishimoto et al. |
| 2013/0238087 A1 | 9/2013 | Taylor |
| 2013/0245615 A1 | 9/2013 | Koltz |
| 2013/0245736 A1 | 9/2013 | Alexander et al. |
| 2013/0253635 A1 | 9/2013 | Straubinger et al. |
| 2013/0253637 A1 | 9/2013 | Wang et al. |
| 2013/0253639 A1 | 9/2013 | Alkhatib |
| 2013/0253641 A1 | 9/2013 | Lattouf |
| 2013/0253642 A1 | 9/2013 | Brecker |
| 2013/0261737 A1 | 10/2013 | Costello |
| 2013/0261738 A1 | 10/2013 | Clague et al. |
| 2013/0268069 A1 | 10/2013 | Zakai et al. |
| 2013/0289695 A1 | 10/2013 | Tian et al. |
| 2013/0304200 A1 | 11/2013 | Mclean et al. |
| 2013/0310928 A1 | 11/2013 | Morriss et al. |
| 2013/0325098 A1 | 12/2013 | Desai et al. |
| 2013/0325121 A1 | 12/2013 | Whatley et al. |
| 2013/0331714 A1 | 12/2013 | Manstrom et al. |
| 2013/0338764 A1 | 12/2013 | Thornton et al. |
| 2013/0338765 A1 | 12/2013 | Braido et al. |
| 2013/0345786 A1 | 12/2013 | Behan |
| 2013/0345803 A1 | 12/2013 | Bergheim, III |

(56) References Cited

U.S. PATENT DOCUMENTS

| | | |
|---|---|---|
| 2014/0005769 A1 | 1/2014 | Tran et al. |
| 2014/0018912 A1 | 1/2014 | Delaloye et al. |
| 2014/0031930 A1 | 1/2014 | Keidar et al. |
| 2014/0039611 A1 | 2/2014 | Lane et al. |
| 2014/0039612 A1 | 2/2014 | Dolan |
| 2014/0039614 A1 | 2/2014 | Delaloye et al. |
| 2014/0044689 A1 | 2/2014 | Liu et al. |
| 2014/0046219 A1 | 2/2014 | Sauter et al. |
| 2014/0046427 A1 | 2/2014 | Michalak |
| 2014/0052237 A1 | 2/2014 | Lane et al. |
| 2014/0052242 A1 | 2/2014 | Revuelta et al. |
| 2014/0081393 A1 | 3/2014 | Hasenkam et al. |
| 2014/0086934 A1 | 3/2014 | Shams |
| 2014/0088685 A1 | 3/2014 | Yevzlin et al. |
| 2014/0088694 A1 | 3/2014 | Rowe et al. |
| 2014/0100420 A1 | 4/2014 | Mortier et al. |
| 2014/0100651 A1 | 4/2014 | Kheradvar et al. |
| 2014/0100653 A1 | 4/2014 | Savage et al. |
| 2014/0107761 A1 | 4/2014 | Gale et al. |
| 2014/0142694 A1 | 5/2014 | Tabor et al. |
| 2014/0155990 A1* | 6/2014 | Nyuli ................. A61F 2/962 623/2.11 |
| 2014/0163668 A1 | 6/2014 | Rafiee |
| 2014/0172085 A1 | 6/2014 | Quadri et al. |
| 2014/0172086 A1 | 6/2014 | Quadri et al. |
| 2014/0186417 A1 | 7/2014 | Trollsas et al. |
| 2014/0194978 A1 | 7/2014 | Seguin et al. |
| 2014/0194981 A1 | 7/2014 | Menk et al. |
| 2014/0194982 A1 | 7/2014 | Kovalsky et al. |
| 2014/0194983 A1 | 7/2014 | Kovalsky et al. |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0214160 A1 | 7/2014 | Naor |
| 2014/0215791 A1 | 8/2014 | Soundararajan et al. |
| 2014/0221823 A1 | 8/2014 | Keogh et al. |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0230515 A1 | 8/2014 | Tuval et al. |
| 2014/0236288 A1 | 8/2014 | Lambrecht et al. |
| 2014/0243966 A1 | 8/2014 | Garde et al. |
| 2014/0249622 A1 | 9/2014 | Carmi et al. |
| 2014/0256035 A1 | 9/2014 | Strasly et al. |
| 2014/0257467 A1 | 9/2014 | Lane et al. |
| 2014/0257475 A1 | 9/2014 | Gross et al. |
| 2014/0257476 A1 | 9/2014 | Montorfano et al. |
| 2014/0277390 A1 | 9/2014 | Ratz et al. |
| 2014/0277402 A1 | 9/2014 | Essinger et al. |
| 2014/0277422 A1 | 9/2014 | Ratz et al. |
| 2014/0277423 A1 | 9/2014 | Alkhatib et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0309731 A1 | 10/2014 | Quadri et al. |
| 2014/0309732 A1 | 10/2014 | Solem |
| 2014/0324160 A1 | 10/2014 | Benichou et al. |
| 2014/0324164 A1 | 10/2014 | Gross et al. |
| 2014/0331475 A1 | 11/2014 | Duffy et al. |
| 2014/0336754 A1 | 11/2014 | Gurskis et al. |
| 2014/0350565 A1 | 11/2014 | Yacoby et al. |
| 2014/0350666 A1 | 11/2014 | Righini |
| 2014/0356519 A1 | 12/2014 | Hossainy et al. |
| 2014/0358223 A1 | 12/2014 | Rafiee et al. |
| 2014/0364404 A1 | 12/2014 | Cleek et al. |
| 2014/0364944 A1 | 12/2014 | Lutter et al. |
| 2014/0370071 A1 | 12/2014 | Chen et al. |
| 2014/0371845 A1 | 12/2014 | Tuval et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379068 A1 | 12/2014 | Thielen et al. |
| 2014/0379077 A1 | 12/2014 | Tuval et al. |
| 2015/0012085 A1 | 1/2015 | Salahieh et al. |
| 2015/0018938 A1 | 1/2015 | Von Segesser et al. |
| 2015/0018944 A1 | 1/2015 | O'connell et al. |
| 2015/0032153 A1 | 1/2015 | Quadri et al. |
| 2015/0045881 A1 | 2/2015 | Lim |
| 2015/0066140 A1 | 3/2015 | Quadri et al. |
| 2015/0081009 A1 | 3/2015 | Quadri et al. |
| 2015/0086603 A1 | 3/2015 | Hossainy et al. |
| 2015/0088252 A1 | 3/2015 | Jenson et al. |
| 2015/0105856 A1 | 4/2015 | Rowe et al. |
| 2015/0142103 A1 | 5/2015 | Vidlund |
| 2015/0148731 A1 | 5/2015 | Mcnamara et al. |
| 2015/0157458 A1 | 6/2015 | Thambar et al. |
| 2015/0209137 A1 | 7/2015 | Quadri et al. |
| 2015/0209141 A1 | 7/2015 | Braido et al. |
| 2015/0216653 A1 | 8/2015 | Freudenthal |
| 2015/0216655 A1 | 8/2015 | Lane et al. |
| 2015/0238315 A1 | 8/2015 | Rabito et al. |
| 2015/0305864 A1 | 10/2015 | Quadri et al. |
| 2015/0328000 A1 | 11/2015 | Ratz et al. |
| 2015/0342736 A1 | 12/2015 | Rabito et al. |
| 2016/0038281 A1 | 2/2016 | Delaloye et al. |
| 2016/0228249 A1 | 8/2016 | Mantanus et al. |
| 2016/0228251 A1 | 8/2016 | Nyuli et al. |
| 2016/0346106 A1 | 12/2016 | Hacker et al. |
| 2017/0056149 A1 | 3/2017 | Rajpara et al. |
| 2018/0168807 A1 | 6/2018 | Nyuli et al. |
| 2019/0091014 A1 | 3/2019 | Arcaro et al. |
| 2019/0117394 A1 | 4/2019 | Morin et al. |
| 2019/0133758 A1 | 5/2019 | Duffy et al. |
| 2019/0254820 A1 | 8/2019 | Nyuli et al. |
| 2020/0222180 A1 | 7/2020 | Lane et al. |
| 2021/0169648 A1 | 6/2021 | Nyuli et al. |
| 2022/0313436 A1* | 10/2022 | Nyuli ................. A61F 2/2412 |

FOREIGN PATENT DOCUMENTS

| | | |
|---|---|---|
| CA | 2304325 A1 | 10/2000 |
| CA | 2874219 A1 | 12/2013 |
| CA | 3050113 A1 | 7/2018 |
| CA | 2874219 C | 7/2020 |
| CN | 102196784 A | 9/2011 |
| CN | 102256568 A | 11/2011 |
| CN | 103037808 A | 4/2013 |
| CN | 113476180 A | 10/2021 |
| DE | 3128704 A1 | 2/1983 |
| DE | 10103955 B4 | 11/2001 |
| DE | 10033858 B4 | 1/2002 |
| DE | 102006052564 B3 | 12/2007 |
| DE | 102006013113 B4 | 12/2008 |
| DE | 102008015781 B4 | 9/2011 |
| DE | 102010051632 B4 | 9/2013 |
| DE | 102005032974 B4 | 11/2013 |
| DE | 202013011734 U1 | 4/2014 |
| DE | 102005052628 B4 | 6/2014 |
| DE | 10301026 B4 | 10/2014 |
| DE | 212013000104 U1 | 11/2014 |
| DE | 102008012438 B4 | 12/2014 |
| DE | 102011107551 B4 | 5/2015 |
| DE | 102011054176 B4 | 2/2016 |
| DE | 102014114762 B3 | 3/2016 |
| DE | 102013208038 B4 | 9/2016 |
| DE | 102010012677 B4 | 8/2017 |
| DE | 202011110951 U1 | 10/2017 |
| DE | 202011110985 U1 | 12/2017 |
| DE | 202016105963 U1 | 1/2018 |
| DE | 10394350 B4 | 5/2018 |
| DE | 102009024648 B4 | 5/2018 |
| DE | 102015206098 B4 | 9/2018 |
| DE | 10065824 B4 | 10/2018 |
| DE | 202017104793 U1 | 11/2018 |
| DE | 102011106928 B4 | 2/2019 |
| DE | 202016008737 U1 | 4/2019 |
| DE | 102013205519 B4 | 5/2019 |
| DE | 102008014730 B4 | 7/2019 |
| DE | 102018102940 B4 | 10/2019 |
| DE | 102009009158 B4 | 11/2020 |
| EP | 0657147 A2 | 6/1995 |
| EP | 1077072 B1 | 11/2003 |

(56) References Cited

FOREIGN PATENT DOCUMENTS

| | | | |
|---|---|---|---|
| EP | 1140244 | B1 | 11/2003 |
| EP | 1214106 | B1 | 11/2003 |
| EP | 1143864 | B1 | 2/2004 |
| EP | 1220651 | B1 | 3/2004 |
| EP | 1265534 | B1 | 6/2004 |
| EP | 1347785 | B1 | 7/2004 |
| EP | 1245202 | B1 | 8/2004 |
| EP | 1161204 | B1 | 9/2004 |
| EP | 1266641 | B1 | 10/2004 |
| EP | 1102567 | B1 | 11/2004 |
| EP | 1117446 | B1 | 11/2004 |
| EP | 1107710 | B1 | 12/2004 |
| EP | 1121070 | B1 | 12/2004 |
| EP | 1217966 | B1 | 12/2004 |
| EP | 1233731 | B1 | 12/2004 |
| EP | 1294318 | B1 | 12/2004 |
| EP | 1237510 | B1 | 1/2005 |
| EP | 1034753 | B1 | 2/2005 |
| EP | 1259194 | B1 | 2/2005 |
| EP | 1121069 | B1 | 3/2005 |
| EP | 1143879 | B1 | 3/2005 |
| EP | 1023879 | B1 | 4/2005 |
| EP | 1339356 | B1 | 4/2005 |
| EP | 1214022 | B1 | 5/2005 |
| EP | 1318774 | B1 | 5/2005 |
| EP | 1088529 | B1 | 6/2005 |
| EP | 1171060 | B1 | 6/2005 |
| EP | 1251803 | B1 | 6/2005 |
| EP | 1259776 | B1 | 6/2005 |
| EP | 1272123 | B1 | 6/2005 |
| EP | 1049422 | B1 | 7/2005 |
| EP | 1230901 | B1 | 8/2005 |
| EP | 1335683 | B1 | 8/2005 |
| EP | 1307246 | B1 | 9/2005 |
| EP | 1267753 | B1 | 10/2005 |
| EP | 1284688 | B1 | 10/2005 |
| EP | 1343536 | B1 | 10/2005 |
| EP | 1027020 | B1 | 11/2005 |
| EP | 1152780 | B1 | 11/2005 |
| EP | 1171059 | B1 | 11/2005 |
| EP | 1237508 | B1 | 11/2005 |
| EP | 1303234 | B1 | 11/2005 |
| EP | 1328215 | B1 | 11/2005 |
| EP | 1341487 | B1 | 11/2005 |
| EP | 1392197 | B1 | 11/2005 |
| EP | 1469797 | B1 | 11/2005 |
| EP | 1255505 | B1 | 12/2005 |
| EP | 1360942 | B1 | 12/2005 |
| EP | 1322260 | B1 | 1/2006 |
| EP | 1359870 | B1 | 1/2006 |
| EP | 1237586 | B1 | 2/2006 |
| EP | 1112043 | B1 | 4/2006 |
| EP | 1309360 | B1 | 4/2006 |
| EP | 1322259 | B1 | 5/2006 |
| EP | 1124592 | B1 | 6/2006 |
| EP | 1237516 | B1 | 6/2006 |
| EP | 1098673 | B1 | 7/2006 |
| EP | 1124591 | B1 | 7/2006 |
| EP | 1083845 | B1 | 8/2006 |
| EP | 1155666 | B1 | 8/2006 |
| EP | 1463462 | B1 | 8/2006 |
| EP | 1684671 | A1 | 8/2006 |
| EP | 1519695 | B1 | 9/2006 |
| EP | 1444993 | B1 | 10/2006 |
| EP | 1117350 | B1 | 11/2006 |
| EP | 1212011 | B1 | 11/2006 |
| EP | 1261294 | B1 | 11/2006 |
| EP | 1318775 | B1 | 11/2006 |
| EP | 1429690 | B1 | 11/2006 |
| EP | 1173111 | B1 | 12/2006 |
| EP | 1239795 | B1 | 12/2006 |
| EP | 1299049 | B1 | 12/2006 |
| EP | 1487382 | B1 | 12/2006 |
| EP | 1112044 | B1 | 1/2007 |
| EP | 1482997 | B1 | 1/2007 |
| EP | 1117352 | B1 | 2/2007 |
| EP | 1128849 | B1 | 2/2007 |
| EP | 1392666 | B1 | 2/2007 |
| EP | 1474077 | B1 | 2/2007 |
| EP | 1251805 | B1 | 3/2007 |
| EP | 1117334 | B1 | 4/2007 |
| EP | 1255510 | B1 | 4/2007 |
| EP | 1263484 | B1 | 5/2007 |
| EP | 1313410 | B1 | 5/2007 |
| EP | 1370200 | B1 | 5/2007 |
| EP | 1560526 | B1 | 6/2007 |
| EP | 1173117 | B1 | 7/2007 |
| EP | 1434615 | B1 | 7/2007 |
| EP | 1465546 | B1 | 7/2007 |
| EP | 1499366 | B1 | 7/2007 |
| EP | 1225948 | B1 | 8/2007 |
| EP | 1519962 | B1 | 9/2007 |
| EP | 1337285 | B1 | 10/2007 |
| EP | 1112042 | B1 | 11/2007 |
| EP | 1148821 | B1 | 11/2007 |
| EP | 1143882 | B1 | 12/2007 |
| EP | 1330189 | B1 | 12/2007 |
| EP | 1489996 | B1 | 12/2007 |
| EP | 1296618 | B1 | 1/2008 |
| EP | 1401356 | B1 | 1/2008 |
| EP | 1629795 | B1 | 1/2008 |
| EP | 1128786 | B1 | 2/2008 |
| EP | 1616532 | B1 | 2/2008 |
| EP | 1289447 | B1 | 3/2008 |
| EP | 1895942 | A2 | 3/2008 |
| EP | 1115353 | B1 | 5/2008 |
| EP | 1330190 | B1 | 5/2008 |
| EP | 1383448 | B1 | 6/2008 |
| EP | 1251804 | B1 | 7/2008 |
| EP | 1294310 | B1 | 7/2008 |
| EP | 1313409 | B1 | 7/2008 |
| EP | 1395202 | B1 | 7/2008 |
| EP | 1395204 | B1 | 7/2008 |
| EP | 1395205 | B1 | 7/2008 |
| EP | 1423066 | B1 | 7/2008 |
| EP | 1560545 | B1 | 7/2008 |
| EP | 1605871 | B1 | 7/2008 |
| EP | 1671608 | B1 | 7/2008 |
| EP | 1690515 | B1 | 7/2008 |
| EP | 1180987 | B1 | 8/2008 |
| EP | 1337386 | B1 | 8/2008 |
| EP | 1492579 | B1 | 9/2008 |
| EP | 1524942 | B1 | 9/2008 |
| EP | 1627091 | B1 | 9/2008 |
| EP | 1827577 | B1 | 9/2008 |
| EP | 1259195 | B1 | 10/2008 |
| EP | 1704834 | B1 | 10/2008 |
| EP | 1146835 | B1 | 11/2008 |
| EP | 1498086 | B1 | 11/2008 |
| EP | 1622548 | B1 | 11/2008 |
| EP | 1235537 | B1 | 12/2008 |
| EP | 1237509 | B1 | 12/2008 |
| EP | 1355590 | B1 | 12/2008 |
| EP | 1455680 | B1 | 12/2008 |
| EP | 1472995 | B1 | 12/2008 |
| EP | 1513474 | B1 | 12/2008 |
| EP | 1562522 | B1 | 12/2008 |
| EP | 1620042 | B1 | 12/2008 |
| EP | 1690514 | B1 | 12/2008 |
| EP | 1258232 | B1 | 1/2009 |
| EP | 1420723 | B1 | 1/2009 |
| EP | 1570809 | B1 | 1/2009 |
| EP | 1395182 | B1 | 2/2009 |
| EP | 1408882 | B1 | 2/2009 |
| EP | 1482868 | B1 | 2/2009 |
| EP | 1255510 | B3 | 3/2009 |
| EP | 1330213 | B1 | 3/2009 |
| EP | 1429651 | B1 | 3/2009 |
| EP | 1610727 | B1 | 4/2009 |
| EP | 1617788 | B1 | 4/2009 |
| EP | 1634547 | B1 | 4/2009 |
| EP | 1790318 | B1 | 4/2009 |
| EP | 2040645 | A1 | 4/2009 |
| EP | 1250165 | B1 | 5/2009 |

(56) References Cited

FOREIGN PATENT DOCUMENTS

| | | | |
|---|---|---|---|
| EP | 1842508 B1 | 6/2009 |
| EP | 1968482 B1 | 6/2009 |
| EP | 2072027 A1 | 6/2009 |
| EP | 1343438 B1 | 7/2009 |
| EP | 1406608 B1 | 7/2009 |
| EP | 1509256 B1 | 7/2009 |
| EP | 1626681 B1 | 7/2009 |
| EP | 1723935 B1 | 7/2009 |
| EP | 1803420 B1 | 7/2009 |
| EP | 2073755 A2 | 7/2009 |
| EP | 1401359 B1 | 8/2009 |
| EP | 1411865 B1 | 8/2009 |
| EP | 1485033 B1 | 8/2009 |
| EP | 1581120 B1 | 8/2009 |
| EP | 1620040 B1 | 8/2009 |
| EP | 1684667 B1 | 8/2009 |
| EP | 1872743 B1 | 8/2009 |
| EP | 1100378 B1 | 9/2009 |
| EP | 1198203 B1 | 9/2009 |
| EP | 1370201 B1 | 9/2009 |
| EP | 1408850 B1 | 9/2009 |
| EP | 1472996 B1 | 9/2009 |
| EP | 1478364 B1 | 9/2009 |
| EP | 1653888 B1 | 9/2009 |
| EP | 1785154 B1 | 9/2009 |
| EP | 1881804 B1 | 9/2009 |
| EP | 1903991 B1 | 9/2009 |
| EP | 1418865 B1 | 10/2009 |
| EP | 1561437 B1 | 10/2009 |
| EP | 1615595 B1 | 10/2009 |
| EP | 1353612 B1 | 11/2009 |
| EP | 1348406 B1 | 12/2009 |
| EP | 1370202 B1 | 12/2009 |
| EP | 1603492 B1 | 12/2009 |
| EP | 1670364 B1 | 12/2009 |
| EP | 1759663 B1 | 12/2009 |
| EP | 1994887 B1 | 12/2009 |
| EP | 1615593 B1 | 1/2010 |
| EP | 1643938 B1 | 1/2010 |
| EP | 1863402 B1 | 1/2010 |
| EP | 1943942 B1 | 1/2010 |
| EP | 2010101 B1 | 1/2010 |
| EP | 2081518 B1 | 1/2010 |
| EP | 1703865 B1 | 2/2010 |
| EP | 1276437 B1 | 3/2010 |
| EP | 1276439 B1 | 3/2010 |
| EP | 1411867 B1 | 3/2010 |
| EP | 1458313 B1 | 3/2010 |
| EP | 1520519 B1 | 3/2010 |
| EP | 1648340 B1 | 3/2010 |
| EP | 1682048 B1 | 3/2010 |
| EP | 1773239 B1 | 3/2010 |
| EP | 1935377 B1 | 3/2010 |
| EP | 1994912 B1 | 3/2010 |
| EP | 1154738 B1 | 4/2010 |
| EP | 1531762 B1 | 4/2010 |
| EP | 1600178 B1 | 4/2010 |
| EP | 1626682 B1 | 4/2010 |
| EP | 1511445 B1 | 5/2010 |
| EP | 1198213 B1 | 6/2010 |
| EP | 1250097 B1 | 6/2010 |
| EP | 1272249 B1 | 6/2010 |
| EP | 1978895 B1 | 6/2010 |
| EP | 1572033 B1 | 7/2010 |
| EP | 1968491 B1 | 7/2010 |
| EP | 2019652 B1 | 7/2010 |
| EP | 1610722 B1 | 8/2010 |
| EP | 1682047 B1 | 8/2010 |
| EP | 1952772 B1 | 8/2010 |
| EP | 1427356 B1 | 9/2010 |
| EP | 1631218 B1 | 9/2010 |
| EP | 1765224 B1 | 9/2010 |
| EP | 1871290 B1 | 9/2010 |
| EP | 1895288 B1 | 9/2010 |
| EP | 1895913 B1 | 9/2010 |
| EP | 2014257 B1 | 9/2010 |
| EP | 1176913 B1 | 10/2010 |
| EP | 1178758 B1 | 10/2010 |
| EP | 1248579 B1 | 10/2010 |
| EP | 1913899 B1 | 10/2010 |
| EP | 1259193 B1 | 11/2010 |
| EP | 1928357 B1 | 11/2010 |
| EP | 1968660 B1 | 11/2010 |
| EP | 2249711 A2 | 11/2010 |
| EP | 1408895 B1 | 12/2010 |
| EP | 1465554 B1 | 12/2010 |
| EP | 1732473 B1 | 12/2010 |
| EP | 1768610 B1 | 12/2010 |
| EP | 1827314 B1 | 12/2010 |
| EP | 1940321 B1 | 12/2010 |
| EP | 1964532 B1 | 12/2010 |
| EP | 2078498 B1 | 12/2010 |
| EP | 1600182 B1 | 1/2011 |
| EP | 1617789 B1 | 1/2011 |
| EP | 1663332 B1 | 1/2011 |
| EP | 2147659 B1 | 1/2011 |
| EP | 2268231 A2 | 1/2011 |
| EP | 2273951 A1 | 1/2011 |
| EP | 1187582 B1 | 2/2011 |
| EP | 1450733 B1 | 2/2011 |
| EP | 1803421 B1 | 2/2011 |
| EP | 1833425 B1 | 2/2011 |
| EP | 2029053 B1 | 2/2011 |
| EP | 2068770 B1 | 2/2011 |
| EP | 1441784 B1 | 3/2011 |
| EP | 1534177 B1 | 3/2011 |
| EP | 1893132 B1 | 3/2011 |
| EP | 1951153 B1 | 3/2011 |
| EP | 2289467 A1 | 3/2011 |
| EP | 2299938 A2 | 3/2011 |
| EP | 1359978 B1 | 4/2011 |
| EP | 1667750 B1 | 4/2011 |
| EP | 1718249 B1 | 4/2011 |
| EP | 1903989 B1 | 4/2011 |
| EP | 2018122 B1 | 4/2011 |
| EP | 1610728 B1 | 5/2011 |
| EP | 2105110 B1 | 5/2011 |
| EP | 1347717 B1 | 6/2011 |
| EP | 2331018 A1 | 6/2011 |
| EP | 1347791 B1 | 7/2011 |
| EP | 1862128 B1 | 7/2011 |
| EP | 2120795 B1 | 7/2011 |
| EP | 2229920 B1 | 7/2011 |
| EP | 1637087 B1 | 8/2011 |
| EP | 2153799 B1 | 8/2011 |
| EP | 2247263 B1 | 8/2011 |
| EP | 2349098 A1 | 8/2011 |
| EP | 2358307 A1 | 8/2011 |
| EP | 1441672 B1 | 9/2011 |
| EP | 1625832 B1 | 9/2011 |
| EP | 2173279 B1 | 9/2011 |
| EP | 2367505 A1 | 9/2011 |
| EP | 2160150 B1 | 10/2011 |
| EP | 2370138 A2 | 10/2011 |
| EP | 1626679 B1 | 11/2011 |
| EP | 1719476 B1 | 11/2011 |
| EP | 1928355 B1 | 11/2011 |
| EP | 2237747 B1 | 11/2011 |
| EP | 2381895 A2 | 11/2011 |
| EP | 2389121 A1 | 11/2011 |
| EP | 1572031 B1 | 12/2011 |
| EP | 1603493 B1 | 12/2011 |
| EP | 1945109 B1 | 12/2011 |
| EP | 1998688 B1 | 12/2011 |
| EP | 2393442 A2 | 12/2011 |
| EP | 2395944 A1 | 12/2011 |
| EP | 1443877 B1 | 1/2012 |
| EP | 2400922 A1 | 1/2012 |
| EP | 1281375 B1 | 2/2012 |
| EP | 1699501 B1 | 2/2012 |
| EP | 1788984 B1 | 2/2012 |
| EP | 1833415 B1 | 2/2012 |
| EP | 1952785 B1 | 2/2012 |
| EP | 2055266 B1 | 2/2012 |

(56) References Cited

FOREIGN PATENT DOCUMENTS

| | | | |
|---|---|---|---|
| EP | 2205184 | B1 | 2/2012 |
| EP | 2416736 | A1 | 2/2012 |
| EP | 1337188 | B1 | 3/2012 |
| EP | 1443974 | B1 | 3/2012 |
| EP | 1542623 | B1 | 3/2012 |
| EP | 1942835 | B1 | 3/2012 |
| EP | 2074964 | B1 | 3/2012 |
| EP | 2244661 | B1 | 3/2012 |
| EP | 2273928 | B1 | 3/2012 |
| EP | 2427144 | A1 | 3/2012 |
| EP | 2429455 | A1 | 3/2012 |
| EP | 1401336 | B1 | 4/2012 |
| EP | 1749544 | B1 | 4/2012 |
| EP | 2119417 | B1 | 4/2012 |
| EP | 2152330 | B1 | 4/2012 |
| EP | 2231069 | B1 | 4/2012 |
| EP | 2437688 | A1 | 4/2012 |
| EP | 2020958 | B1 | 5/2012 |
| EP | 2192875 | B1 | 5/2012 |
| EP | 2218425 | B1 | 5/2012 |
| EP | 2445450 | A2 | 5/2012 |
| EP | 1411847 | B1 | 6/2012 |
| EP | 1727499 | B1 | 6/2012 |
| EP | 2082690 | B1 | 6/2012 |
| EP | 1740747 | B1 | 7/2012 |
| EP | 1861044 | B1 | 7/2012 |
| EP | 2052699 | B1 | 7/2012 |
| EP | 2470121 | A2 | 7/2012 |
| EP | 2471492 | A1 | 7/2012 |
| EP | 1887975 | B1 | 8/2012 |
| EP | 2000116 | B1 | 8/2012 |
| EP | 2222247 | B1 | 8/2012 |
| EP | 2486894 | A1 | 8/2012 |
| EP | 1605870 | B1 | 9/2012 |
| EP | 1887980 | B1 | 9/2012 |
| EP | 2497445 | A1 | 9/2012 |
| EP | 1740126 | B1 | 10/2012 |
| EP | 1865889 | B1 | 10/2012 |
| EP | 2033593 | B1 | 10/2012 |
| EP | 2124824 | B1 | 10/2012 |
| EP | 2139431 | B1 | 10/2012 |
| EP | 2506777 | A1 | 10/2012 |
| EP | 2512952 | A2 | 10/2012 |
| EP | 1430853 | B1 | 11/2012 |
| EP | 1928512 | B1 | 11/2012 |
| EP | 2008615 | B1 | 11/2012 |
| EP | 2088965 | B1 | 11/2012 |
| EP | 2522307 | A1 | 11/2012 |
| EP | 1557138 | B1 | 12/2012 |
| EP | 1924221 | B1 | 12/2012 |
| EP | 2023859 | B1 | 12/2012 |
| EP | 2250970 | B1 | 12/2012 |
| EP | 2285317 | B1 | 12/2012 |
| EP | 2537486 | A1 | 12/2012 |
| EP | 1494731 | B1 | 1/2013 |
| EP | 1610752 | B1 | 1/2013 |
| EP | 1796597 | B1 | 1/2013 |
| EP | 1919397 | B1 | 1/2013 |
| EP | 1942834 | B1 | 1/2013 |
| EP | 2015709 | B1 | 1/2013 |
| EP | 2079400 | B1 | 1/2013 |
| EP | 2238947 | B1 | 1/2013 |
| EP | 2241287 | B1 | 1/2013 |
| EP | 2359774 | B1 | 1/2013 |
| EP | 2538878 | A1 | 1/2013 |
| EP | 2538883 | A1 | 1/2013 |
| EP | 1512383 | B1 | 2/2013 |
| EP | 1578474 | B1 | 2/2013 |
| EP | 1648339 | B1 | 2/2013 |
| EP | 1750622 | B1 | 2/2013 |
| EP | 1994482 | B1 | 2/2013 |
| EP | 2250975 | B1 | 2/2013 |
| EP | 2257242 | B1 | 2/2013 |
| EP | 2265225 | B1 | 2/2013 |
| EP | 2558032 | A1 | 2/2013 |
| EP | 1659992 | B1 | 3/2013 |
| EP | 1701668 | B1 | 3/2013 |
| EP | 2151216 | B1 | 3/2013 |
| EP | 2340075 | B1 | 3/2013 |
| EP | 2568924 | A2 | 3/2013 |
| EP | 1781183 | B1 | 4/2013 |
| EP | 1786367 | B1 | 4/2013 |
| EP | 1850795 | B1 | 4/2013 |
| EP | 1861041 | B1 | 4/2013 |
| EP | 2319458 | B1 | 4/2013 |
| EP | 2526898 | B1 | 4/2013 |
| EP | 2537487 | B1 | 4/2013 |
| EP | 2575681 | A1 | 4/2013 |
| EP | 1901682 | B1 | 5/2013 |
| EP | 1951166 | B1 | 5/2013 |
| EP | 1994913 | B1 | 5/2013 |
| EP | 2231070 | B1 | 5/2013 |
| EP | 2401970 | B1 | 5/2013 |
| EP | 2409651 | B1 | 5/2013 |
| EP | 2594230 | A1 | 5/2013 |
| EP | 1694246 | B1 | 6/2013 |
| EP | 1948087 | B1 | 6/2013 |
| EP | 2135559 | B1 | 6/2013 |
| EP | 1115335 | B1 | 7/2013 |
| EP | 1663339 | B1 | 7/2013 |
| EP | 1864687 | B1 | 7/2013 |
| EP | 1977719 | B1 | 7/2013 |
| EP | 2111337 | B1 | 7/2013 |
| EP | 2298237 | B1 | 7/2013 |
| EP | 2309949 | B1 | 7/2013 |
| EP | 2608741 | A2 | 7/2013 |
| EP | 2611389 | A2 | 7/2013 |
| EP | 1599151 | B1 | 8/2013 |
| EP | 1761211 | B1 | 8/2013 |
| EP | 2047871 | B1 | 8/2013 |
| EP | 2142144 | B1 | 8/2013 |
| EP | 2150206 | B1 | 8/2013 |
| EP | 2319459 | B1 | 8/2013 |
| EP | 2397108 | B1 | 8/2013 |
| EP | 2623068 | A1 | 8/2013 |
| EP | 1758523 | B1 | 9/2013 |
| EP | 1545392 | B1 | 10/2013 |
| EP | 1638627 | B1 | 10/2013 |
| EP | 1779868 | B1 | 10/2013 |
| EP | 2073756 | B1 | 10/2013 |
| EP | 2111190 | B1 | 10/2013 |
| EP | 1848375 | B1 | 11/2013 |
| EP | 1928356 | B1 | 11/2013 |
| EP | 1933766 | B1 | 11/2013 |
| EP | 2109417 | B1 | 11/2013 |
| EP | 2194925 | B1 | 11/2013 |
| EP | 2387977 | B1 | 11/2013 |
| EP | 2476394 | B1 | 11/2013 |
| EP | 2529701 | B1 | 11/2013 |
| EP | 1945142 | B1 | 12/2013 |
| EP | 2387972 | B1 | 12/2013 |
| EP | 2477555 | B1 | 12/2013 |
| EP | 2670349 | A2 | 12/2013 |
| EP | 2117476 | B1 | 1/2014 |
| EP | 2526895 | B1 | 1/2014 |
| EP | 2526899 | B1 | 1/2014 |
| EP | 2529696 | B1 | 1/2014 |
| EP | 2529697 | B1 | 1/2014 |
| EP | 2529698 | B1 | 1/2014 |
| EP | 2529699 | B1 | 1/2014 |
| EP | 2679198 | A1 | 1/2014 |
| EP | 1395214 | B1 | 2/2014 |
| EP | 1499266 | B1 | 2/2014 |
| EP | 1838241 | B1 | 2/2014 |
| EP | 2520250 | B1 | 2/2014 |
| EP | 2526977 | B1 | 2/2014 |
| EP | 2693985 | A1 | 2/2014 |
| EP | 2699302 | A2 | 2/2014 |
| EP | 1629794 | B1 | 3/2014 |
| EP | 1919398 | B1 | 3/2014 |
| EP | 2099508 | B1 | 3/2014 |
| EP | 2399549 | B1 | 3/2014 |
| EP | 2422823 | B1 | 3/2014 |
| EP | 2706958 | A1 | 3/2014 |

(56) References Cited

FOREIGN PATENT DOCUMENTS

| | | | |
|---|---|---|---|
| EP | 1804860 B1 | 4/2014 |
| EP | 1926455 B1 | 4/2014 |
| EP | 2081519 B1 | 4/2014 |
| EP | 2117477 B1 | 4/2014 |
| EP | 2405966 B1 | 4/2014 |
| EP | 2420205 B1 | 4/2014 |
| EP | 2593048 B1 | 4/2014 |
| EP | 2713894 A2 | 4/2014 |
| EP | 2713955 A2 | 4/2014 |
| EP | 2723273 A2 | 4/2014 |
| EP | 1499265 B1 | 5/2014 |
| EP | 1594569 B1 | 5/2014 |
| EP | 2029056 B1 | 5/2014 |
| EP | 2257243 B1 | 5/2014 |
| EP | 1791500 B1 | 6/2014 |
| EP | 2073753 B1 | 6/2014 |
| EP | 2306933 B1 | 6/2014 |
| EP | 2331017 B1 | 6/2014 |
| EP | 2337522 B1 | 6/2014 |
| EP | 2389897 B1 | 6/2014 |
| EP | 2606723 B1 | 6/2014 |
| EP | 2739250 A1 | 6/2014 |
| EP | 1487350 B1 | 7/2014 |
| EP | 1977718 B1 | 7/2014 |
| EP | 2117469 B1 | 7/2014 |
| EP | 2124826 B1 | 7/2014 |
| EP | 2258316 B1 | 7/2014 |
| EP | 2747708 A1 | 7/2014 |
| EP | 2750630 A1 | 7/2014 |
| EP | 2750631 A1 | 7/2014 |
| EP | 1667604 B1 | 8/2014 |
| EP | 1786368 B1 | 8/2014 |
| EP | 2211779 B1 | 8/2014 |
| EP | 2217174 B1 | 8/2014 |
| EP | 2293740 B1 | 8/2014 |
| EP | 2367504 B1 | 8/2014 |
| EP | 2453942 B1 | 8/2014 |
| EP | 2475328 B1 | 8/2014 |
| EP | 2545884 B1 | 8/2014 |
| EP | 2571460 B1 | 8/2014 |
| EP | 2763708 A2 | 8/2014 |
| EP | 2765954 A1 | 8/2014 |
| EP | 1935378 B1 | 9/2014 |
| EP | 2246011 B1 | 9/2014 |
| EP | 2422749 B1 | 9/2014 |
| EP | 2531139 B1 | 9/2014 |
| EP | 2609893 B1 | 9/2014 |
| EP | 2777616 A1 | 9/2014 |
| EP | 2779945 A1 | 9/2014 |
| EP | 1853199 B1 | 10/2014 |
| EP | 2133039 B1 | 10/2014 |
| EP | 2549955 B1 | 10/2014 |
| EP | 2549956 B1 | 10/2014 |
| EP | 2651335 B1 | 10/2014 |
| EP | 2785281 A1 | 10/2014 |
| EP | 2793743 A1 | 10/2014 |
| EP | 2793752 A1 | 10/2014 |
| EP | 2049721 B1 | 11/2014 |
| EP | 2142143 B1 | 11/2014 |
| EP | 2229921 B1 | 11/2014 |
| EP | 2288403 B1 | 11/2014 |
| EP | 2415421 B1 | 11/2014 |
| EP | 1551274 B1 | 12/2014 |
| EP | 1768735 B1 | 12/2014 |
| EP | 1959865 B1 | 12/2014 |
| EP | 2077718 B1 | 12/2014 |
| EP | 2303185 B1 | 12/2014 |
| EP | 2334857 B1 | 12/2014 |
| EP | 2365840 B1 | 12/2014 |
| EP | 2420207 B1 | 12/2014 |
| EP | 2422750 B1 | 12/2014 |
| EP | 2707073 B1 | 12/2014 |
| EP | 1768630 B1 | 1/2015 |
| EP | 2254515 B1 | 1/2015 |
| EP | 2641569 B1 | 1/2015 |
| EP | 2709559 B1 | 1/2015 |
| EP | 2825203 A1 | 1/2015 |
| EP | 1903990 B1 | 2/2015 |
| EP | 2255753 B1 | 2/2015 |
| EP | 2335649 B1 | 2/2015 |
| EP | 2522308 B1 | 2/2015 |
| EP | 2591754 B1 | 2/2015 |
| EP | 2835112 A1 | 2/2015 |
| EP | 1861045 B1 | 3/2015 |
| EP | 2029057 B1 | 3/2015 |
| EP | 2193761 B1 | 3/2015 |
| EP | 2379010 B1 | 3/2015 |
| EP | 2416737 B1 | 3/2015 |
| EP | 1791495 B1 | 4/2015 |
| EP | 2298252 B1 | 4/2015 |
| EP | 2536359 B1 | 4/2015 |
| EP | 2538879 B1 | 4/2015 |
| EP | 2609894 B1 | 4/2015 |
| EP | 2693984 B1 | 4/2015 |
| EP | 2712633 B1 | 4/2015 |
| EP | 2747707 B1 | 4/2015 |
| EP | 2862546 A1 | 4/2015 |
| EP | 2863842 A1 | 4/2015 |
| EP | 1465555 B1 | 5/2015 |
| EP | 1924224 B1 | 5/2015 |
| EP | 1992369 B1 | 5/2015 |
| EP | 2410947 B1 | 5/2015 |
| EP | 2484311 B1 | 5/2015 |
| EP | 2654616 B1 | 5/2015 |
| EP | 2866741 A1 | 5/2015 |
| EP | 1646332 B1 | 6/2015 |
| EP | 2745805 B1 | 6/2015 |
| EP | 2749254 B1 | 6/2015 |
| EP | 2877123 A2 | 6/2015 |
| EP | 2882374 A1 | 6/2015 |
| EP | 2884906 A1 | 6/2015 |
| EP | 1729685 B1 | 7/2015 |
| EP | 1976439 B1 | 7/2015 |
| EP | 2068767 B1 | 7/2015 |
| EP | 2068769 B1 | 7/2015 |
| EP | 2444031 B1 | 7/2015 |
| EP | 2455041 B1 | 7/2015 |
| EP | 2498719 B1 | 7/2015 |
| EP | 2558030 B1 | 7/2015 |
| EP | 2752209 B1 | 7/2015 |
| EP | 2892467 A1 | 7/2015 |
| EP | 1702247 B1 | 8/2015 |
| EP | 1729688 B1 | 8/2015 |
| EP | 1887979 B1 | 8/2015 |
| EP | 2032079 B1 | 8/2015 |
| EP | 2219558 B1 | 8/2015 |
| EP | 2234657 B1 | 8/2015 |
| EP | 2250976 B1 | 8/2015 |
| EP | 2262447 B1 | 8/2015 |
| EP | 2303384 B1 | 8/2015 |
| EP | 2387365 B1 | 8/2015 |
| EP | 2560579 B1 | 8/2015 |
| EP | 2575621 B1 | 8/2015 |
| EP | 2590595 B1 | 8/2015 |
| EP | 2709560 B1 | 8/2015 |
| EP | 2755603 B1 | 8/2015 |
| EP | 2906147 A1 | 8/2015 |
| EP | 1534185 B1 | 9/2015 |
| EP | 1765225 B1 | 9/2015 |
| EP | 1778127 B1 | 9/2015 |
| EP | 2094194 B1 | 9/2015 |
| EP | 2201911 B1 | 9/2015 |
| EP | 2306934 B1 | 9/2015 |
| EP | 2397113 B1 | 9/2015 |
| EP | 2453843 B1 | 9/2015 |
| EP | 2459127 B1 | 9/2015 |
| EP | 2675396 B1 | 9/2015 |
| EP | 2675397 B1 | 9/2015 |
| EP | 2736454 B1 | 9/2015 |
| EP | 2790609 B1 | 9/2015 |
| EP | 2805693 B1 | 9/2015 |
| EP | 2911611 A1 | 9/2015 |
| EP | 2916781 A2 | 9/2015 |
| EP | 1734903 B1 | 10/2015 |

(56) References Cited

FOREIGN PATENT DOCUMENTS

| | | | |
|---|---|---|---|
| EP | 1863546 B1 | 10/2015 |
| EP | 1900343 B1 | 10/2015 |
| EP | 2081515 B1 | 10/2015 |
| EP | 2191792 B1 | 10/2015 |
| EP | 2254513 B1 | 10/2015 |
| EP | 2381896 B1 | 10/2015 |
| EP | 2450008 B1 | 10/2015 |
| EP | 2544626 B1 | 10/2015 |
| EP | 2561830 B1 | 10/2015 |
| EP | 2600798 B1 | 10/2015 |
| EP | 2626039 B1 | 10/2015 |
| EP | 2647354 B1 | 10/2015 |
| EP | 2729093 B1 | 10/2015 |
| EP | 2836165 B1 | 10/2015 |
| EP | 1863545 B1 | 11/2015 |
| EP | 2303395 B1 | 11/2015 |
| EP | 2497446 B1 | 11/2015 |
| EP | 2772228 B1 | 11/2015 |
| EP | 1482869 B1 | 12/2015 |
| EP | 1551473 B1 | 12/2015 |
| EP | 1748745 B1 | 12/2015 |
| EP | 1755459 B1 | 12/2015 |
| EP | 1850796 B1 | 12/2015 |
| EP | 1922030 B1 | 12/2015 |
| EP | 1954212 B1 | 12/2015 |
| EP | 2424472 B1 | 12/2015 |
| EP | 2470120 B1 | 12/2015 |
| EP | 2542179 B1 | 12/2015 |
| EP | 2948100 A1 | 12/2015 |
| EP | 1991168 B1 | 1/2016 |
| EP | 2254512 B1 | 1/2016 |
| EP | 2422748 B1 | 1/2016 |
| EP | 2964153 A1 | 1/2016 |
| EP | 2967700 A1 | 1/2016 |
| EP | 2967807 A2 | 1/2016 |
| EP | 2967834 A1 | 1/2016 |
| EP | 2967856 A1 | 1/2016 |
| EP | 2967860 A1 | 1/2016 |
| EP | 2967866 A2 | 1/2016 |
| EP | 2977026 A1 | 1/2016 |
| EP | 1754684 B1 | 2/2016 |
| EP | 1835948 B1 | 2/2016 |
| EP | 2012712 B1 | 2/2016 |
| EP | 2285318 B1 | 2/2016 |
| EP | 2731550 B1 | 2/2016 |
| EP | 2926766 B1 | 2/2016 |
| EP | 2982337 A1 | 2/2016 |
| EP | 1585463 B1 | 3/2016 |
| EP | 1638621 B1 | 3/2016 |
| EP | 1804726 B1 | 3/2016 |
| EP | 1865886 B1 | 3/2016 |
| EP | 1887982 B1 | 3/2016 |
| EP | 2150205 B1 | 3/2016 |
| EP | 2278944 B1 | 3/2016 |
| EP | 2291126 B1 | 3/2016 |
| EP | 2517674 B1 | 3/2016 |
| EP | 2520253 B1 | 3/2016 |
| EP | 2526897 B1 | 3/2016 |
| EP | 2621409 A4 | 3/2016 |
| EP | 2670353 B1 | 3/2016 |
| EP | 2674130 B1 | 3/2016 |
| EP | 2780042 B1 | 3/2016 |
| EP | 2991584 A1 | 3/2016 |
| EP | 2991588 A1 | 3/2016 |
| EP | 2994072 A1 | 3/2016 |
| EP | 2994075 A1 | 3/2016 |
| EP | 2996632 A1 | 3/2016 |
| EP | 2996633 A1 | 3/2016 |
| EP | 2996641 A1 | 3/2016 |
| EP | 2999435 A1 | 3/2016 |
| EP | 1420730 B1 | 4/2016 |
| EP | 1545371 B1 | 4/2016 |
| EP | 1592367 B1 | 4/2016 |
| EP | 1708649 B1 | 4/2016 |
| EP | 1871300 B1 | 4/2016 |
| EP | 2168536 B1 | 4/2016 |
| EP | 2399550 B1 | 4/2016 |
| EP | 2433591 B1 | 4/2016 |
| EP | 2478871 B1 | 4/2016 |
| EP | 2536355 B1 | 4/2016 |
| EP | 2572676 B1 | 4/2016 |
| EP | 2606852 B1 | 4/2016 |
| EP | 2621408 B1 | 4/2016 |
| EP | 2626041 B1 | 4/2016 |
| EP | 2633821 B1 | 4/2016 |
| EP | 2670354 B1 | 4/2016 |
| EP | 2702965 B1 | 4/2016 |
| EP | 2704669 B1 | 4/2016 |
| EP | 2815725 B1 | 4/2016 |
| EP | 3007651 A1 | 4/2016 |
| EP | 3010564 A1 | 4/2016 |
| EP | 2194933 B1 | 5/2016 |
| EP | 2237746 B1 | 5/2016 |
| EP | 2378947 B1 | 5/2016 |
| EP | 2542184 B1 | 5/2016 |
| EP | 2572684 B1 | 5/2016 |
| EP | 2582326 B1 | 5/2016 |
| EP | 2618784 B1 | 5/2016 |
| EP | 2654623 B1 | 5/2016 |
| EP | 2656816 B1 | 5/2016 |
| EP | 2680791 B1 | 5/2016 |
| EP | 2693986 B1 | 5/2016 |
| EP | 2806805 B1 | 5/2016 |
| EP | 2866739 B1 | 5/2016 |
| EP | 2889020 B1 | 5/2016 |
| EP | 2926767 B1 | 5/2016 |
| EP | 2949292 B1 | 5/2016 |
| EP | 3019092 A1 | 5/2016 |
| EP | 1734902 B1 | 6/2016 |
| EP | 1906884 B1 | 6/2016 |
| EP | 2111800 B1 | 6/2016 |
| EP | 2160156 B1 | 6/2016 |
| EP | 2190379 B1 | 6/2016 |
| EP | 2193762 B1 | 6/2016 |
| EP | 2416739 B1 | 6/2016 |
| EP | 2453969 B1 | 6/2016 |
| EP | 2515800 B1 | 6/2016 |
| EP | 2558031 B1 | 6/2016 |
| EP | 2563236 B1 | 6/2016 |
| EP | 2572675 B1 | 6/2016 |
| EP | 2626040 B1 | 6/2016 |
| EP | 2704668 B1 | 6/2016 |
| EP | 2777611 B1 | 6/2016 |
| EP | 2815724 B1 | 6/2016 |
| EP | 2854710 B1 | 6/2016 |
| EP | 2901966 B1 | 6/2016 |
| EP | 3024527 A2 | 6/2016 |
| EP | 1605866 B1 | 7/2016 |
| EP | 1933756 B1 | 7/2016 |
| EP | 2393452 B1 | 7/2016 |
| EP | 2410948 B1 | 7/2016 |
| EP | 2412397 B1 | 7/2016 |
| EP | 2724690 B1 | 7/2016 |
| EP | 2815723 B1 | 7/2016 |
| EP | 2870945 B1 | 7/2016 |
| EP | 3040054 A1 | 7/2016 |
| EP | 3042635 A1 | 7/2016 |
| EP | 3043745 A1 | 7/2016 |
| EP | 3043747 A1 | 7/2016 |
| EP | 3043755 A1 | 7/2016 |
| EP | 1401358 B1 | 8/2016 |
| EP | 1915105 B1 | 8/2016 |
| EP | 1937186 B1 | 8/2016 |
| EP | 2292186 B1 | 8/2016 |
| EP | 2379012 B1 | 8/2016 |
| EP | 2385809 B1 | 8/2016 |
| EP | 2536345 B1 | 8/2016 |
| EP | 2537490 B1 | 8/2016 |
| EP | 2549954 B1 | 8/2016 |
| EP | 2618779 B1 | 8/2016 |
| EP | 2670352 B1 | 8/2016 |
| EP | 2829235 B1 | 8/2016 |
| EP | 2853238 B1 | 8/2016 |
| EP | 2866738 B1 | 8/2016 |

(56) References Cited

FOREIGN PATENT DOCUMENTS

| | | | |
|---|---|---|---|
| EP | 2906150 | B1 | 8/2016 |
| EP | 3052053 | A1 | 8/2016 |
| EP | 3060174 | A1 | 8/2016 |
| EP | 3061421 | A1 | 8/2016 |
| EP | 3061422 | A1 | 8/2016 |
| EP | 1156755 | B1 | 9/2016 |
| EP | 1492478 | B1 | 9/2016 |
| EP | 1912697 | B1 | 9/2016 |
| EP | 2393449 | B1 | 9/2016 |
| EP | 2670356 | B1 | 9/2016 |
| EP | 2793969 | B1 | 9/2016 |
| EP | 2809271 | B1 | 9/2016 |
| EP | 2896425 | B1 | 9/2016 |
| EP | 3068345 | A1 | 9/2016 |
| EP | 3068346 | A1 | 9/2016 |
| EP | 3071148 | A1 | 9/2016 |
| EP | 2023858 | B1 | 10/2016 |
| EP | 2112912 | B1 | 10/2016 |
| EP | 2640319 | B1 | 10/2016 |
| EP | 2663257 | B1 | 10/2016 |
| EP | 2727612 | B1 | 10/2016 |
| EP | 2760384 | B1 | 10/2016 |
| EP | 2806829 | B1 | 10/2016 |
| EP | 2858599 | B1 | 10/2016 |
| EP | 2918250 | B1 | 10/2016 |
| EP | 2922592 | A4 | 10/2016 |
| EP | 2934387 | B1 | 10/2016 |
| EP | 3076901 | A1 | 10/2016 |
| EP | 1539047 | B1 | 11/2016 |
| EP | 2282700 | B1 | 11/2016 |
| EP | 2400926 | B1 | 11/2016 |
| EP | 2467104 | B1 | 11/2016 |
| EP | 2525743 | B1 | 11/2016 |
| EP | 2549953 | B1 | 11/2016 |
| EP | 2575696 | B1 | 11/2016 |
| EP | 2598045 | B1 | 11/2016 |
| EP | 2670355 | B1 | 11/2016 |
| EP | 2676640 | B1 | 11/2016 |
| EP | 2680792 | B1 | 11/2016 |
| EP | 2707053 | B1 | 11/2016 |
| EP | 2717803 | B1 | 11/2016 |
| EP | 2773297 | B1 | 11/2016 |
| EP | 2801387 | B1 | 11/2016 |
| EP | 2844192 | B1 | 11/2016 |
| EP | 2849679 | B1 | 11/2016 |
| EP | 2877122 | B1 | 11/2016 |
| EP | 2908778 | B1 | 11/2016 |
| EP | 2922500 | B1 | 11/2016 |
| EP | 2922501 | B1 | 11/2016 |
| EP | 2967854 | B1 | 11/2016 |
| EP | 3020365 | B1 | 11/2016 |
| EP | 3090703 | A1 | 11/2016 |
| EP | 3096713 | A1 | 11/2016 |
| EP | 1645244 | B1 | 12/2016 |
| EP | 1667614 | B1 | 12/2016 |
| EP | 1684656 | B1 | 12/2016 |
| EP | 1684670 | B1 | 12/2016 |
| EP | 1750592 | B1 | 12/2016 |
| EP | 1883375 | B1 | 12/2016 |
| EP | 2293739 | B1 | 12/2016 |
| EP | 2339988 | B1 | 12/2016 |
| EP | 2512375 | B1 | 12/2016 |
| EP | 2754417 | B1 | 12/2016 |
| EP | 2754418 | B1 | 12/2016 |
| EP | 2755562 | B1 | 12/2016 |
| EP | 2889019 | B1 | 12/2016 |
| EP | 3010442 | B1 | 12/2016 |
| EP | 3099271 | A1 | 12/2016 |
| EP | 3107495 | A1 | 12/2016 |
| EP | 3107498 | A2 | 12/2016 |
| EP | 3107500 | A1 | 12/2016 |
| EP | 1893127 | B1 | 1/2017 |
| EP | 1951352 | B1 | 1/2017 |
| EP | 2109419 | B1 | 1/2017 |
| EP | 2185107 | B1 | 1/2017 |
| EP | 2266503 | B1 | 1/2017 |
| EP | 2340055 | B1 | 1/2017 |
| EP | 2395941 | B1 | 1/2017 |
| EP | 2400923 | B1 | 1/2017 |
| EP | 2629699 | B1 | 1/2017 |
| EP | 2645963 | B1 | 1/2017 |
| EP | 2654622 | B1 | 1/2017 |
| EP | 2706952 | B1 | 1/2017 |
| EP | 2760347 | B1 | 1/2017 |
| EP | 2771064 | B1 | 1/2017 |
| EP | 2780077 | B1 | 1/2017 |
| EP | 2809272 | B1 | 1/2017 |
| EP | 2934385 | B1 | 1/2017 |
| EP | 2986255 | B1 | 1/2017 |
| EP | 3119351 | A1 | 1/2017 |
| EP | 1507493 | B1 | 2/2017 |
| EP | 2563238 | B1 | 2/2017 |
| EP | 2752170 | B1 | 2/2017 |
| EP | 2760371 | B1 | 2/2017 |
| EP | 2793709 | B1 | 2/2017 |
| EP | 2793748 | B1 | 2/2017 |
| EP | 2793763 | B1 | 2/2017 |
| EP | 2832317 | B1 | 2/2017 |
| EP | 2921135 | B1 | 2/2017 |
| EP | 2967931 | B1 | 2/2017 |
| EP | 2974693 | B1 | 2/2017 |
| EP | 3025680 | B1 | 2/2017 |
| EP | 3025681 | B1 | 2/2017 |
| EP | 3125826 | A1 | 2/2017 |
| EP | 3125827 | A2 | 2/2017 |
| EP | 3128927 | A1 | 2/2017 |
| EP | 3131502 | A1 | 2/2017 |
| EP | 1845895 | B1 | 3/2017 |
| EP | 2190385 | B1 | 3/2017 |
| EP | 2266504 | B1 | 3/2017 |
| EP | 2341871 | B1 | 3/2017 |
| EP | 2379011 | B1 | 3/2017 |
| EP | 2379013 | B1 | 3/2017 |
| EP | 2640316 | B1 | 3/2017 |
| EP | 2731552 | B1 | 3/2017 |
| EP | 2756109 | B1 | 3/2017 |
| EP | 2773298 | B1 | 3/2017 |
| EP | 2832316 | B1 | 3/2017 |
| EP | 2854718 | B1 | 3/2017 |
| EP | 2881083 | B1 | 3/2017 |
| EP | 2934390 | B1 | 3/2017 |
| EP | 2934391 | B1 | 3/2017 |
| EP | 3010564 | A4 | 3/2017 |
| EP | 3145451 | A2 | 3/2017 |
| EP | 3146938 | A1 | 3/2017 |
| EP | 2014239 | B1 | 4/2017 |
| EP | 2111189 | B1 | 4/2017 |
| EP | 2393451 | B1 | 4/2017 |
| EP | 2617388 | B1 | 4/2017 |
| EP | 2629700 | B1 | 4/2017 |
| EP | 2832318 | B1 | 4/2017 |
| EP | 2893904 | B1 | 4/2017 |
| EP | 2982340 | B1 | 4/2017 |
| EP | 3000436 | B1 | 4/2017 |
| EP | 3001979 | B1 | 4/2017 |
| EP | 3043749 | B1 | 4/2017 |
| EP | 3045147 | B1 | 4/2017 |
| EP | 3054893 | B1 | 4/2017 |
| EP | 3154474 | A1 | 4/2017 |
| EP | 3156007 | A1 | 4/2017 |
| EP | 3157469 | A1 | 4/2017 |
| EP | 1855614 | B1 | 5/2017 |
| EP | 2001402 | B1 | 5/2017 |
| EP | 2032080 | B1 | 5/2017 |
| EP | 2262451 | B1 | 5/2017 |
| EP | 2470119 | B1 | 5/2017 |
| EP | 2478869 | B1 | 5/2017 |
| EP | 2538880 | B1 | 5/2017 |
| EP | 2545850 | B1 | 5/2017 |
| EP | 2600799 | B1 | 5/2017 |
| EP | 2717926 | B1 | 5/2017 |
| EP | 2726024 | B1 | 5/2017 |
| EP | 2805678 | B1 | 5/2017 |
| EP | 2809270 | B1 | 5/2017 |

(56) References Cited

FOREIGN PATENT DOCUMENTS

| | | | |
|---|---|---|---|
| EP | 2918245 | B1 | 5/2017 |
| EP | 2953579 | B1 | 5/2017 |
| EP | 2976043 | B1 | 5/2017 |
| EP | 2979666 | B1 | 5/2017 |
| EP | 3011931 | B1 | 5/2017 |
| EP | 3025682 | B1 | 5/2017 |
| EP | 3033135 | B1 | 5/2017 |
| EP | 3167847 | A1 | 5/2017 |
| EP | 3169245 | A1 | 5/2017 |
| EP | 3169276 | A1 | 5/2017 |
| EP | 2351541 | B1 | 6/2017 |
| EP | 2384165 | B1 | 6/2017 |
| EP | 2400924 | B1 | 6/2017 |
| EP | 2419041 | B1 | 6/2017 |
| EP | 2419050 | B1 | 6/2017 |
| EP | 2489331 | B1 | 6/2017 |
| EP | 2493417 | B1 | 6/2017 |
| EP | 2560585 | B1 | 6/2017 |
| EP | 2611387 | B1 | 6/2017 |
| EP | 2645967 | B1 | 6/2017 |
| EP | 2677965 | B1 | 6/2017 |
| EP | 2760349 | B1 | 6/2017 |
| EP | 2826443 | B1 | 6/2017 |
| EP | 2906148 | B1 | 6/2017 |
| EP | 2929860 | B1 | 6/2017 |
| EP | 2934669 | B1 | 6/2017 |
| EP | 2967852 | B1 | 6/2017 |
| EP | 3076901 | A4 | 6/2017 |
| EP | 3174502 | A1 | 6/2017 |
| EP | 3178443 | A1 | 6/2017 |
| EP | 3178445 | A1 | 6/2017 |
| EP | 3184081 | A1 | 6/2017 |
| EP | 1624810 | B1 | 7/2017 |
| EP | 2026703 | B1 | 7/2017 |
| EP | 2293718 | B1 | 7/2017 |
| EP | 2339989 | B1 | 7/2017 |
| EP | 2344076 | B1 | 7/2017 |
| EP | 2486893 | B1 | 7/2017 |
| EP | 2536356 | B1 | 7/2017 |
| EP | 2548534 | B1 | 7/2017 |
| EP | 2608742 | B1 | 7/2017 |
| EP | 2673038 | B1 | 7/2017 |
| EP | 2676638 | B1 | 7/2017 |
| EP | 2774630 | B1 | 7/2017 |
| EP | 2825107 | B1 | 7/2017 |
| EP | 2841020 | B1 | 7/2017 |
| EP | 2934386 | B1 | 7/2017 |
| EP | 2943151 | B1 | 7/2017 |
| EP | 3058894 | B1 | 7/2017 |
| EP | 3071151 | B1 | 7/2017 |
| EP | 3191025 | A1 | 7/2017 |
| EP | 3193740 | A2 | 7/2017 |
| EP | 3193782 | A1 | 7/2017 |
| EP | 1530441 | B1 | 8/2017 |
| EP | 1722716 | B1 | 8/2017 |
| EP | 1971289 | B1 | 8/2017 |
| EP | 2323591 | B1 | 8/2017 |
| EP | 2344070 | B1 | 8/2017 |
| EP | 2393442 | A4 | 8/2017 |
| EP | 2413842 | B1 | 8/2017 |
| EP | 2427143 | B1 | 8/2017 |
| EP | 2459077 | B1 | 8/2017 |
| EP | 2480167 | B1 | 8/2017 |
| EP | 2482749 | B1 | 8/2017 |
| EP | 2496181 | B1 | 8/2017 |
| EP | 2568925 | B1 | 8/2017 |
| EP | 2617389 | B1 | 8/2017 |
| EP | 2713954 | B1 | 8/2017 |
| EP | 2755602 | B1 | 8/2017 |
| EP | 2800602 | B1 | 8/2017 |
| EP | 2809263 | B1 | 8/2017 |
| EP | 2830536 | B1 | 8/2017 |
| EP | 2841009 | B1 | 8/2017 |
| EP | 2844190 | B1 | 8/2017 |
| EP | 2849681 | B1 | 8/2017 |
| EP | 2858600 | B1 | 8/2017 |
| EP | 2897556 | B1 | 8/2017 |
| EP | 2934388 | B1 | 8/2017 |
| EP | 2979667 | B1 | 8/2017 |
| EP | 3197397 | A1 | 8/2017 |
| EP | 3202371 | A1 | 8/2017 |
| EP | 3206629 | A1 | 8/2017 |
| EP | 1799093 | B1 | 9/2017 |
| EP | 2010103 | B1 | 9/2017 |
| EP | 2114304 | B1 | 9/2017 |
| EP | 2344090 | B1 | 9/2017 |
| EP | 2398421 | B1 | 9/2017 |
| EP | 2437687 | B1 | 9/2017 |
| EP | 2453970 | B1 | 9/2017 |
| EP | 2509538 | B1 | 9/2017 |
| EP | 2713956 | B1 | 9/2017 |
| EP | 2772227 | B1 | 9/2017 |
| EP | 2787924 | B1 | 9/2017 |
| EP | 2803335 | B1 | 9/2017 |
| EP | 2811939 | B1 | 9/2017 |
| EP | 2830537 | B1 | 9/2017 |
| EP | 2865355 | B1 | 9/2017 |
| EP | 2872047 | B1 | 9/2017 |
| EP | 2934389 | B1 | 9/2017 |
| EP | 3213715 | A1 | 9/2017 |
| EP | 3213716 | A1 | 9/2017 |
| EP | 3215061 | A1 | 9/2017 |
| EP | 3220856 | A2 | 9/2017 |
| EP | 1945141 | B1 | 10/2017 |
| EP | 2317956 | B1 | 10/2017 |
| EP | 2613737 | B1 | 10/2017 |
| EP | 2620125 | B1 | 10/2017 |
| EP | 2720642 | B1 | 10/2017 |
| EP | 2741682 | B1 | 10/2017 |
| EP | 2872077 | B1 | 10/2017 |
| EP | 3021925 | B1 | 10/2017 |
| EP | 3231395 | A1 | 10/2017 |
| EP | 3232989 | A1 | 10/2017 |
| EP | 1651148 | B1 | 11/2017 |
| EP | 1913901 | B1 | 11/2017 |
| EP | 2222248 | B1 | 11/2017 |
| EP | 2296581 | B1 | 11/2017 |
| EP | 2326264 | B1 | 11/2017 |
| EP | 2427142 | B1 | 11/2017 |
| EP | 2456483 | B1 | 11/2017 |
| EP | 2493423 | B1 | 11/2017 |
| EP | 2611391 | B1 | 11/2017 |
| EP | 2618780 | B1 | 11/2017 |
| EP | 2658480 | B1 | 11/2017 |
| EP | 2710978 | B1 | 11/2017 |
| EP | 2832315 | B1 | 11/2017 |
| EP | 2954875 | B1 | 11/2017 |
| EP | 2967861 | B1 | 11/2017 |
| EP | 2982338 | B1 | 11/2017 |
| EP | 3027144 | B1 | 11/2017 |
| EP | 3043746 | B1 | 11/2017 |
| EP | 3049026 | B1 | 11/2017 |
| EP | 3068311 | B1 | 11/2017 |
| EP | 3110368 | B1 | 11/2017 |
| EP | 3110369 | B1 | 11/2017 |
| EP | 3132773 | B1 | 11/2017 |
| EP | 3238662 | A1 | 11/2017 |
| EP | 3247312 | A1 | 11/2017 |
| EP | 1667603 | B1 | 12/2017 |
| EP | 1874954 | B1 | 12/2017 |
| EP | 2427145 | B1 | 12/2017 |
| EP | 2542185 | B1 | 12/2017 |
| EP | 2723274 | B1 | 12/2017 |
| EP | 2736455 | B1 | 12/2017 |
| EP | 2736457 | B1 | 12/2017 |
| EP | 2830534 | B1 | 12/2017 |
| EP | 2830535 | B1 | 12/2017 |
| EP | 2911592 | B1 | 12/2017 |
| EP | 2916772 | B1 | 12/2017 |
| EP | 2967922 | B1 | 12/2017 |
| EP | 3009105 | B1 | 12/2017 |
| EP | 3088037 | B1 | 12/2017 |
| EP | 3115023 | B1 | 12/2017 |
| EP | 3251633 | A1 | 12/2017 |

(56) References Cited

FOREIGN PATENT DOCUMENTS

| | | | |
|---|---|---|---|
| EP | 3253332 | A2 | 12/2017 |
| EP | 3256073 | A1 | 12/2017 |
| EP | 3256074 | A1 | 12/2017 |
| EP | 3256076 | A1 | 12/2017 |
| EP | 3256178 | A1 | 12/2017 |
| EP | 1492458 | B1 | 1/2018 |
| EP | 1768604 | B1 | 1/2018 |
| EP | 1951154 | B1 | 1/2018 |
| EP | 2091465 | B1 | 1/2018 |
| EP | 2345380 | B1 | 1/2018 |
| EP | 2456363 | B1 | 1/2018 |
| EP | 2531143 | B1 | 1/2018 |
| EP | 2621407 | B1 | 1/2018 |
| EP | 2694123 | B1 | 1/2018 |
| EP | 2775962 | B1 | 1/2018 |
| EP | 2874568 | B1 | 1/2018 |
| EP | 2967863 | B1 | 1/2018 |
| EP | 2967869 | B1 | 1/2018 |
| EP | 3033047 | B1 | 1/2018 |
| EP | 3037065 | B1 | 1/2018 |
| EP | 3049025 | B1 | 1/2018 |
| EP | 3052052 | B1 | 1/2018 |
| EP | 3078350 | B1 | 1/2018 |
| EP | 3267946 | A1 | 1/2018 |
| EP | 3269331 | A1 | 1/2018 |
| EP | 3273911 | A1 | 1/2018 |
| EP | 3275404 | A1 | 1/2018 |
| EP | 2197512 | B1 | 2/2018 |
| EP | 2248486 | B1 | 2/2018 |
| EP | 2344066 | B1 | 2/2018 |
| EP | 2381854 | B1 | 2/2018 |
| EP | 2667823 | B1 | 2/2018 |
| EP | 2699169 | B1 | 2/2018 |
| EP | 2714177 | B1 | 2/2018 |
| EP | 2736544 | B1 | 2/2018 |
| EP | 2846736 | B1 | 2/2018 |
| EP | 2886082 | B1 | 2/2018 |
| EP | 2886084 | B1 | 2/2018 |
| EP | 2931178 | B1 | 2/2018 |
| EP | 2934392 | B1 | 2/2018 |
| EP | 3150173 | B1 | 2/2018 |
| EP | 3277222 | A1 | 2/2018 |
| EP | 3280358 | A1 | 2/2018 |
| EP | 3281608 | A1 | 2/2018 |
| EP | 3283009 | A1 | 2/2018 |
| EP | 3283011 | A1 | 2/2018 |
| EP | 3287099 | A1 | 2/2018 |
| EP | 1959864 | B1 | 3/2018 |
| EP | 2513200 | B1 | 3/2018 |
| EP | 2608815 | B1 | 3/2018 |
| EP | 2858711 | B1 | 3/2018 |
| EP | 2938292 | B1 | 3/2018 |
| EP | 2943132 | B1 | 3/2018 |
| EP | 2983620 | B1 | 3/2018 |
| EP | 3003219 | B1 | 3/2018 |
| EP | 3005979 | B1 | 3/2018 |
| EP | 3037064 | B1 | 3/2018 |
| EP | 3046511 | B1 | 3/2018 |
| EP | 3142603 | B1 | 3/2018 |
| EP | 3288479 | A1 | 3/2018 |
| EP | 3288491 | A1 | 3/2018 |
| EP | 3288494 | A1 | 3/2018 |
| EP | 3288497 | A2 | 3/2018 |
| EP | 3288498 | A1 | 3/2018 |
| EP | 3288499 | A1 | 3/2018 |
| EP | 3290004 | A1 | 3/2018 |
| EP | 3290007 | A1 | 3/2018 |
| EP | 3294214 | A1 | 3/2018 |
| EP | 3294215 | A1 | 3/2018 |
| EP | 3294218 | A1 | 3/2018 |
| EP | 3298970 | A1 | 3/2018 |
| EP | 3298987 | A1 | 3/2018 |
| EP | 2209440 | B1 | 4/2018 |
| EP | 2536357 | B1 | 4/2018 |
| EP | 2605725 | B1 | 4/2018 |
| EP | 2608743 | B1 | 4/2018 |
| EP | 2709561 | B1 | 4/2018 |
| EP | 2787925 | B1 | 4/2018 |
| EP | 2789314 | B1 | 4/2018 |
| EP | 2900150 | B1 | 4/2018 |
| EP | 2908779 | B1 | 4/2018 |
| EP | 2922502 | B1 | 4/2018 |
| EP | 2964441 | B1 | 4/2018 |
| EP | 2967868 | B1 | 4/2018 |
| EP | 2979665 | B1 | 4/2018 |
| EP | 2994073 | B1 | 4/2018 |
| EP | 3095394 | B1 | 4/2018 |
| EP | 3128927 | A4 | 4/2018 |
| EP | 3134033 | B1 | 4/2018 |
| EP | 3137146 | A4 | 4/2018 |
| EP | 3280482 | A4 | 4/2018 |
| EP | 3302297 | A2 | 4/2018 |
| EP | 3302362 | A1 | 4/2018 |
| EP | 3302367 | A1 | 4/2018 |
| EP | 3308745 | A1 | 4/2018 |
| EP | 3310301 | A1 | 4/2018 |
| EP | 3311774 | A1 | 4/2018 |
| EP | 3311783 | A1 | 4/2018 |
| EP | 1945112 | B1 | 5/2018 |
| EP | 2007313 | B1 | 5/2018 |
| EP | 2316381 | B2 | 5/2018 |
| EP | 2377469 | B1 | 5/2018 |
| EP | 2531115 | B1 | 5/2018 |
| EP | 2561831 | B1 | 5/2018 |
| EP | 2605724 | B1 | 5/2018 |
| EP | 2723277 | B1 | 5/2018 |
| EP | 2741711 | B1 | 5/2018 |
| EP | 2755573 | B1 | 5/2018 |
| EP | 2768429 | B1 | 5/2018 |
| EP | 2819618 | B1 | 5/2018 |
| EP | 2833836 | B1 | 5/2018 |
| EP | 2886083 | B1 | 5/2018 |
| EP | 2926840 | B1 | 5/2018 |
| EP | 2943157 | B1 | 5/2018 |
| EP | 2948099 | B1 | 5/2018 |
| EP | 3000437 | B1 | 5/2018 |
| EP | 3145448 | B1 | 5/2018 |
| EP | 3154475 | B1 | 5/2018 |
| EP | 3316819 | A1 | 5/2018 |
| EP | 3316821 | A1 | 5/2018 |
| EP | 3322381 | A1 | 5/2018 |
| EP | 3322383 | A1 | 5/2018 |
| EP | 3323353 | A1 | 5/2018 |
| EP | 3323439 | A1 | 5/2018 |
| EP | 3324892 | A1 | 5/2018 |
| EP | 3326584 | A1 | 5/2018 |
| EP | 2150312 | B1 | 6/2018 |
| EP | 2379322 | B1 | 6/2018 |
| EP | 2400925 | B1 | 6/2018 |
| EP | 2552355 | B1 | 6/2018 |
| EP | 2560589 | B1 | 6/2018 |
| EP | 2563277 | B1 | 6/2018 |
| EP | 2661305 | B1 | 6/2018 |
| EP | 2736456 | B1 | 6/2018 |
| EP | 2782523 | B1 | 6/2018 |
| EP | 3056170 | B1 | 6/2018 |
| EP | 3062745 | B1 | 6/2018 |
| EP | 3130320 | B1 | 6/2018 |
| EP | 3187150 | B1 | 6/2018 |
| EP | 3334378 | A1 | 6/2018 |
| EP | 3334380 | A1 | 6/2018 |
| EP | 3334381 | A1 | 6/2018 |
| EP | 3335670 | A1 | 6/2018 |
| EP | 3337424 | A1 | 6/2018 |
| EP | 2478872 | B1 | 7/2018 |
| EP | 2563278 | B1 | 7/2018 |
| EP | 2616004 | B1 | 7/2018 |
| EP | 2779943 | B1 | 7/2018 |
| EP | 2802290 | B1 | 7/2018 |
| EP | 2816980 | B1 | 7/2018 |
| EP | 2938293 | B1 | 7/2018 |
| EP | 3107496 | B1 | 7/2018 |
| EP | 3178450 | B1 | 7/2018 |
| EP | 3212097 | B1 | 7/2018 |

(56) References Cited

FOREIGN PATENT DOCUMENTS

| | | | |
|---|---|---|---|
| EP | 3340923 | A1 | 7/2018 |
| EP | 3340934 | A1 | 7/2018 |
| EP | 3340936 | A1 | 7/2018 |
| EP | 3340945 | A1 | 7/2018 |
| EP | 3342355 | A1 | 7/2018 |
| EP | 3342377 | A1 | 7/2018 |
| EP | 3346952 | A1 | 7/2018 |
| EP | 3348235 | A1 | 7/2018 |
| EP | 3349693 | A1 | 7/2018 |
| EP | 2536354 | B1 | 8/2018 |
| EP | 2616006 | B1 | 8/2018 |
| EP | 2797556 | B1 | 8/2018 |
| EP | 2822473 | B1 | 8/2018 |
| EP | 2854711 | B1 | 8/2018 |
| EP | 2866847 | B1 | 8/2018 |
| EP | 2918246 | B1 | 8/2018 |
| EP | 2967845 | B1 | 8/2018 |
| EP | 2999436 | B1 | 8/2018 |
| EP | 3013281 | B1 | 8/2018 |
| EP | 3060170 | B1 | 8/2018 |
| EP | 3104811 | B1 | 8/2018 |
| EP | 3143944 | B1 | 8/2018 |
| EP | 3157467 | B1 | 8/2018 |
| EP | 3193791 | B1 | 8/2018 |
| EP | 3241526 | B1 | 8/2018 |
| EP | 3355800 | A1 | 8/2018 |
| EP | 3360513 | A1 | 8/2018 |
| EP | 3360514 | A1 | 8/2018 |
| EP | 3361988 | A1 | 8/2018 |
| EP | 2114305 | B1 | 9/2018 |
| EP | 2155115 | B1 | 9/2018 |
| EP | 2601910 | B1 | 9/2018 |
| EP | 2617390 | B1 | 9/2018 |
| EP | 2734157 | B1 | 9/2018 |
| EP | 2968674 | B1 | 9/2018 |
| EP | 2999415 | B1 | 9/2018 |
| EP | 3106130 | B1 | 9/2018 |
| EP | 3151763 | B1 | 9/2018 |
| EP | 3213717 | B1 | 9/2018 |
| EP | 3245985 | B1 | 9/2018 |
| EP | 3367979 | A1 | 9/2018 |
| EP | 3370649 | A1 | 9/2018 |
| EP | 3370650 | A1 | 9/2018 |
| EP | 1827256 | B1 | 10/2018 |
| EP | 1850790 | B1 | 10/2018 |
| EP | 2063823 | B1 | 10/2018 |
| EP | 2124825 | B1 | 10/2018 |
| EP | 2249746 | B1 | 10/2018 |
| EP | 2254514 | B1 | 10/2018 |
| EP | 2285309 | B1 | 10/2018 |
| EP | 2455042 | B1 | 10/2018 |
| EP | 2571561 | B1 | 10/2018 |
| EP | 2616008 | B1 | 10/2018 |
| EP | 2647393 | B1 | 10/2018 |
| EP | 2739214 | B1 | 10/2018 |
| EP | 2739247 | B1 | 10/2018 |
| EP | 2776114 | B1 | 10/2018 |
| EP | 2836171 | B1 | 10/2018 |
| EP | 2842581 | B1 | 10/2018 |
| EP | 2870946 | B1 | 10/2018 |
| EP | 2923665 | B1 | 10/2018 |
| EP | 2964277 | B1 | 10/2018 |
| EP | 3001978 | B1 | 10/2018 |
| EP | 3010562 | B1 | 10/2018 |
| EP | 3072475 | B1 | 10/2018 |
| EP | 3081161 | B1 | 10/2018 |
| EP | 3081195 | B1 | 10/2018 |
| EP | 3099345 | B1 | 10/2018 |
| EP | 3120809 | B1 | 10/2018 |
| EP | 3238663 | B1 | 10/2018 |
| EP | 3384879 | A1 | 10/2018 |
| EP | 3388027 | A1 | 10/2018 |
| EP | 3390706 | A1 | 10/2018 |
| EP | 1708650 | B1 | 11/2018 |
| EP | 1945143 | B1 | 11/2018 |
| EP | 2205183 | B1 | 11/2018 |
| EP | 2663258 | B1 | 11/2018 |
| EP | 2790615 | B1 | 11/2018 |
| EP | 2854709 | B1 | 11/2018 |
| EP | 2898859 | B1 | 11/2018 |
| EP | 2921139 | B1 | 11/2018 |
| EP | 2928538 | B1 | 11/2018 |
| EP | 3075354 | B1 | 11/2018 |
| EP | 3082949 | B1 | 11/2018 |
| EP | 3145452 | B1 | 11/2018 |
| EP | 3216424 | B1 | 11/2018 |
| EP | 3260084 | B1 | 11/2018 |
| EP | 3398562 | A1 | 11/2018 |
| EP | 3400908 | A1 | 11/2018 |
| EP | 3405139 | A1 | 11/2018 |
| EP | 1858450 | B1 | 12/2018 |
| EP | 2150208 | B1 | 12/2018 |
| EP | 2326261 | B1 | 12/2018 |
| EP | 2344075 | B1 | 12/2018 |
| EP | 2370028 | B1 | 12/2018 |
| EP | 2555709 | B1 | 12/2018 |
| EP | 2564812 | B1 | 12/2018 |
| EP | 2777618 | B1 | 12/2018 |
| EP | 2814427 | B1 | 12/2018 |
| EP | 2829240 | B1 | 12/2018 |
| EP | 2911594 | B1 | 12/2018 |
| EP | 2911729 | B1 | 12/2018 |
| EP | 2954876 | B1 | 12/2018 |
| EP | 2958520 | B1 | 12/2018 |
| EP | 2958605 | B1 | 12/2018 |
| EP | 3010446 | B1 | 12/2018 |
| EP | 3064174 | B1 | 12/2018 |
| EP | 3206628 | B1 | 12/2018 |
| EP | 3242629 | B1 | 12/2018 |
| EP | 3260085 | B1 | 12/2018 |
| EP | 3266416 | B1 | 12/2018 |
| EP | 3326583 | B1 | 12/2018 |
| EP | 3410987 | A1 | 12/2018 |
| EP | 3415120 | A1 | 12/2018 |
| EP | 3417813 | A1 | 12/2018 |
| EP | 2129332 | B1 | 1/2019 |
| EP | 2196159 | B1 | 1/2019 |
| EP | 2370025 | B1 | 1/2019 |
| EP | 2549957 | B1 | 1/2019 |
| EP | 2819619 | B1 | 1/2019 |
| EP | 2849680 | B1 | 1/2019 |
| EP | 2856972 | B1 | 1/2019 |
| EP | 2866742 | B1 | 1/2019 |
| EP | 2884946 | B1 | 1/2019 |
| EP | 2948102 | B1 | 1/2019 |
| EP | 2979664 | B1 | 1/2019 |
| EP | 3043748 | B1 | 1/2019 |
| EP | 3145449 | B1 | 1/2019 |
| EP | 3288491 | A4 | 1/2019 |
| EP | 3332743 | B1 | 1/2019 |
| EP | 3429507 | A1 | 1/2019 |
| EP | 3432832 | A1 | 1/2019 |
| EP | 3432834 | A1 | 1/2019 |
| EP | 1895943 | B1 | 2/2019 |
| EP | 2070490 | B1 | 2/2019 |
| EP | 2308425 | B1 | 2/2019 |
| EP | 2379009 | B1 | 2/2019 |
| EP | 2575685 | B1 | 2/2019 |
| EP | 2688562 | B1 | 2/2019 |
| EP | 2714068 | B1 | 2/2019 |
| EP | 2720641 | B1 | 2/2019 |
| EP | 2760375 | B1 | 2/2019 |
| EP | 2862590 | B1 | 2/2019 |
| EP | 2925259 | B1 | 2/2019 |
| EP | 2931179 | B1 | 2/2019 |
| EP | 3005983 | B1 | 2/2019 |
| EP | 3023117 | B1 | 2/2019 |
| EP | 3184083 | B1 | 2/2019 |
| EP | 3202333 | B1 | 2/2019 |
| EP | 3261583 | B1 | 2/2019 |
| EP | 3278832 | B1 | 2/2019 |
| EP | 3435919 | A1 | 2/2019 |
| EP | 3441045 | A1 | 2/2019 |
| EP | 3442469 | A1 | 2/2019 |

(56) References Cited

FOREIGN PATENT DOCUMENTS

| | | | |
|---|---|---|---|
| EP | 3445290 | A1 | 2/2019 |
| EP | 1771132 | B1 | 3/2019 |
| EP | 1959866 | B1 | 3/2019 |
| EP | 2120794 | B1 | 3/2019 |
| EP | 2259728 | B1 | 3/2019 |
| EP | 2344074 | B1 | 3/2019 |
| EP | 2552356 | B1 | 3/2019 |
| EP | 2598044 | B1 | 3/2019 |
| EP | 2659861 | B1 | 3/2019 |
| EP | 2670357 | B1 | 3/2019 |
| EP | 2898902 | B1 | 3/2019 |
| EP | 2948098 | B1 | 3/2019 |
| EP | 2948101 | B1 | 3/2019 |
| EP | 2967865 | B1 | 3/2019 |
| EP | 2974695 | B1 | 3/2019 |
| EP | 3027243 | B1 | 3/2019 |
| EP | 3116446 | B1 | 3/2019 |
| EP | 3145445 | B1 | 3/2019 |
| EP | 3151783 | B1 | 3/2019 |
| EP | 3151784 | B1 | 3/2019 |
| EP | 3278768 | B1 | 3/2019 |
| EP | 3320943 | B1 | 3/2019 |
| EP | 3448314 | A1 | 3/2019 |
| EP | 3448315 | A1 | 3/2019 |
| EP | 3454785 | A1 | 3/2019 |
| EP | 3454786 | A1 | 3/2019 |
| EP | 3454789 | A1 | 3/2019 |
| EP | 3454794 | A1 | 3/2019 |
| EP | 3457987 | A1 | 3/2019 |
| EP | 3457988 | A1 | 3/2019 |
| EP | 3457990 | A1 | 3/2019 |
| EP | 3459499 | A2 | 3/2019 |
| EP | 1793745 | B1 | 4/2019 |
| EP | 1855623 | B1 | 4/2019 |
| EP | 2129333 | B1 | 4/2019 |
| EP | 2149349 | B1 | 4/2019 |
| EP | 2438888 | B1 | 4/2019 |
| EP | 2484309 | B1 | 4/2019 |
| EP | 2519268 | B1 | 4/2019 |
| EP | 2528545 | B1 | 4/2019 |
| EP | 2536358 | B1 | 4/2019 |
| EP | 2661239 | B1 | 4/2019 |
| EP | 2709563 | B1 | 4/2019 |
| EP | 2736451 | B1 | 4/2019 |
| EP | 2810619 | B1 | 4/2019 |
| EP | 2810622 | B1 | 4/2019 |
| EP | 2879589 | B1 | 4/2019 |
| EP | 2921198 | B1 | 4/2019 |
| EP | 2986256 | B1 | 4/2019 |
| EP | 3090704 | B1 | 4/2019 |
| EP | 3116445 | B1 | 4/2019 |
| EP | 3141217 | B1 | 4/2019 |
| EP | 3193745 | B1 | 4/2019 |
| EP | 3241525 | B1 | 4/2019 |
| EP | 3344167 | A4 | 4/2019 |
| EP | 3461531 | A1 | 4/2019 |
| EP | 3466373 | A1 | 4/2019 |
| EP | 3471662 | A1 | 4/2019 |
| EP | 1703870 | B1 | 5/2019 |
| EP | 1708642 | B1 | 5/2019 |
| EP | 2240121 | B1 | 5/2019 |
| EP | 2663259 | B1 | 5/2019 |
| EP | 2695586 | B1 | 5/2019 |
| EP | 2726018 | B1 | 5/2019 |
| EP | 2954872 | B1 | 5/2019 |
| EP | 3071150 | B1 | 5/2019 |
| EP | 3110370 | B1 | 5/2019 |
| EP | 3111890 | B1 | 5/2019 |
| EP | 3182932 | B1 | 5/2019 |
| EP | 3192472 | B1 | 5/2019 |
| EP | 3238661 | B1 | 5/2019 |
| EP | 3284503 | B1 | 5/2019 |
| EP | 3302364 | B1 | 5/2019 |
| EP | 3315094 | B1 | 5/2019 |
| EP | 3316818 | B1 | 5/2019 |
| EP | 3474778 | A1 | 5/2019 |
| EP | 3476366 | A1 | 5/2019 |
| EP | 3476424 | A1 | 5/2019 |
| EP | 3478224 | A1 | 5/2019 |
| EP | 3479797 | A1 | 5/2019 |
| EP | 3481335 | A1 | 5/2019 |
| EP | 3481336 | A1 | 5/2019 |
| EP | 3481338 | A1 | 5/2019 |
| EP | 3481339 | A1 | 5/2019 |
| EP | 3482718 | A1 | 5/2019 |
| EP | 3484412 | A1 | 5/2019 |
| EP | 3485847 | A1 | 5/2019 |
| EP | 3485848 | A1 | 5/2019 |
| EP | 3485933 | A1 | 5/2019 |
| EP | 3487420 | A1 | 5/2019 |
| EP | 3487451 | A1 | 5/2019 |
| EP | 3487452 | A1 | 5/2019 |
| EP | 3488822 | A1 | 5/2019 |
| EP | 1624792 | B1 | 6/2019 |
| EP | 1737394 | B1 | 6/2019 |
| EP | 1858451 | B1 | 6/2019 |
| EP | 1895944 | B1 | 6/2019 |
| EP | 1968487 | B1 | 6/2019 |
| EP | 2004095 | B1 | 6/2019 |
| EP | 2010102 | B1 | 6/2019 |
| EP | 2131788 | B1 | 6/2019 |
| EP | 2560580 | B1 | 6/2019 |
| EP | 2618782 | B1 | 6/2019 |
| EP | 2868296 | B1 | 6/2019 |
| EP | 2961358 | B1 | 6/2019 |
| EP | 2967847 | B1 | 6/2019 |
| EP | 2985006 | B1 | 6/2019 |
| EP | 3033048 | B1 | 6/2019 |
| EP | 3119451 | B1 | 6/2019 |
| EP | 3131503 | B1 | 6/2019 |
| EP | 3213718 | B1 | 6/2019 |
| EP | 3275390 | B1 | 6/2019 |
| EP | 3300692 | B1 | 6/2019 |
| EP | 3326585 | B1 | 6/2019 |
| EP | 3338737 | B1 | 6/2019 |
| EP | 3357457 | B1 | 6/2019 |
| EP | 3372198 | B1 | 6/2019 |
| EP | 3490465 | A1 | 6/2019 |
| EP | 3490500 | A1 | 6/2019 |
| EP | 3490659 | A1 | 6/2019 |
| EP | 3496626 | A1 | 6/2019 |
| EP | 3496664 | A1 | 6/2019 |
| EP | 3498224 | A1 | 6/2019 |
| EP | 3501454 | A1 | 6/2019 |
| EP | 3501456 | A1 | 6/2019 |
| EP | 1659981 | B1 | 7/2019 |
| EP | 1924223 | B1 | 7/2019 |
| EP | 2249745 | B1 | 7/2019 |
| EP | 2296744 | B1 | 7/2019 |
| EP | 2331019 | B1 | 7/2019 |
| EP | 2368527 | B1 | 7/2019 |
| EP | 2509542 | B1 | 7/2019 |
| EP | 2555710 | B1 | 7/2019 |
| EP | 2575682 | B1 | 7/2019 |
| EP | 2575683 | B1 | 7/2019 |
| EP | 2640431 | B1 | 7/2019 |
| EP | 2641572 | B1 | 7/2019 |
| EP | 2649964 | B1 | 7/2019 |
| EP | 2767260 | B1 | 7/2019 |
| EP | 2777615 | B1 | 7/2019 |
| EP | 2838476 | B1 | 7/2019 |
| EP | 2861186 | B1 | 7/2019 |
| EP | 2877124 | B1 | 7/2019 |
| EP | 2877132 | B1 | 7/2019 |
| EP | 2921565 | B1 | 7/2019 |
| EP | 2938291 | B1 | 7/2019 |
| EP | 2999433 | B1 | 7/2019 |
| EP | 3145450 | B1 | 7/2019 |
| EP | 3254644 | B1 | 7/2019 |
| EP | 3315093 | B1 | 7/2019 |
| EP | 3344189 | B1 | 7/2019 |
| EP | 3503813 | A1 | 7/2019 |
| EP | 3503846 | A1 | 7/2019 |
| EP | 3503847 | A1 | 7/2019 |

(56) References Cited

FOREIGN PATENT DOCUMENTS

| | | |
|---|---|---|
| EP | 3503848 A1 | 7/2019 |
| EP | 3505077 A1 | 7/2019 |
| EP | 3512465 A1 | 7/2019 |
| EP | 3515365 A1 | 7/2019 |
| EP | 1861043 B1 | 8/2019 |
| EP | 2303190 B1 | 8/2019 |
| EP | 2593171 B1 | 8/2019 |
| EP | 2632393 B1 | 8/2019 |
| EP | 2663355 B1 | 8/2019 |
| EP | 2665509 B1 | 8/2019 |
| EP | 2688525 B1 | 8/2019 |
| EP | 2699201 B1 | 8/2019 |
| EP | 2755564 B1 | 8/2019 |
| EP | 2769681 B1 | 8/2019 |
| EP | 2793751 B1 | 8/2019 |
| EP | 2900177 B1 | 8/2019 |
| EP | 2967536 B1 | 8/2019 |
| EP | 3050541 B1 | 8/2019 |
| EP | 3102152 B1 | 8/2019 |
| EP | 3157607 B1 | 8/2019 |
| EP | 3231392 B1 | 8/2019 |
| EP | 3284411 B1 | 8/2019 |
| EP | 3328318 B1 | 8/2019 |
| EP | 3348233 B1 | 8/2019 |
| EP | 3366262 B1 | 8/2019 |
| EP | 3527170 A1 | 8/2019 |
| EP | 3530236 A1 | 8/2019 |
| EP | 2358297 B1 | 9/2019 |
| EP | 2368525 B1 | 9/2019 |
| EP | 2542186 B1 | 9/2019 |
| EP | 2656863 B1 | 9/2019 |
| EP | 3003221 B1 | 9/2019 |
| EP | 3003452 B1 | 9/2019 |
| EP | 3220971 B1 | 9/2019 |
| EP | 3223874 B1 | 9/2019 |
| EP | 3288495 B1 | 9/2019 |
| EP | 3311776 B1 | 9/2019 |
| EP | 3334379 B1 | 9/2019 |
| EP | 3531975 A1 | 9/2019 |
| EP | 3534840 A1 | 9/2019 |
| EP | 3534841 A1 | 9/2019 |
| EP | 3534845 A2 | 9/2019 |
| EP | 3535010 A1 | 9/2019 |
| EP | 3538026 A1 | 9/2019 |
| EP | 3538027 A1 | 9/2019 |
| EP | 3539508 A1 | 9/2019 |
| EP | 3539509 A1 | 9/2019 |
| EP | 3541325 A1 | 9/2019 |
| EP | 3542758 A1 | 9/2019 |
| EP | 1740265 B1 | 10/2019 |
| EP | 2039756 B1 | 10/2019 |
| EP | 2456506 B1 | 10/2019 |
| EP | 2470122 B1 | 10/2019 |
| EP | 2613738 B1 | 10/2019 |
| EP | 2637607 B1 | 10/2019 |
| EP | 2674174 B1 | 10/2019 |
| EP | 2811923 B1 | 10/2019 |
| EP | 2901967 B1 | 10/2019 |
| EP | 3010431 B1 | 10/2019 |
| EP | 3019091 B1 | 10/2019 |
| EP | 3019123 B1 | 10/2019 |
| EP | 3057522 B1 | 10/2019 |
| EP | 3067075 B1 | 10/2019 |
| EP | 3146937 B1 | 10/2019 |
| EP | 3238777 B1 | 10/2019 |
| EP | 3359211 B1 | 10/2019 |
| EP | 3388026 B1 | 10/2019 |
| EP | 3432806 B1 | 10/2019 |
| EP | 3496626 A4 | 10/2019 |
| EP | 3544548 A1 | 10/2019 |
| EP | 3547936 A1 | 10/2019 |
| EP | 3547966 A1 | 10/2019 |
| EP | 3549555 A1 | 10/2019 |
| EP | 3552585 A1 | 10/2019 |
| EP | 3556323 A1 | 10/2019 |
| EP | 3558165 A1 | 10/2019 |
| EP | 3558168 A1 | 10/2019 |
| EP | 3558169 A2 | 10/2019 |
| EP | 2043559 B1 | 11/2019 |
| EP | 2358308 B1 | 11/2019 |
| EP | 2405863 B1 | 11/2019 |
| EP | 2701633 B1 | 11/2019 |
| EP | 2898857 B1 | 11/2019 |
| EP | 2967853 B1 | 11/2019 |
| EP | 3009104 B1 | 11/2019 |
| EP | 3021792 B1 | 11/2019 |
| EP | 3076900 B1 | 11/2019 |
| EP | 3111889 B1 | 11/2019 |
| EP | 3142607 B1 | 11/2019 |
| EP | 3167850 B1 | 11/2019 |
| EP | 3397205 B1 | 11/2019 |
| EP | 3572045 A1 | 11/2019 |
| EP | 3572117 A1 | 11/2019 |
| EP | 3479800 A4 | 12/2019 |
| EP | 3576677 A1 | 12/2019 |
| EP | 3579761 A2 | 12/2019 |
| EP | 3582697 A1 | 12/2019 |
| EP | 3583922 A1 | 12/2019 |
| EP | 3445443 A4 | 1/2020 |
| EP | 3590471 A1 | 1/2020 |
| EP | 3590472 A1 | 1/2020 |
| EP | 3592284 A1 | 1/2020 |
| EP | 3592288 A1 | 1/2020 |
| EP | 3592289 A1 | 1/2020 |
| EP | 3593763 A1 | 1/2020 |
| EP | 3595588 A1 | 1/2020 |
| EP | 3600159 A1 | 2/2020 |
| EP | 3606472 A1 | 2/2020 |
| EP | 2241287 B2 | 3/2020 |
| EP | 2376013 B1 | 3/2020 |
| EP | 2911593 B1 | 3/2020 |
| EP | 2995279 B1 | 3/2020 |
| EP | 3009103 B1 | 3/2020 |
| EP | 3038664 B1 | 3/2020 |
| EP | 3167848 B1 | 3/2020 |
| EP | 3175822 B1 | 3/2020 |
| EP | 3179960 B1 | 3/2020 |
| EP | 3280479 B1 | 3/2020 |
| EP | 3616651 A1 | 3/2020 |
| EP | 3619136 A1 | 3/2020 |
| EP | 3626208 A1 | 3/2020 |
| EP | 1667614 B2 | 4/2020 |
| EP | 2119417 B2 | 4/2020 |
| EP | 2155114 B1 | 4/2020 |
| EP | 2299937 B1 | 4/2020 |
| EP | 2331016 B1 | 4/2020 |
| EP | 2376013 B8 | 4/2020 |
| EP | 2413843 B1 | 4/2020 |
| EP | 2854705 B1 | 4/2020 |
| EP | 2918249 B1 | 4/2020 |
| EP | 2922593 B1 | 4/2020 |
| EP | 2950753 B1 | 4/2020 |
| EP | 2967810 B1 | 4/2020 |
| EP | 3110367 B1 | 4/2020 |
| EP | 3111888 B1 | 4/2020 |
| EP | 3128927 B1 | 4/2020 |
| EP | 3134032 B1 | 4/2020 |
| EP | 3142606 B1 | 4/2020 |
| EP | 3270825 B1 | 4/2020 |
| EP | 3300696 B1 | 4/2020 |
| EP | 3316823 B1 | 4/2020 |
| EP | 3334487 B1 | 4/2020 |
| EP | 3342355 B1 | 4/2020 |
| EP | 3373863 B1 | 4/2020 |
| EP | 3459498 B1 | 4/2020 |
| EP | 3470105 B1 | 4/2020 |
| EP | 3628239 A1 | 4/2020 |
| EP | 3632338 A1 | 4/2020 |
| EP | 3639792 A1 | 4/2020 |
| EP | 3639888 A1 | 4/2020 |
| EP | 3643273 A1 | 4/2020 |
| EP | 1895942 B1 | 5/2020 |
| EP | 2120821 B1 | 5/2020 |
| EP | 2437688 B1 | 5/2020 |

(56) References Cited

FOREIGN PATENT DOCUMENTS

| | | | |
|---|---|---|---|
| EP | 2785281 | B1 | 5/2020 |
| EP | 2852354 | B1 | 5/2020 |
| EP | 2884906 | B1 | 5/2020 |
| EP | 2999412 | B1 | 5/2020 |
| EP | 3060174 | B1 | 5/2020 |
| EP | 3071147 | B1 | 5/2020 |
| EP | 3104812 | B1 | 5/2020 |
| EP | 3139861 | B1 | 5/2020 |
| EP | 3232989 | B1 | 5/2020 |
| EP | 3294219 | B1 | 5/2020 |
| EP | 3298970 | B1 | 5/2020 |
| EP | 3302366 | B1 | 5/2020 |
| EP | 3323389 | B1 | 5/2020 |
| EP | 3332744 | B1 | 5/2020 |
| EP | 3402440 | B1 | 5/2020 |
| EP | 3417813 | B1 | 5/2020 |
| EP | 3417831 | B1 | 5/2020 |
| EP | 3457987 | B1 | 5/2020 |
| EP | 3484413 | B1 | 5/2020 |
| EP | 3531975 | B1 | 5/2020 |
| EP | 3644866 | A1 | 5/2020 |
| EP | 3646822 | A1 | 5/2020 |
| EP | 3646824 | A1 | 5/2020 |
| EP | 3646825 | A1 | 5/2020 |
| EP | 3648706 | A1 | 5/2020 |
| EP | 3656354 | A1 | 5/2020 |
| EP | 1648339 | B2 | 6/2020 |
| EP | 2072027 | B1 | 6/2020 |
| EP | 2331016 | B8 | 6/2020 |
| EP | 2616007 | B1 | 6/2020 |
| EP | 2967856 | B1 | 6/2020 |
| EP | 3042635 | B1 | 6/2020 |
| EP | 3060165 | B1 | 6/2020 |
| EP | 3280338 | B1 | 6/2020 |
| EP | 3283010 | B1 | 6/2020 |
| EP | 3400908 | B1 | 6/2020 |
| EP | 3494928 | B1 | 6/2020 |
| EP | 3498225 | B1 | 6/2020 |
| EP | 3583920 | B1 | 6/2020 |
| EP | 3659553 | A1 | 6/2020 |
| EP | 3668450 | A1 | 6/2020 |
| EP | 3668452 | A1 | 6/2020 |
| EP | 3669828 | A1 | 6/2020 |
| EP | 3669829 | A1 | 6/2020 |
| EP | 2271284 | B1 | 7/2020 |
| EP | 2291145 | B1 | 7/2020 |
| EP | 2512952 | B1 | 7/2020 |
| EP | 2558029 | B1 | 7/2020 |
| EP | 2693985 | B1 | 7/2020 |
| EP | 2858708 | B1 | 7/2020 |
| EP | 2862546 | B1 | 7/2020 |
| EP | 2967807 | B1 | 7/2020 |
| EP | 2967866 | B1 | 7/2020 |
| EP | 3061421 | B1 | 7/2020 |
| EP | 3107497 | B1 | 7/2020 |
| EP | 3139862 | B1 | 7/2020 |
| EP | 3423000 | B1 | 7/2020 |
| EP | 3441045 | B1 | 7/2020 |
| EP | 3451972 | B1 | 7/2020 |
| EP | 3501454 | B1 | 7/2020 |
| EP | 3512466 | B1 | 7/2020 |
| EP | 3616652 | B1 | 7/2020 |
| EP | 3672528 | A1 | 7/2020 |
| EP | 3672529 | A1 | 7/2020 |
| EP | 3673925 | A1 | 7/2020 |
| EP | 3679894 | A1 | 7/2020 |
| EP | 3681439 | A1 | 7/2020 |
| EP | 3681441 | A1 | 7/2020 |
| EP | 3682852 | A1 | 7/2020 |
| EP | 3682854 | A1 | 7/2020 |
| EP | 3685802 | A1 | 7/2020 |
| EP | 2367505 | B1 | 8/2020 |
| EP | 2497445 | B1 | 8/2020 |
| EP | 2537486 | B1 | 8/2020 |
| EP | 2777616 | B1 | 8/2020 |
| EP | 3007651 | B1 | 8/2020 |
| EP | 3052053 | B1 | 8/2020 |
| EP | 3237033 | B1 | 8/2020 |
| EP | 3388005 | B1 | 8/2020 |
| EP | 3410986 | B1 | 8/2020 |
| EP | 3451974 | B1 | 8/2020 |
| EP | 3463192 | B1 | 8/2020 |
| EP | 3554423 | B1 | 8/2020 |
| EP | 3568089 | A4 | 8/2020 |
| EP | 3573544 | B1 | 8/2020 |
| EP | 3634255 | B1 | 8/2020 |
| EP | 3689299 | A1 | 8/2020 |
| EP | 3691567 | A1 | 8/2020 |
| EP | 3695810 | A1 | 8/2020 |
| EP | 3697346 | A1 | 8/2020 |
| EP | 2485795 | B1 | 9/2020 |
| EP | 3125777 | B1 | 9/2020 |
| EP | 3182930 | B1 | 9/2020 |
| EP | 3285690 | B1 | 9/2020 |
| EP | 3459500 | B1 | 9/2020 |
| EP | 3570782 | B1 | 9/2020 |
| EP | 3700467 | A1 | 9/2020 |
| EP | 3711711 | A1 | 9/2020 |
| EP | 3714936 | A1 | 9/2020 |
| EP | 2979667 | B2 | 10/2020 |
| EP | 3193783 | B1 | 10/2020 |
| EP | 3490501 | B1 | 10/2020 |
| EP | 3720363 | A1 | 10/2020 |
| EP | 2387973 | B1 | 11/2020 |
| EP | 2427144 | B1 | 11/2020 |
| EP | 2506777 | B1 | 11/2020 |
| EP | 2793743 | B1 | 11/2020 |
| EP | 2825203 | B1 | 11/2020 |
| EP | 2863842 | B1 | 11/2020 |
| EP | 2967700 | B1 | 11/2020 |
| EP | 2977026 | B1 | 11/2020 |
| EP | 3139864 | B1 | 11/2020 |
| EP | 3145451 | B1 | 11/2020 |
| EP | 3156007 | B1 | 11/2020 |
| EP | 3244834 | B1 | 11/2020 |
| EP | 3298987 | B1 | 11/2020 |
| EP | 3302362 | B1 | 11/2020 |
| EP | 3311777 | B1 | 11/2020 |
| EP | 3316819 | B1 | 11/2020 |
| EP | 3361988 | B1 | 11/2020 |
| EP | 3503813 | B1 | 11/2020 |
| EP | 3527170 | B1 | 11/2020 |
| EP | 3530236 | B1 | 11/2020 |
| EP | 3590471 | B1 | 11/2020 |
| EP | 3593762 | B1 | 11/2020 |
| EP | 3737336 | A1 | 11/2020 |
| EP | 3740162 | A1 | 11/2020 |
| EP | 2370138 | B1 | 12/2020 |
| EP | 2445450 | B1 | 12/2020 |
| EP | 2739250 | B1 | 12/2020 |
| EP | 2877123 | B1 | 12/2020 |
| EP | 2967834 | B1 | 12/2020 |
| EP | 2996632 | B1 | 12/2020 |
| EP | 3090703 | B1 | 12/2020 |
| EP | 3191025 | B1 | 12/2020 |
| EP | 3202371 | B1 | 12/2020 |
| EP | 3316822 | B1 | 12/2020 |
| EP | 3334382 | B1 | 12/2020 |
| EP | 3337424 | B1 | 12/2020 |
| EP | 3367896 | B1 | 12/2020 |
| EP | 3368582 | B1 | 12/2020 |
| EP | 3397208 | B1 | 12/2020 |
| EP | 3476366 | B1 | 12/2020 |
| EP | 3481303 | B1 | 12/2020 |
| EP | 3538028 | B1 | 12/2020 |
| EP | 3539510 | B1 | 12/2020 |
| EP | 3544548 | B1 | 12/2020 |
| EP | 3545906 | B1 | 12/2020 |
| EP | 3572117 | B1 | 12/2020 |
| EP | 3593763 | B1 | 12/2020 |
| EP | 3744291 | A1 | 12/2020 |
| EP | 3749254 | A1 | 12/2020 |
| EP | 1906883 | B1 | 1/2021 |
| EP | 2334261 | B1 | 1/2021 |

(56) References Cited

FOREIGN PATENT DOCUMENTS

| | | | |
|---|---|---|---|
| EP | 2349096 | B1 | 1/2021 |
| EP | 2568924 | B1 | 1/2021 |
| EP | 2699202 | B1 | 1/2021 |
| EP | 2713894 | B1 | 1/2021 |
| EP | 2835112 | B1 | 1/2021 |
| EP | 3040054 | B1 | 1/2021 |
| EP | 3131502 | B1 | 1/2021 |
| EP | 3197397 | B1 | 1/2021 |
| EP | 3256178 | B1 | 1/2021 |
| EP | 3290007 | B1 | 1/2021 |
| EP | 3316821 | B1 | 1/2021 |
| EP | 3337412 | B1 | 1/2021 |
| EP | 3432834 | B1 | 1/2021 |
| EP | 3454786 | B1 | 1/2021 |
| EP | 3474778 | B1 | 1/2021 |
| EP | 3528748 | B1 | 1/2021 |
| EP | 3547966 | B1 | 1/2021 |
| EP | 3603576 | B1 | 1/2021 |
| EP | 3760164 | A1 | 1/2021 |
| EP | 3763331 | A1 | 1/2021 |
| EP | 2273951 | B1 | 2/2021 |
| EP | 2379008 | B1 | 2/2021 |
| EP | 2996641 | B1 | 2/2021 |
| EP | 3043747 | B1 | 2/2021 |
| EP | 3340936 | B1 | 2/2021 |
| EP | 3457985 | B1 | 2/2021 |
| EP | 3503847 | B1 | 2/2021 |
| EP | 3538027 | B1 | 2/2021 |
| EP | 3558168 | B1 | 2/2021 |
| EP | 3581232 | B1 | 2/2021 |
| EP | 3656354 | B1 | 2/2021 |
| EP | 3697324 | B1 | 2/2021 |
| EP | 3773329 | A1 | 2/2021 |
| EP | 2299938 | B1 | 3/2021 |
| EP | 2470121 | B1 | 3/2021 |
| EP | 2564811 | B1 | 3/2021 |
| EP | 2679198 | B1 | 3/2021 |
| EP | 3068346 | B1 | 3/2021 |
| EP | 3160394 | B1 | 3/2021 |
| EP | 3169245 | B1 | 3/2021 |
| EP | 3178443 | B1 | 3/2021 |
| EP | 3184081 | B1 | 3/2021 |
| EP | 3226956 | B1 | 3/2021 |
| EP | 3324892 | B1 | 3/2021 |
| EP | 3334354 | B1 | 3/2021 |
| EP | 3402446 | B1 | 3/2021 |
| EP | 3442469 | B1 | 3/2021 |
| EP | 3503851 | B1 | 3/2021 |
| EP | 3506855 | B1 | 3/2021 |
| EP | 3531979 | B1 | 3/2021 |
| EP | 3535010 | B1 | 3/2021 |
| EP | 3581151 | B1 | 3/2021 |
| EP | 3590472 | B1 | 3/2021 |
| EP | 3593760 | B1 | 3/2021 |
| EP | 3646825 | B1 | 3/2021 |
| EP | 3649985 | B1 | 3/2021 |
| EP | 3791795 | A1 | 3/2021 |
| EP | 3791828 | A1 | 3/2021 |
| EP | 3796875 | A1 | 3/2021 |
| EP | 1734872 | B1 | 4/2021 |
| EP | 2594230 | B1 | 4/2021 |
| EP | 2624785 | B1 | 4/2021 |
| EP | 2670349 | B1 | 4/2021 |
| EP | 2793752 | B1 | 4/2021 |
| EP | 2823769 | B1 | 4/2021 |
| EP | 2964152 | B1 | 4/2021 |
| EP | 3253331 | B1 | 4/2021 |
| EP | 3290004 | B1 | 4/2021 |
| EP | 3311778 | B1 | 4/2021 |
| EP | 3367979 | B1 | 4/2021 |
| EP | 3454794 | B1 | 4/2021 |
| EP | 3487420 | B1 | 4/2021 |
| EP | 3558165 | B1 | 4/2021 |
| EP | 3616651 | B1 | 4/2021 |
| EP | 3619136 | B1 | 4/2021 |
| EP | 3626208 | B1 | 4/2021 |
| EP | 3632379 | B1 | 4/2021 |
| EP | 3646823 | B1 | 4/2021 |
| EP | 3646824 | B1 | 4/2021 |
| EP | 3653173 | B1 | 4/2021 |
| EP | 1951155 | B1 | 5/2021 |
| EP | 2073755 | B1 | 5/2021 |
| EP | 2948100 | B1 | 5/2021 |
| EP | 3099270 | B1 | 5/2021 |
| EP | 3150172 | B1 | 5/2021 |
| EP | 3178445 | B1 | 5/2021 |
| EP | 3310301 | B1 | 5/2021 |
| EP | 3582697 | B1 | 5/2021 |
| EP | 3592295 | B1 | 5/2021 |
| EP | 3639888 | B1 | 5/2021 |
| EP | 3669828 | B1 | 5/2021 |
| EP | 2471492 | B1 | 6/2021 |
| EP | 2486894 | B1 | 6/2021 |
| EP | 2750630 | B1 | 6/2021 |
| EP | 3247312 | B1 | 6/2021 |
| EP | 3294215 | B1 | 6/2021 |
| EP | 3323353 | B1 | 6/2021 |
| EP | 3360513 | B1 | 6/2021 |
| EP | 3488821 | B1 | 6/2021 |
| EP | 3549555 | B1 | 6/2021 |
| EP | 3576677 | B1 | 6/2021 |
| EP | 3632338 | B1 | 6/2021 |
| EP | 3834879 | A1 | 6/2021 |
| EP | 2381895 | B1 | 7/2021 |
| EP | 2611389 | B1 | 7/2021 |
| EP | 2779945 | B1 | 7/2021 |
| EP | 3193740 | B1 | 7/2021 |
| EP | 3206629 | B1 | 7/2021 |
| EP | 3277222 | B1 | 7/2021 |
| EP | 3400907 | B1 | 7/2021 |
| EP | 3435919 | B1 | 7/2021 |
| EP | 3522800 | B1 | 7/2021 |
| EP | 3539508 | B1 | 7/2021 |
| EP | 3539509 | B1 | 7/2021 |
| EP | 3572044 | B1 | 7/2021 |
| EP | 3592289 | B1 | 7/2021 |
| EP | 3668450 | B1 | 7/2021 |
| EP | 3681439 | B1 | 7/2021 |
| EP | 3691567 | B1 | 7/2021 |
| EP | 3789077 | A4 | 7/2021 |
| EP | 3846740 | A1 | 7/2021 |
| EP | 2558032 | B1 | 8/2021 |
| EP | 2992857 | B1 | 8/2021 |
| EP | 2994075 | B1 | 8/2021 |
| EP | 3038539 | B1 | 8/2021 |
| EP | 3287099 | B1 | 8/2021 |
| EP | 3348235 | B1 | 8/2021 |
| EP | 3643273 | B1 | 8/2021 |
| EP | 3646822 | B1 | 8/2021 |
| EP | 3658215 | B1 | 8/2021 |
| EP | 3659553 | B1 | 8/2021 |
| EP | 3723665 | B1 | 8/2021 |
| EP | 3744290 | B1 | 8/2021 |
| EP | 3860530 | A1 | 8/2021 |
| EP | 3863567 | A1 | 8/2021 |
| EP | 2329796 | B1 | 9/2021 |
| EP | 3125827 | B1 | 9/2021 |
| EP | 3137146 | B1 | 9/2021 |
| EP | 3288494 | B1 | 9/2021 |
| EP | 3288497 | B1 | 9/2021 |
| EP | 3454784 | B1 | 9/2021 |
| EP | 3456293 | B1 | 9/2021 |
| EP | 3503848 | B1 | 9/2021 |
| EP | 3512465 | B1 | 9/2021 |
| EP | 3544664 | B1 | 9/2021 |
| EP | 3568089 | B1 | 9/2021 |
| EP | 3592288 | B1 | 9/2021 |
| EP | 3606472 | B1 | 9/2021 |
| EP | 3669829 | B1 | 9/2021 |
| EP | 3672528 | B1 | 9/2021 |
| EP | 3833302 | A4 | 9/2021 |
| EP | 3870110 | A1 | 9/2021 |
| EP | 3881801 | A1 | 9/2021 |
| EP | 2723273 | B1 | 10/2021 |

(56) References Cited

FOREIGN PATENT DOCUMENTS

| | | | |
|---|---|---|---|
| EP | 3267946 | B1 | 10/2021 |
| EP | 3334381 | B1 | 10/2021 |
| EP | 3639792 | B1 | 10/2021 |
| EP | 3886762 | A1 | 10/2021 |
| EP | 3892240 | A1 | 10/2021 |
| EP | 3900679 | A1 | 10/2021 |
| EP | 2331018 | B1 | 11/2021 |
| EP | 2429455 | B1 | 11/2021 |
| EP | 2538878 | B1 | 11/2021 |
| EP | 2699302 | B1 | 11/2021 |
| EP | 2706958 | B1 | 11/2021 |
| EP | 2892467 | B1 | 11/2021 |
| EP | 2999434 | B1 | 11/2021 |
| EP | 3024527 | B1 | 11/2021 |
| EP | 3061422 | B1 | 11/2021 |
| EP | 3107500 | B1 | 11/2021 |
| EP | 3110468 | B1 | 11/2021 |
| EP | 3154474 | B1 | 11/2021 |
| EP | 3213715 | B1 | 11/2021 |
| EP | 3256076 | B1 | 11/2021 |
| EP | 3288499 | B1 | 11/2021 |
| EP | 3360514 | B1 | 11/2021 |
| EP | 3429507 | B1 | 11/2021 |
| EP | 3445443 | B1 | 11/2021 |
| EP | 3454785 | B1 | 11/2021 |
| EP | 3505077 | B1 | 11/2021 |
| EP | 3672529 | B1 | 11/2021 |
| EP | 3760164 | B1 | 11/2021 |
| EP | 3912596 | A1 | 11/2021 |
| EP | 2358307 | B1 | 12/2021 |
| EP | 2765954 | B1 | 12/2021 |
| EP | 2777608 | B1 | 12/2021 |
| EP | 2991584 | B1 | 12/2021 |
| EP | 3283011 | B1 | 12/2021 |
| EP | 3288479 | B1 | 12/2021 |
| EP | 3344167 | B1 | 12/2021 |
| EP | 3410987 | B1 | 12/2021 |
| EP | 3481339 | B1 | 12/2021 |
| EP | 3482718 | B1 | 12/2021 |
| EP | 3490465 | B1 | 12/2021 |
| EP | 3498224 | B1 | 12/2021 |
| EP | 3503846 | B1 | 12/2021 |
| EP | 3592284 | B1 | 12/2021 |
| EP | 3624705 | B1 | 12/2021 |
| EP | 3749254 | B1 | 12/2021 |
| EP | 3914191 | A1 | 12/2021 |
| EP | 3915493 | A1 | 12/2021 |
| EP | 2400922 | B1 | 1/2022 |
| EP | 2545885 | B1 | 1/2022 |
| EP | 2747708 | B1 | 1/2022 |
| EP | 2763708 | B1 | 1/2022 |
| EP | 2994072 | B1 | 1/2022 |
| EP | 3220856 | B1 | 1/2022 |
| EP | 3288498 | B1 | 1/2022 |
| EP | 3534840 | B1 | 1/2022 |
| EP | 3558169 | B1 | 1/2022 |
| EP | 3668452 | B1 | 1/2022 |
| EP | 3682854 | B1 | 1/2022 |
| EP | 3697346 | B1 | 1/2022 |
| EP | 3700467 | B1 | 1/2022 |
| EP | 2611388 | B1 | 4/2022 |
| EP | 2916781 | B1 | 4/2022 |
| EP | 3487451 | B1 | 4/2022 |
| EP | 3628239 | B1 | 4/2022 |
| EP | 3644866 | B1 | 4/2022 |
| EP | 3796873 | B1 | 4/2022 |
| EP | 2268231 | B1 | 5/2022 |
| EP | 2856973 | B1 | 5/2022 |
| EP | 2962664 | B1 | 5/2022 |
| EP | 3311774 | B1 | 5/2022 |
| EP | 3335670 | B1 | 5/2022 |
| EP | 3403616 | B1 | 5/2022 |
| EP | 3445290 | B1 | 5/2022 |
| EP | 3541316 | B1 | 5/2022 |
| EP | 3648709 | B1 | 5/2022 |
| EP | 3695810 | B1 | 5/2022 |
| EP | 3721811 | B1 | 5/2022 |
| EP | 3773271 | B1 | 5/2022 |
| EP | 2538893 | B1 | 6/2022 |
| EP | 2575681 | B1 | 6/2022 |
| EP | 2583640 | B1 | 6/2022 |
| EP | 3071149 | B1 | 6/2022 |
| EP | 3253332 | B1 | 6/2022 |
| EP | 3283009 | B1 | 6/2022 |
| EP | 3296979 | B1 | 6/2022 |
| EP | 3298988 | B1 | 6/2022 |
| EP | 3342377 | B1 | 6/2022 |
| EP | 3365349 | B1 | 6/2022 |
| EP | 3397206 | B1 | 6/2022 |
| EP | 3426194 | B1 | 6/2022 |
| EP | 3595588 | B1 | 6/2022 |
| EP | 3636312 | B1 | 6/2022 |
| EP | 3661436 | B1 | 6/2022 |
| EP | 3790501 | B1 | 6/2022 |
| EP | 3846740 | B1 | 6/2022 |
| EP | 3849472 | B1 | 6/2022 |
| EP | 3897454 | B1 | 6/2022 |
| EP | 2621409 | B1 | 7/2022 |
| EP | 2787926 | B1 | 7/2022 |
| EP | 2838473 | B1 | 7/2022 |
| EP | 2950752 | B1 | 7/2022 |
| EP | 3060171 | B1 | 7/2022 |
| EP | 3206631 | B1 | 7/2022 |
| EP | 3245980 | B1 | 7/2022 |
| EP | 3256073 | B1 | 7/2022 |
| EP | 3311783 | B1 | 7/2022 |
| EP | 3347182 | B1 | 7/2022 |
| EP | 3389557 | B1 | 7/2022 |
| EP | 3463120 | B1 | 7/2022 |
| EP | 3579788 | B1 | 7/2022 |
| EP | 3756623 | B1 | 7/2022 |
| EP | 3796872 | B1 | 7/2022 |
| EP | 3796876 | B1 | 7/2022 |
| EP | 2313152 | B1 | 8/2022 |
| EP | 2688516 | B1 | 8/2022 |
| EP | 2849678 | B1 | 8/2022 |
| EP | 2950751 | B1 | 8/2022 |
| EP | 2964153 | B1 | 8/2022 |
| EP | 3019092 | B1 | 8/2022 |
| EP | 3184082 | B1 | 8/2022 |
| EP | 3231395 | B1 | 8/2022 |
| EP | 3266417 | B1 | 8/2022 |
| EP | 3407834 | B1 | 8/2022 |
| EP | 3458136 | B1 | 8/2022 |
| EP | 3459499 | B1 | 8/2022 |
| EP | 3471662 | B1 | 8/2022 |
| EP | 3484412 | B1 | 8/2022 |
| EP | 3534841 | B1 | 8/2022 |
| EP | 3541328 | B1 | 8/2022 |
| EP | 3672532 | B1 | 8/2022 |
| EP | 3718509 | B1 | 8/2022 |
| EP | 3769721 | B1 | 8/2022 |
| EP | 3789077 | B1 | 8/2022 |
| EP | 3908228 | B1 | 8/2022 |
| EP | 3915493 | B1 | 8/2022 |
| EP | 3967274 | B1 | 8/2022 |
| EP | 2670351 | B1 | 9/2022 |
| EP | 2777617 | B1 | 9/2022 |
| EP | 2810620 | B1 | 9/2022 |
| EP | 2922592 | B1 | 9/2022 |
| EP | 3038567 | B1 | 9/2022 |
| EP | 3096713 | B1 | 9/2022 |
| EP | 3448315 | B1 | 9/2022 |
| EP | 3481335 | B1 | 9/2022 |
| EP | 3520715 | B1 | 9/2022 |
| FR | 2815844 | B1 | 1/2003 |
| FR | 2826863 | B1 | 9/2003 |
| FR | 2828091 | B1 | 11/2003 |
| FR | 2847800 | B1 | 10/2005 |
| FR | 2858543 | B1 | 2/2006 |
| FR | 2828263 | B1 | 5/2007 |
| FR | 2874812 | B1 | 6/2007 |
| FR | 2874813 | B1 | 6/2007 |
| FR | 2883721 | B1 | 6/2007 |

(56) References Cited

FOREIGN PATENT DOCUMENTS

| | | |
|---|---|---|
| FR | 2894131 B1 | 12/2008 |
| FR | 2899096 B1 | 12/2008 |
| FR | 2910269 B1 | 2/2009 |
| FR | 2909857 B1 | 3/2009 |
| FR | 2906454 B1 | 4/2009 |
| FR | 2906998 B1 | 4/2009 |
| FR | 2913879 B1 | 6/2009 |
| FR | 2916959 B1 | 9/2009 |
| FR | 2892939 B1 | 1/2010 |
| FR | 2915678 B1 | 4/2010 |
| FR | 2930137 B1 | 4/2010 |
| FR | 2915903 B1 | 6/2010 |
| FR | 2916627 B1 | 9/2010 |
| FR | 2920664 B1 | 9/2010 |
| FR | 2932376 B1 | 4/2011 |
| FR | 2947716 B1 | 9/2011 |
| FR | 2945440 B1 | 12/2012 |
| FR | 2951549 B1 | 8/2013 |
| FR | 2964855 B1 | 10/2013 |
| FR | 2977792 B1 | 10/2013 |
| FR | 2980968 B1 | 12/2013 |
| FR | 2986149 B1 | 12/2014 |
| FR | 2997288 B1 | 1/2015 |
| FR | 2998167 B1 | 1/2015 |
| FR | 2996747 B1 | 2/2015 |
| FR | 2996748 B1 | 2/2015 |
| FR | 3004638 B1 | 5/2015 |
| FR | 2982763 B1 | 7/2015 |
| FR | 2991162 B1 | 7/2015 |
| FR | 3006582 B1 | 7/2015 |
| FR | 3001121 B1 | 1/2016 |
| FR | 2998166 B1 | 2/2016 |
| FR | 3021862 B1 | 5/2016 |
| FR | 3004917 B1 | 6/2016 |
| FR | 3006884 B1 | 6/2016 |
| FR | 3023704 B1 | 8/2016 |
| FR | 3008885 B1 | 12/2016 |
| FR | 3033494 B1 | 3/2017 |
| FR | 3057154 B1 | 10/2018 |
| FR | 3058631 B1 | 1/2019 |
| FR | 3058632 B1 | 1/2019 |
| FR | 3060292 B1 | 1/2019 |
| FR | 3063631 B1 | 3/2019 |
| FR | 3020265 B1 | 9/2019 |
| FR | 3072013 B1 | 9/2019 |
| GB | 243370 A | 8/1926 |
| GB | 1264471 A | 2/1972 |
| GB | 1315844 A | 5/1973 |
| GB | 2245495 A | 1/1992 |
| GB | 2398245 A | 8/2004 |
| GB | 2407146 B | 4/2006 |
| GB | 2398245 B | 3/2007 |
| GB | 2433700 B | 12/2007 |
| GB | 2478498 B | 7/2012 |
| GB | 2530487 B | 12/2016 |
| GB | 2517609 B | 5/2017 |
| GB | 2538749 B | 8/2017 |
| GB | 2538072 B | 11/2017 |
| GB | 2536538 B | 7/2018 |
| GB | 2548891 B | 7/2018 |
| JP | 2002540889 A | 12/2002 |
| JP | 2003530143 A | 10/2003 |
| JP | 2008541865 A | 11/2008 |
| JP | 6042432 B2 | 11/2016 |
| JP | 6329535 B2 | 4/2018 |
| WO | WO-9749355 A1 | 12/1997 |
| WO | WO-9819633 A1 | 5/1998 |
| WO | WO-0053104 A1 | 9/2000 |
| WO | WO-0061034 A1 | 10/2000 |
| WO | WO-0135861 A1 | 5/2001 |
| WO | WO-0135870 A1 | 5/2001 |
| WO | WO-0172239 A2 | 10/2001 |
| WO | WO-0211646 A1 | 2/2002 |
| WO | WO-0236048 A1 | 5/2002 |
| WO | WO-03028522 A2 | 4/2003 |
| WO | WO-03092554 A1 | 11/2003 |
| WO | WO-2004014257 A1 | 2/2004 |
| WO | WO-2004014474 A1 | 2/2004 |
| WO | WO-2004058097 A2 | 7/2004 |
| WO | WO-2005011534 A1 | 2/2005 |
| WO | WO-2005041810 A2 | 5/2005 |
| WO | WO-2005087140 A1 | 9/2005 |
| WO | WO-2006070372 A2 | 7/2006 |
| WO | WO-2006085304 A2 | 8/2006 |
| WO | WO-2006089236 A1 | 8/2006 |
| WO | WO-2006097931 A2 | 9/2006 |
| WO | WO-2006127765 A1 | 11/2006 |
| WO | WO-2007025028 A1 | 3/2007 |
| WO | WO-2007034488 A2 | 3/2007 |
| WO | WO-2007058857 A2 | 5/2007 |
| WO | WO-2007122459 A2 | 11/2007 |
| WO | WO-2007123658 A1 | 11/2007 |
| WO | WO-2007134290 A2 | 11/2007 |
| WO | WO-2008005535 A2 | 1/2008 |
| WO | WO-2008013915 A2 | 1/2008 |
| WO | WO-2008070797 A2 | 6/2008 |
| WO | WO-2008091515 A2 | 7/2008 |
| WO | WO-2008103722 A2 | 8/2008 |
| WO | WO-2008150529 A1 | 12/2008 |
| WO | WO-2009026563 A2 | 2/2009 |
| WO | WO-2009033469 A1 | 3/2009 |
| WO | WO-2009045331 A1 | 4/2009 |
| WO | WO-2009052188 A1 | 4/2009 |
| WO | WO-2009053497 A1 | 4/2009 |
| WO | WO-2009091509 A1 | 7/2009 |
| WO | WO-2009094500 A1 | 7/2009 |
| WO | WO-2009134701 A2 | 11/2009 |
| WO | WO-2009137359 A1 | 11/2009 |
| WO | WO-2009149462 A2 | 12/2009 |
| WO | WO-2009155561 A2 | 12/2009 |
| WO | WO-2010004546 A1 | 1/2010 |
| WO | WO-2010008549 A1 | 1/2010 |
| WO | WO-2010040009 A1 | 4/2010 |
| WO | WO-2010037141 A1 | 4/2010 |
| WO | WO-2010057262 A1 | 5/2010 |
| WO | WO-2010096176 A1 | 8/2010 |
| WO | WO-2010098857 A1 | 9/2010 |
| WO | WO-2010121076 A2 | 10/2010 |
| WO | WO-2010130789 A1 | 11/2010 |
| WO | WO-2010138853 A2 | 12/2010 |
| WO | WO-2011025945 A1 | 3/2011 |
| WO | WO-2011109813 A2 | 9/2011 |
| WO | WO-2011137531 A9 | 11/2011 |
| WO | WO-2011137531 A1 | 11/2011 |
| WO | WO-2012035279 A1 | 3/2012 |
| WO | WO-2012106491 A1 | 8/2012 |
| WO | WO-2012162228 A1 | 11/2012 |
| WO | WO-2012177942 A2 | 12/2012 |
| WO | WO-2013016513 A1 | 1/2013 |
| WO | WO-2017040684 A1 | 3/2017 |

OTHER PUBLICATIONS

US 8,221,315 B2, 07/2012, Lambrecht et al. (withdrawn)
"European Application Serial No. 13796278.3, Response filed Sep. 14, 22 to Communication Pursuant to Article 94(3) EPC dated May 4, 22", Claims not amended in response filed, 3 pgs.
"50 Early- to Late-Stage Medical Device Companies Seeking Investment and Partnering Opportunities to Present in 3 Weeks at Investment in Innovation (In3) Medical Device Summit", [Online] Retrieved from the internet: <Businesswire.com>, (May 27, 2008), 3 pgs.
"U.S. Appl. No. 13/904,827, Examiner Interview Summary dated Feb. 11, 2016", 3 pgs.
"U.S. Appl. No. 13/904,827, Non Final Office Action dated Sep. 1, 2015", 24 pgs.
"U.S. Appl. No. 13/904,827, Notice of allowance dated Mar. 15, 2016", 8 pgs.
"U.S. Appl. No. 13/904,827, Response filed Jul. 10, 2015 to Restriction Requirement dated Jun. 18, 2015", 1 pgs.
"U.S. Appl. No. 13/904,827, Response filed Dec. 1, 2015 to Non Final Office Action dated Sep. 1, 2015", 7 pgs.

(56) References Cited

OTHER PUBLICATIONS

"U.S. Appl. No. 13/904,827, Restriction Requirement dated Jun. 18, 2015", 6 pgs.
"U.S. Appl. No. 15/134,164, Final Office Action dated Jul. 21, 2017", 15 pgs.
"U.S. Appl. No. 15/134,164, Non Final Office Action dated Jan. 11, 2017", 16 pgs.
"U.S. Appl. No. 15/134,164, Notice of Allowance dated Nov. 7, 2017", 8 pgs.
"U.S. Appl. No. 15/134,164, Response filed Apr. 11, 2017 to Non Final Office Action dated Jan. 11, 2017", 9 pgs.
"U.S. Appl. No. 15/134,164, Response filed Oct. 20, 2017 to Final Office Action dated Jul. 21, 2017", 8 pgs.
"U.S. Appl. No. 15/890,119, Non Final Office Action dated Jun. 4, 2018", 8 pgs.
"U.S. Appl. No. 15/890,119, Notice of Allowability dated May 2, 2019", 2 pgs.
"U.S. Appl. No. 15/890,119, Notice of Allowance dated Dec. 10, 2018", 8 pgs.
"U.S. Appl. No. 15/890,119, Preliminary Amendment filed Apr. 25, 2018", 4 pgs.
"U.S. Appl. No. 15/890,119, Response to Non Final Office Action dated Jun. 4, 2018 filed Sep. 17, 2018", 7 pgs.
"U.S. Appl. No. 16/295,913 Supplemental Preliminary Amendment filed Jul. 17, 2019", 5 pgs.
"U.S. Appl. No. 16/295,913, Notice of Allowance dated Nov. 6, 2020", 10 pgs.
"U.S. Appl. No. 17/168,818, Notice of Allowance dated Mar. 15, 2022", 13 pgs.
"U.S. Appl. No. 17/168,818, Notice of Non-Compliant Amendment dated Nov. 26, 2021", 2 pgs.
"U.S. Appl. No. 17/168,818, Response filed Jan. 12, 2022 to Notice of Non-Compliant Amendment dated Nov. 26, 2021", 5 pgs.
"U.S. Appl. No. 17/168,818, Response filed Nov. 12, 2021 to Restriction Requirement dated Sep. 20, 2021", 6 pgs.
"U.S. Appl. No. 17/168,818, Restriction Requirement dated Sep. 20, 2021", 7 pgs.
"Australian Application Serial No. 20135270351, First Examination Report dated Jul. 28, 2017", 3 pgs.
"Canadian Application Serial No. 2,874,219, Office Action dated Feb. 26, 2019", 4 pgs.
"Canadian Application Serial No. 2,874,219, Response Filed Aug. 13, 2019 to Office Action dated Feb. 26, 2019", 83 pgs.
"Canadian Application Serial No. 3,080,648, Office Action dated Jun. 14, 2021", 3 pgs.
"Canadian Application Serial No. 3,080,648, Response filed Oct. 14, 2021 to Office Action dated Jun. 14, 2021", 14 pgs.
"Canadian Application Serial No. 3,080,648, Voluntary Amendment Filed May 19, 2022", 16 pgs.
"CardiAQ Valve Technologies", Medical Devices Today, [Online], Retrieved from the Internet: <http:/www.medicaldevicestoday.com/2009/07/medical-device-start-up-cardiaq-valve-technologies-percutaneous-mitral-valve-replacement.html>Accessed: Mar. 8, 2012, (Jul. 17, 2009), 2 pgs.
"CardiAQ Valve Technologies ("CVT") to disclose data during 'EuroPCR 2010' about the world's first successful in vivo transcatheter delivery of a mitral heart valve implant", Irvine, California, Businesswire. com, (May 20, 2010), 2 pgs.
"CardiAQ Valve Technologies to pursue first-in-man studies of its transcatheter mitral valve system", Cardiac Interventions Today, (Jan. 12, 2010), 2 pgs.
"CardiAQ Valve Technologies: Percutaneous Mitral Valve Replacement", Start Up Windhover Review of Emerging Medical Ventures, vol. 14. No.6, (Jun. 2009), 48-49.
"CardiAQ's Complaint and Jury Demand; U.S. District Court—District of Massachusetts", *CardiAQ Valve, Technologies Inc. v. Neovasc Inc. and Neovasc Tiara*, (Jun. 6, 2014), 22 pgs.
"CardiAQ's First Amended Complaint and Jury Demand", U.S. District Court—District of Massachusetts *CardiAQ Valve, Technologies Inc. v. Neovasc Inc. and Neovasc Tiara Inc*, (Aug. 12, 2014), 21 pgs.
"CardiAQ's Objection in Patent Vindication Action in regard to EP 2566416", Administrative Court of Munich; *CardiAQ Valve Technologies, Inc., v. Neovasc Tiara Inc*, (Jun. 25, 2014), 22 pgs.
"CardiAQ's Second Amended Complaint and Jury Demand", U.S. District Court—District of Massachusetts; *CardiAQ Valve, Technologies Inc. v. Neovasc Inc. and Neovasc Tiara Inc*, (Jan. 15, 2015), 25 pgs.
"Chinese Application Serial No. 201610647657.6, Decision of Reexamination dated Mar. 31, 2021", with machine translation, 22 pgs.
"Chinese Application Serial No. 201610647657.6, Decision of Rejection dated Sep. 3, 2019", with English translation of claims, 6 pgs.
"Chinese Application Serial No. 201610647657.6, Office Action dated Feb. 27, 2019", with English translation of claims, 12 pgs.
"Chinese Application Serial No. 201610647657.6, Office Action dated Jun. 13, 2018", with English translation, 9 pgs.
"Chinese Application Serial No. 201610647657.6, Office Action dated Sep. 12, 2017", w/English Translation, 10 pgs.
"Chinese Application Serial No. 201610647657.6, Response filed May 14, 2019 to Office Action dated Feb. 27, 2019", w/ English claims, 14 pgs.
"Chinese Application Serial No. 201610647657.6, Response filed Oct. 26, 2018 to Office Action dated Sep. 17, 2018", with English translation of claims, 14 pgs.
"Chinese Application Serial No. 201610647657.6, Response filed Dec. 18, 2019 to Decision of Rejection dated Sep. 3, 2019", with machine translation, 15 pgs.
"Chinese Application Serial No. 202110686668.6, Voluntary Amendment filed Jan. 13, 2022", w/ English Claims, 20 pgs.
"Company Fact Sheet—CardiAQ Valve Technologies", (2009), 1 pg.
"Company Overview—CardiAQ Valve Technologies", (Jun. 25, 2009), 17 pgs.
"CoreValve USA", An advanced TAVR design, Medtronic.com, Accessed Jan. 27, 2015, (Jan. 27, 2015), 2 pgs.
"Court's Memorandum & Order; U.S. District Court—District of Massachusetts", *CardiAQ Valve, Technologies Inc. v. Neovasc Inc. and Neovasc Tiara Inc*, (Nov. 6, 2014), 14 pgs.
"CVT's Transcatheter Mitral Valve Implanation (TMVI) platform might be the 'next big thing' in the cardiac cath lab", CardiAQ Valve Technologies (CVT) Elects Michael Mack, MD, to its Scientific Advisory Board, (Jun. 2, 2009), 4 pgs.
"Defendants Neovasc Inc.'s and Neovasc Tiara Inc.'s Answer to Plaintiffs First Amended Complaint", *CardiAQ Valve, Technologies Inc. v. Neovasc Inc. and Neovasc Tiara Inc*, (Nov. 20, 2014), 20 pgs.
"Defendants Neovasc Inc.'s and Neovasc Tiara Inc.'s Answer to Plaintiffs Second Amended Complaint", *CardiAQ Valve, Technologies Inc. v. Neovasc Inc. and Neovasc Tiara Inc*., (Jan. 29, 2015), 22 pgs.
"Edwards Lifesciences 2005 annual report", (Accessed Jan. 27, 2015), 24 pgs.
"Edwards Lifesciences 2005 Annual Report", (Jan. 27, 2015), 24 pgs.
"Engager system. Precise Valve positioning", TAVR, (Jan. 28, 2015), 2 pgs.
"European Application Serial No. 06827638.5, Extended European Search Report dated Feb. 28, 2013", 6 pgs.
"European Application Serial No. 11798780.0, Extended European Search Report dated Jan. 30, 2014", 7 pgs.
"European Application Serial No. 13796278.3, Communication Pursuant to Article 94(3) EPC dated May 4, 2022", 4 pgs.
"European Application Serial No. 13796278.3, Extended European Search Report dated Sep. 14, 2015", 6 pgs.
"European Application Serial No. 13796278.3, Invitation pursuant to Article 94(3) and Rule 71(1) EPC dated May 6, 2021", 4 pgs.
"European Application Serial No. 13796278.3, Response filed Mar. 24, 15 to Communication pursuant to Rules 161(1) and 162 EPC dated Jan. 23, 2015", 1 pg.

(56) References Cited

OTHER PUBLICATIONS

"European Application Serial No. 13796278.3, Response filed Apr. 8, 2016 to Extended European Search Report dated Sep. 14, 2015", 26 pgs.
"European Application Serial No. 13796278.3, Response filed Sep. 7, 2021 to Communication pursuant to Article 94(3) dated May 6, 2021", 9 pgs.
"Exhibits accompanying CardiAQ's Objection in Patent Vindication Action in regard to EP 2566416", (Jun. 25, 2014), 306 pgs.
"Exhibits accompanying Neovasc's Statement of Defense in Patent Vindication Action in regard to EP 2566416", (Dec. 9, 2014), 67 pgs.
"International Application Serial No. PCT/CA2013/000530, International Preliminary Report on Patentability dated Dec. 11, 2014", 7 pgs.
"International Application Serial No. PCT/CA2013/000530, International Search Report dated Sep. 4, 2013", 3 pgs.
"International Application Serial No. PCT/CA2013/000530, Written Opinion dated Sep. 4, 2013", 5 pgs.
"International Application Serial No. PCT/US2006/043526, International Search Report dated Jun. 25, 2008", 1 pg.
"International Application Serial No. PCT/US2006/043526, Written Opinion dated Jun. 25, 2008", 3 pgs.
"International Application Serial No. PCT/US2007/016855, International Search Report dated Mar. 26, 2008", 1 pg.
"International Application Serial No. PCT/US2007/016855, Written Opinion dated Mar. 26, 2008", 3 pgs.
"International Application Serial No. PCT/US2009/058893, International Search Report dated Dec. 11, 2009", 5 pgs.
"International Application Serial No. PCT/US2009/058893, Written Opinion dated Dec. 11, 2009", 5 pgs.
"International Application Serial No. PCT/US2009/059299, International Search Report dated Dec. 18, 2009", 5 pgs.
"International Application Serial No. PCT/US2009/059299, Written Opinion dated Dec. 18, 2009", 8 pgs.
"International Application Serial No. PCT/US2010/031313, International Search Report dated Dec. 22, 2010", 4 pgs.
"International Application Serial No. PCT/US2010/031313, Written Opinion dated Dec. 22, 2010", 3 pgs.
"International Application Serial No. PCT/US2011/041306, International Search Report dated Feb. 29, 2012", 8 pgs.
"International Application Serial No. PCT/US2011/041306, Written Opinion dated Feb. 29, 2012", 5 pgs.
"Japanese Application Serial No. 2015-514301, Office Action dated Apr. 3, 2017", with English translation of claims, 4 pgs.
"Japanese Application Serial No. 2015-514301, Response filed Oct. 2, 2017", with English translation, 7 pgs.
"Japanese Application Serial No. 2015-514301, Voluntary Amendment filed May 27, 2016", with English translation of claims, 14 pgs.
"Neovasc corporate presentation", [Online], Retrieved from the Internet: <http://www.neovasc.com/investors/documents/Neovasc-Corporate-Presentation-October-2009.pdf>, (Oct. 2009), 21 pgs.
"Neovasc Ostial Products Overview", [Online], Retrieved from the Internet: <https://web.archive.org/web/20090930050359/https://www.neovasc.com/vascular-products/ostialproducts/default.php>, (Sep. 30, 2008), 1 pg.
"Neovasc Surgical Products: An Operating Division of Neovasc Inc", (Apr. 2009), 17 pgs.
"Neovasc's Statement of Defense in Patent Vindication Action in regard to EP 2566416; Administrative Court of Munich", *CardiAQ Valve Technologies, Inc., v. Neovasc Tiara Inc*, (Dec. 9, 2014), 39 pgs.
"The Jena Valve—the prosthesis", Jena Valve Technology, (Jan. 28, 2015), 1 pg.
"Update—CardiAQ Valve Technologies", (Jun. 6, 2010), 12 pgs.
Al-Attar, "Next generation surgical aortic biological prostheses: sutureless valves", European Society of Cardiology, (Dec. 21, 2011), 3 pgs.

Banai, et al., "Tiara: a novel catheter-based mitral valve bioprosthesis: initial experiments and short-term pre-clinical results", J Am Coll Cardiol, 60(15), (2012), 1430-1.
Bavaria, "CardiAQ Valve Technologies (CVT) discloses successful results of acute in vivo study of its novel transcatheter mitral valve implantation (TMVI) system", [Online], Retrieved from the Internet: <http://eon.businesswire.com/news/eon/20090928005120/en/CardiAQ-Valve-Technologies/Heart/heart-failure>, (Sep. 28, 2009), 2 pgs.
Bavaria, "CardiAQ Valve Technologies. TCT Company Overview", Transcatheter Cardiovascular Therapeutics Conference. San Francisco, CA, (Sep. 21-25, 2009), 11 pgs.
Berreklouw, et al., "Sutureless mitral valve replacement with bioprostheses and Nitinol attachment rings: feasibility in acute pig experiments", J Thorac Cardiovasc Surg, (Feb. 4, 2011), 390-5.
Boudjemline, et al., "Steps toward the percutaneous replacement of atrioventricular valves an experimental study", J Am Coll Cardiol, (2005), 360-5.
Brinkman, "Transcatheter cardiac valve interventions", Surg Clin North Am, (2009), 951-66.
Carpentier-Edwards, "Why compromise in the mitral position?", Edwards Lifesciences, (2004), 4 pgs.
Chiam, et al., "Percutaneous transcatheter aortic valve implantation: assessing results judging outcomes, and planning trials: the interventionalist perspective", JACC Cardiovasc Interv, (2008), 341-50.
Condado, et al., "Percutaneous treatment of heart valves", Rev Esp Cardiol, (2006), 1225-31.
De Backer, et al., "Percutaneous transcatheter mitral valve replacement: an overview of devices in preclinical and early clinical evaluation", Circ Cardiovasc Interv, (Jun. 2014), 400-9 pgs.
Fanning, et al., "Transcatheter aortic valve implantation (TAVI): valve design and evolution", Int J Cardiol, (Oct. 3, 2013), 1822-31.
Feldman, et al., "Prospects for percutaneous valve therapies", Circulation, (2007), 2866-77.
Fitzgerald, "Tomorrow's technology: percutaneous mitral valve replacement, chordal shortening and beyond", Transcatheter Valve Therapies (TVT) Conference. Seattle, WA, (Jun. 7, 2010), 8 pgs.
Gillespie, et al., "Sutureless mitral valve replacement: initial steps toward a percutaneous procedure", Ann Thorac Surg 96(2), (2013), 4 pgs.
Grube, et al., "Percutaneous aortic valve replacement for severe aortic stenosis in high-risk patients using the second- and current third-generation self-expanding Core Valve prosthesis: device success and 30-day clinical outcome", J Am Coll Cardiol, (Jun. 6, 2007), 69-76 pgs.
Grube, et al., "Percutaneous implantation of the Core Valve self-expanding valve prosthesis in high-risk patients with aortic valve disease: the Siegburg first-in-man study", Circulation, (Oct. 2, 2006), 1616-24.
Harmon, et al., "Effect of acute myocardial infarction on the angle between the mitral and aortic valve plane", Am J Cardiol, 84(3), (Aug. 1999), 342-4.
Herrman, "Trancatheter mitral valve implantation", Cardiac Interventions Today, (Aug./Sep. 2009), 82-85.
Horvath, et al., "Transapical aortic valve replacement under real-time magnetic resonance imaging guidance: experimental results with balloon-expandable and self-expanding stents", Eur J Cardiothorac Surg, (Jun. 2011), 822-8 pgs.
Ionasec, "Personalized modeling and assessment of the aortic-mitral coupling from 4D TEE and CT", Med Image Comput Comput Assist Interv, (2009), 767-75 pgs.
Karimi, et al., "Percutaneous Valve Therapies", Chapter 11, (2007), 11 pgs.
Kronemyer, "CardiAQ Valve Technologies: Percutaneous Mitral Valve Replacement", Windhover Review of Emerging Medical Ventures, vol. 14, No. 6, (Jun. 2009), 48-49 pgs.
Kumar, et al., "Design considerations and quantitative assessment for the development of percutaneous mitral valve stent", Med Eng Phys, (Apr. 16, 2014), 882-8.
Lansac, et al., "Dynamic balance of the aortomitral junction", J Thorac Cardiovasc Surg, 123(5), (2002), 911-8 pgs.

(56) References Cited

OTHER PUBLICATIONS

Lauten, et al., "Experimental evaluation of the JenaClip transcatheter aortic valve", Catheter Cardiovasc Interv, 74(3), (Sep. 1, 2009), 514-19.
Leon, et al., "Transcatheter aortic valve replacement in patients with critical aortic stenosis: rationale, device descriptions, early clinical experiences, and perspectives", Semin Thorac Cardiovasc Surg, 18(2), (2006), 165-74.
Lozonschi, et al., "Transapical mitral valved stent implantation", Ann Thorac Surg, 86(3), (2008), 745-8.
Lutter, et al., "Off-pump transapical mitral valve replacement", Eur J Cardiothorac Surg, (2009), 124-8.
Lutter, et al., "Transapical mitral valve implantation: the Lutter valve", Heart Lung Vessel, (2013), 6 pgs.
Lutter, G, et al., "Transcatheter Mitral Valve Replacement—Early Animal Results", Universitatsklinikum, Schleswig-Holstein, (Aug. 28, 2012), 51 pgs.
Ma, et al., "Double-crowned valved stents for off-pump mitral valve replacement", Eur J Cardiothorac Surg, (Aug. 2005), 194-8.
Mack, "Advantages and limitations of surgical mitral valve replacement; lessons for the transcatheter approach", Texas Cardiovascular Innovative Ventures (TCIV) Conference. Dallas, TX, (Jun. 7, 2010), 32 pgs.
Mack, Michael, et al., "Antegrade Transcatheter Mitral valve Implantation: A Short-term Experience in Swine Model", Applicant believes this may have been presented, (May 2011), 10 pgs.
Maisano, "Mitral transcatheter technologies", Rambam Maimonides Med J, 4(3), (Jul. 25, 2013), 12 pgs.
Masson, et al., "Percutaneous treatment of mitral regurgitation", Circ Cardiovasc Interv, (2009), 140-6 pgs.
Navia, et al., "Sutureless implantation a expandable mitral stent-valve prosthesis in acute animal model", TCT728. JACC vol. 58, No. 20, (Nov. 8, 2011), 1 pg.
Nkomo, et al., "Burden of valvular heart diseases: a population-based study", Lancet, 368(9540), (Sep. 16, 2006), 1005-11 pgs.
Ormiston, et al., "Size and motion of the mitral valve annulus in man", A two-dimensional echocardiographic method and findings in normal subjects. Circulation, (1981), 113-20 pgs.
Orton, "Mitralseal: hybrid trancatheter mitral valve replacement", Colorado State University, [Online] Retrieved from the internet: <https://www.acvs.org/files/proceedings/2011/data/papers/102.pdf.>, (2011), 311-312.
Ostrovsky, "Transcatheter mitral valve implantation technology from CardiAQ", [Online], Retrieved from the Internet: <http://medgadget.com/2010/01/transcatheter_mitral_valveimplantation_technologyfrom_cardiaq.html>, Accessed Jun. 27, 2012 from, (Jan. 15, 2010), 2 pgs.
Ostrovsky, Gene, "A Trial of Zenith Fenestrated AAA Endovascular Graft Goes On", [Online] Retrieved from the internet <http://www.medgadget.com/2008/08/a_trial_of_zenith_fenestrated_aaa_endovascular_graft_goes_on.html.>, (Aug. 1, 2008), 9 pgs.
Otto, "Evaluation and management of chronic mitral regurgitation", Clinical practice N Engl J Med, (2001), 740-6 pgs.
Piazza, et al., "Anatomy of the aortic valvar complex and its implications for transcatheter implantation of the aortic valve", Circ Cardiovasc Interv, (Aug. 2008), 74-81.
Pluth, et al., "Aortic and mitral valve replacement with cloth-covered Braunwald-Cutter prosthesis", A three-year follow-up. Ann Thorac Surg, (Sep. 1975), 239-48.
Preston-Maher, et al., "A Technical Review of Minimally Invasive Mitral Valve Replacements", Cardiovasc Eng Technol, (Nov. 2, 20145), 11 pgs.
Quadri, et al., "CVT is developing a non-surgical apporach to replacing mitral valves that may be the alternative to open-chest surgery", CardiAQ Valve Technologies, (May 8, 2009), 1 pg.
Quadri, Arshad, "Transcatheter Mitral Valve Implantation (TMVI) (An Acute In Vivo Study", Applicant believes this may have been presented, (Sep. 22, 2010), 19 pgs.
Ratz, et al., "Any experiences making an expandable stent frame?", Forums: Modeling, Multiple forum postings, [Online] Retrieved from the internet: <http://www.arch-pub.com/Any-experiences-making-an-expandable-stent-frame_10601513.html.>, (Feb. 3, 2009), 5 pgs.
Ratz, "CardiAQ Valve Technologies. Innovations in heartvalve therapy", IN3 San Francisco PowerPoint presentation in 19 slides, (Jun. 18, 2008), 19 pgs.
Ratz, Brent J, et al., "Fabric, Skin, Cloth expansion . . . best approach?", [Online], Retrieved from the Internet: <http://forums.autodesk.com/t5/modeling/fabric-skin-cloth-expansion-best-approach/td-p/4062607>, (Feb. 18, 2009), 3 pgs.
Ratz, Brent J, et al., "Isolating Interpolation", Architecture Forums: Animation and Rigging, Forum, (Feb. 9, 2009), 2 pgs.
Ratz, Brent J, et al., "In3 Company Overview", (Jun. 24, 2009), 15 pgs.
Ratz, Brent J, "LSI EMT Spotlight", (May 15, 2009), 21 pgs.
Ribiero, "Balloon-expandable prostheses for transcatheter aortic valve replacement", Prog Cardiovasc Dis, (Mar. 1, 2014), 583-95.
Ross, "Renal Ostial Stent System with Progressi-flex Technology, Evasc Medical Systems", Applicant requests the Examiner to consider this reference to be prior art, (Jun. 2009), 1 pg.
Ruiz, "Overview of novel transcatheter valve technologies", Glimpse into the future. New transcatheter mitral valve treatment. Euro PCR. Paris, France, (May 27, 2010), 14 pgs.
Seidel, et al., "A mitral valve prosthesis and a study of thrombosis on heart valves in dogs", J Surg Res, (May 1962), 168-75.
Shuto, et al., "Percutaneous transvenous Melody valve-in-ring procedure for mitral valve replacement", J Am Coll Cardiol, (Dec. 2011), 2475-80.
Sondergaard, et al., "First-in-human CardiAQ transcatheter mitral valve implantation via transapical approach", TCT-811. JACC vol. 64, No. 11 Suppl B, (Sep. 13, 2014), 1 pg.
Spencer, et al., "Surgical treatment of valvular heart disease", Part V. Prosthetic replacement of the mitral valve. American Heart Journal, (Oct. 1968), 576-580.
Spillner, et al., "New sutureless 'atrial mitral-valve prosthesis' for minimally invasive mitral valve therapy", Textile Research Journal, (2010), 7 pgs.
Timek, et al., "Aorto-mitral annular dynamics", Ann Thorac Surg, (Dec. 2003), 1944-50.
Tsang, et al., "Changes in aortic-mitral coupling with severe aortic stenosis", JACC vol. 55. Issue 1A, (Mar. 9, 2010), 1 pg.
Van Mieghem, "Anatomy of the mitral valvular complex and its implications for transcatheter interventions for mitral regurgitation", J Am Coll Cardiol, (2010), 617-26 pgs.
Veronesi, "A study of functional anatomy of aortic-mitral valve coupling using 3D matrix transesophageal echocardiography", Circ Cardiovasc Imaging, (Dec. 2, 2008), 24-31 pgs.
Vu, et al., "Novel sutureless mitral valve implantation method involving a bayonet insertion and release mechanism: A proof of concept study in pigs", J Thorac Cardiovasc Surg, (2012), 985-8.
Walther, Thomas, et al., "Transapical approach for sutureless stent-fixed aortic valve implantation: experimental results", European Journal of Cardio-thoracic Surgery, 29, (2006), 703-708.
Webb, J. G, et al., "Transcatheter aortic valve implantation: The evolution of prostheses, delivery systems and approaches", Archives of Cardiovascular Disease, 105(3), (2012), 153-159.
Yamada, et al., "The left ventricular ostium: an anatomic concept relevant to idiopathic ventricular arrhythmias", Circ Arrhythm Electrophysiol, (2009), 396-404 pgs.
U.S. Appl. No. 13/904,827 U.S. Pat. No. 9,345,573, filed May 29, 2013, Methods and Apparatus for Loading a Prosthesis Onto a Delivery System.
U.S. Appl. No. 15/134,164 U.S. Pat. No. 10,016,275, filed Apr. 20, 2016, Methods and Apparatus for Loading a Prosthesis Onto a Delivery System.
U.S. Appl. No. 15/890,119 U.S. Pat. No. 10,314,705, filed Feb. 6, 2018, Methods and Apparatus for Loading a Prosthesis Onto a Delivery System.
U.S. Appl. No. 16/295,913 U.S. Pat. No. 10,940,001, filed Mar. 7, 2019, Methods and Apparatus for Loading a Prosthesis Onto a Delivery System.

(56) References Cited

OTHER PUBLICATIONS

U.S. Appl. No. 17/168,818 U.S. Pat. No. 11,389,294, filed Feb. 5, 2021, Methods and Apparatus for Loading a Prosthesis Onto a Delivery System.

* cited by examiner

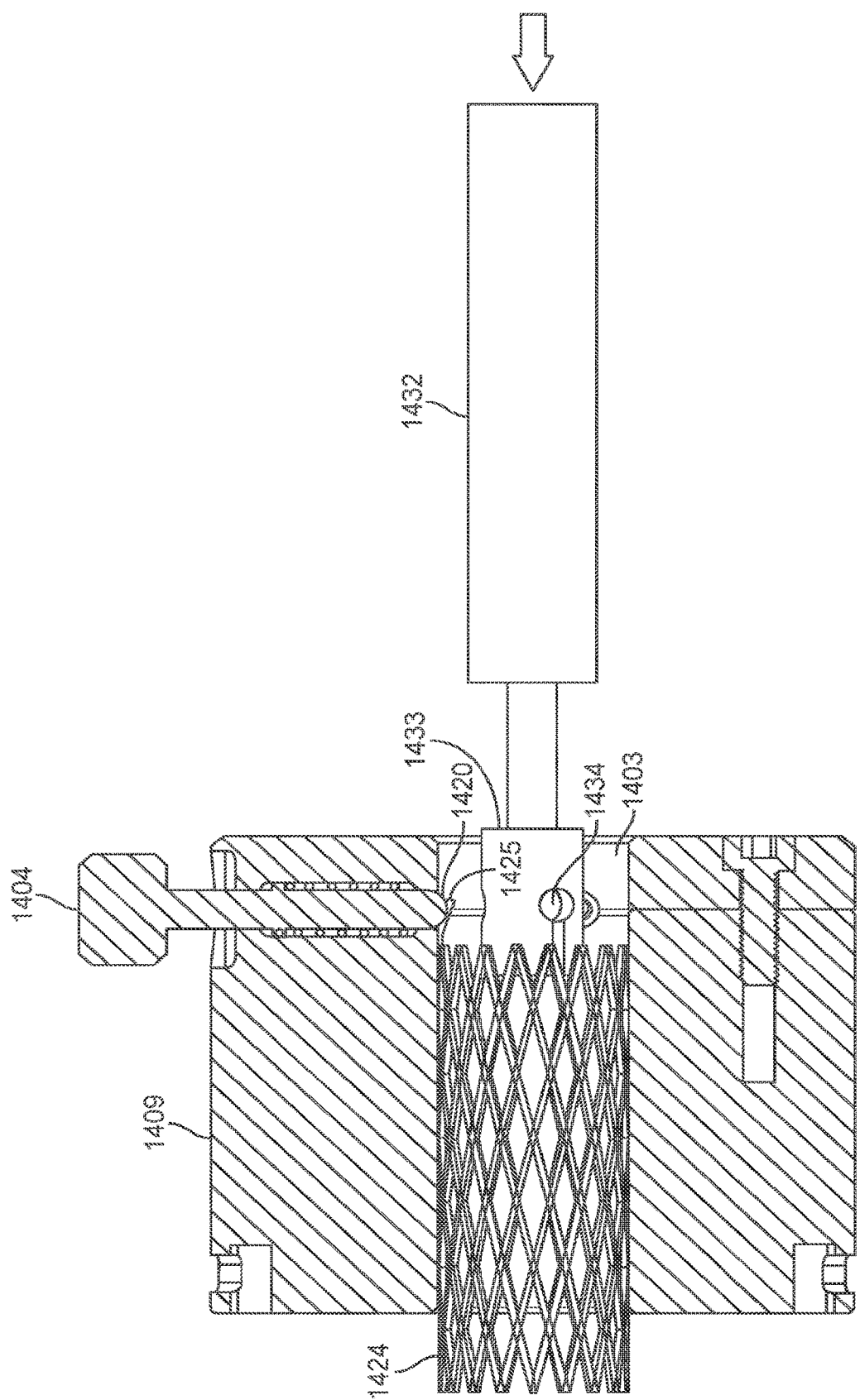

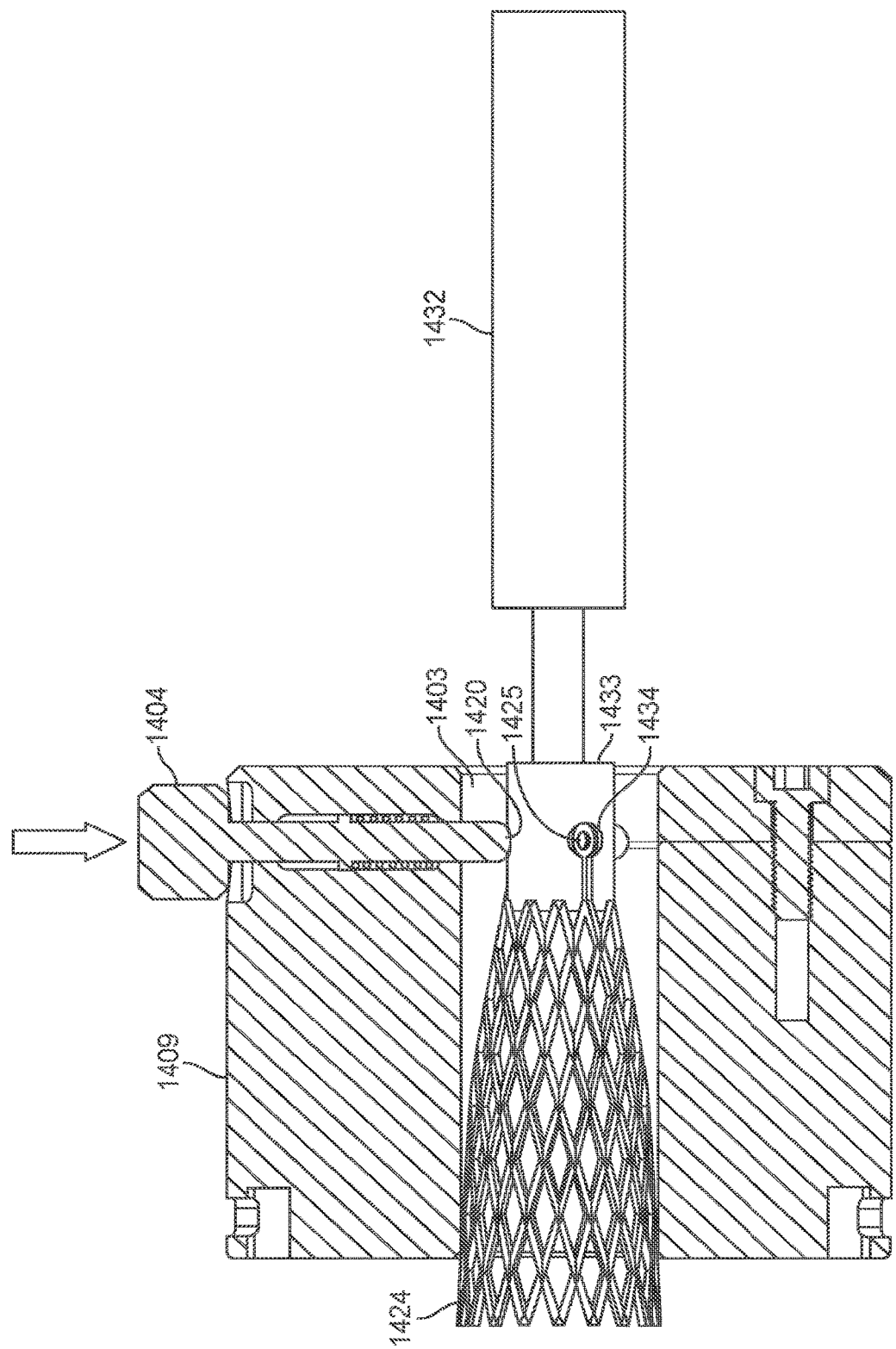

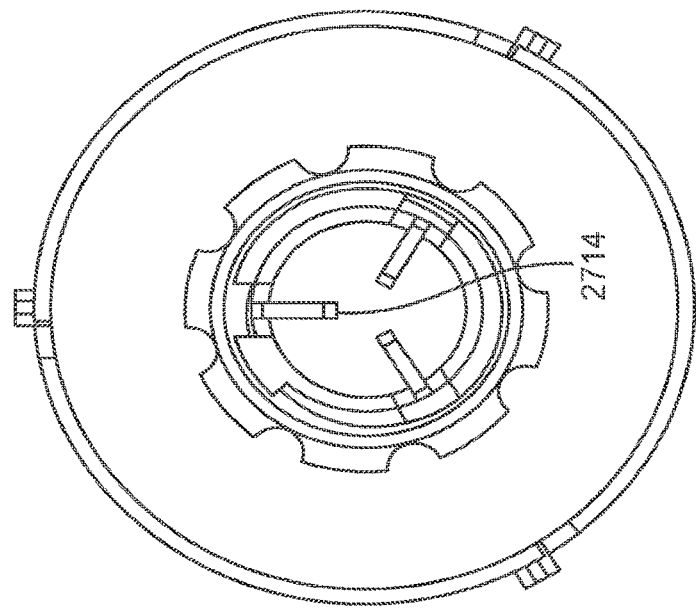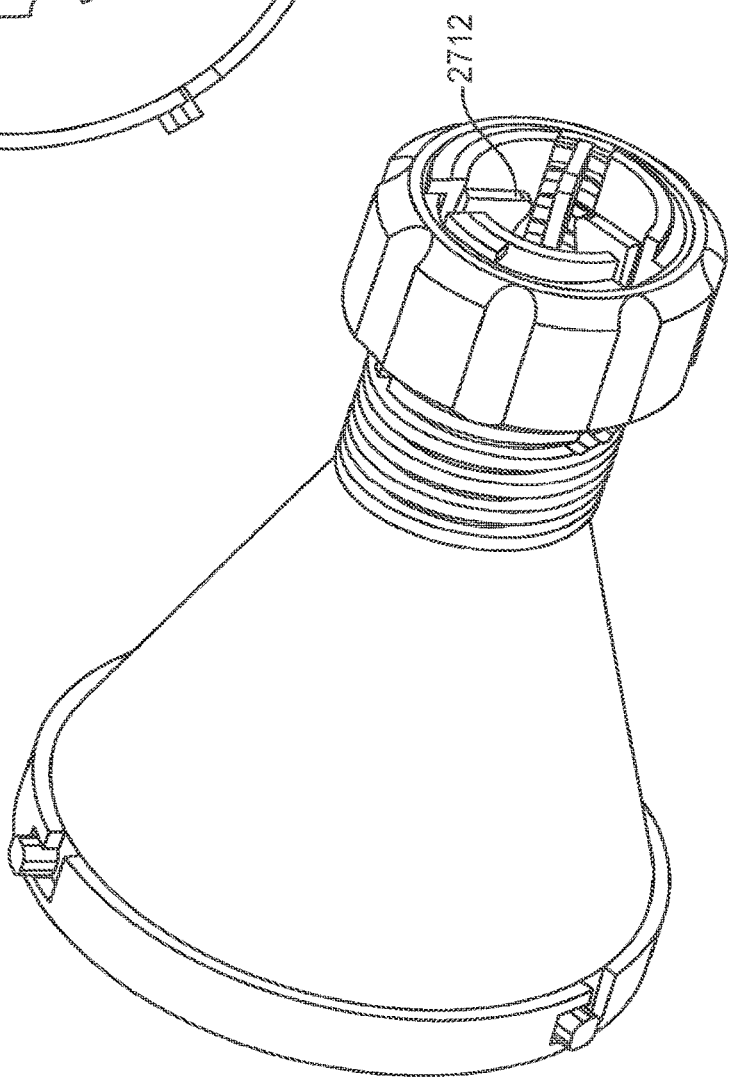
FIG. 29B
FIG. 29A

METHODS AND APPARATUS FOR LOADING A PROSTHESIS ONTO A DELIVERY SYSTEM

CROSS-REFERENCE

The present application is a continuation of U.S. patent application Ser. No. 17/168,818, filed on Feb. 5, 2021, which application is a continuation of U.S. patent application Ser. No. 16/295,913, filed on Mar. 7, 2019, now U.S. Pat. No. 10,940,001 issued on Mar. 9, 2021, which is a continuation of U.S. patent application Ser. No. 15/890,119, filed on Feb. 6, 2018, now U.S. Pat. No. 10,314,705 issued on Jun. 11, 2019, which is a continuation of U.S. patent application Ser. No. 15/134,164, filed on Apr. 20, 2016, now U.S. Pat. No. 10,016,275 issued on Jul. 10, 2018, which is a divisional of U.S. patent application Ser. No. 13/904,827, filed on May 29, 2013, now U.S. Pat. No. 9,345,573 issued on May 24, 2016, which claims the benefit of U.S. Provisional Application No. 61/653,273 filed on May 30, 2012, the entire contents of which are incorporated herein by reference.

BACKGROUND OF THE INVENTION

1. Field of the Invention

The present invention generally relates to medical devices and methods, and more particularly relates to devices and methods for loading a prosthesis onto a delivery system. The prosthesis may be any device but in preferred embodiments is used to treat valve insufficiency, such as mitral insufficiency, also referred to as mitral regurgitation. The delivery system may be any system used to deliver the prosthesis either by traditional surgical implantation methods, or by less invasive percutaneous catheter or minimally invasive transapical methods.

The heart of vertebrate animals is divided into four chambers, and is equipped with four valves (the mitral, aortic, pulmonary and tricuspid valves) that ensure that blood pumped by the heart flows in a forward direction through the cardiovascular system. The mitral valve of a healthy heart prevents the backflow of blood from the left ventricle into the left atrium of the heart, and comprises two flexible leaflets (anterior and posterior) that close when the left ventricle contracts. The leaflets are attached to a fibrous annulus, and their free edges are tethered by subvalvular chordae tendineae to papillary muscles in the left ventricle to prevent them from prolapsing into the left atrium during the contraction of the left ventricle.

Various cardiac diseases or degenerative changes may cause dysfunction in any of these portions of the mitral valve apparatus, causing the mitral valve to become abnormally narrowed or dilated, or to allow blood to leak (also referred to as regurgitate) from the left ventricle back into the left atrium. Any such impairments compromise cardiac sufficiency, and can be debilitating or life threatening.

Numerous surgical methods and devices have accordingly been developed to treat mitral valve dysfunction, including open-heart surgical techniques for replacing, repairing or re-shaping the native mitral valve apparatus, and the surgical implantation of various prosthetic devices such as annuloplasty rings to modify the anatomy of the native mitral valve. More recently, less invasive transcatheter techniques for the delivery of replacement mitral valve assemblies have been developed. In such techniques, a prosthetic valve is generally mounted in a crimped state on the end of a flexible catheter and advanced through a blood vessel or the body of the patient until the valve reaches the implantation site. The prosthetic valve is then expanded to its functional size at the site of the defective native valve.

While these devices and methods are promising treatments for valvar insufficiency, they can be difficult to deliver, and difficult to load onto the delivery system. Therefore, it would be desirable to provide improved devices and methods for coupling the prosthesis with the delivery system. At least some of these objectives will be met by the devices and methods disclosed below.

2. Description of the Background Art

By way of example, PCT international patent number PCT/US2008/0544 0 (published as PCT international publication no. WO2008/103722), the disclosure of which is hereby incorporated by reference, describes a transcatheter mitral valve prosthesis that comprises a resilient ring, a plurality of leaflet membranes mounted with respect to the ring so as to permit blood flow therethrough in one direction, and a plurality of tissue-engaging positioning elements movably mounted with respect to the ring and dimensioned to grip the anatomical structure of the heart valve annulus, heart valve leaflets, and/or heart wall. Each of the positioning elements defines respective proximal, intermediate, and distal tissue engaging regions cooperatively configured and dimensioned to simultaneously engage separate corresponding areas of the tissue of an anatomical structure, and may include respective first, second, and third elongate tissue-piercing elements. The valve prosthesis may also include a skirt mounted with respect to the resilient ring for sealing a periphery of the valve prosthesis against a reverse flow of blood around the valve prosthesis.

PCT international patent number PCT/US2009/041754 (published as PCT international publication no. WO2009/134701), the disclosure of which is hereby incorporated by reference, describes a prosthetic mitral valve assembly that comprises an anchor or outer support frame with a flared upper end and a tapered portion to fit the contours of the native mitral valve, and a tissue-based one-way valve mounted therein. The assembly is adapted to expand radially outwardly and into contact with the native heart tissue to create a pressure fit, and further includes tension members anchoring the leaflets of the valve assembly to a suitable location on the heart to function as prosthetic chordae tendineae.

Also known are prosthetic mitral valve assemblies that utilize a claw structure for attachment of the prosthesis to the heart (see, for example, U.S. patent application publication no. US2007/0016286 to Hermann et al., the disclosure of which is hereby incorporated by reference), as are prosthetic mitral valve assemblies that rely on the application of axial rather than radial clamping forces to facilitate the self-positioning and self-anchoring of the prosthesis with respect to the native anatomical structure.

Another method which has been proposed as a treatment of mitral valve regurgitation is the surgical bow tie method, which recently has been adapted into a minimally invasive catheter based treatment where an implant is used to clip the valve leaflets together. This procedure is more fully disclosed in the scientific and patent literature, such as in U.S. Pat. No. 6,629,534 to St. Goar et al., the entire contents of which are incorporated herein by reference.

Other relevant publications include U.S. Patent Publication No. 2011/0015731 to Carpentier et al. and WO 2011137531 to Lane et al. While some of these devices and methods are promising, there still is a need for improved devices and methods that will further allow more accurate positioning of a prosthetic valve and that will also more securely anchor the valve in place. In addition to needing improved devices, there is also a need for improved delivery systems and improved tools or devices and methods for loading the devices onto their respective delivery systems. At least some of these objectives will be met by the exemplary embodiments disclosed herein.

SUMMARY OF THE INVENTION

The present invention generally relates to medical devices and methods, and more particularly relates to devices and methods for loading a prosthesis onto a delivery system. The prosthesis may be any device but in preferred embodiments is used to treat valve insufficiency, such as mitral insufficiency, also referred to as mitral regurgitation. The delivery system may be any system used to deliver the prosthesis either by traditional surgical implantation methods, or by less invasive percutaneous catheter or minimally invasive transapical methods. While the present disclosure focuses on fixtures for loading the prosthesis onto a delivery system, this is not intended to be limiting. The prosthetic valves disclosed herein may also be used to treat other body valves including other heart valves or venous valves. Exemplary heart valves include the aortic valve, the triscupsid valve, or the pulmonary valve. The loading devices disclosed herein may be used to load any prosthesis onto any delivery system.

In a first aspect of the present invention, a device for loading a prosthesis onto a delivery system comprises a first housing comprising a first inlet, a first outlet, and a first central bore extending therebetween. The first housing has one or more actuators configured to actuate radially inward or outward, and the one or more actuators are adapted to selectively compress a discrete portion of the prosthesis radially inward when the prosthesis is disposed in the first central bore and while adjacent portions of the prosthesis remain uncompressed by the one or more actuators.

The first central bore may comprise a constant diameter region or a first tapered region adapted to radially collapse the prosthesis from a first initial diameter to a smaller diameter when the prosthesis is passed therethrough. The one or more actuators may comprise three actuators circumferentially disposed around the first housing about every 120 degrees. The one or more actuators may be operably coupled together such that they are actuated simultaneously. The device may further comprise a collar that is threadably engaged with the first housing. Rotating the collar actuates the one or more actuators. The one or more actuators may comprise spring loaded actuators biased to return to a position disposed radially outward from the first central bore. The first housing may further comprise a plurality of engagement elements for engaging an adjacent housing. The device may also include a support element that is releasably engaged with the first housing. The inner support element may be configured to support an inner surface of the prosthesis.

The device may further comprise a second housing coupleable end-to-end with the first housing. The second housing may comprise a second inlet, a second outlet, and a second central bore extending therebetween. The second central bore may have a second tapered region that is adapted to radially collapse the prosthesis from a second initial diameter to a second smaller diameter as the prosthesis is advanced through the second central bore. The second central bore may further comprise a second constant diameter region in communication with the first central bore and proximal thereof. The second central bore may further comprise a filleted region disposed between the second tapered region and the second constant diameter region. The second central bore may be at least partially cylindrically shaped. The second housing may comprise a plurality of engagement elements for releasably engaging the second housing with an adjacent housing, or a plurality of engagement receptacles for receiving engagement elements on an adjacent housing. The plurality of engagement elements may comprise three engagement tabs arranged circumferentially around the first housing approximately every 120 degrees. Passage of the prosthesis through the second central bore may shape the prosthesis to have a circular cross-section.

The device may further comprise a third housing coupleable end-to-end with the first or the second housing. The third housing may comprise a third inlet, a third outlet, and a third central bore extending therebetween and in communication with the first central bore or the second central bore. The third central bore may have a third tapered region adapted to radially collapse the prosthesis from a third diameter to a diameter smaller than the third diameter as the prosthesis is advanced through the third central bore. The third central bore may further comprise a third constant diameter region in communication with the third tapered region and distal thereto. The third central bore may also comprise a filleted region disposed between the third tapered region and the third constant diameter region. The third central bore may be at least partially cylindrically shaped. The third housing may comprise a plurality of engagement elements for releasably engaging an adjacent housing. The third housing may comprise a plurality of engagement receptacles for receiving engagement elements on an adjacent housing. The plurality of engagement elements may comprise three engagement tabs arranged circumferentially around the first housing approximately every 120 degrees. Passage of the prosthesis through the third central bore may shape the prosthesis to have a circular cross-section.

The prosthesis may comprise a prosthetic heart valve, and may comprise a plurality of anchoring tabs, and wherein actuation of the one or more actuators is adapted to move the plurality of anchoring tabs radially inward. The plurality of anchoring tabs may be adapted to be releasably engaged with retaining features on the delivery catheter. The plurality of anchoring tabs may comprise commissure posts on a prosthetic heart valve.

In another aspect of the present invention, a system for loading a prosthesis onto a delivery system comprises the loading device described above in addition to a prosthetic heart valve and a delivery device.

In still another aspect of the present invention, a method for loading a prosthesis onto a delivery system comprises providing a prosthetic valve having a plurality of commissure posts coupled thereto, wherein the prosthetic valve comprises an unbiased diameter, and reducing the unbiased diameter of the prosthetic valve in selected discrete regions, the selected discrete regions comprising the commissure posts. The method also includes loading the reduced diameter prosthetic valve onto a delivery device.

Reducing the unbiased diameter of the prosthetic valve may comprise actuating one or more actuators on a first housing, wherein the one or more actuators may selectively engage discrete regions of the prosthetic valve. The method may further comprise passing the prosthetic valve through a constant diameter portion of a central channel in the first housing. Actuating the one or more actuators may comprise depressing one or more pins or fingers radially inward to engage the discrete regions of the prosthetic valve. The discrete regions may move radially inward into a reduced profile. Depressing may comprise simultaneously depressing the one or more pins or fingers.

The method may further comprise reducing diameter of the prosthetic valve from the unbiased diameter to a first diameter less than the unbiased diameter. Reducing diameter of the prosthetic valve from the unbiased diameter to the first diameter may comprise passing the prosthetic valve through a tapered central channel. Passing the prosthetic valve through the tapered central channel may comprise pushing or pulling the prosthetic valve therethrough. Passing the prosthetic valve through the tapered central channel may comprise shaping the prosthetic valve to have a circular cross-section.

The method may further comprise reducing diameter of the prosthetic valve from the first diameter to a second diameter less than the first diameter. Reducing diameter from the first diameter to the second diameter may comprise passing the prosthetic valve through a second tapered central channel. Passing the prosthetic valve through the second tapered central channel may comprise pushing or pulling the prosthetic valve therethrough.

The delivery device may comprise an inner shaft and an outer shaft slidably disposed thereover, and loading the reduced diameter prosthetic valve may comprise disposing the prosthetic valve between the inner shaft and outer shafts. Loading the reduced diameter prosthetic valve may comprise releasably engaging the commissure posts with the delivery device.

The prosthetic valve may be fabricated from a nickel titanium alloy, and the method may further comprise cooling the prosthetic valve to a temperature less than or equal to the austenitic finish temperature of the prosthetic valve. Cooling the prosthetic valve may comprise cooling the prosthetic valve in chilled saline. The diameter of the prosthetic valve may be reduced from the unbiased diameter to the first diameter in a first housing, and the diameter of the prosthetic valve may be reduced from the first diameter to the second diameter in a second housing, and the method may further comprise coupling the first housing with the second housing. The first housing and the second housing may be uncoupled from one another after the diameter has been reduced to the first diameter. The method may also comprise supporting an inner surface of the prosthesis with a support element.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 24 is a partial cross-sectional view of the prosthesis in FIG. 19 positioned in the third stage of the loading system of FIG. 14 and with a delivery system also engaged with the loading system.

FIG. 25 is a partial cross-sectional view of the prosthesis in FIG. 19 after actuation of the loading system of FIG. 14.

FIGS. 29A-29B illustrate the loading system of FIG. 27 after actuation.

DETAILED DESCRIPTION OF THE INVENTION

Specific embodiments of the disclosed device, delivery system, and method will now be described with reference to the drawings. Nothing in this detailed description is intended to imply that any particular component, feature, or step is essential to the invention.

Figure 1:
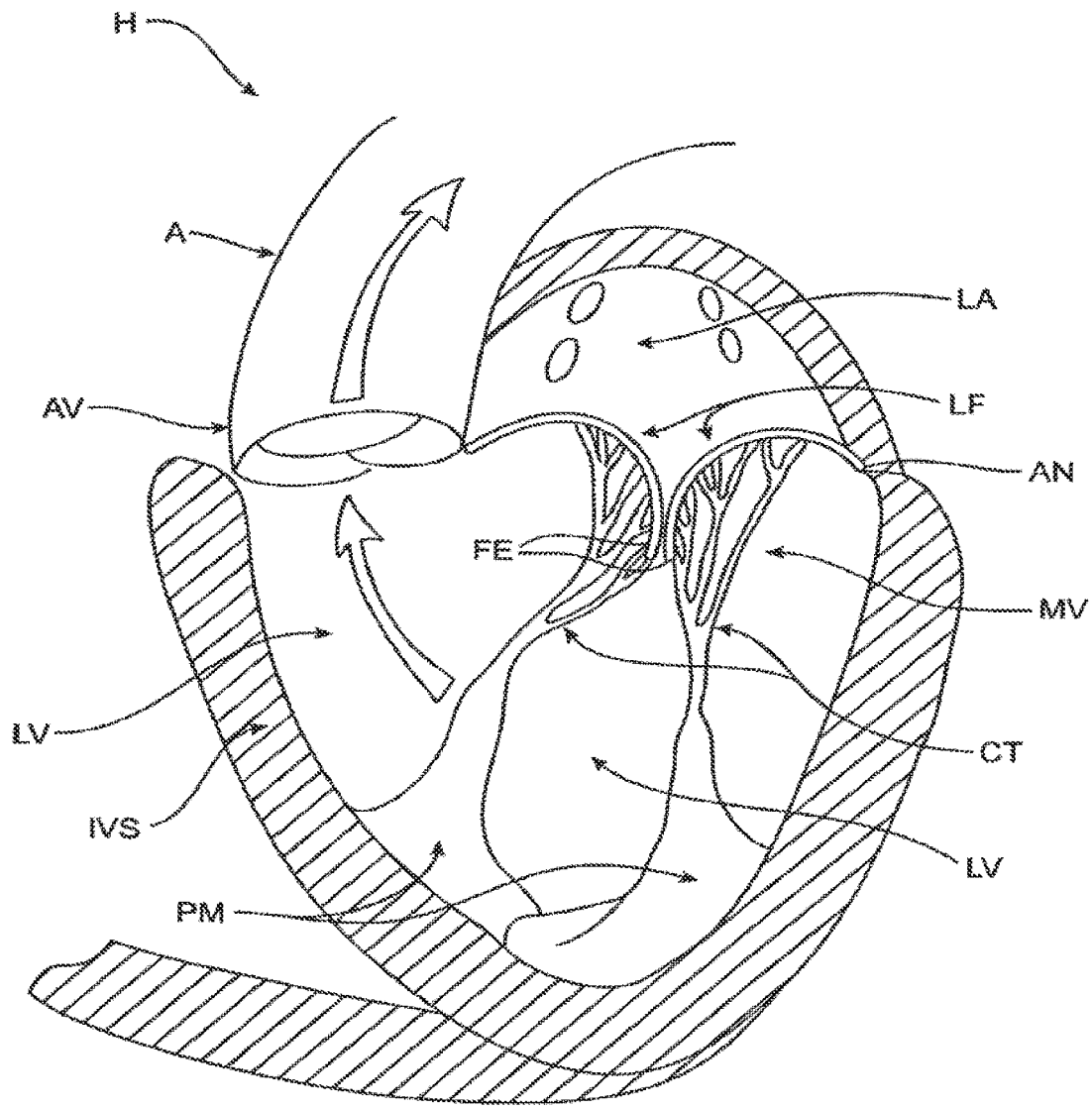
FIG. 1 is a schematic illustration of the left ventricle of a heart showing blood flow during systole with arrows.

Cardiac Anatomy. The left ventricle LV of a normal heart H in systole is illustrated in FIG. 1. The left ventricle LV is contracting and blood flows outwardly through the aortic valve AV, a tricuspid valve in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1. The opposite ends of the leaflets LF are attached to the surrounding heart structure along an annular region referred to as the annulus AN. The free edges FE of the leaflets LF are secured to the lower portions of the left ventricle LV through chordae tendineae CT (also referred to herein as the chordae) which include a plurality of branching tendons secured over the lower surfaces of each of the valve leaflets LF. The chordae CT in turn, are attached to the papillary muscles PM which extend upwardly from the lower portions of the left ventricle and interventricular septum IVS.

Figure 2:
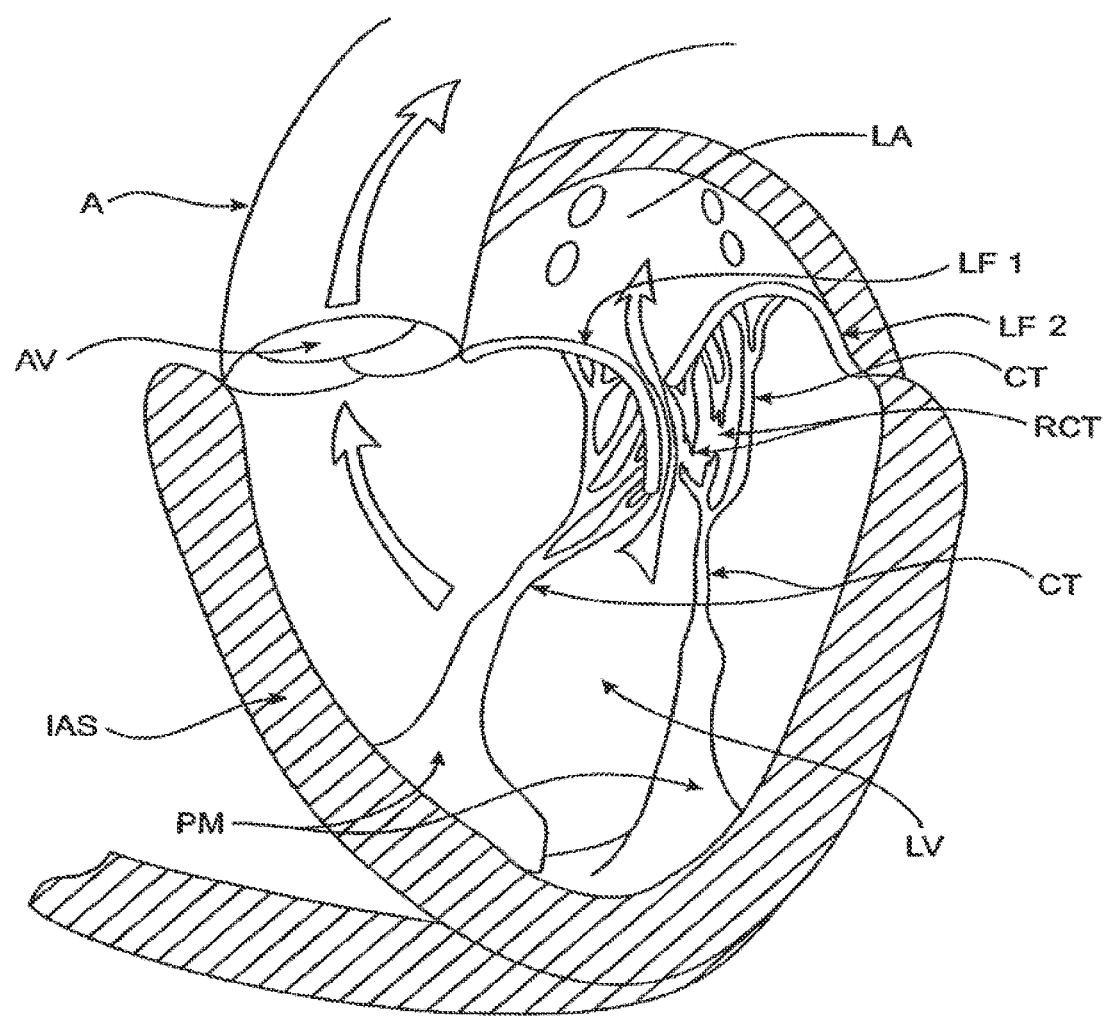
FIG. 2 is a schematic illustration of the left ventricle of a heart having prolapsed leaflets in the mitral valve.
Figure 3:
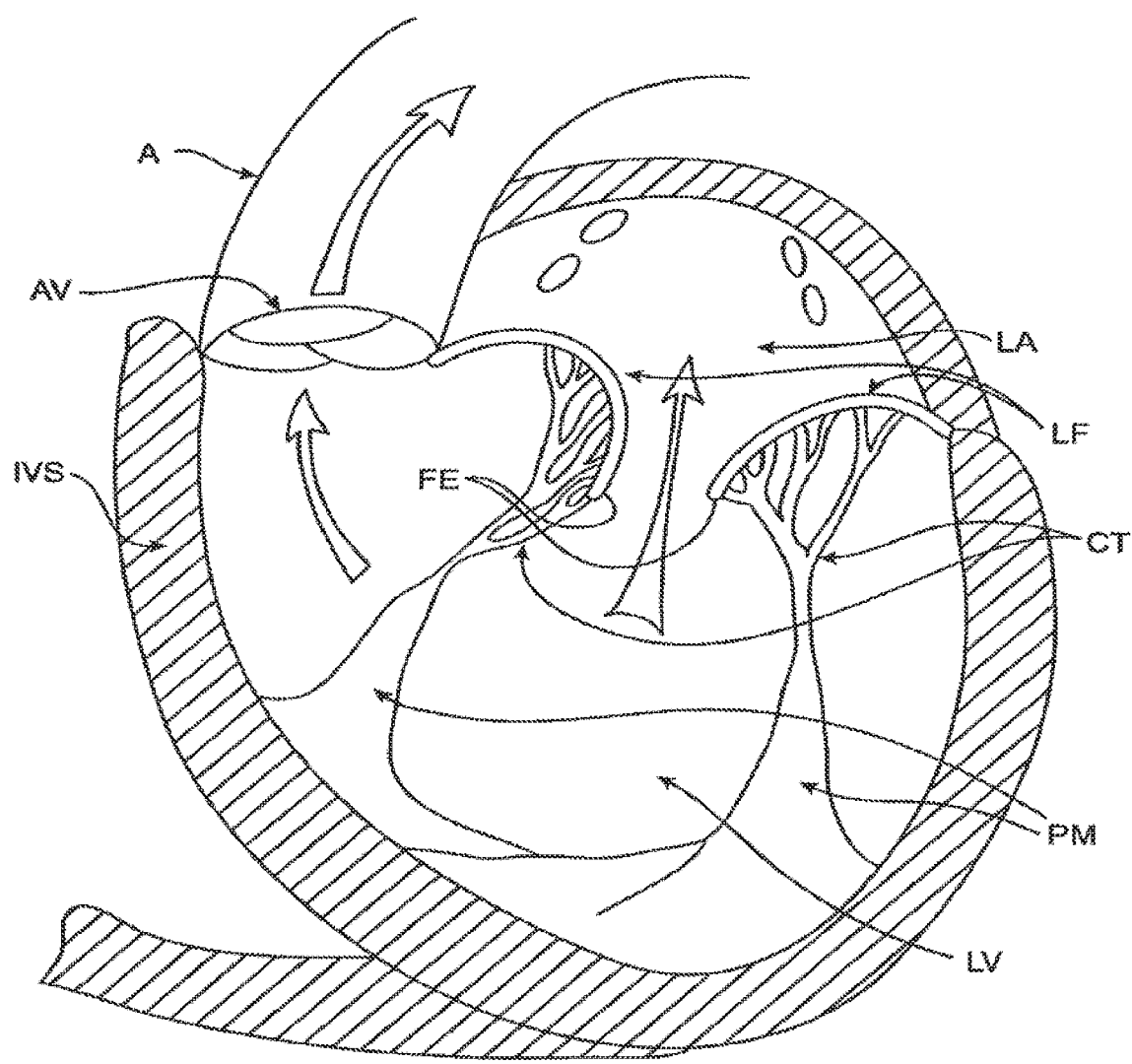
FIG. 3 is a schematic illustration of a heart in a patient suffering from cardiomyopathy where the heart is dilated and the leaflets do not meet.
Figure 4:
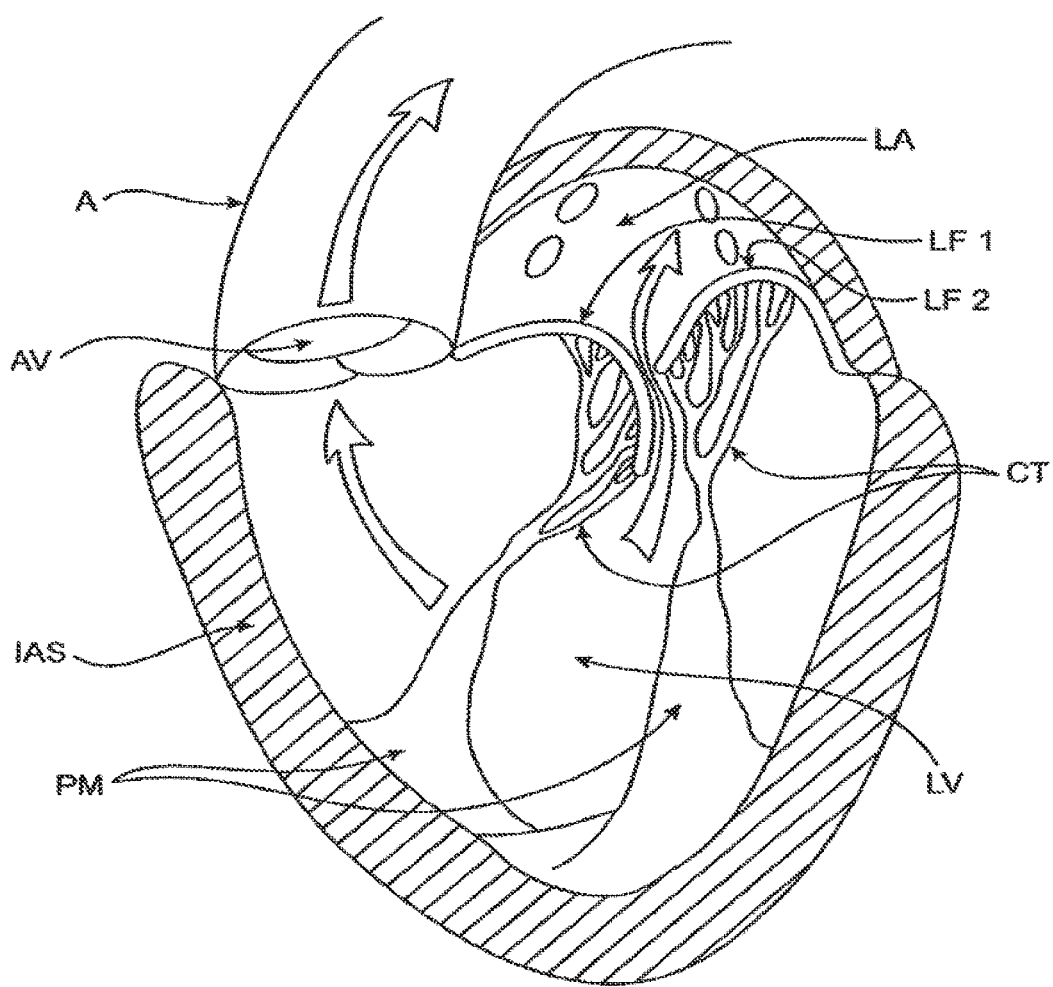
FIG. 4 illustrates mitral valve regurgitation in the left ventricle of a heart having impaired papillary muscles.

Referring now to FIGS. 2-4, a number of structural defects in the heart can cause mitral valve regurgitation. Ruptured chordae RCT, as shown in FIG. 2, can cause a valve leaflet LF2 to prolapse since inadequate tension is transmitted to the leaflet via the chordae. While the other leaflet LF1 maintains a normal profile, the two valve leaflets do not properly meet and leakage from the left ventricle LV into the left atrium LA will occur, as shown by the arrow.

Figure 3A:
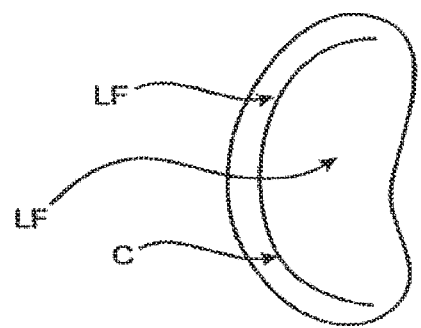
FIG. 3A shows normal closure of the valve leaflets.
Figure 3B:
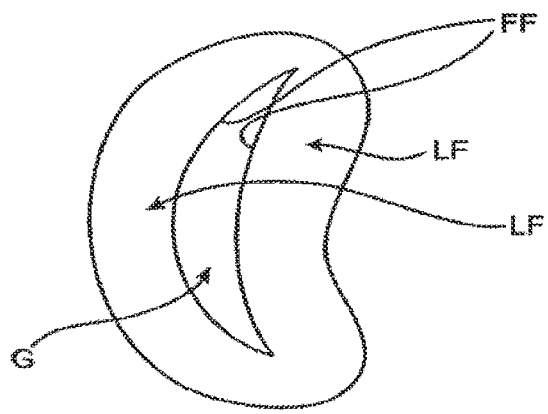
FIG. 3B shows abnormal closure of the valve leaflets.

Regurgitation also occurs in the patients suffering from cardiomyopathy where the heart is dilated and the increased size prevents the valve leaflets LF from meeting properly, as shown in FIG. 3. The enlargement of the heart causes the mitral annulus to become enlarged, making it impossible for the free edges FE to meet during systole. The free edges of the anterior and posterior leaflets normally meet along a line of coaptation C as shown in FIG. 3A, but a significant gap G can be left in patients suffering from cardiomyopathy, as shown in FIG. 3B.

Mitral valve regurgitation can also occur in patients who have suffered ischemic heart disease where the functioning of the papillary muscles PM is impaired, as illustrated in FIG. 4. As the left ventricle LV contracts during systole, the papillary muscles PM do not contract sufficiently to effect proper closure. The leaflets LF1 and LF2 then prolapse, as illustrated. Leakage again occurs from the left ventricle LV to the left atrium LA, as shown by the arrow.

Figure 5A:
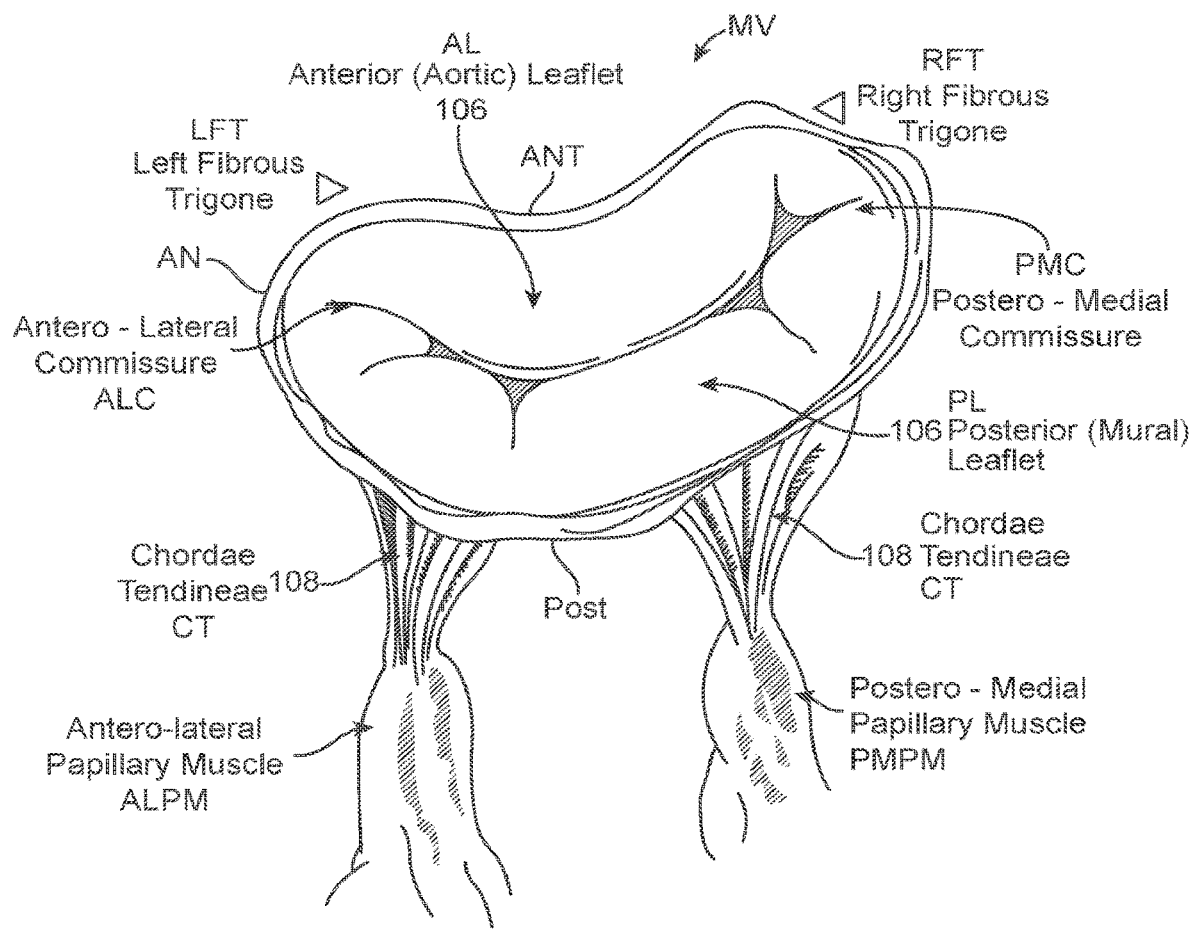
FIGS. 5A-5B illustrate anatomy of the mitral valve.
Figure 5B:
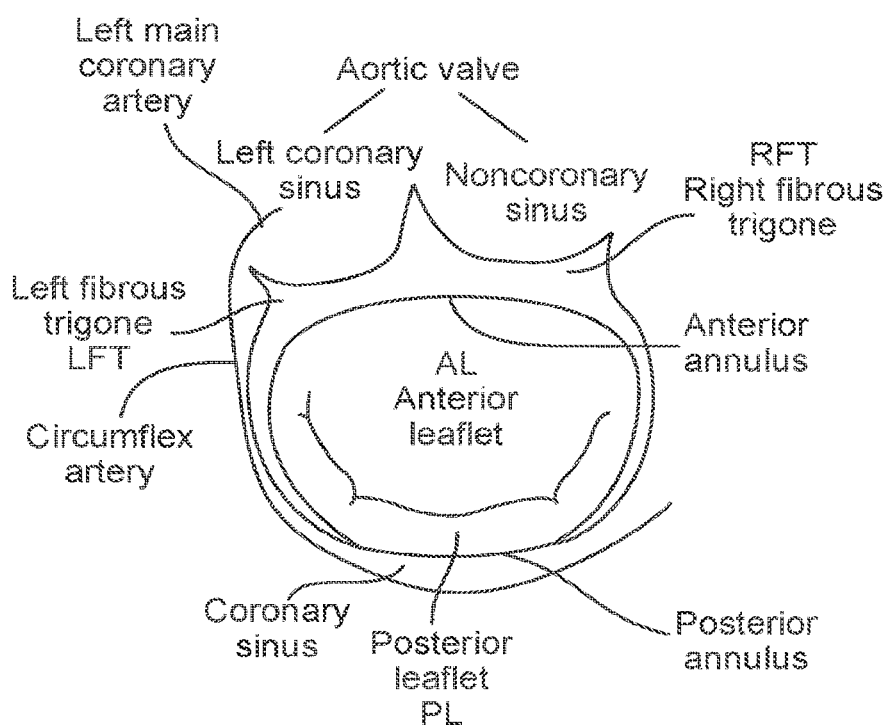

FIG. 5A more clearly illustrates the anatomy of a mitral valve MV which is a bicuspid valve having an anterior side ANT and a posterior side POST. The valve includes an anterior (aortic) leaflet AL and a posterior (mural) leaflet PL. Chordae tendineae CT couple the valve leaflets AL. PL with the antero-lateral papillary muscle ALPM and the postero-medial papillary muscle PMPM. The valve leaflets AL, PL join one another along a line referred to as the antero-lateral commissure ALC and the posterior-medial commissure PMC. The annulus AN circumscribes the valve leaflets, and two regions adjacent an anterior portion of the annulus, on opposite sides of the anterior leaflet are referred to as the left fibrous trigone LFT and also the right fibrous trigone RFT. These areas are indicted generally by the solid triangles. FIG. 5B more clearly illustrates the left and right fibrous trigones. LFT, RFT.

While various surgical techniques as well as implantable devices have been proposed and appear to be promising treatments for mitral regurgitation, surgical approaches can require a lengthy recovery period, and implantable devices have varying clinical results. Therefore, there still is a need for improved devices, delivery systems, loading fixtures, and methods for treating mitral regurgitation. While the embodiments disclosed herein are directed to an implantable prosthetic mitral valve for treating mitral regurgitation, one of skill in the art will appreciate that this is not intended to be limiting, and the devices and methods disclosed herein may also be used to treat other cardiac valves such as the tricuspid valve, aortic valve, pulmonary valve, etc, as well as other valves in the body such as venous valves.

Prosthetic Valve. Prosthetic valves have been surgically implanted in the heart as a treatment for mitral regurgitation. Some of these valves have been valves harvested from animals such as porcine valves, and others have been prosthetic mechanical valves with or without a tissue covering. More recently, minimally invasive catheter technology has been used to deliver prosthetic valves to the heart. These valves typically include an anchor for securing the valve to the patient's heart, and a valve mechanism, either a mechanical valve, a valve with animal tissue, or combinations thereof. The prosthetic valve once implanted, takes over for malfunctioning native valve, thereby reducing or eliminating valvar insufficiency. While some of these valves appear promising, there still is a need for improved valves. Positioning and anchoring the prosthetic valve in the native anatomy remains a challenge. The following discloses exemplary embodiments of a prosthetic valve, a delivery system for the prosthetic valve, and methods of delivering the valve that overcome some of the challenges associated with existing prosthetic valves.

Figure 6:
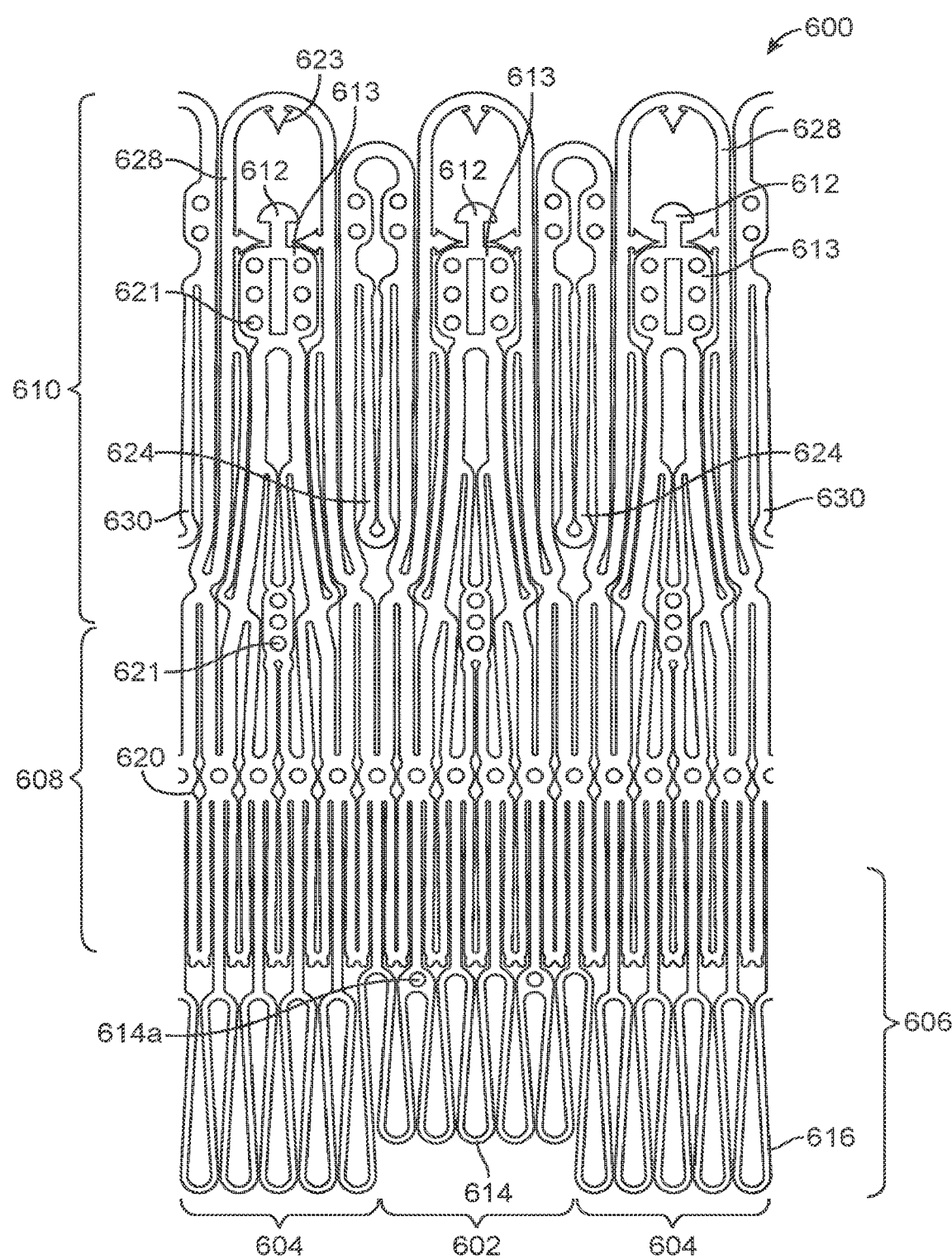
FIG. 6 illustrates an exemplary embodiment of an uncovered frame in a prosthetic cardiac valve, with the frame flattened out and unrolled.

FIG. 6 illustrates an exemplary embodiment of a prosthetic cardiac valve in the collapsed configuration. Coverings from the frame (e.g. fabric or tissue) has been removed to permit observation of the underlying frame 600. The frame has been unrolled and flattened out. The prosthetic valve frame 600 has an atrial region 606, an annular region 608, and a ventricular region 610. The frame 600 is formed from a plurality of interconnected struts that form a series of peaks and valleys which can expand and contract relative to one another thereby permitting the frame to be loaded onto a delivery catheter in a collapsed configuration, and then radially expanded at a target treatment site for implantation. Preferred embodiments are self-expanding and may be fabricated using superelastic nitinol or other self-expanding materials. Shape memory alloys that spring open above a transition temperature may also be used, and expandable members may also be used to expand the frame when plastic deformation (e.g. balloon expansion) is required to open the frame.

Atrial region 606 has a skirt 616 which includes a plurality of interconnected struts that form a series of peaks and valleys. In this region, the struts are skew relative to one another and thus the resulting cell pattern has an enlarged end and the opposite end tapers to a smaller end. In preferred embodiments, the anterior portion of the atrial skirt does not have a flanged region like the posterior portion, thus the anterior portion 602 of the atrial region may have shorter struts than the posterior region 604. Thus the peaks and valleys in the anterior portion are axially offset from those in the remaining posterior portion of the atrial region. This may be advantageous as it prevents the struts in the anterior portion of the atrial skirt from protruding upwards potentially impinging against the left atrium and causing perforations. Additionally, the shortened struts and offset peaks and valleys form an alignment element 614 that can assist the physician visualize delivery of the prosthetic valve to the mitral valve and alignment of the prosthetic valve prior to expansion of the prosthetic valve. Optional radiopaque markers 614a are disposed on either side of the offset peaks and valleys and further help with visualization during implantation of the valve. The atrial region preferably self-expands to either a cylindrical shape, or it may have a D-shaped cross-section where the anterior portion 602 is substantially flat, and the posterior portion 604 is cylindrically shaped. This allows the atrial skirt to conform to the anatomy of the native mitral valve, thereby preventing obstruction of the left ventricular outflow tract. Additionally, the atrial skirt may also be formed so that upon expansion, the skirt flares outward and forms a flange that can rest against a superior surface of the mitral valve. The flanged region is preferably along the posterior portion of the atrial skirt, and the anterior portion of the atrial skirt remains flangeless. Or, the flange may extend entirely around the atrial skirt. The atrial region is connected to the adjacent annular region 608 with connecting struts which are preferably linear and substantially parallel to the longitudinal axis of the frame.

The annular region 608 is also comprised of a plurality of axially oriented and interconnected struts that form peaks and valleys that allow radial expansion. The struts are preferably parallel with one another and parallel with the longitudinal axis of the frame. The annular region may also be self-expanding and expand into a cylindrical shape, or more preferably the annular region may expand to have a D-shaped cross-section as described above with respect to the atrial region. Thus, the annular region may similarly have a flat anterior portion, and a cylindrically shaped posterior portion. Upon delivery, the annular region is aligned with and expanded into engagement with the mitral valve annulus. Connector struts join the annular region with the ventricular region 610.

The ventricular region 610 also includes a plurality of interconnected struts that form peaks and valleys. Additionally, the struts in the ventricular region form the leaflet commissures 613 which are covered with fabric, pericardial tissue, or other materials to form the prosthetic valve leaflets. Holes in the commissures allow suture to be attached thereto. Struts in the ventricular region also form a ventricular skirt 628 which expands outward to engage the anterior and posterior mitral valve leaflets, and struts in the ventricular region also form the anterior tabs 624 and the posterior tab 630. The anterior tabs are designed to capture the anterior mitral valve leaflet between an inner surface of the anterior tab and outer surface of the ventricular skirt. Any adjacent chordae tendineae may also be captured therebetween. Also, the tip of the anterior tab engages the fibrous trigone on an anterior portion of the mitral valve, one on the left and one on the right side. The posterior tab similarly captures the posterior mitral valve leaflet between an inner surface of the posterior tab and an outer surface of the ventricular skirt, along with any adjacent chordae tendineae. This will be described in more detail below.

By controlling strut length or axial position of the anterior or posterior tabs along the frame, deployment of the tabs may be controlled. Thus in this exemplary embodiment, because the length of the struts in the anterior tabs and posterior tabs 624, 630 as well as their relative position along the frame are the same as one another, when a constraining sheath is retracted away from the tabs, the anterior and posterior tabs will partially spring outward together. As the constraining sheath is further retracted, the remainder of the anterior tabs will self-expand radially outward. Further retraction of the constraining sheath then allows the remainder of the posterior tab to finish its radial expansion, and finally the ventricular skirt will radially expand outward. While strut lengths and axial position of the posterior tab and the ventricular skirt are similar, internal struts connect the ventricular skirt with the commissures, and this delays expansion of the ventricular skirt slightly, thus the posterior tab finishes expansion before the ventricular skirt. Using this sequence of deploying the prosthetic valve may allow the valve to more accurately delivered and also more securely anchored into position.

Suture holes 621 are disposed along the struts of the annular region as well as the ventricular region to allow attachment of a cover such as pericardium or a polymer such as Dacron or ePTFE. The suture holes may also be disposed along any other part of the frame. Barbs 623 are disposed along the ventricular skirt 628 to help anchor the prosthetic valve to adjacent tissue. Commissure tabs or tabs 612 are disposed on the tips of the commissures 613 and may be used to releasably couple the commissures with a delivery system as will be described below. This allows the frame to expand first, and then the commissures may be released from the delivery system afterwards. One of skill in the art will appreciate that a number of strut geometries may be used, and additionally that strut dimensions such as length, width, thickness, etc. may be adjusted in order to provide the anchor with the desired mechanical properties such as stiffness, radial crush strength, commissure deflection, etc. Therefore, the illustrated geometry is not intended to be limiting.

The frame may be formed by EDM, laser cutting, photochemical etching, or other techniques known in the art. Hypodermic tubing or flat sheets may be used to form the frame. Once the frame has been cut and formed into a cylinder, it may be radially expanded into a desired geometry and heat treated using known processes to set the shape. Thus, the prosthetic valve may be loaded onto a delivery catheter in a collapsed configuration and constrained in the collapsed configuration with a constraining sheath. Removal of the constraining sheath will allow the anchor to self-expand into its unbiased pre-set shape. In other embodiments, an expandable member such as a balloon may be used to radially expand the anchor into its preferred expanded configuration.

Figure 7:
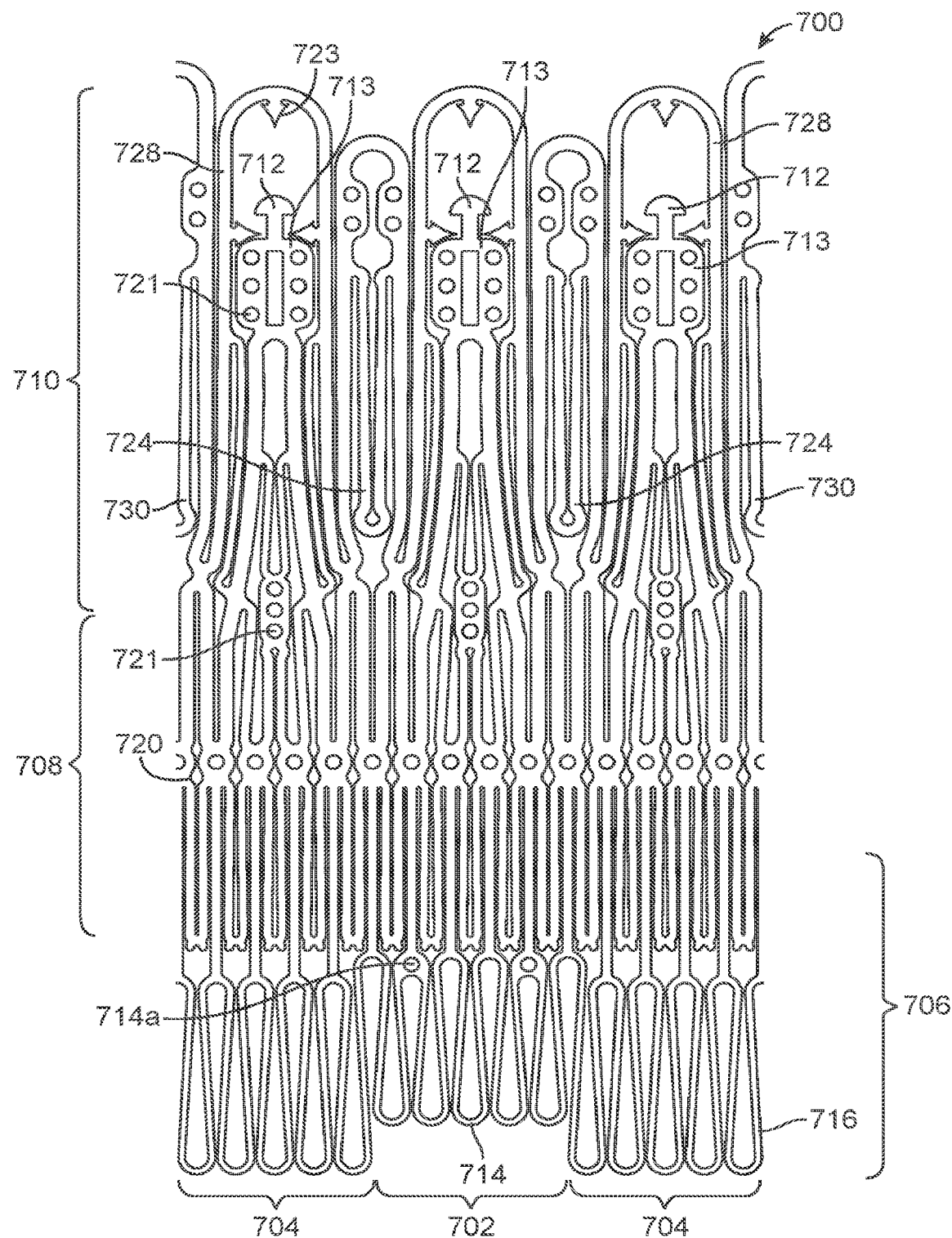
FIG. 7 illustrates another exemplary embodiment of an uncovered frame in a prosthetic cardiac valve, with the frame flattened out and unrolled.

FIG. 7 illustrates another exemplary embodiment of a prosthetic cardiac valve in the collapsed configuration, and similar to the previous embodiment with the major difference being the strut lengths in the anterior tabs, posterior tab, and ventricular skirt. Varying the strut lengths allow the sequence of expansion of the anterior and posterior tabs and ventricular skirt to be controlled. Coverings from the frame (e.g. fabric or tissue) has been removed to permit observation of the underlying frame 700. The frame has been unrolled and flattened out. The prosthetic valve frame 700 has an atrial region 706, an annular region 708, and a ventricular region 710. The frame 700 is formed from a plurality of interconnected struts that form a series of peaks and valleys which can expand and contract relative to one another thereby permitting the frame to be loaded onto a delivery catheter in a collapsed configuration, and then radially expanded at a target treatment site for implantation. Preferred embodiments are self-expanding and may be fabricated using superelastic nitinol or other self-expanding materials. Shape memory alloys that spring open above a transition temperature may also be used, and expandable members may also be used to expand the frame when plastic deformation (e.g. balloon expansion) is required to open the frame.

Atrial region 706 has a skirt 716 which includes a plurality of interconnected struts that form a series of peaks and valleys. In this region, the struts are skew relative to one another and thus the resulting cell pattern has an enlarged end and the opposite end tapers to a smaller end. An anterior portion 702 of the atrial region has shorter struts than the posterior region 704. Thus the peaks and valleys in the anterior portion are axially offset from those in the remaining posterior portion of the atrial region. This allows creation of an alignment element 714 to help the physician deliver the prosthetic valve to the mitral valve and align the prosthetic valve prior to expansion of the prosthetic valve. Other aspects of the atrial region 706 are similar to those of the atrial region 606 in FIG. 6. Optional radiopaque markers 714*a* are disposed on either side of the offset peaks and valleys and help with visualization during implantation of the valve. The atrial region preferably self-expands to either a cylindrical shape, or it may have a D-shaped cross-section where the anterior portion 702 is substantially flat, and the posterior portion 704 is cylindrically shaped. This allows the atrial skirt to conform to the anatomy of the native mitral valve, thereby preventing obstruction of the left ventricular outflow tract. Additionally, the atrial skirt may also be formed so that upon expansion, the skirt flares outward and forms a flange that can rest against a superior surface of the mitral valve. The flanged region is preferably along the posterior portion of the atrial skirt, and the anterior portion of the atrial skirt remains flangeless. Or, the flange may extend entirely around the atrial skirt. The atrial region is connected to the adjacent annular region 708 with connecting struts which are preferably linear and substantially parallel to the longitudinal axis of the frame.

The annular region 708 is also comprised of a plurality of axially oriented and interconnected struts that form peaks and valleys that allow radial expansion. The struts are preferably parallel with one another and parallel with the longitudinal axis of the frame. The annular region may also be self-expanding and expand into a cylindrical shape, or more preferably the annular region may expand to have a D-shaped cross-section as described above with respect to the atrial region. Thus, the annular region may similarly have a flat anterior portion, and a cylindrically shaped posterior portion. Upon delivery, the annular region is aligned with and expanded into engagement with the mitral valve annulus. Connector struts join the annular region with the ventricular region 710.

The ventricular region 710 also includes a plurality of interconnected struts that form peaks and valleys. Additionally, the struts in the ventricular region form the leaflet commissures 713 which are covered with fabric, pericardial tissue, or other materials to form the prosthetic valve leaflets. Holes in the commissures allow suture to be attached thereto. Struts in the ventricular region also form a ventricular skirt 728 which expands outward to engage the anterior and posterior mitral valve leaflets, and struts in the ventricular region also form the anterior tabs 724 and the posterior tab 730. The anterior tabs are designed to capture the anterior mitral valve leaflet between an inner surface of the anterior tab and outer surface of the ventricular skirt. Any adjacent chordae tendineae may also be captured therebetween. Also, the tip of the anterior tab engages the fibrous trigone on an anterior portion of the mitral valve, one on the left and one on the right side. The posterior tab similarly captures the posterior mitral valve leaflet between an inner surface of the posterior tab and an outer surface of the ventricular skirt, along with any adjacent chordae tendineae. This will be described in more detail below.

By controlling strut length or axial position of the anterior or posterior tabs along the frame, deployment of the tabs may be controlled. Thus in this exemplary embodiment, because the length of the struts in the anterior tabs and posterior tabs 724, 730 as well as their relative position along the frame are the same as one another, when a constraining sheath is retracted away from the tabs, the anterior and posterior tabs will partially spring outward together. As the constraining sheath is further retracted, the remainder of the anterior tabs will self-expand radially outward because they are the shortest relative to the struts in the ventricular skirt and the posterior tab. Further retraction of the constraining sheath then allows the ventricular skirt to radially expand, and finally further retraction of the sheath allows the remainder of the posterior tab to finish it's radial expansion. Using this sequence of deploying the prosthetic valve may allow the valve to more accurately be delivered and also more securely anchored into position.

Suture holes 721 are disposed along the struts of the annular region as well as the ventricular region to allow attachment of a cover such as pericardium or a polymer such as Dacron or ePTFE. The suture holes may also be disposed along any other part of the frame. Barbs 723 are disposed along the ventricular skirt 728 to help anchor the prosthetic valve to adjacent tissue. Commissure tabs or tabs 712 are disposed on the tips of the commissures 713 and may be used to releasably couple the commissures with a delivery system as will be described below. This allows the frame to expand first, and then the commissures may be released from the delivery system afterwards. One of skill in the art will appreciate that a number of strut geometries may be used, and additionally that strut dimensions such as length, width, thickness, etc. may be adjusted in order to provide the anchor with the desired mechanical properties such as stiffness, radial crush strength, commissure deflection, etc. Therefore, the illustrated geometry is not intended to be limiting. The frame may be formed similarly as described above with respect to FIG. 6.

Figure 8:
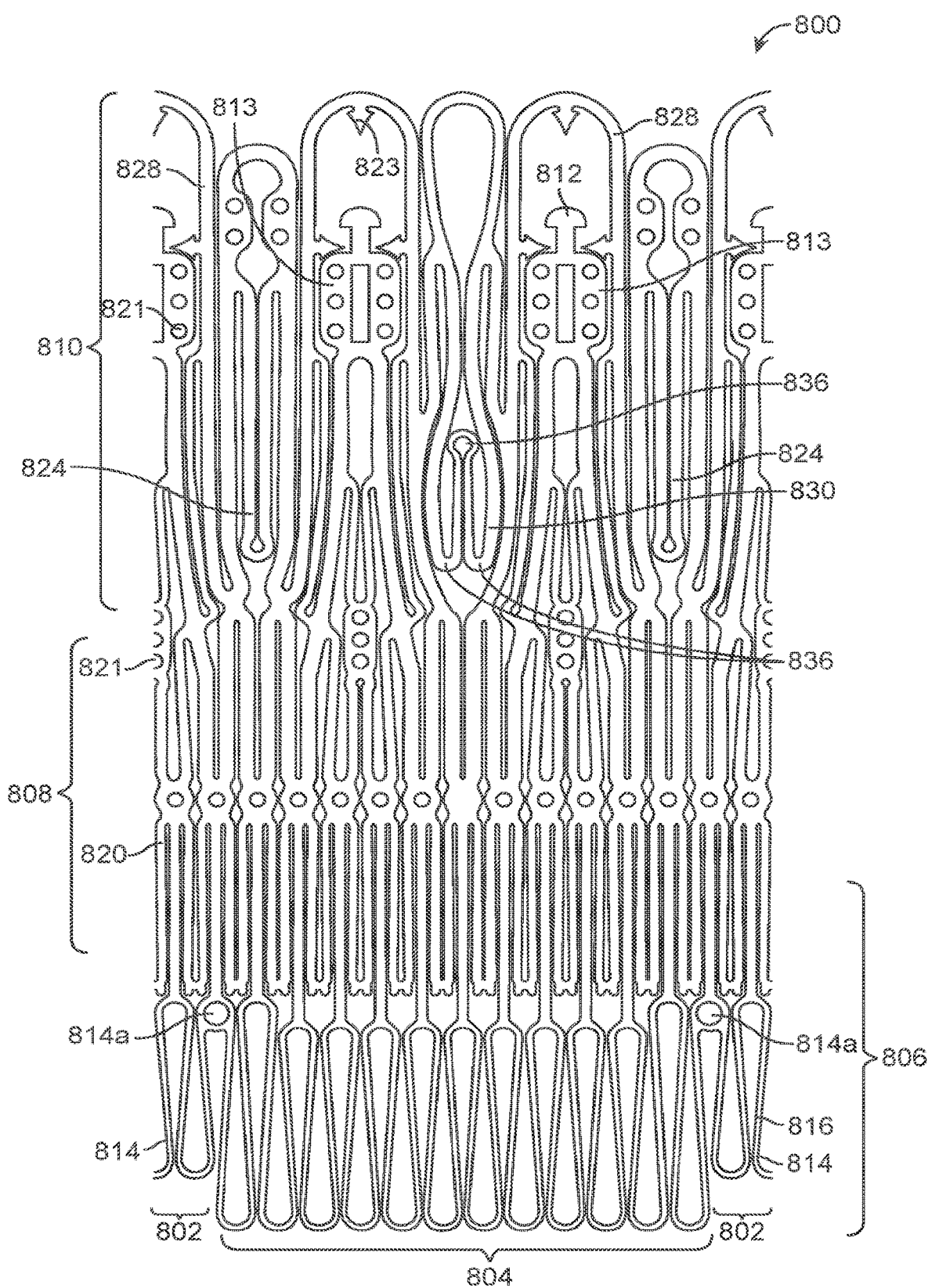
FIG. 8 illustrates still another exemplary embodiment of an uncovered frame in a prosthetic cardiac valve, with the frame flattened out and unrolled.

FIG. 8 illustrates another exemplary embodiment of a prosthetic cardiac valve in the collapsed configuration, and is similar to the previous embodiments, with the major difference being that the posterior tab is designed to expand to form an elongate horizontal section which allows engagement and anchoring of the posterior tab with the sub-annular region between the posterior leaflet and the ventricular wall. Thus, the elongate horizontal section contacts a larger region of the sub-annular region as compared with a posterior tab that only has a tapered tip formed from a single hinge between struts. This provides enhanced anchoring of the prosthetic valve. In this exemplary embodiment, the anterior tabs will completely self-expand first, followed by the posterior tab and then the ventricular skirt. However, in some situations external factors such as the delivery system, anatomy, etc. may alter the sequence of expansion, and therefore this is not intended to be limiting. Coverings from the frame (e.g. fabric or tissue) have been removed to permit observation of the underlying frame 800. The frame has been unrolled and flattened out. The prosthetic valve frame 800 has an atrial region 806, an annular region 808, and a ventricular region 810. The frame 800 is formed from a plurality of interconnected struts that form a series of peaks and valleys which can expand and contract relative to one another thereby permitting the frame to be loaded onto a delivery catheter in a collapsed configuration, and then radially expanded at a target treatment site for implantation. Preferred embodiments are self-expanding and may be fabricated using superelastic nitinol or other self-expanding materials. Shape memory alloys that spring open above a transition temperature may also be used, and expandable members may also be used to expand the frame when plastic deformation (e.g. balloon expansion) is required to open the frame.

Atrial region 806 has a skirt 816 which includes a plurality of interconnected struts that form a series of peaks and valleys. In this region, the struts are skew relative to one another and thus the resulting cell pattern has an enlarged end and the opposite end tapers to a smaller end. An anterior portion 802 of the atrial region has shorter struts than the posterior region 804. Thus the peaks and valleys in the anterior portion are axially offset from those in the remaining posterior portion of the atrial region. This allows creation of an alignment element 814 to help the physician deliver the prosthetic valve to the mitral valve and align the prosthetic valve prior to expansion of the prosthetic valve. Other aspects of the atrial region 806 are similar to those of the atrial region 606 in FIG. 6. Optional radiopaque markers 814a are disposed on either side of the offset peaks and valleys and help with visualization during implantation of the valve. The atrial region preferably self-expands to either a cylindrical shape, or it may have a D-shaped cross-section where the anterior portion 802 is substantially flat, and the posterior portion 804 is cylindrically shaped. This allows the atrial skirt to conform to the anatomy of the native mitral valve, thereby preventing obstruction of the left ventricular outflow tract. Additionally, the atrial skirt may also be formed so that upon expansion, the skirt flares outward and forms a flange that can rest against a superior surface of the mitral valve. The flanged region is preferably along the posterior portion of the atrial skirt, and the anterior portion of the atrial skirt remains flangeless. Or, the flange may extend entirely around the atrial skirt. The atrial region is connected to the adjacent annular region 808 with connecting struts which are preferably linear and substantially parallel to the longitudinal axis of the frame.

The annular region 808 is also comprised of a plurality of axially oriented and interconnected struts that form peaks and valleys that allow radial expansion. The struts are preferably parallel with one another and parallel with the longitudinal axis of the frame. The annular region may also be self-expanding and expand into a cylindrical shape, or more preferably the annular region may expand to have a D-shaped cross-section as described above with respect to the atrial region. Thus, the annular region may similarly have a flat anterior portion, and a cylindrically shaped posterior portion. Upon delivery, the annular region is aligned with and expanded into engagement with the mitral valve annulus. Connector struts join the annular region with the ventricular region 810.

The ventricular region 810 also includes a plurality of interconnected struts that form peaks and valleys. Additionally, the struts in the ventricular region form the leaflet commissures 813 which are covered with fabric, pericardial tissue, or other materials to form the prosthetic valve leaflets. Holes in the commissures allow suture to be attached thereto. Struts in the ventricular region also form a ventricular skirt 828 which expands outward to engage the anterior and posterior mitral valve leaflets, and struts in the ventricular region also form the anterior tabs 824 and the posterior tab 830. The anterior tabs are designed to capture the anterior mitral valve leaflet between an inner surface of the anterior tab and outer surface of the ventricular skirt. Any adjacent chordae tendineae may also be captured therebetween. Also, the tip of the anterior tab engages the fibrous trigone on an anterior portion of the mitral valve, one on the left and one on the right side. The posterior tab similarly captures the posterior mitral valve leaflet between an inner surface of the posterior tab and an outer surface of the ventricular skirt, along with any adjacent chordae tendineae. This will be described in more detail below. The posterior tab is similar to the posterior tabs described above in FIGS. 6-7, except that in this embodiment, the posterior tab comprises four interconnected struts as opposed to two interconnected struts. Thus, in this embodiment the plurality of interconnected struts form three hinged regions 836 along the tab. Upon expansion of the posterior tab, the hinged regions will also expand, thereby forming an elongate horizontal section which allows engagement and anchoring of the posterior tab with the sub-annular region between the posterior leaflet and the ventricular wall. This may help position and anchor the prosthetic valve better than posterior tabs which only have a smaller footprint or a single tapered tip for engagement with the posterior portion of the mitral valve. The posterior leaflet in this embodiment, may be substituted with any of the other posterior tabs described in this specification.

By controlling strut length or axial position of the anterior or posterior tabs along the frame, deployment of the tabs may be controlled. Thus in this exemplary embodiment, because the length of the struts in the anterior tabs and posterior tabs 824, 830 as well as their relative position along the frame are the same as one another, when a constraining sheath is retracted away from the tabs, the anterior and posterior tabs will partially spring outward together. As the constraining sheath is further retracted, the remainder of the anterior tabs will self-expand radially outward because they are the shortest relative to the struts in the ventricular skirt and the posterior tab. Further retraction of the constraining sheath then allows the remainder of the posterior tab to finish self-expanding, followed by self-expansion of the ventricular skirt. Using this sequence of deploying the prosthetic valve may allow the valve to more accurately be delivered and also more securely anchored into position.

Suture holes 821 are disposed along the struts of the annular region as well as the ventricular region to allow attachment of a cover such as pericardium or a polymer such as Dacron or ePTFE. The suture holes may also be disposed along any other part of the frame. Barbs 823 are disposed along the ventricular skirt 828 to help anchor the prosthetic valve to adjacent tissue. Commissure tabs or tabs 812 are disposed on the tips of the commissures 813 and may be used to releasably couple the commissures with a delivery system as will be described below. This allows the frame to expand first, and then the commissures may be released from the delivery system afterwards. One of skill in the art will appreciate that a number of strut geometries may be used, and additionally that strut dimensions such as length, width, thickness, etc. may be adjusted in order to provide the anchor with the desired mechanical properties such as stiffness, radial crush strength, commissure deflection, etc. Therefore, the illustrated geometry is not intended to be limiting. The frame may be formed similarly as described above with respect to those previously described above.

Figure 9A:
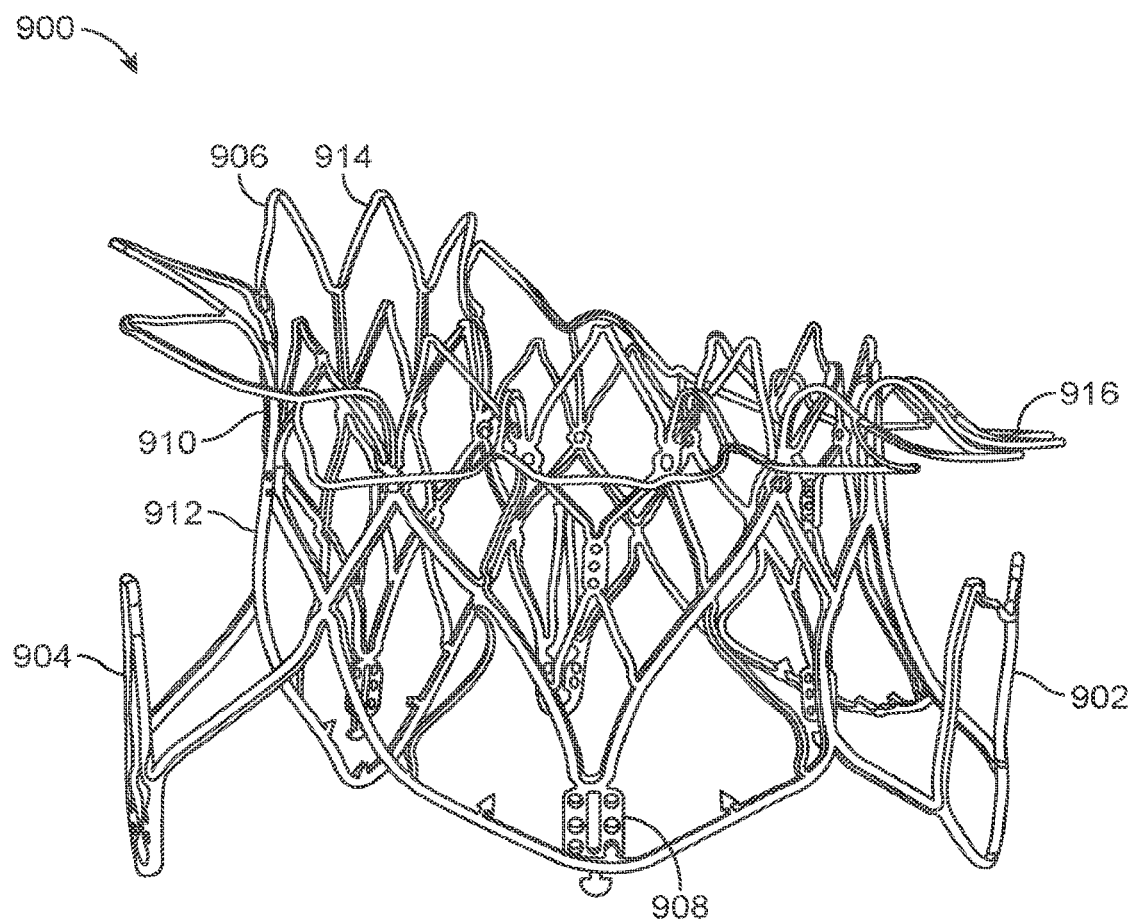
FIG. 9A illustrates a perspective view of an uncovered frame in a prosthetic cardiac valve after it has expanded.
Figure 9B:
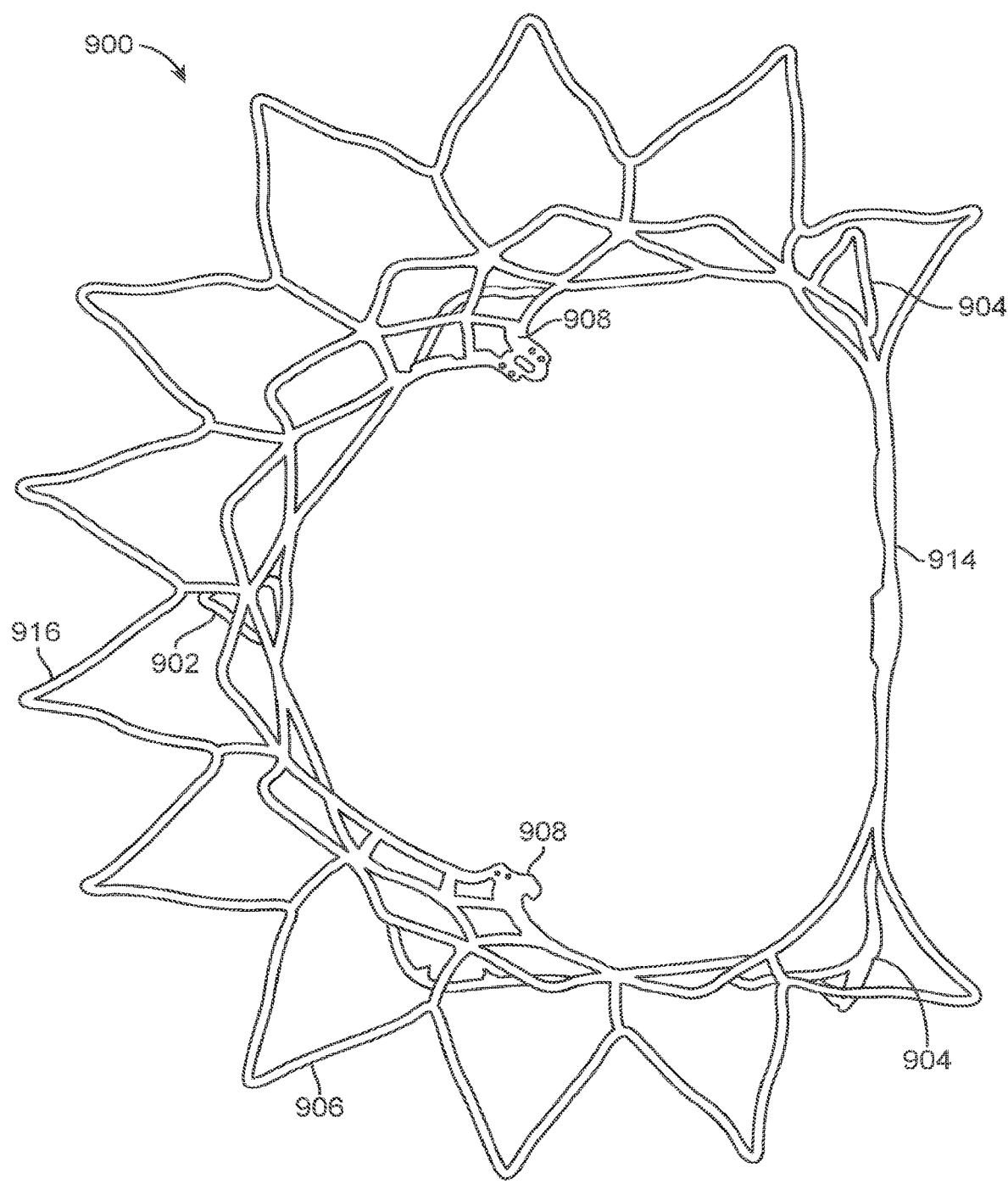
FIG. 9B illustrates a top view of the embodiment in FIG. 9A.

FIG. 9A illustrates the frame 900 of a prosthetic cardiac valve after it has expanded. Any of the frame embodiments described above may take this form as each of the above frames have similar geometry but they expand in different order. The frame includes the atrial skirt 906 with anterior portion 914 and posterior portion 916. A flanged region is formed around the posterior portion and the anterior portion remains flangeless. Additionally, the anterior portion is generally flat, while the posterior portion is cylindrically shaped, thereby forming a D-shaped cross-section which accommodates the mitral valve anatomy. FIG. 9B is a top view of the embodiment in FIG. 9A and more clearly illustrates the D-shaped cross-section.

The frame also includes the annular region 910 and ventricular skirt 912. Anterior tabs 904 (only one visible in this view) is fully expanded such that a space exists between the inner surface of the anterior tab and and outer surface of the ventricular skirt. This allows the anterior leaflet and adjacent chordae to be captured therebetween. Similarly, the posterior tab 902 is also fully deployed, with a similar space between the inner surface of the posterior tab 902 and an outer surface of the ventricular skirt. This allows the posterior leaflet and adjacent chordae tendineae to be captured therebetween. The commissure posts 908 are also visible and are disposed in the inner channel formed by the frame. The commissure posts are used to form the prosthetic mitral valve leaflets. The overall shape of the expanded frame is D-shaped, with the anterior portion flat and the posterior portion cylindrically shaped.

Figure 10:
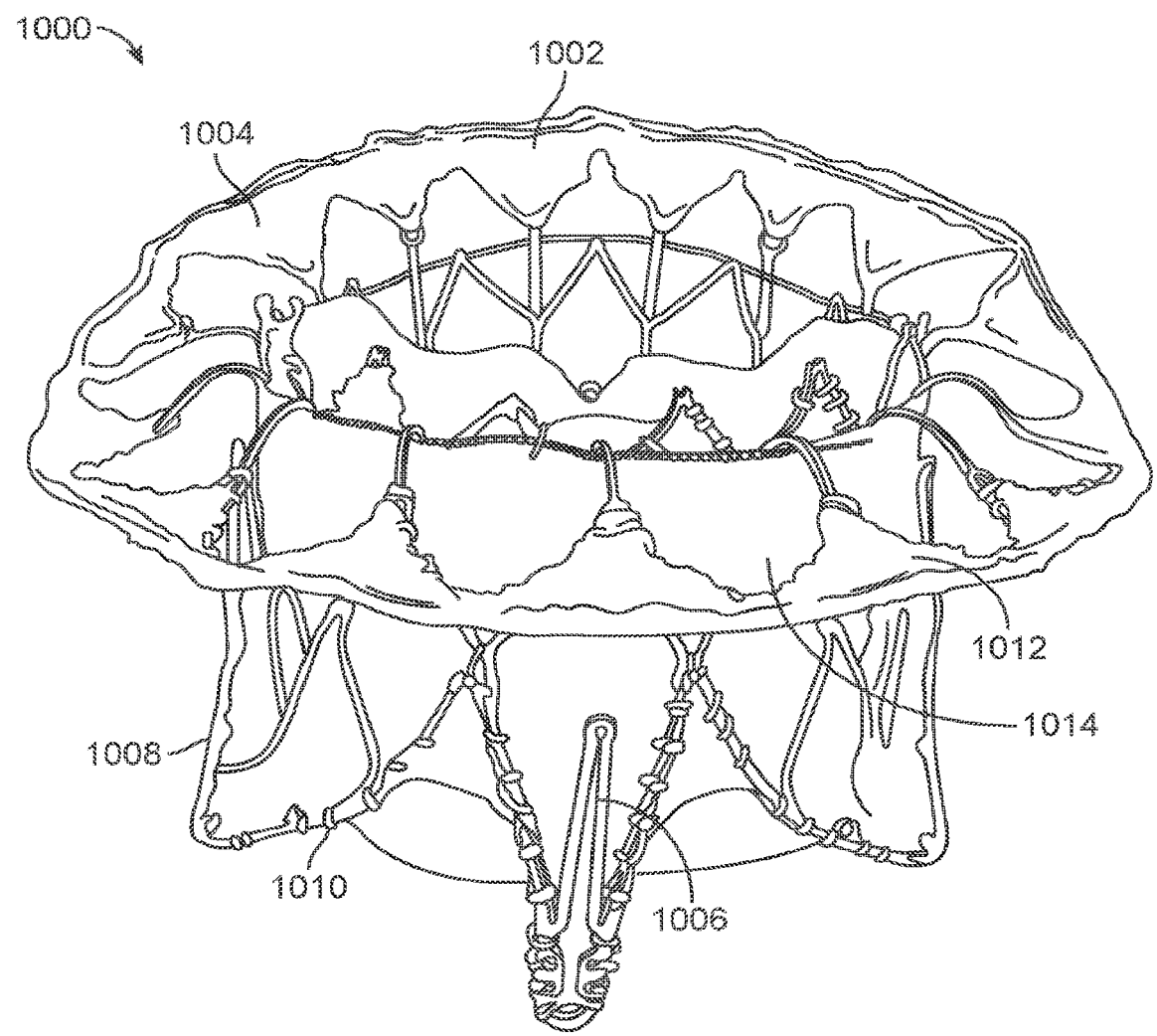
FIG. 10 illustrates the frame of FIG. 9A with the covering thereby forming a prosthetic cardiac valve.

FIG. 10 illustrates the expanded frame covered with a cover 1002 such as pericardial tissue or a polymer such as ePTFE or a fabric like Dacron attached to the frame, thereby forming the prosthetic cardiac valve 1000. The atrial skirt may be entirely covered by a material, or in preferred embodiments, the covering is only disposed between adjacent struts 1012 in adjacent cells in the flanged portion of the atrial skirt. The area 1014 between adjacent struts within the same cell remain uncovered. This allows blood flow to remain substantially uninterrupted while the prosthetic valve is being implanted. Suture 1010 may be used to attach the cover to the frame. In this view, only the posterior tab 1006 is visible on the posterior portion of the prosthetic valve along with ventricular skirt 1008 and atrial skirt 1004.

Delivery System. FIGS. 11A-11D illustrate an exemplary embodiment of a delivery system that may be used to deliver any of the prosthetic cardiac valves disclosed in this specification. While the delivery system is designed to preferably deliver the prosthetic cardiac valve transapically, one of skill in the art will appreciate that it may also be modified so that the prosthetic valve may be delivered via a catheter transluminally, such using a transseptal route. One of skill in the art will appreciate that using a transseptal route may require the relative motion of the various shafts to be modified in order to accommodate the position of the delivery system relative to the mitral valve.

Figure 11A:
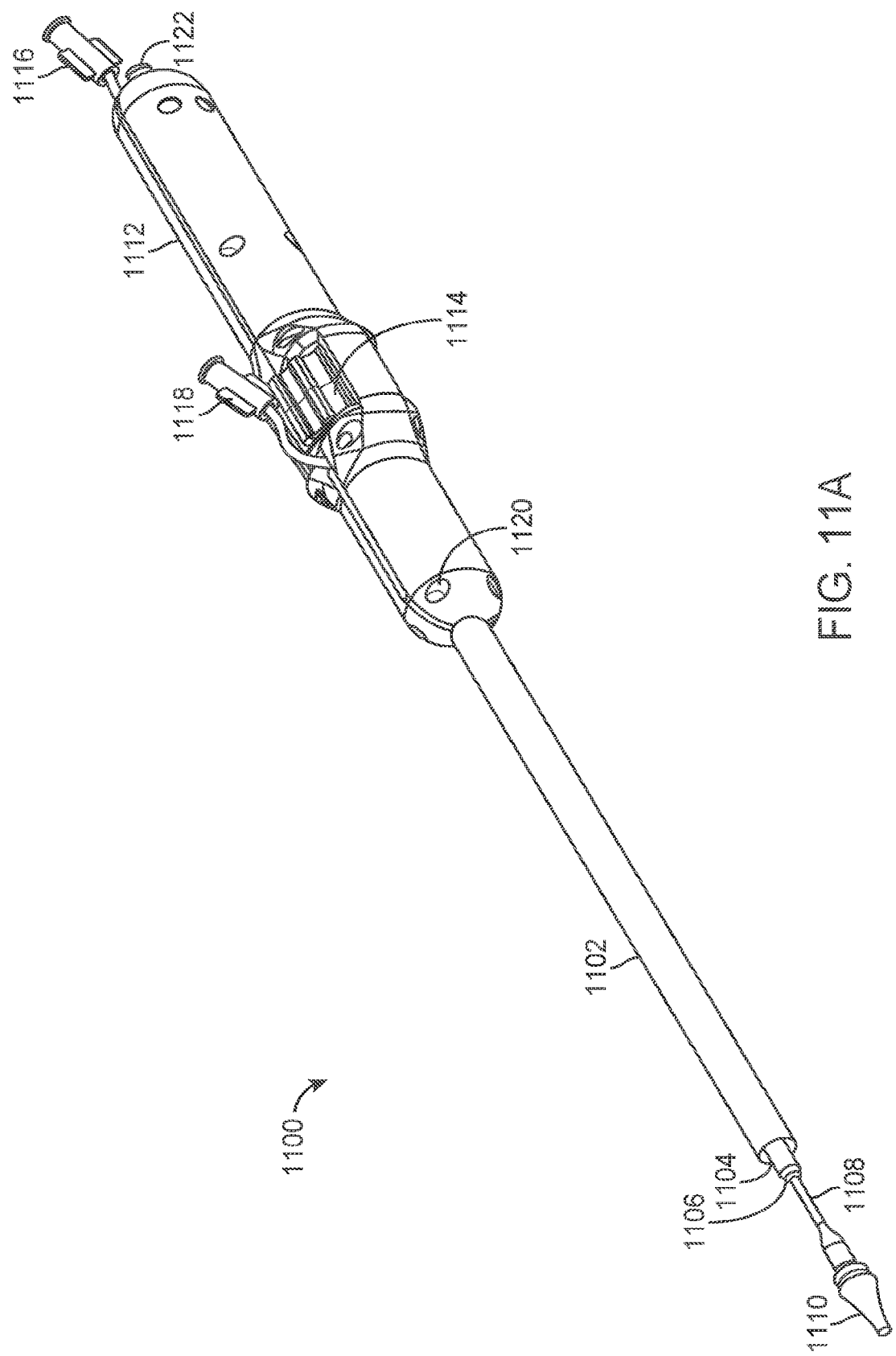
FIGS. 11A-11D illustrate an exemplary embodiment of a delivery system used to transapically deliver a prosthetic cardiac valve.
Figure 11B:
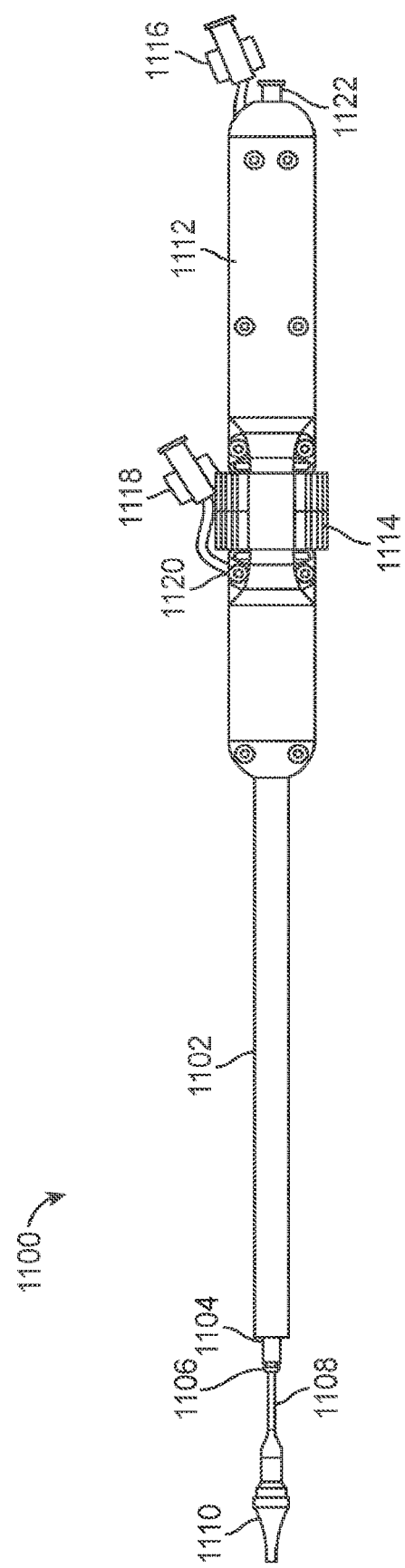

FIG. 11A illustrates a perspective view of delivery system 1100. The delivery system 1100 includes a handle 1112 near a proximal end of the delivery system and a distal tissue penetrating tip 1110. Four elongate shafts are included in the delivery system and include an outer sheath catheter shaft 1102, a bell catheter shaft 1104 which is slidably disposed in the outer sheath catheter shaft 1102, a hub catheter shaft 1106 which remains stationary relative to the other shafts, but the bell catheter shaft slides relative to the hub shaft, and finally an inner guidewire catheter shaft 1108 which is also fixed relative to the other shafts and has a lumen sized to receive a guidewire which passes therethrough and exits the distal tissue penetrating tip. An actuator mechanism 1114 is used to control movement of the various shafts as will be explained in greater detail below, and flush lines 1116, 1118 with luer connectors are used to flush the annular regions between adjacent shafts. Flush line 1118 is used to flush the annular space between the outer sheath catheter shaft 1102 and the bell catheter shaft 1104. Flush line 1116 is used to flush the annular space between the bell catheter 1104 and the hub catheter 1106. The inner guidewire catheter shaft 1108 is stationary relative to the hub catheter 1106 therefore the annular space may be sealed with an o-ring or other material. Luer connector 1122 allows flushing of the guidewire lumen and a hemostatic valve such as a Tuohy-Borst may be coupled to the luer connector to allow a guidewire to be advanced through the guidewire catheter shaft while maintaining hemostasis. Screws 1120 keep the handle housing coupled together. FIG. 11B illustrates a sideview of the delivery system 1100.

Figure 11C:
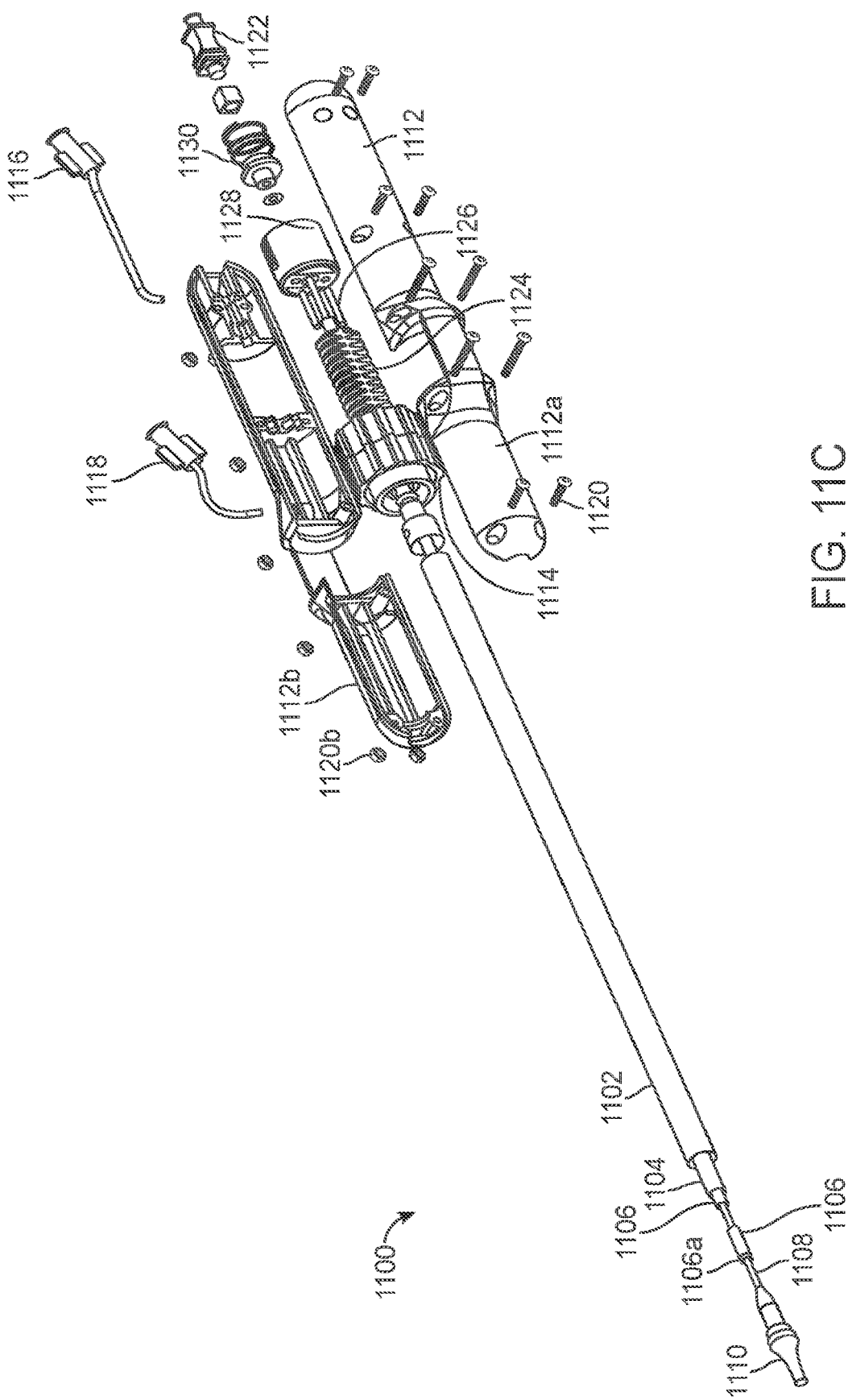

FIG. 11C is a partial exploded view of the delivery system 1100 and more clearly illustrates the components in the handle 1112 and how they interact. The handle 1112 includes a housing having two halves 1112a, 1112b which hold all the components. The handle is preferably held together with screws 1120 and nuts 1120b, although it may also be sealed using other techniques such as a press fit, snap fit, adhesive bonding, ultrasonic welding, etc. Rotation of actuator wheel 1114 is translated into linear motion of threaded insert 1124. The outer sheath catheter shaft 1102 is coupled to the threaded insert 1124, therefore rotation of actuator wheel 1114 in one direction will advance the sheath catheter shaft 1102, and rotation in the opposite direction will retract the sheath catheter shaft 1102. Further rotation of actuator wheel 1114 retracts threaded insert 1124 enough to bump into pins 1126 which are coupled to insert 1128, thereby also moving insert 1128. The bell catheter shaft 1106 is coupled to insert 1128, therefore further rotation of the actuator wheel 1114 will move the outer shaft 1102 and also move the bell catheter shaft 1106. Rotation of the actuator wheel in the opposite direction advances the sheath and threaded insert 1124 disengages from pins 1126. Spring 1130 returns insert 1128 to its unbiased position, thereby returning the bell catheter shaft to its unbiased position.

Any of the prosthetic cardiac valves disclosed herein may be carried by delivery system 1100. The atrial skirt, annular skirt, anterior tabs, posterior tab and ventricular skirt are loaded over the bell catheter shaft and disposed under the outer sheath catheter shaft 1102. The ventricular skirt is loaded proximally so that it is closest to the handle 1112 and the atrial skirt is loaded most distally so it is closest to the tip 1110. Therefore, retraction of outer sheath catheter shaft 1102 plays a significant part in controlling deployment of the prosthetic cardiac valve. The atrial skirt therefore expands first when the outer sheath catheter is retracted. The prosthetic valve commissures may be coupled with a hub 1106a on the distal portion of hub catheter 1106 and then the bell catheter shaft is disposed thereover, thereby releasably engaging the commissures with the delivery catheter. Once other portions of the prosthetic cardiac valve have expanded, the commissures may be released.

Figure 11D:
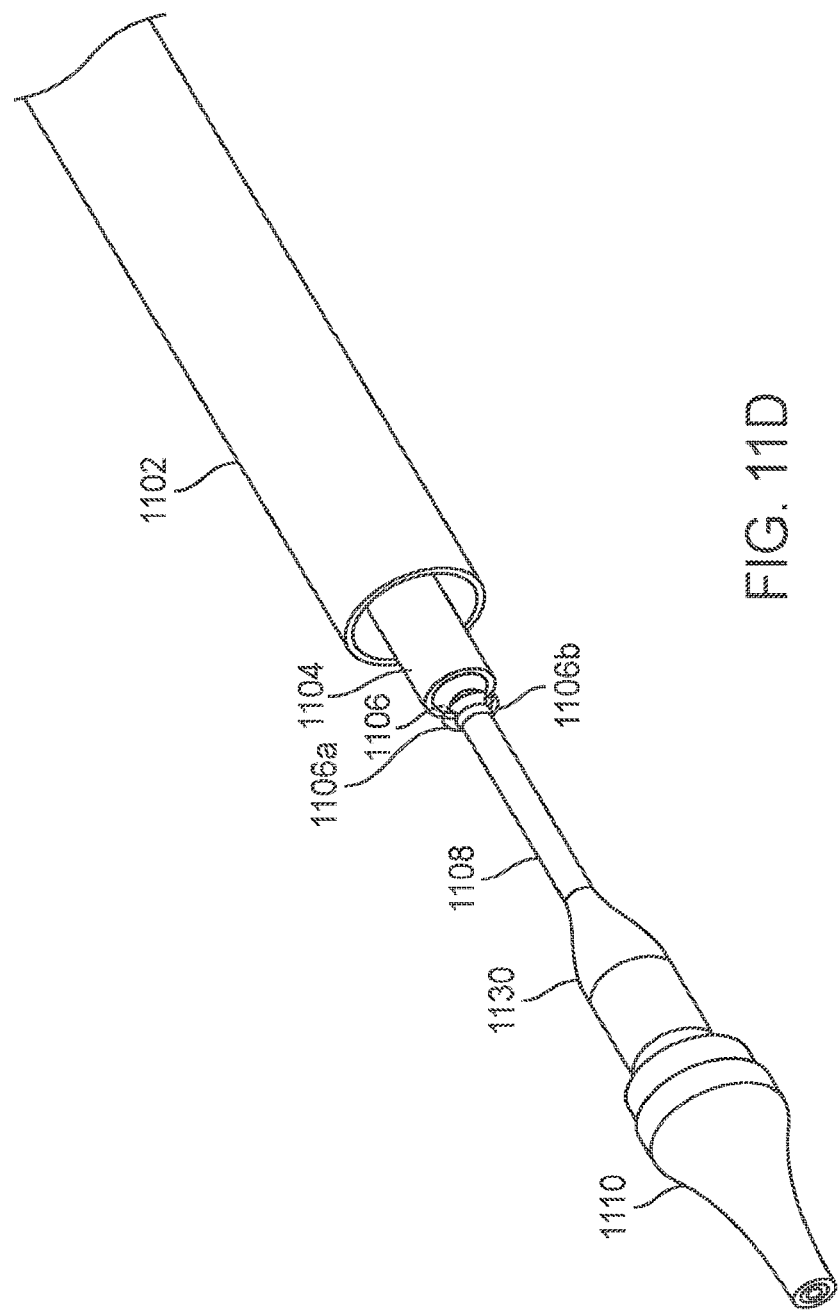

FIG. 11D highlights the distal portion of the delivery system 1100. Outer sheath catheter shaft 1102 advances and retracts relative to bell catheter shaft 1104 which is slidably disposed in the outer sheath catheter shaft 1102. Hub catheter shaft 1106 is shown slidably disposed in bell catheter shaft 1104 and with bell catheter shaft 1104 retracted so as to expose the hub 1106a having slots 1106b that hold the prosthetic valve commissures. Inner guidewire catheter shaft 1108 is the innermost shaft and has a tapered conical section 1130 which provides a smooth transition for the prosthetic valve and prevents unwanted bending or buckling of the prosthetic cardiac valve frame. Tissue penetrating tip 1110 is adapted to penetrate tissue, especially in a cardiac transapical procedure.

Loading Fixture. The prosthetic valve may be loaded manually by a physician onto the delivery system, but this can be challenging since the valve must be properly oriented relative to the delivery system and then the commissure posts must also be engaged with the slots or receptacles on the delivery system, and captured therein. This may require multiple operators to simultaneously manipulate the prosthesis as well as the delivery system and its actuator mechanisms. Therefore, it would be advantageous to provide a fixture to facilitate loading of the prosthetic valve onto the delivery system. FIGS. 14-18B illustrate an exemplary embodiment of a loading fixture (also referred to herein as a loading device) that may be used to couple a prosthesis such as a prosthetic valve with a delivery system. The prosthesis may be any prosthesis including the prosthetic valve described in this disclosure. Similarly, the delivery system may be any delivery system, including those described herein.

Figure 14:
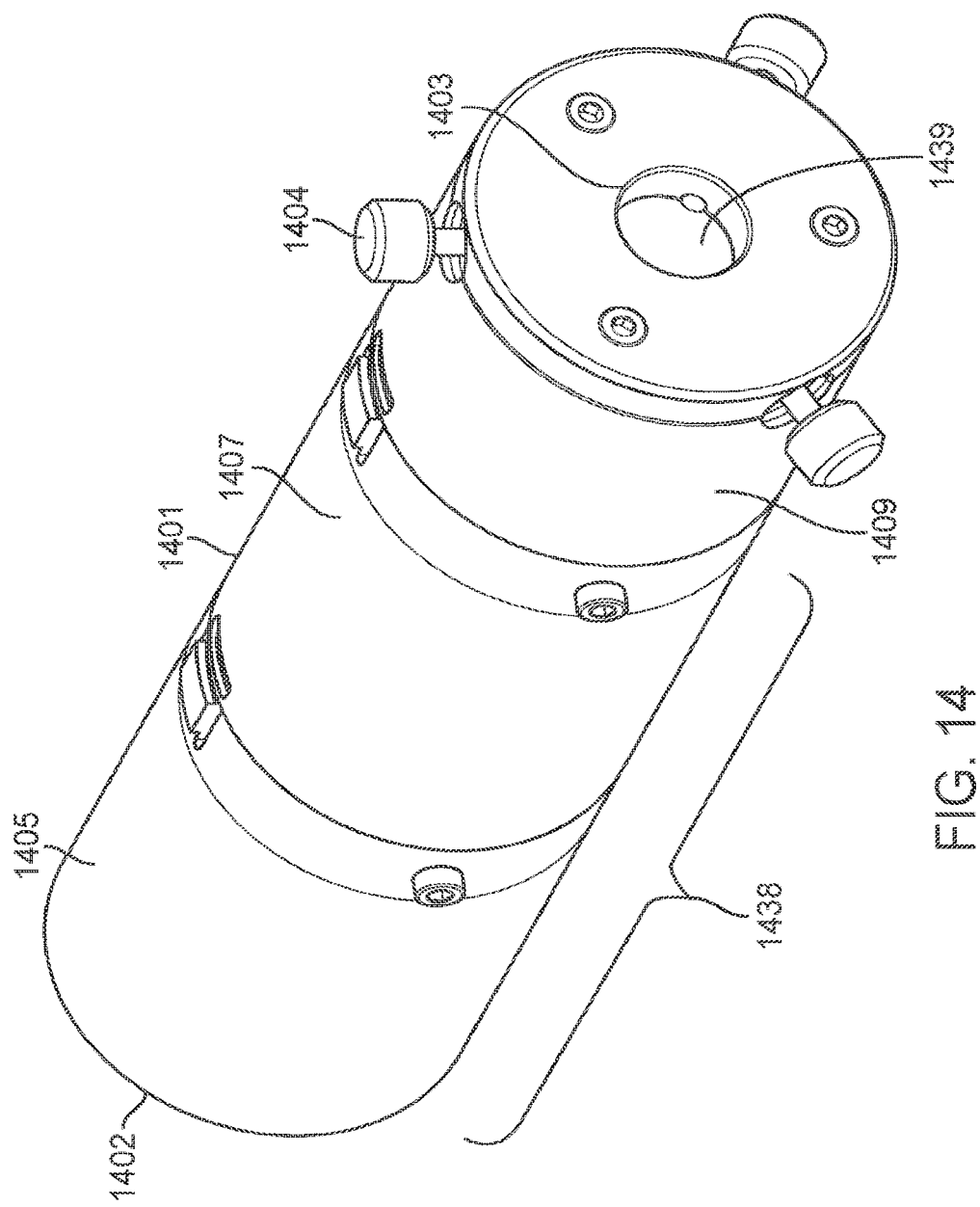
FIG. 14 is a perspective view of an exemplary loading system for the loading of a prosthetic valve with commissures into a delivery system.

FIG. 14 illustrates the loading device 1401 having a body 1438 which includes three interlocking stages or housings including a first housing 1405 (also referred to herein as the A stage or A housing), second housing 1407 (also referred to herein as the B stage or B housing), and third housing 1409 (also referred to herein as the C stage or C housing). The loading device 1401 allows a prosthesis such as a prosthetic valve to be inserted into one end of the loading device and as the prosthesis is passed therethrough, its overall diameter is reduced and selected regions of the prosthesis are further compressed radially inward when the loading device is actuated. This allows engagement of the prosthesis with the delivery system prior to delivery.

An internal channel 1439 begins at the first housing 1405 with an inlet orifice 1402 and terminates at the third housing 1409 at an outlet orifice 1403. Three hand operated and spring loaded actuators 1404 are located in the third housing 1409 and are used to depress certain portions of a prosthesis such as a prosthetic heart valve in order to load the valve onto a delivery system, the details of which are described in greater detail below.

Figure 15:
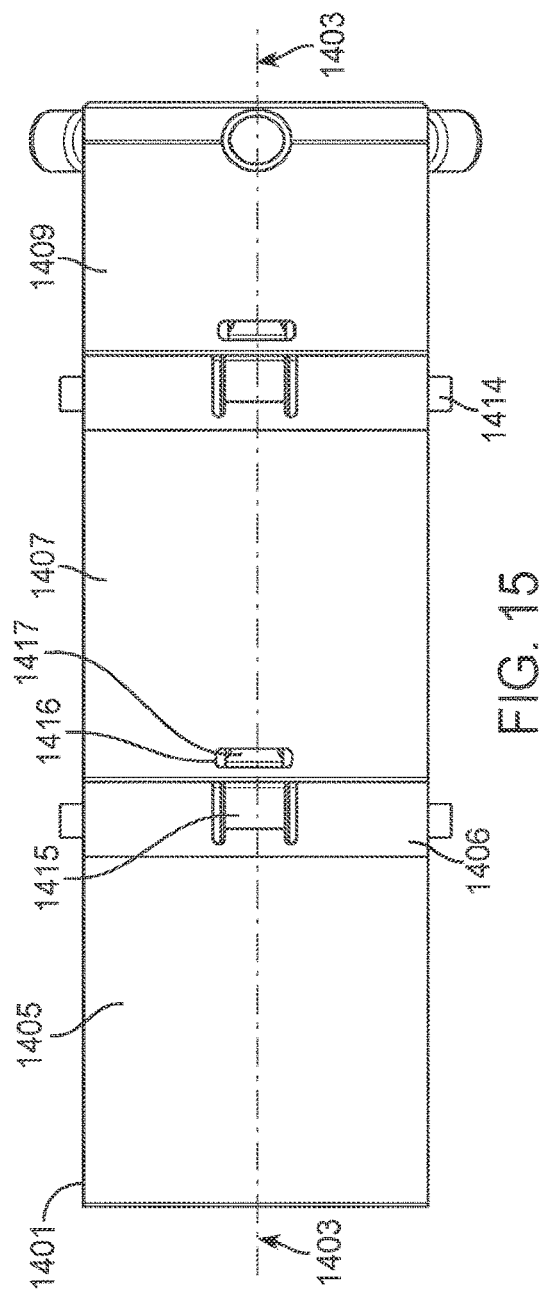
FIG. 15 is a side view of the loading system in FIG. 14.

As can be seen in FIG. 15, A stage 1405 includes a fitment ring 1406 which provides a number of cantilevered tabs 1415 that are used to mate with a locking window 1416 of the subsequent stage by virtue of a snap fit 1417. Each fitment ring 1406 is fastened to a respective stage with threaded fasteners 1414. By depressing the cantilevered tabs 1415, the snap fit 1417 is released from the locking window 1416 and the respective stages (1405, 1407, or 1409) may be separated so that each stage of the device can be manipulated individually.

Figure 16:
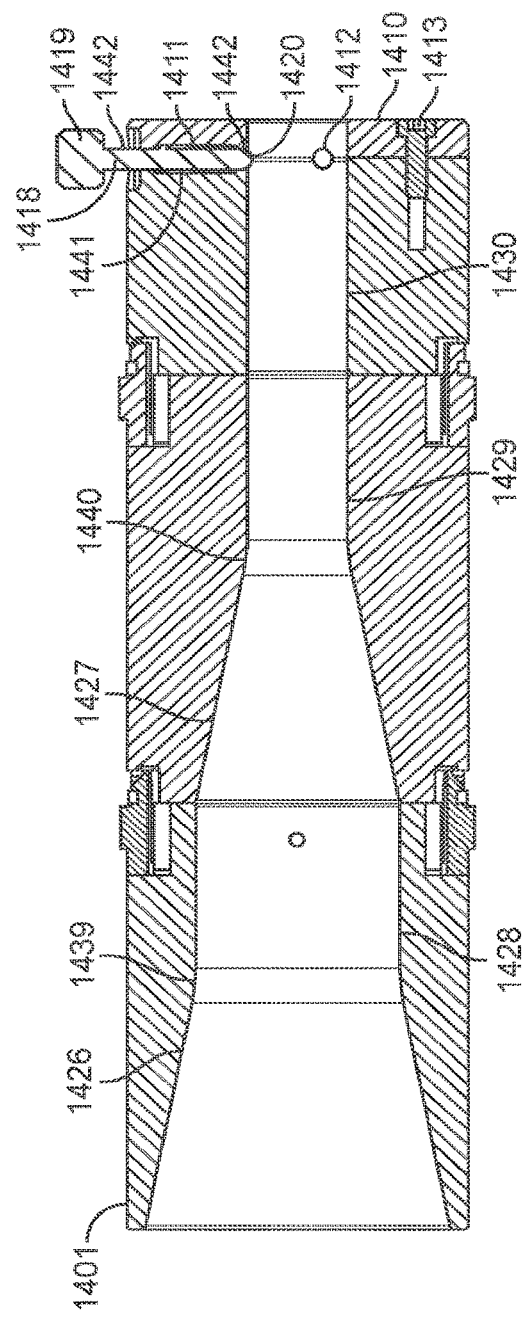
FIG. 16 cross-sectional view of the loading system in FIG. 14.

FIG. 16 shows a cross-sectional view of the loading system 1401 shown in FIG. 15. In order to begin compression of a prosthetic heart valve, the A stage 1405 first has an internally tapered section 1426 which by way of a filleted transition zone 1439 is coupled with a flat section 1428 of constant diameter. Passing through the A stage 1405 has the effect of reducing a prosthetic heart valve diameter from a first larger input value to a second smaller output value, and also helps to shape-set the frame or scaffold portion of the valve into having a circular cross section. The B stage 1407 first has an internally tapered section 1427 which by way of a filleted transition zone 1440 is coupled with a flat section 1429 of constant diameter. Passing through the B stage 1407 has the effect of again reducing a prosthetic heart valve diameter from a first larger input value (the output diameter of the A stage 1405) to a second smaller and final output value.

The internal mechanical components of the loading system 1401 are displayed in cross-sectional view in FIG. 15. As a valve is pushed from the B stage 1407 to the C stage 1409, it retains the output diameter that was set in the B stage 1407. In order to deflect certain portions of the heart valve such as commissures, anchors or otherwise necessary locating features, spring loaded actuators 1404 must be depressed, the act of which transfers linear displacement to the locating features of the prosthetic valve. Spring loaded actuators 1404 may be arranged in variably different circumferential configurations, for example three of such actuators 1404 could be equally spaced by 120' in order to deflect three separate locating features of a heart valve prosthesis. Let this design by no means be limited to three of such actuators, or any specific positioning scheme, as the design can be modified to incorporate any reasonable number and position of such actuators operating on specific portions of stents. By travelling through a constant diameter channel 1430 in the C stage 1409, a prosthetic heart valve can be brought into contact with the tips 1420 of the spring loaded actuators 1404. The spring loaded actuator 1404 is comprised of a button 1419 which can be depressed, a shaft 1418 on which a spring 1411 is housed, a shoulder 1421 against which the spring 1411 abuts to provide return force, a cylindrical pocket 1441 in which the spring 1411 has room to compress, and bearing surfaces 1442 which allow the shaft 1418 to translate freely between an uncompressed and a compressed state, and a tip 1420 that protrudes out of a hole 1412 and comes into contact with a heart valve to permit compression.

As seen in FIG. 16, a capping plate 1410 is fastened to the C stage 1409 by threaded fasteners 1413. The capping plate 1410 acts with the C stage 1409 to house the springs 1411 and spring loaded actuators 1404.

Figure 17:
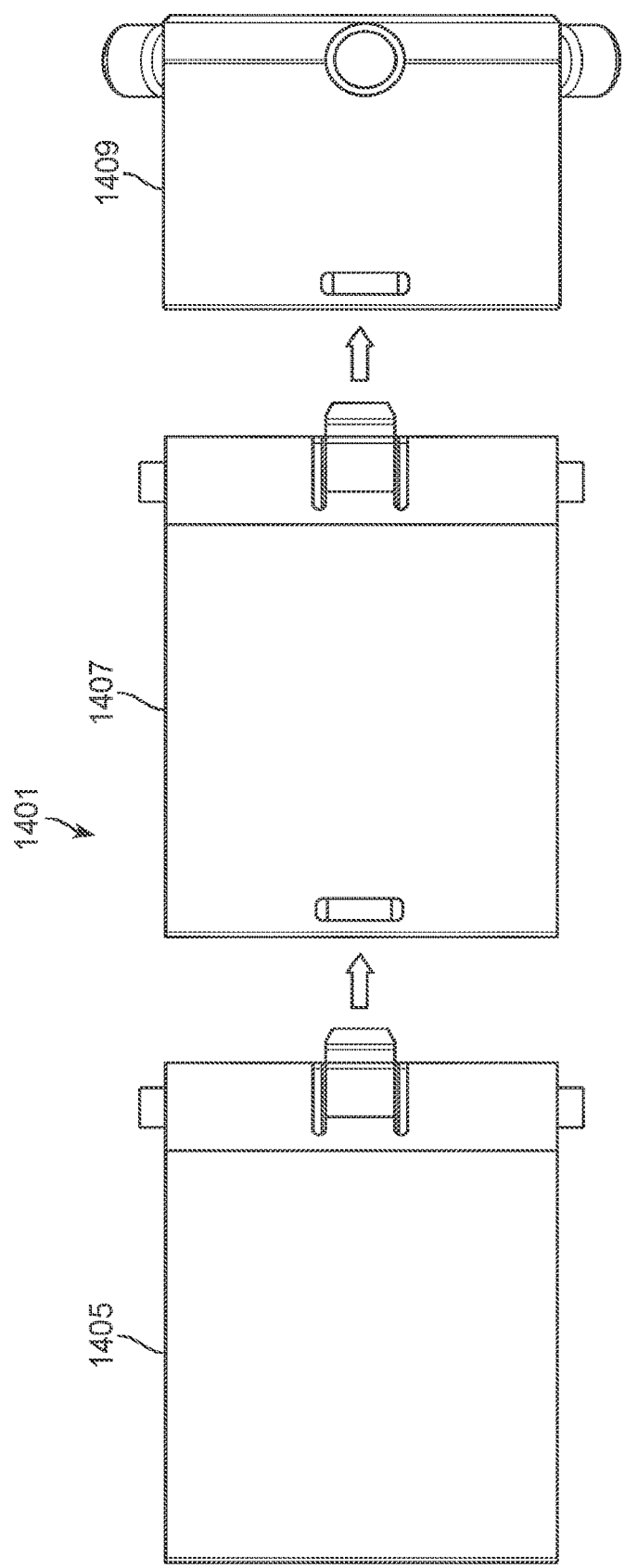
FIG. 17 is a partially exploded side view of the loading system in FIG. 14.

FIG. 17 illustrates the manner through which the A stage 1405, the B stage 1407 and the C stage 1409 are combined, and details the locations of relevant attachment mechanisms as discussed previously.

Figure 18B:
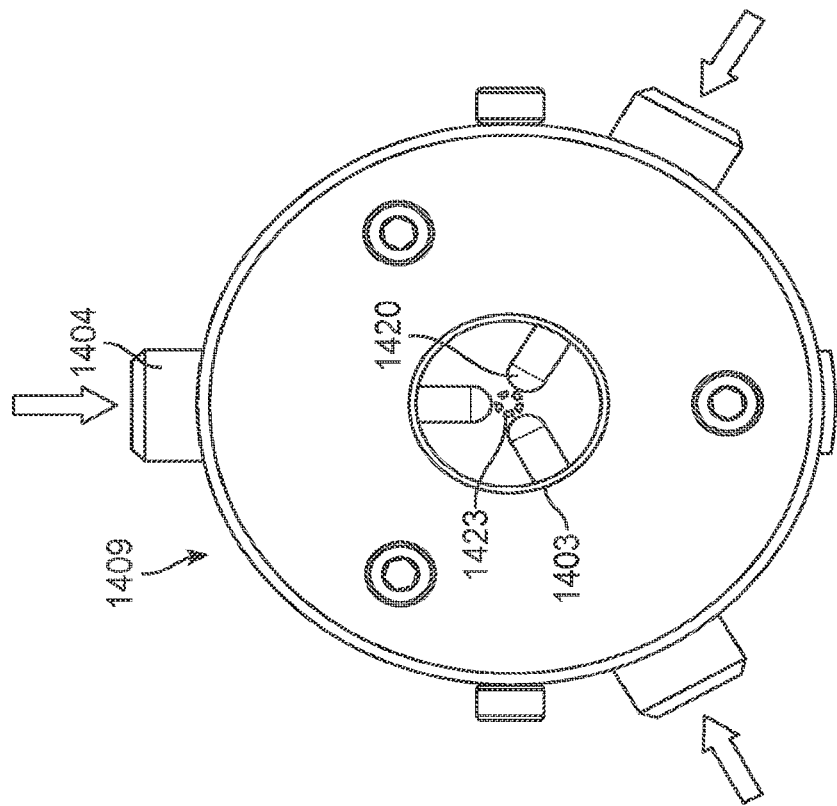
FIG. 18B is and end view of the loading system in FIG. 14 in an actuated configuration.
Figure 18A:
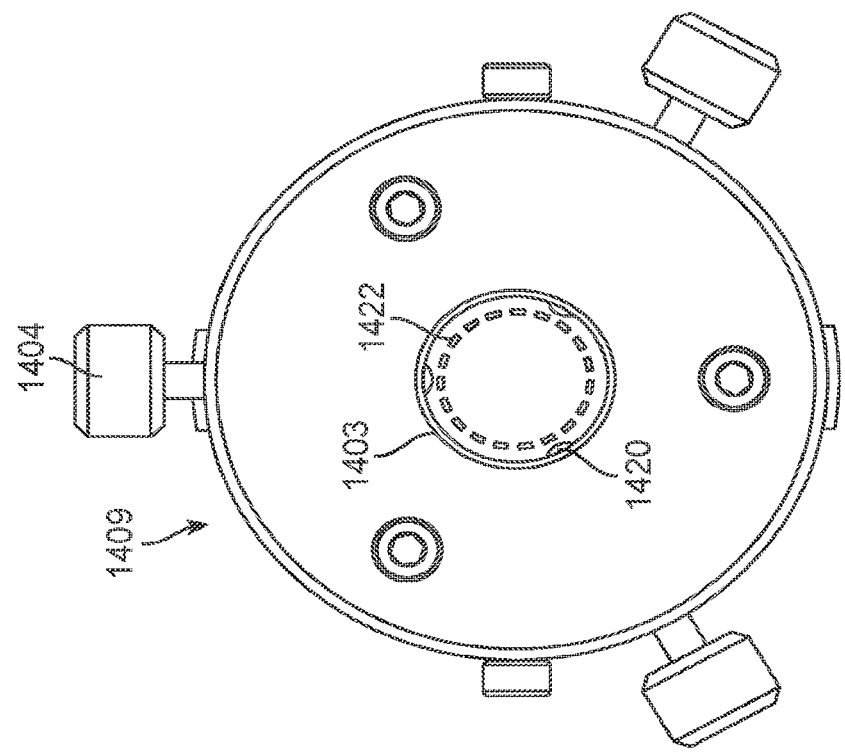
FIG. 18A is an end view of the loading system in FIG. 14 in an unactuated configuration.

As seen in FIG. 18A, the end view of the C stage 1409 has an outlet orifice 1403. An uncompressed diametral circle 1422, representing the initial large diameter at which the tips 1420 of the spring loaded actuators 1404 are normally located is also illustrated. It is then shown in FIG. 18B that upon actuation, the tips 1420 of the spring loaded actuators 1404 translate and conform to a smaller, compressed diametral circle 1423. This is the mechanism through which selective prosthetic valve deflection is achieved in order to mate portions of the prosthetic valve with the delivery system.

One of skill in the art will appreciate that the loading device is not limited to three separate housings. Alternative embodiments of the device may include a single housing that incorporates some or all of the features of the three individual housings. Single housing embodiments are illustrated in FIGS. 27-33 and described below. An exemplary embodiment of a single housing loading device is described in greater detail below. Other alternative embodiments may include either the A or B housing and the C housing, and this configuration may be as two couplable housings, or a single integrated housing. In still other embodiments, the entire diameter reduction may be accomplished with a single tapered channel in a single housing and the selective deflection may be in that same housing or in a separate housing. One of skill in the art will appreciate that any combination or permutation of the three housings and their corresponding features may be used in a loading device to load a prosthesis onto a delivery system.

Figure 19:
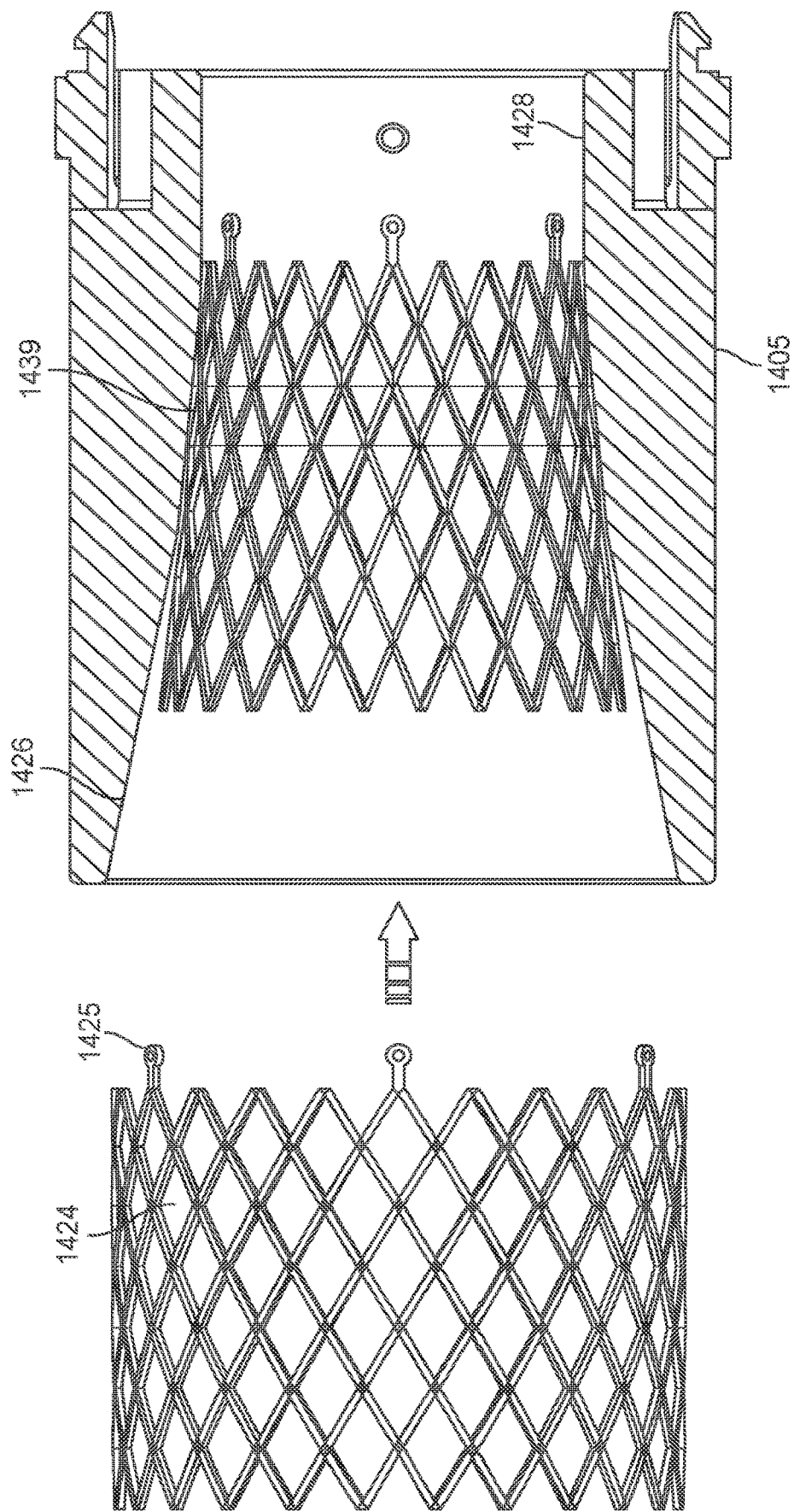
FIG. 19 is a partial cross-sectional view of a prosthesis with commissures being inserted into the first stage of the loading system of FIG. 14.

FIGS. 19-26B illustrate an exemplary method of using the loading device described above for loading a prosthetic valve such as those described herein onto a delivery system such as those described herein. FIG. 19 illustrates the initial interaction between the A stage 1405 and a generic prosthetic heart valve 1424. In this example, the generic heart valve 1424 includes three anchoring tabs 1425 which are required for location and attachment of this valve model to a delivery system. These three anchoring tabs 1425 may be equivalent to the commissure posts or struts previously described above with respect to the disclosed prosthetic mitral valve. As the generic prosthetic heart valve 1424 is manually pushed through the A stage 1405, the valve slides down an internally tapered section 1426, past a filleted transition zone 1439, and into a flat section 1428 of constant diameter. In order to safely reduce the diameter of a heart valve prosthesis that is at least partially manufactured from alloys such as Nitinol it is first necessary to cool the prosthesis in chilled saline, in order to bring the device below a temperature known as the austenitic finish temperature, which is specific to each alloy and dependant upon manufacturing processes. This is the temperature at which the crystalline structure of Nitinol becomes arranged in a manner that allows for plastic deformation, with little risk of permanent damage due to strain. When the generic prosthetic heart valve 1424 is positioned in the flat section 1428 and manually adjusted to acquire a circular shape, the A stage 1405 is ready to be attached to the B stage 1407, and this step of the procedure will be detailed below.

Figure 20:
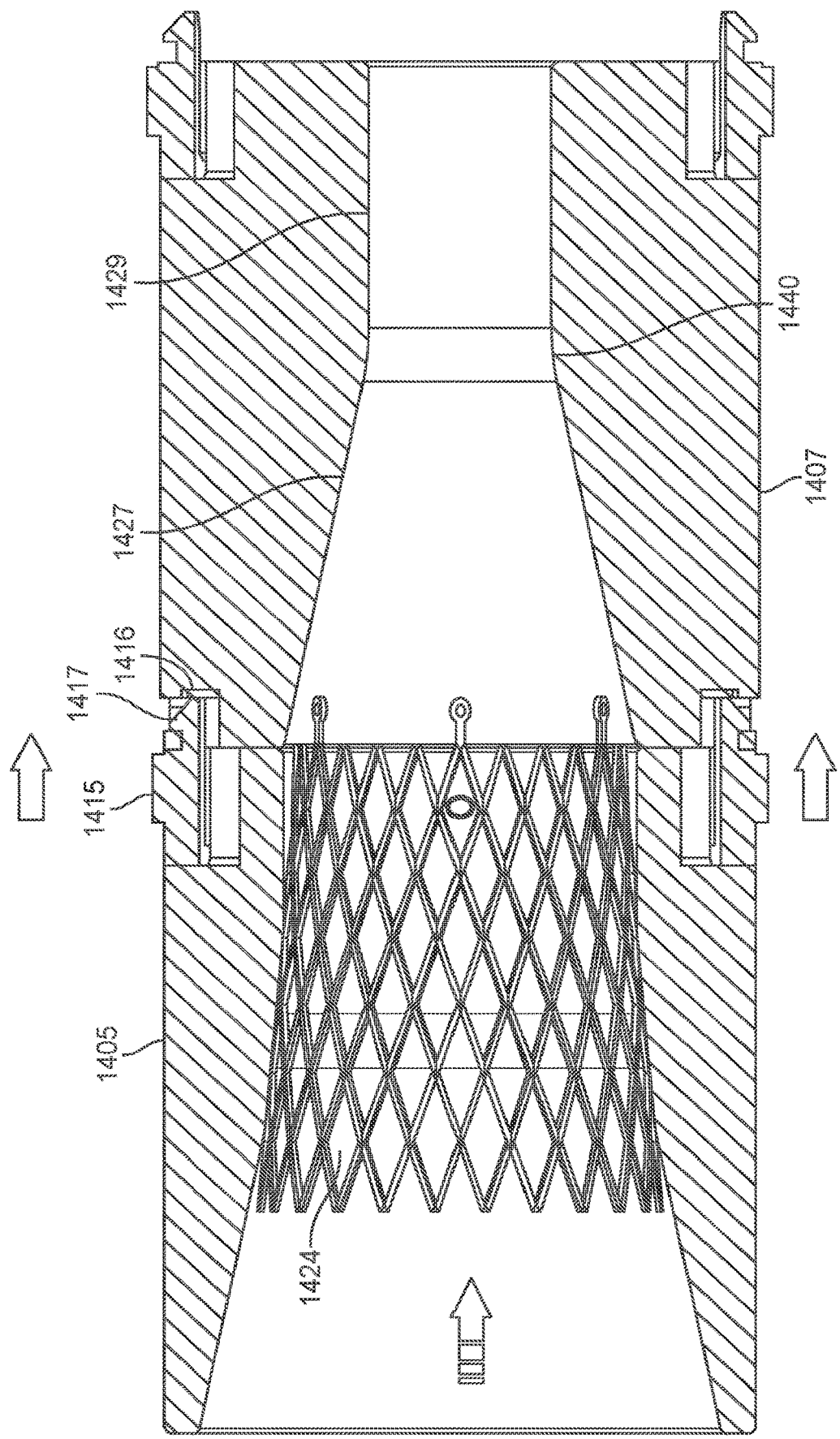
FIG. 20 is a partial cross-sectional view the prosthesis in FIG. 19 travelling from the first to the second stage of the loading system of FIG. 14.
Figure 21:
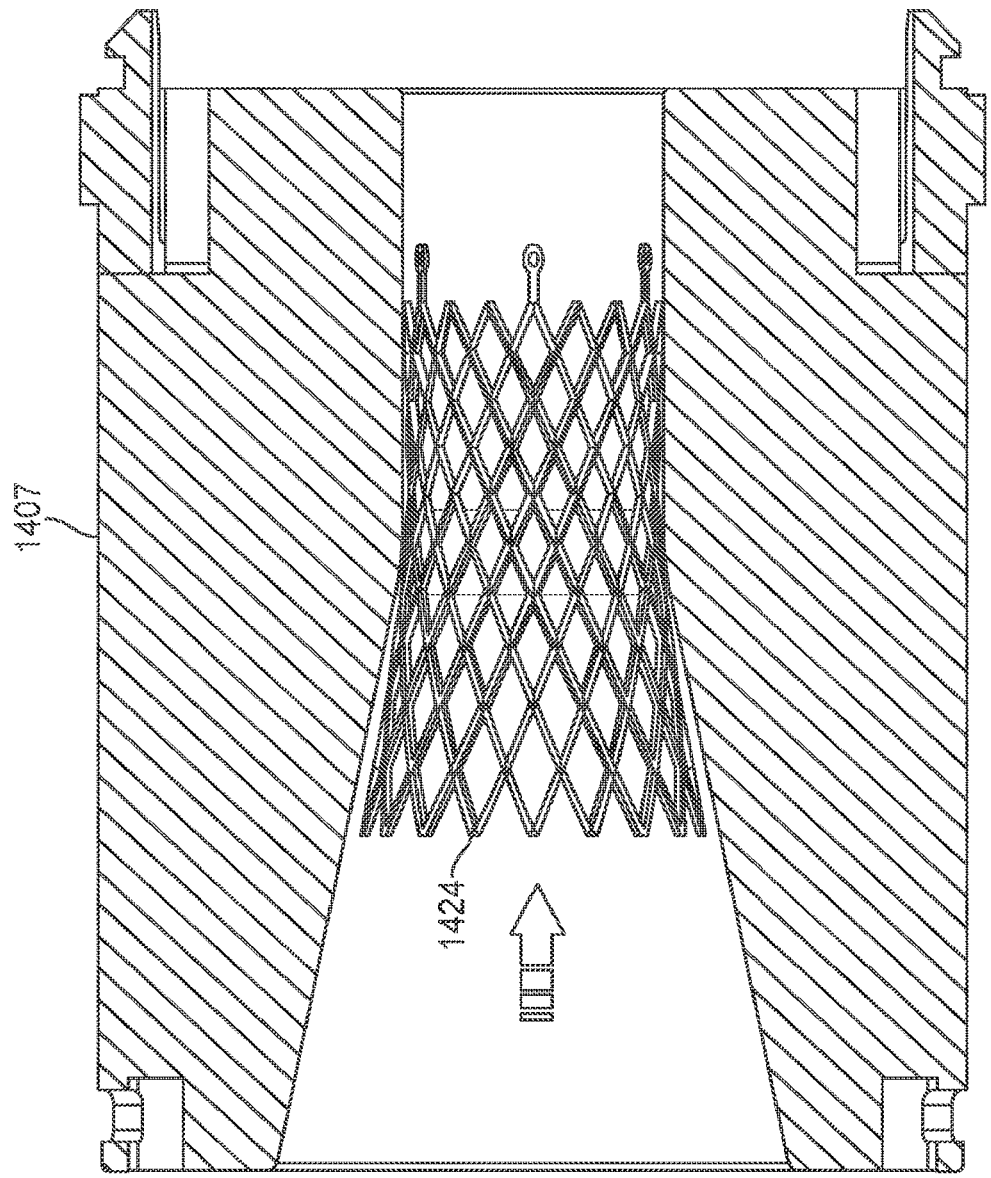
FIG. 21 is a partial cross-sectional view of the prosthesis in FIG. 19 travelling through the second stage of the loading system of FIG. 14.

As shown in FIG. 20, the A stage 1045 is latched onto the B stage 1407 by way of pressing cantilevered tabs 1415 on the A stage 1405 that end in snap fits 1417 into respective locking windows 1416 that reside on the B stage 1407. After latching the A stage 1405 onto the B stage 1407, the generic prosthetic heart valve 1424 can be advanced across the junction and into an internally tapered section 1427, past a filleted transition zone 1440 and finally into a flat section 1429 of constant and final diameter. This step of the procedure can be more readily appreciated if viewed in FIG. 21, as it becomes necessary to detach the A stage 1405 from the B stage 1407 as the generic prosthetic heart valve 1424 assumes its end location in the B stage 1407.

Figure 22:
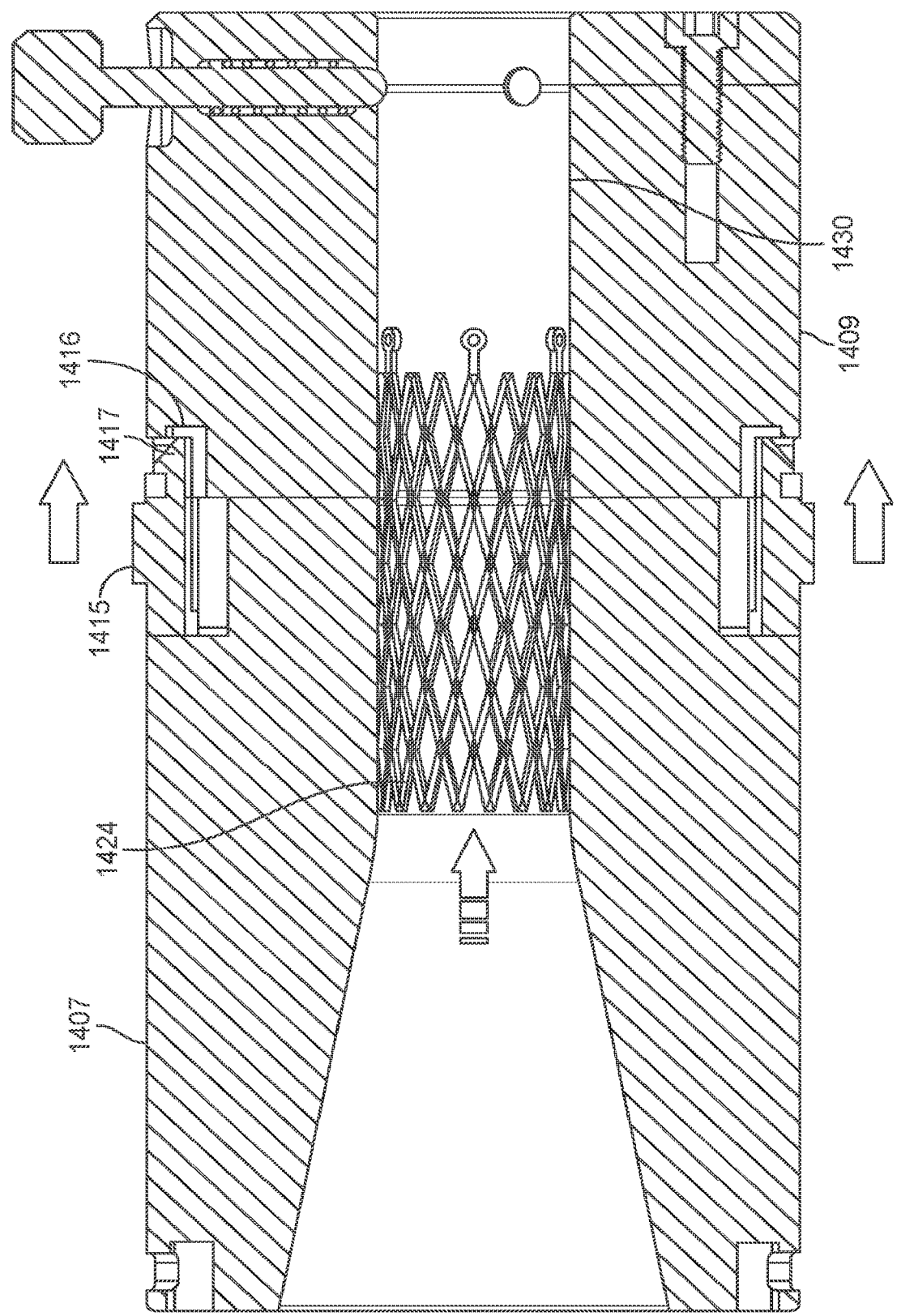
FIG. 22 is a partial cross-sectional view of the prosthesis in FIG. 19 travelling from the second to the third stage of the loading system in FIG. 14.

As shown in FIG. 22, the B stage 1407 is latched onto the C stage 1409 by way of pressing cantilevered tabs 1415 on the B stage 1407 that end in snap fits 1417 into respective locking windows 1416 that reside on the C stage 1409. After latching the B stage 1407 onto the C stage 1409, the generic prosthetic heart valve 1424 can be advanced across the junction and into a flat section 1430 of constant and final diameter. The diameter of the flat section 1430 is designed to optimally compress the valve 1424 to the smallest diameter that would still allow passage of a respective delivery system or components thereof, and still allow access to the relevant stent features required for valve loading and anchoring to the delivery system.

Figure 23:
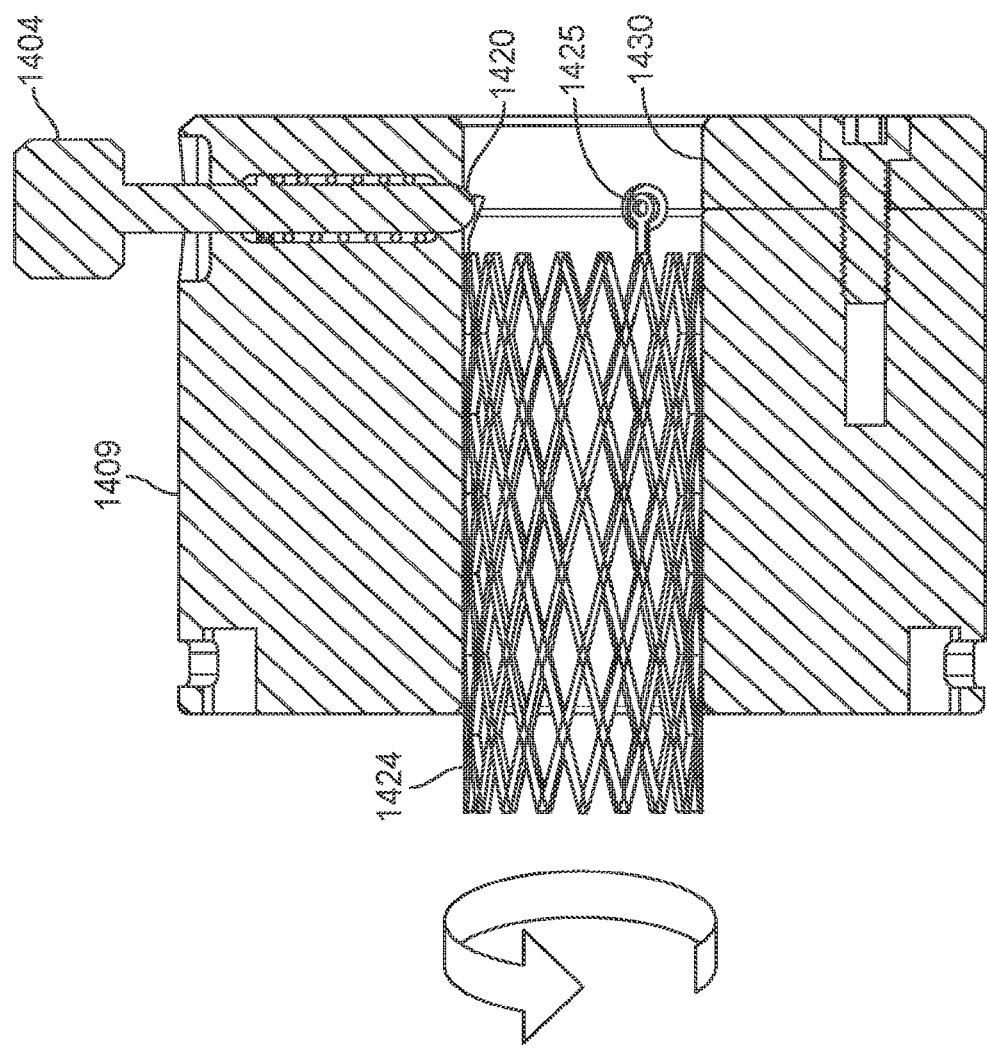
FIG. 23 is a partial cross-sectional view of the prosthesis in FIG. 19 positioned within the third stage of the loading system of FIG. 14.

The final compressed location of a generic prosthetic heart valve 1424 within the C stage 1409 can be seen in FIG. 23. Before accurate anchoring tab 1425 deflection can be performed, it may first be necessary to rotate the valve 1424 within the flat section 1430 of constant diameter so as to align all anchoring tabs 1425 with the tips 1420 of respective spring loaded actuators 1404. This practice is illustrated in FIG. 23. After performing anchoring tab 1425 alignment, accurate spring loaded actuator 1404 operation becomes possible.

As can be seen in FIG. 24, a generic delivery system 1432 can be introduced to the outlet orifice 1403 of the C stage 1409, and retaining pockets (also referred to herein as receptacles or slots) 1434 located in an anchoring hub 1433 can be brought into alignment with the anchoring tabs 1425 of a generic prosthetic heart valve 1424.

FIG. 25 illustrates the mechanism by which the tips 1420 of the spring loaded actuators 1404 are pressed into the anchoring tabs 1425 of a generic prosthetic heart valve 1424, so as to deflect them by bending, and force the anchoring tabs 1425 into respective retaining pockets 1434 located in the anchoring hub 1433 of a generic delivery system 1432.

Figure 26A:
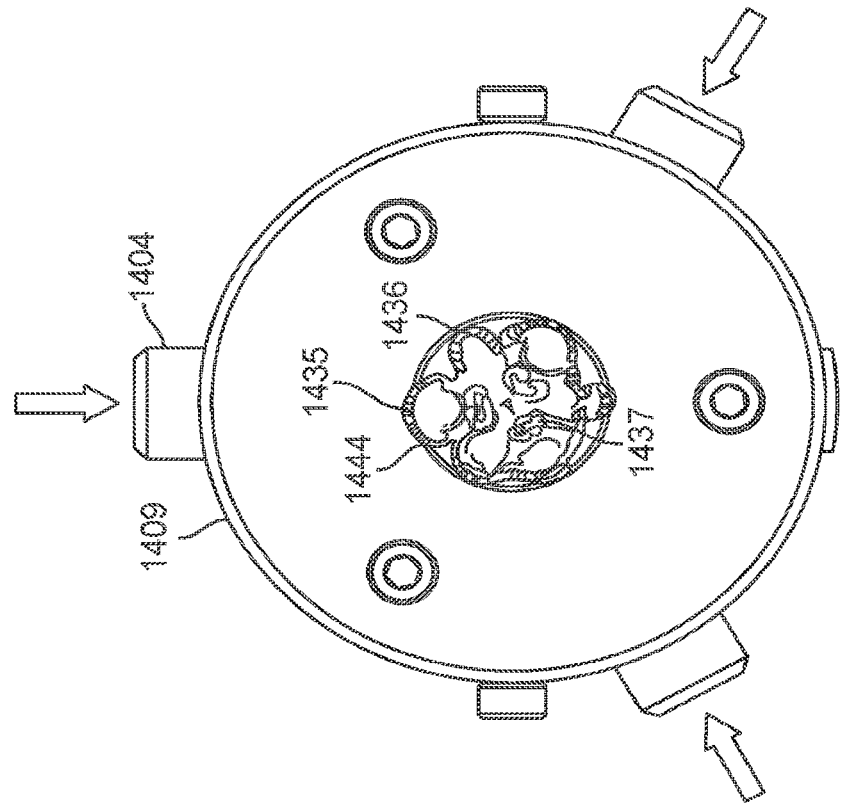
FIG. 26A is an end view of the loading system in FIG. 14 showing a prosthesis in a collapsed but undeflected configuration.

FIG. 26A shows an end view of the C stage 1409, with a prosthetic heart valve 1444 such as those previously described above, compressed and in place prior to final deflection. Relevant features of the prosthetic heart valve 1444 include the ventricular skirt 1435, trigonal tabs 1436, and commissure anchors (also referred to as commissure posts or struts) 1437, details of which can be found elsewhere in this specification.

Figure 26B:
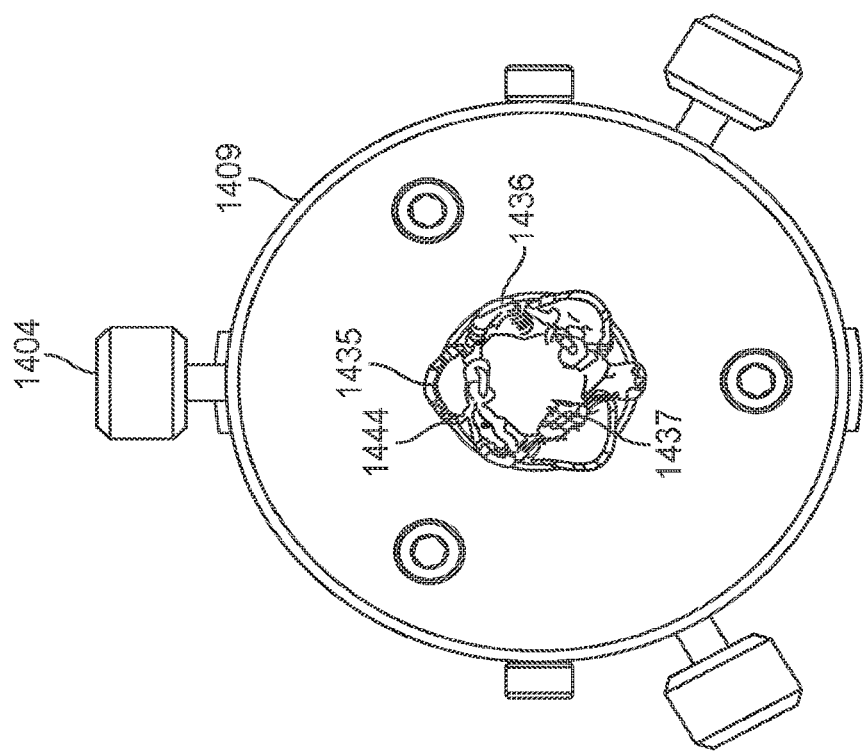
FIG. 26B is an end view of the loading system in FIG. 14 with a prosthesis in a collapsed and deflected configuration.

FIG. 26B shows an end view of the C stage 1409, with a prosthetic heart valve 1444 compressed and in place after final deflection. Note that relevant features such as the ventricular skirt 1435, and trigonal tabs 1436 have not been displaced by any portion of the spring loaded actuators 1404, and that only the commissure anchors 1437 have been displaced to a final reduced diameter and made available to respective features on the respective delivery system, details of which are disclosed elsewhere in this specification. Once the commissure anchors 1437 have been deflected radially inward and positioned in the corresponding receptacles on the delivery catheter, an outer shaft or sheath may be slidably disposed thereover in order to capture the commissure anchors. Another outer shaft or sheath may then be slidably disposed over the remainder of the prosthetic valve to capture it and hold it in position during delivery. Release of the prosthetic valve is described below.

FIGS. 27-29B illustrate another exemplary embodiment of a loading system. While this embodiment is similar to the embodiment previously described, this embodiment has the advantage of providing support to both internal and external surfaces of the prosthesis during loading, and also the actuators are simultaneously actuated.

Figure 27:
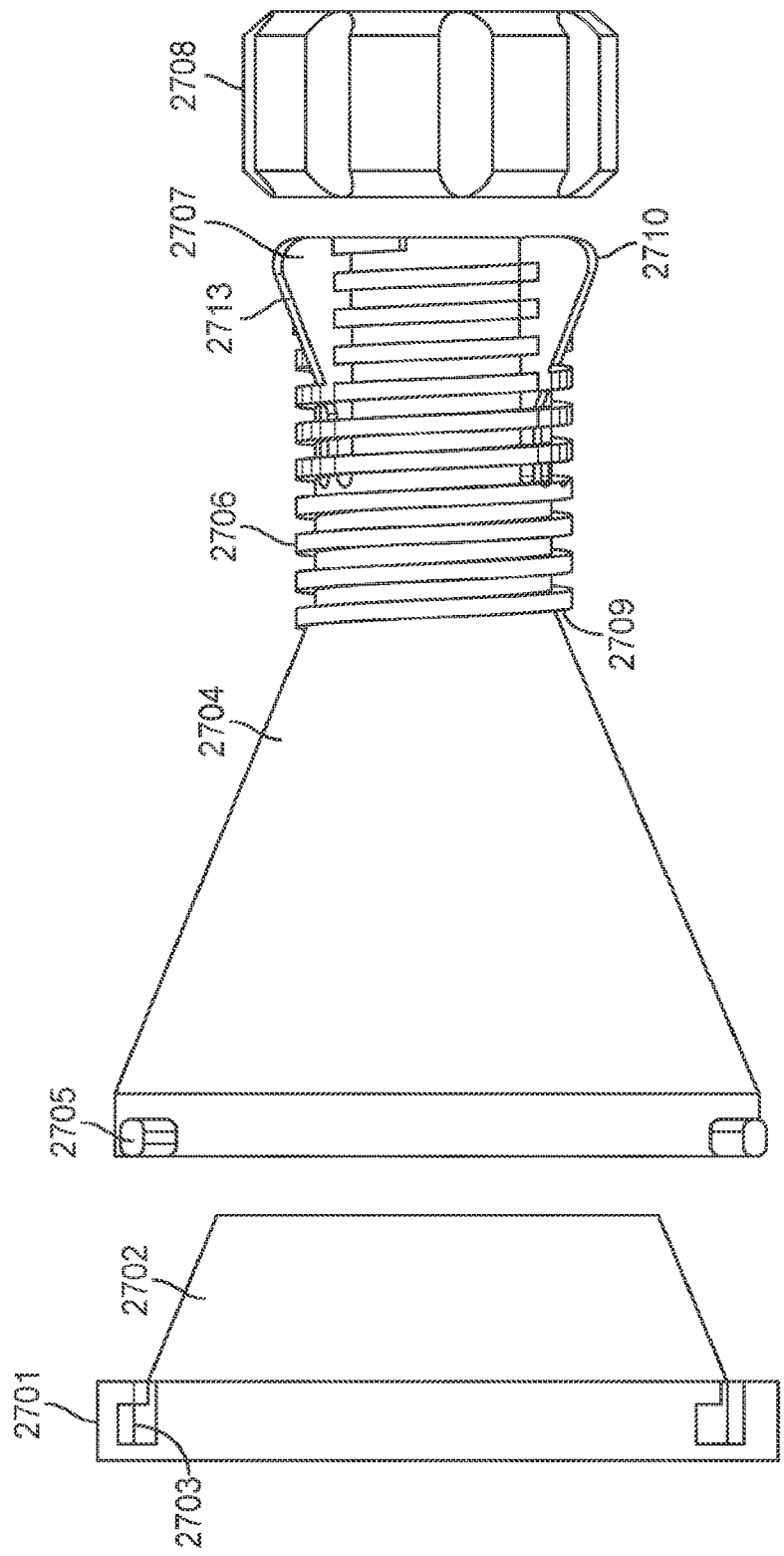
FIG. 27 illustrates another exemplary embodiment of a loading system.

As seen in FIG. 27, a variation of the valve loading system is detailed. An inner cone 2701 provides support for the internal surface of a valve or prosthesis to be loaded. The important features of inner cone 2701 include a conical inclined plane 2702, and twistable locking mechanism 2703 such as a bayonet lock. The conical inclined plane 2702 aids in seating a valve to be loaded, while the twistable locking mechanism 2703 allows the inner cone 2701 to be securely fastened to an outer cone 2704, through a twisting motion that will be further described below.

Three locking pegs 2705 on the circumference of the outer cone 2704 allow the base of the outer cone 2704 to be mated to the locking mechanism 2703 of the inner cone 2701. A threaded section 2706 of the outer cone 2704 begins at an initial end 2709 and terminates at a final end 2710, and is threaded in a manner that allows for mating to a displacement nut 2708 which has matching internal threads. As the displacement nut 2708 is screwed forward from initial end 2709 to final end 2710, the leading edge of the displacement nut 2708 forces a fin or other finger-like member 2707 to be pushed down due to the inclined plane that comprises the rib 2713 of the fin 2707, and the sliding motion of the displacement nut 2708 as it rides over the fin 2707. A plurality of fins 2707 may be spaced circumferentially about the outer cone 2708 at the final end 2710 in order to affect the desired mechanism. This embodiment preferably has three fins spaced generally 120 degrees apart.

Figure 28B:
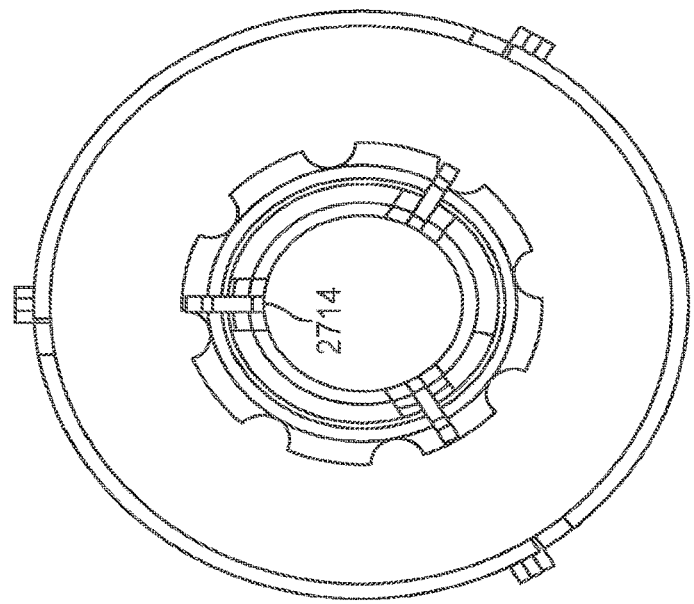
FIGS. 28A-28B illustrate the loading system of FIG. 27 prior to actuation.
Figure 28A:
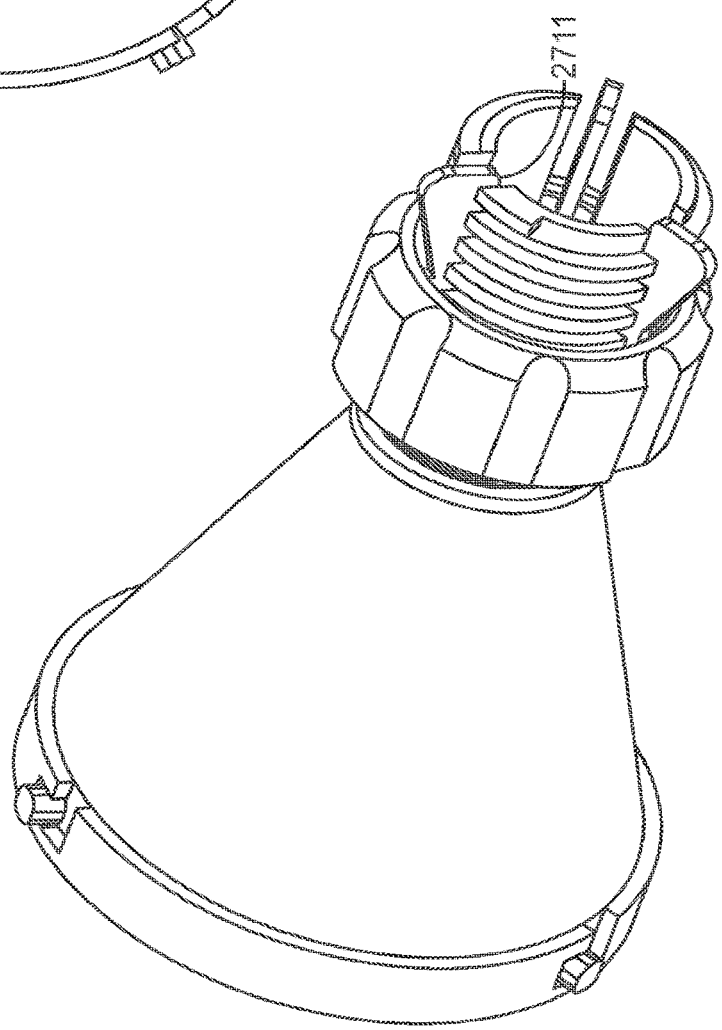

As seen in FIG. 28A and FIG. 28B, end views of the device provide further detail of the inherent mechanical relationships between relevant parts. Pad 2714 is seen in FIG. 28B resting in an un-deflected position 2711. As the displacement nut 2708 rides over the threaded section 2706, the position of pad 2714 moves radially inward to a deflected position 2712, as seen in FIG. 29A. A plurality of pads 2714 may be spaced circumferentially about the outer cone 2708 at the final end 2710 in order to affect the desired mechanism in conjunction with an equal plurality of fins 2707.

Figure 30:
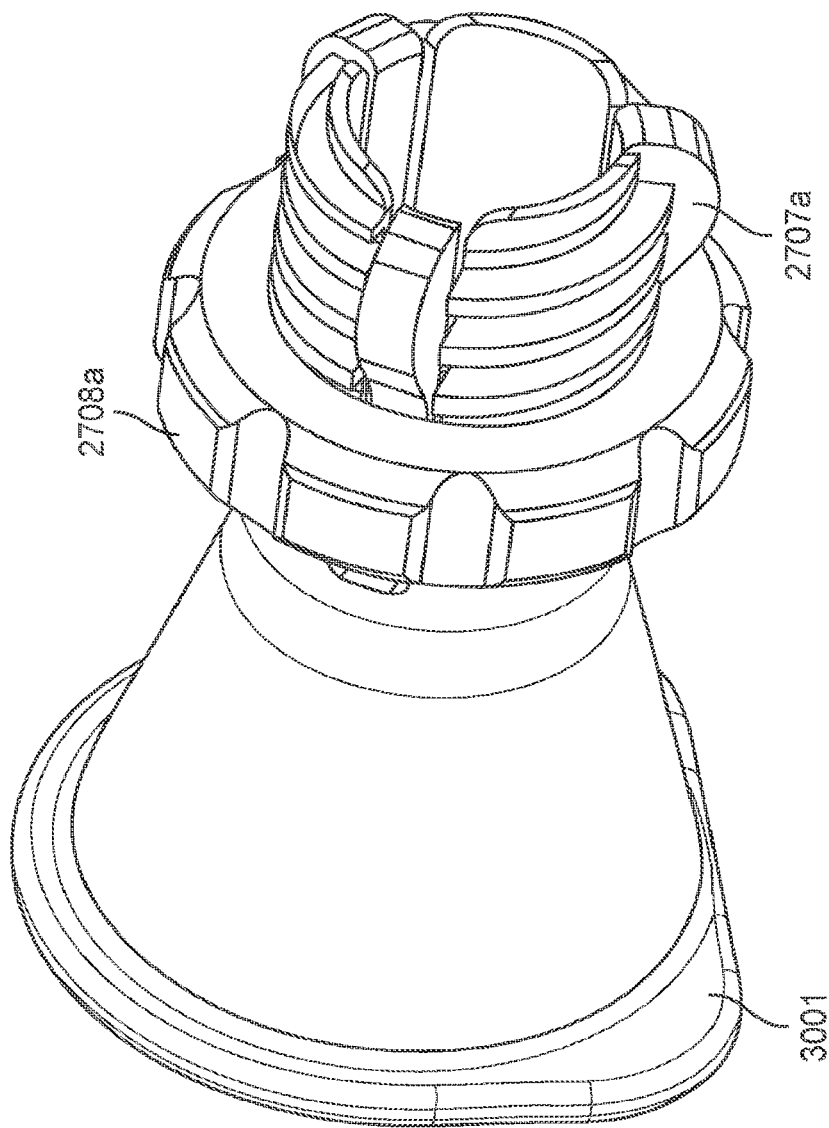
FIGS. 30-33 illustrate still another exemplary embodiment of a loading system.

FIGS. 30-33 illustrate another exemplary embodiment of a loading fixture. FIG. 30 is a perspective view of the loading system. The fingers 2707a are thicker than previous embodiments and also have a cammed profile instead of a ramped profile. Also, the displacement nut 2708a is thinner than previous embodiments. These features help the operator to smoothly actuate the displacement nut and radially collapse a portion of the prosthesis for loading onto a delivery system. Additionally, this embodiment includes a "D" shaped flange 3001 on the inlet side of the cone (this feature can also be seen in FIG. 33) which can be used for valve alignment purposes. Other alignment features will be illustrated in FIGS. 31-32. Thus the operator will know that the flat portion of the "D" shaped flange is also the flat portion of the "D" shaped prosthesis.

Figure 31:
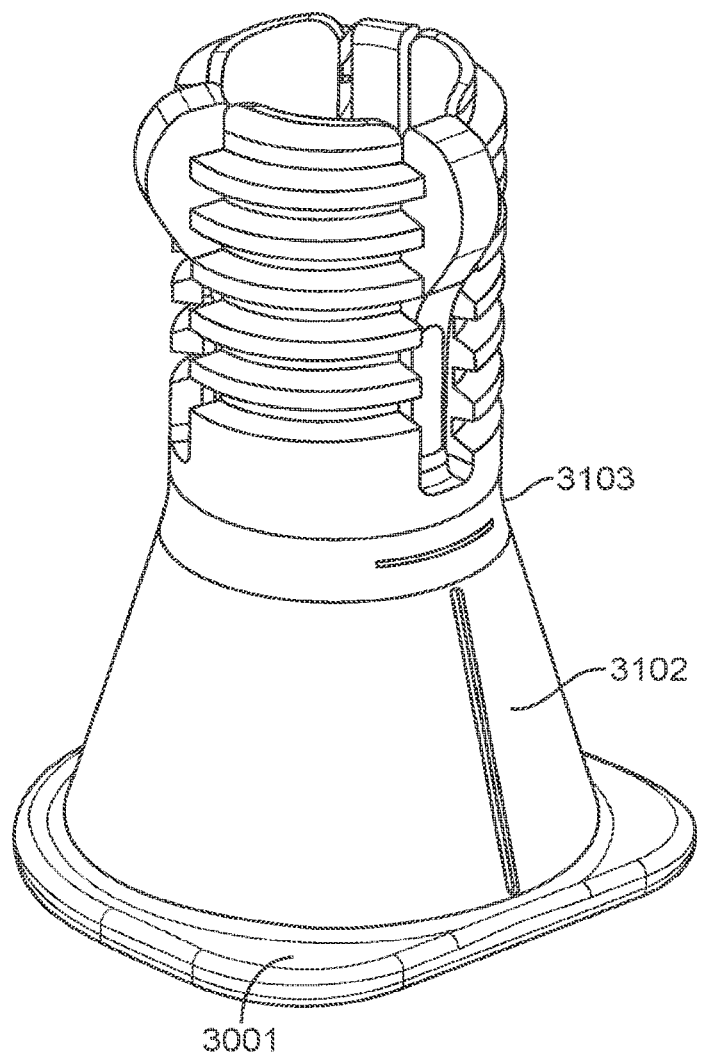

FIG. 31 is an isometric view of the loading cone with the displacement nut removed, illustrating optional features which may be used in any of the loading fixture embodiments. A vertical slot 3102 appearing on the tapered portion of the loading cone acts as a landmark for a suture (not illustrated) on the prosthetic valve to be aligned with. This allows the valve to be accurately located during loading. A horizontal slot 3103 appearing on the tapered transition portion of the loading cone acts as a landmark with which the atrial skirt region of the stent can be registered against, in order to accurately locate the valve prior to commissure capture. The loading cone may be formed of an optically clear polymer such as polycarbonate which allows the user to see valve features/landmarks throughout the loading process.

Figure 32:
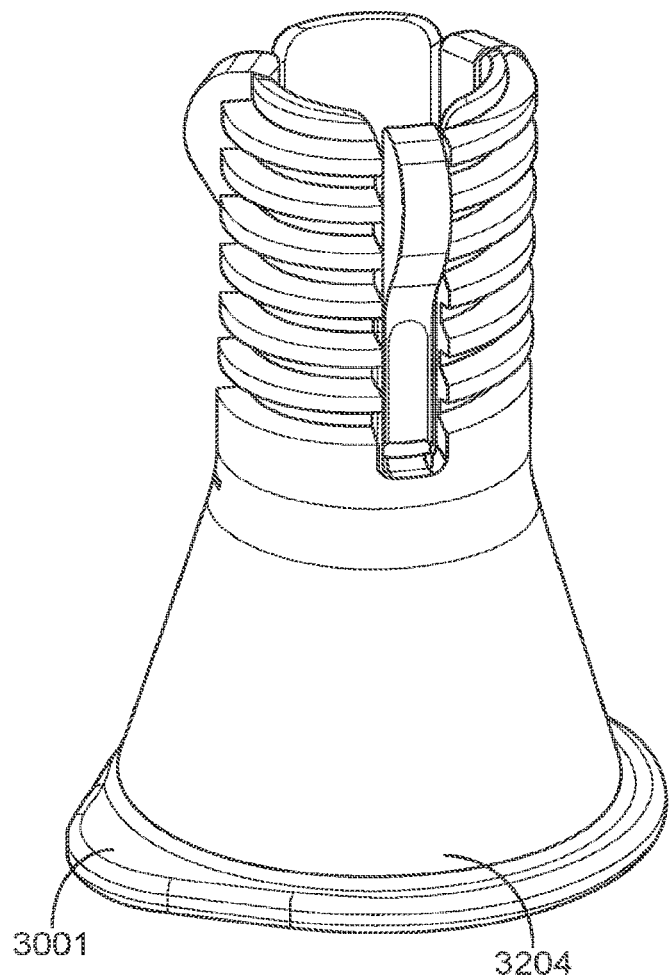

FIG. 32 is an isometric view of the loading cone. An optional size designation 3004 has been stamped on the tapered section of the cone adjacent to the D-shaped flange 3001. Indicia allow a user to easily identify and select the appropriate loading fixture.

Figure 33:
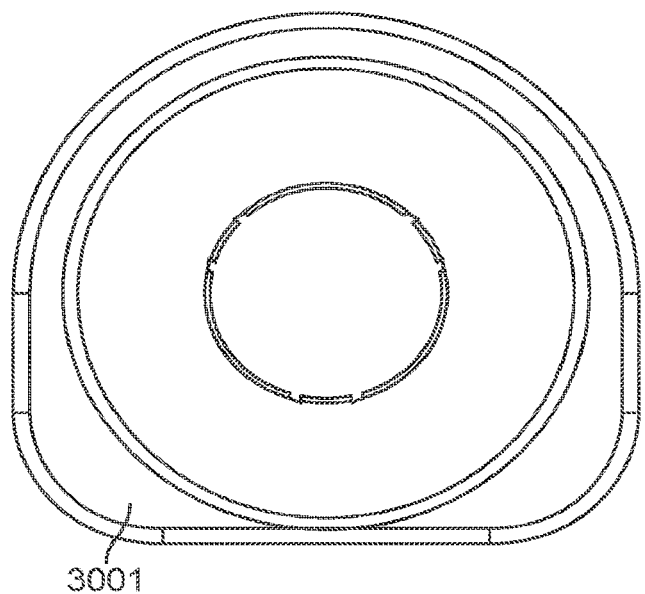

FIG. 33 is an end view of the loading cone. The D-shaped flange 3001 can clearly be seen in this view. When loading a valve into the loading cone, an operator may orient the flat side of the valve with the flat portion of the D-shaped flange prior to insertion.

The embodiment of FIGS. 30-33 provides a single stage for collapsing a prosthetic valve and therefore is easier than a multiple stage loading fixture. The prosthetic valve may be chilled in cold saline during loading as previously discussed above. Because this embodiment is smaller and has fewer parts than other embodiments, it is lighter and easier to use, and also manufacturing costs are reduced. It may be actuated with a single hand while other embodiments may require more than one hand.

Delivery Method. A number of methods may be used to deliver a prosthetic cardiac valve to the heart. Exemplary methods of delivering a prosthetic mitral valve may include a transluminal delivery route which may also be a transseptal technique which crosses the septum between the right and left sides of the heart, or in more preferred embodiments, a transapical route may be used such as illustrated in FIGS. 12A-12L. The delivery device previously described above may be used to deliver any of the embodiments of prosthetic valves described herein, or other delivery devices and other prosthetic valves may also be used, such as those disclosed in U.S. patent application Ser. No. 13/096,572, previously incorporated herein by reference. However, in this preferred exemplary embodiment, the prosthetic cardiac valve of FIG. 6 is used so that the anterior tabs deploy first, followed by the posterior tab, and then the ventricular skirt.

Figure 12A:
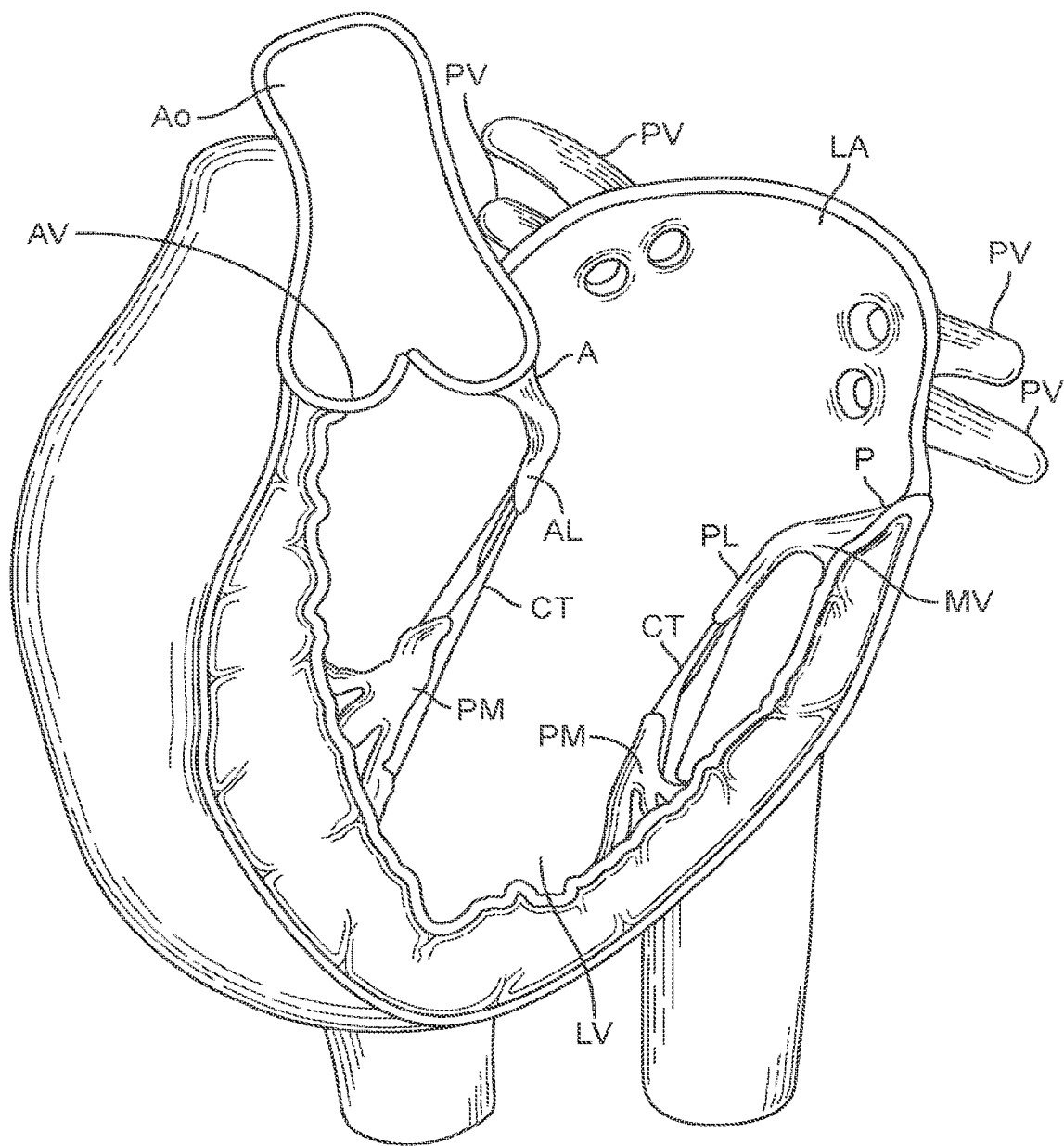
FIGS. 12A-12L illustrate an exemplary method of implanting a prosthetic cardiac valve.

FIG. 12A illustrates the basic anatomy of the left side of a patient's heart including the left atrium LA and left ventricle LV. Pulmonary veins PV return blood from the lungs to the left atrium and the blood is then pumped from the left atrium into the left ventricle across the mitral valve MV. The mitral valve includes an anterior leaflet AL on an anterior side A of the valve and a posterior leaflet PL on a posterior side P of the valve. The leaflets are attached to chordae tendineae CT which are subsequently secured to the heart walls with papillary muscles PM. The blood is then pumped out of the left ventricle into the aorta Ao with the aortic valve AV preventing regurgitation.

Figure 12B:
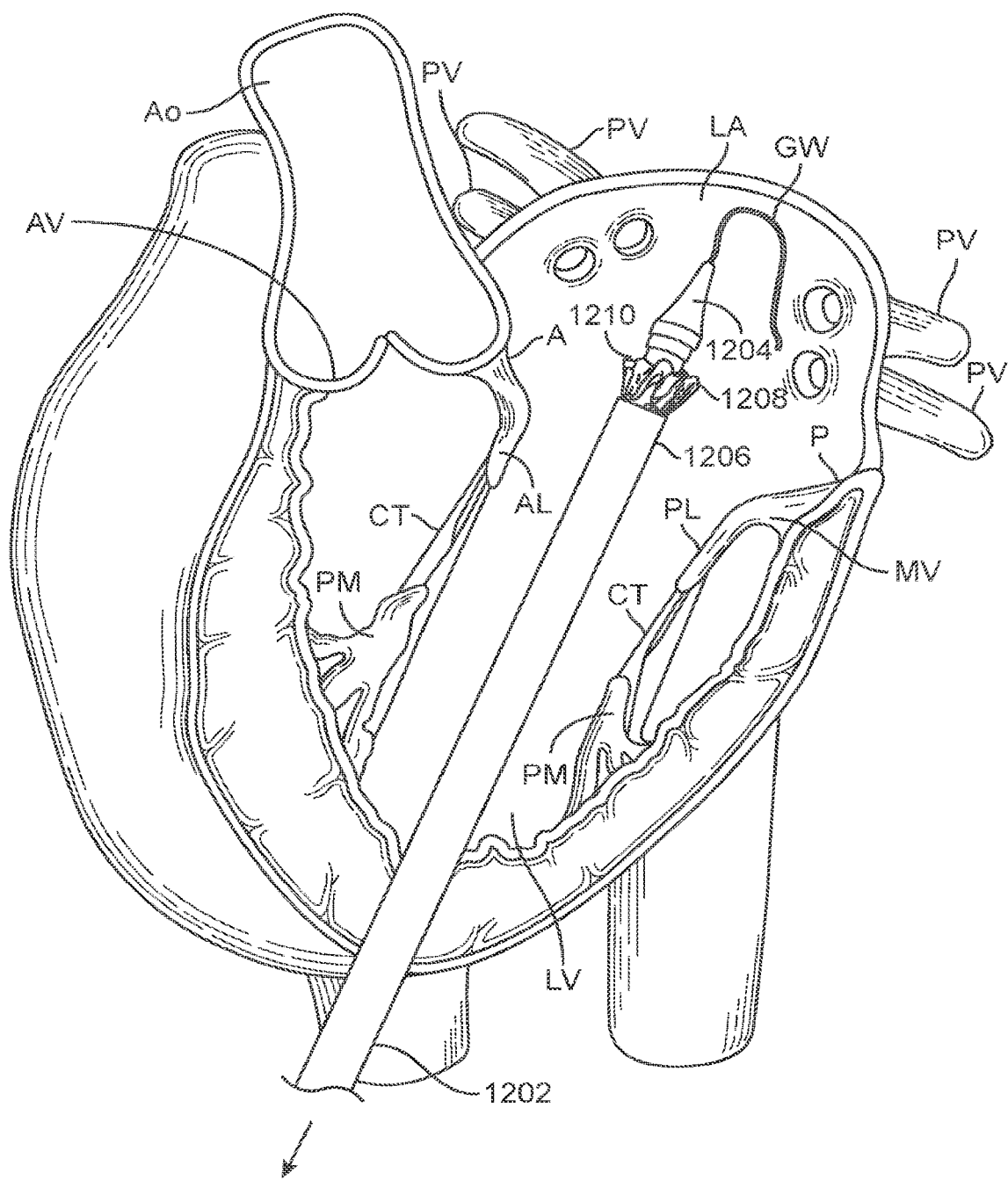
Figure 12C:
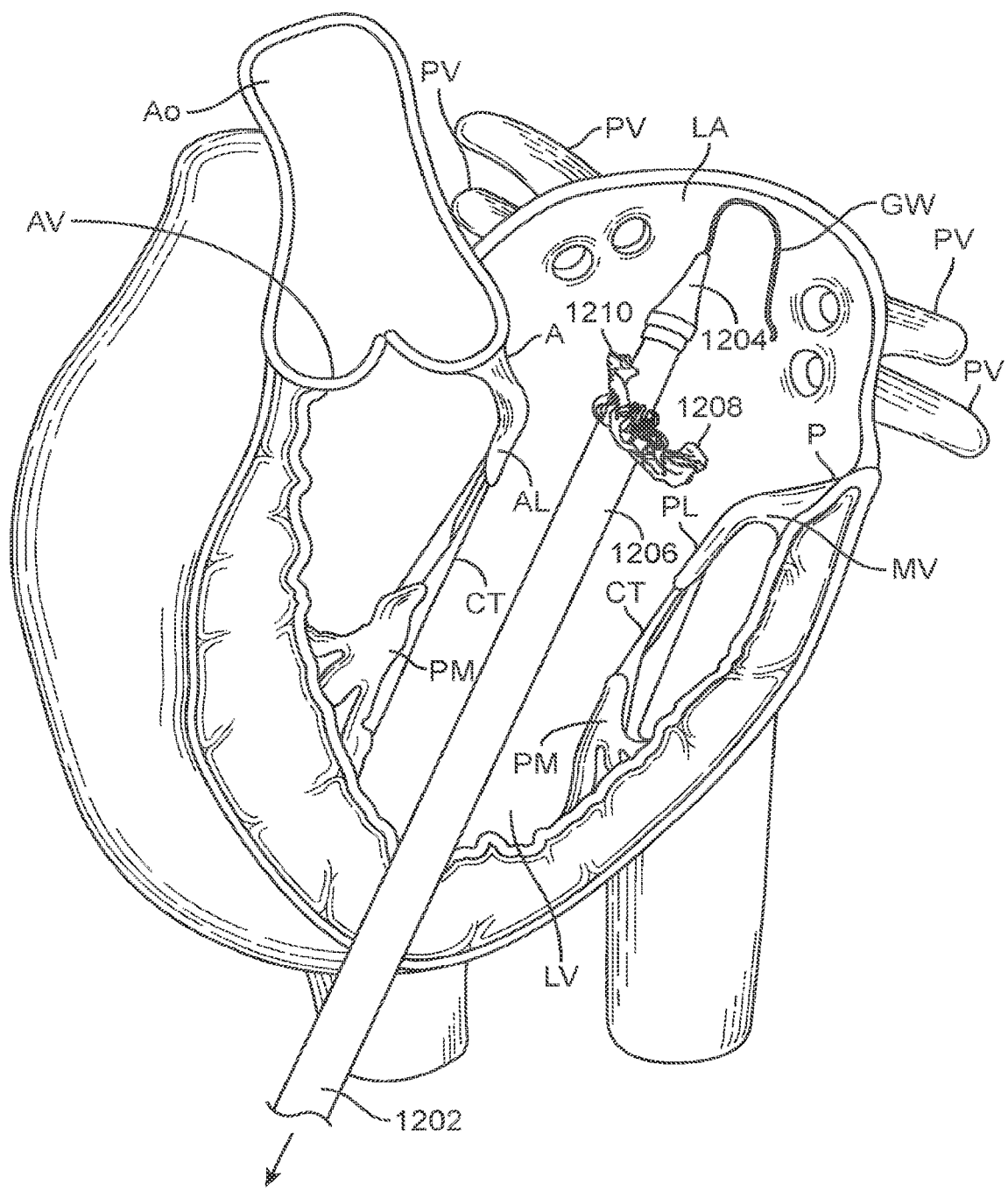
Figure 12D:
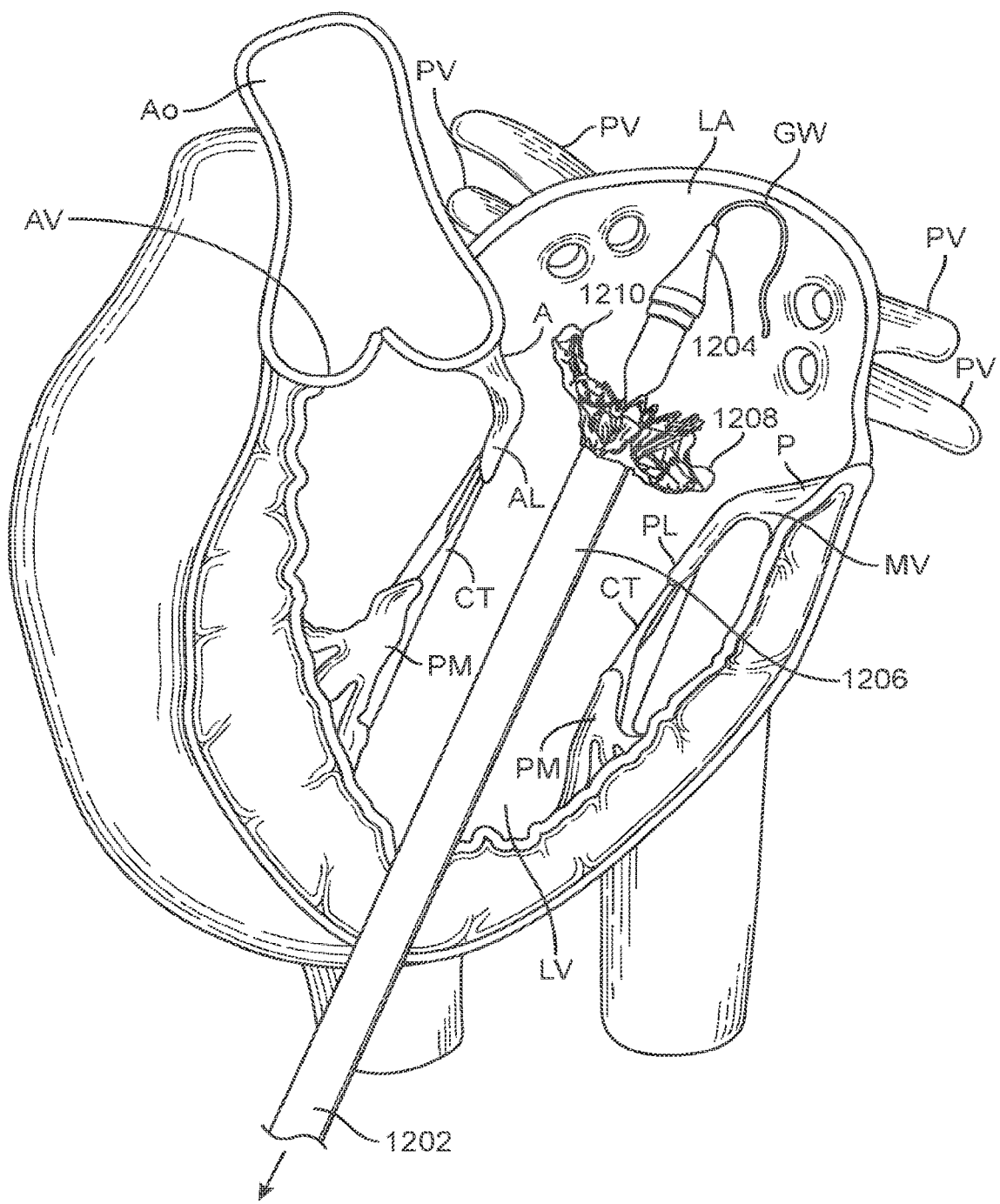

FIG. 12B illustrates transapical delivery of a delivery system 1202 through the apex of the heart into the left atrium LA. The delivery system 1202 may be advanced over a guidewire GW into the left atrium, and a tissue penetrating tip 1204 helps the delivery system pass through the apex of the heart by dilating the tissue and forming a larger channel for the remainder of the delivery system to pass through. The delivery catheter carries prosthetic cardiac valve 1208. Once the distal portion of the delivery system has been advanced into the left atrium, the outer sheath 1206 may be retracted proximally (e.g. toward the operator) thereby removing the constraint from the atrial portion of the prosthetic valve 1208. This allows the atrial skirt 1210 to self-expand radially outward. In FIG. 12C, as the outer sheath is further retracted, the atrial skirt continues to self-expand and peek out, until it fully deploys as seen in FIG. 12D. The atrial skirt may have a cylindrical shape or it may be D-shaped as discussed above with a flat anterior portion and a cylindrical posterior portion so as to avoid interfering with the aortic valve and other aspects of the left ventricular outflow tract. The prosthetic cardiac valve may be advanced upstream or downstream to properly position the atrial skirt. In preferred embodiments, the atrial skirt forms a flange that rests against a superior surface of the mitral valve and this anchors the prosthetic valve and prevents it unwanted movement downstream into the left ventricle.

Figure 12E:
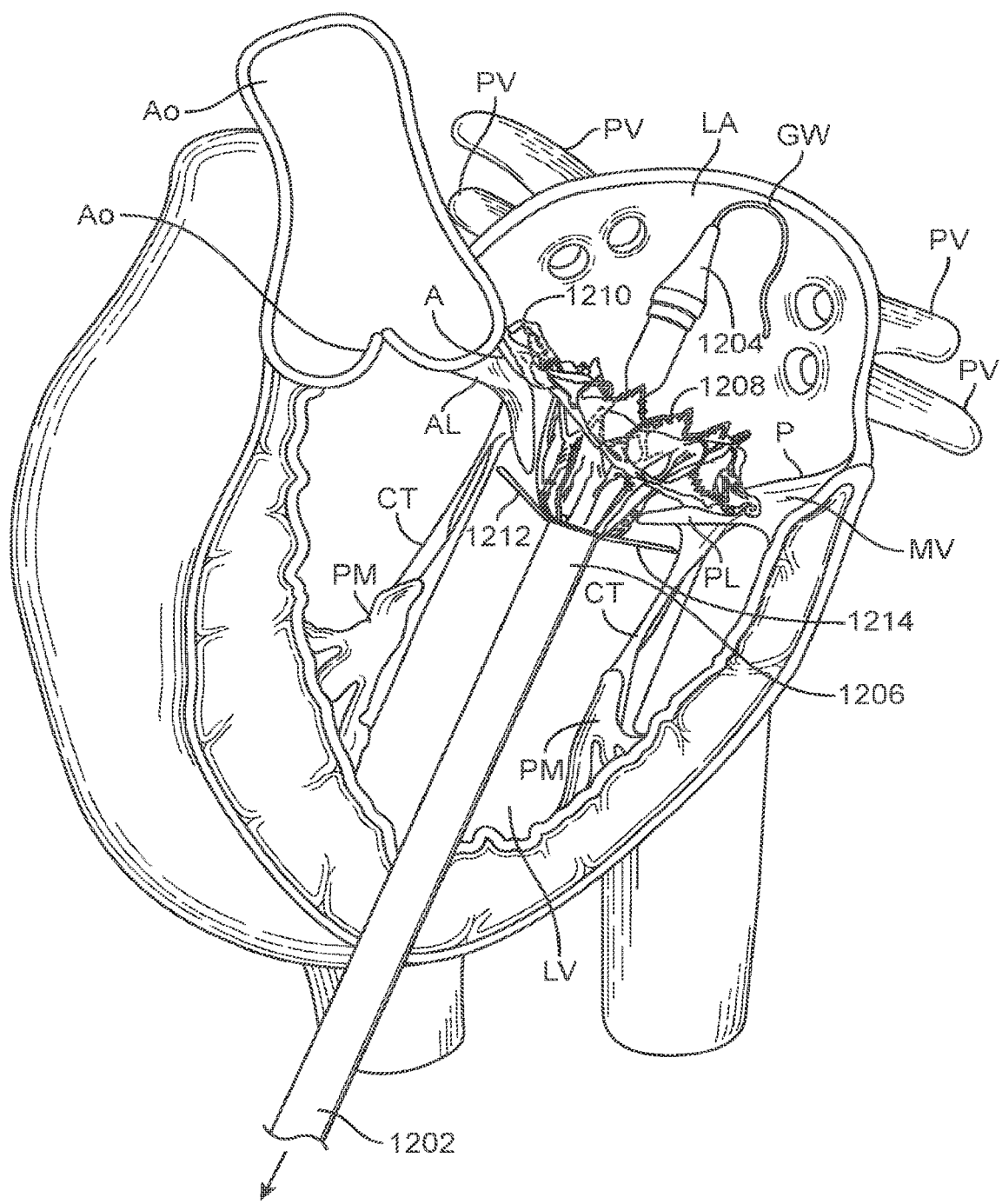
Figure 12F:
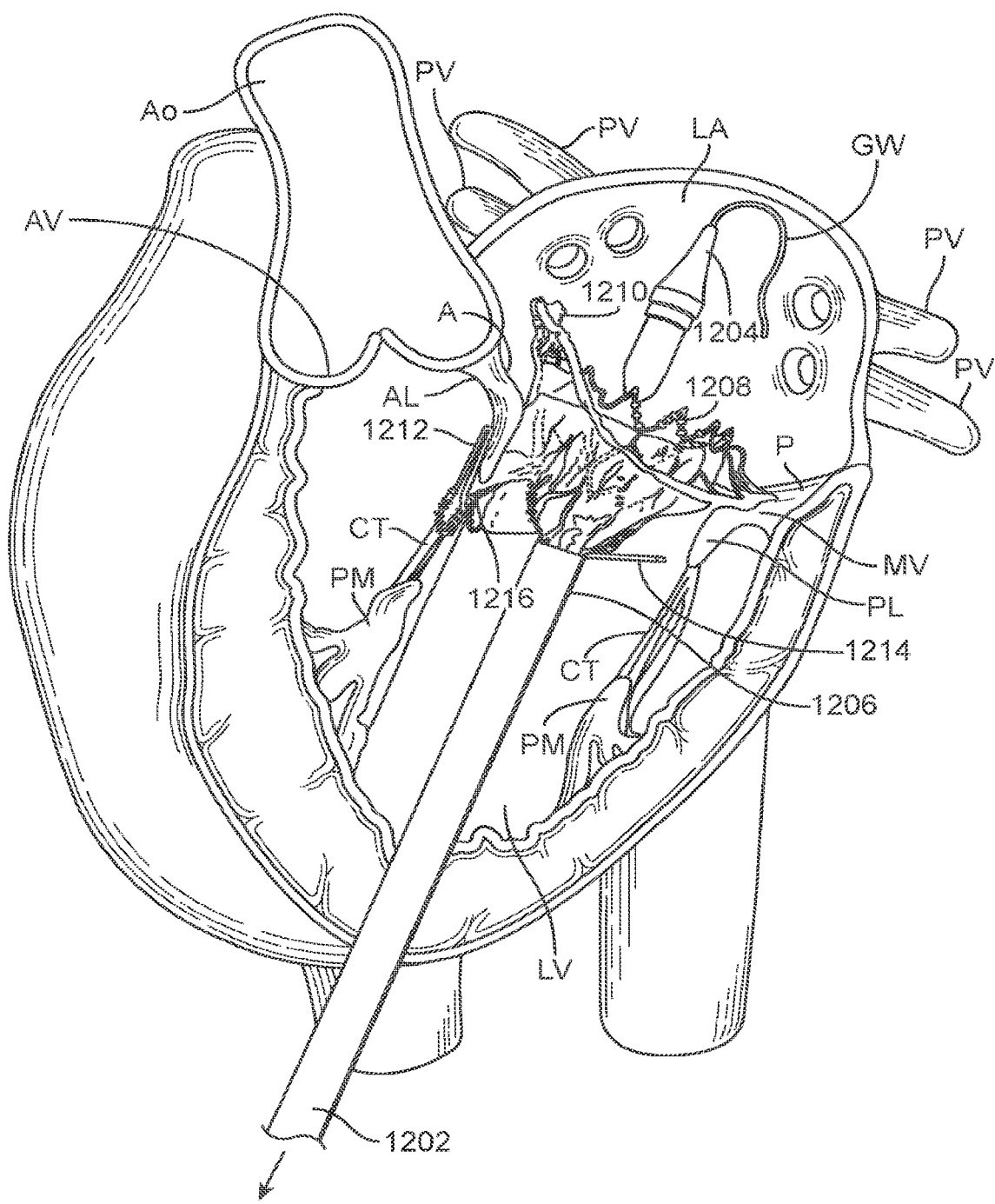

As the outer sheath 1206 continues to be proximally retracted, the annular region of the prosthetic cardiac valve self-expands next into engagement with the valve annulus. The annular region also preferably has the D-shaped geometry, although it may also be cylindrical or have other geometries to match the native anatomy. In FIG. 12E, retraction of sheath 1206 eventually allows both the anterior 1212 and posterior 1214 tabs to partially self-expand outward preferably without engaging the anterior or posterior leaflets or the chordae tendineae. In this embodiment, further retraction of the outer sheath 1206 then allows both the anterior tabs 1212 (only one visible in this view) to complete their self-expansion so that the anterior leaflet is captured between an inner surface of each of the anterior tabs and an outer surface of the ventricular skirt 1216, as illustrated in FIG. 12F. The posterior tab 1214 remains partially open, but has not completed its expansion yet. Additionally, the tips of the anterior tabs also anchor into the left and right fibrous trigones of the mitral valve, as will be illustrated in greater detail below.

Figure 12G:
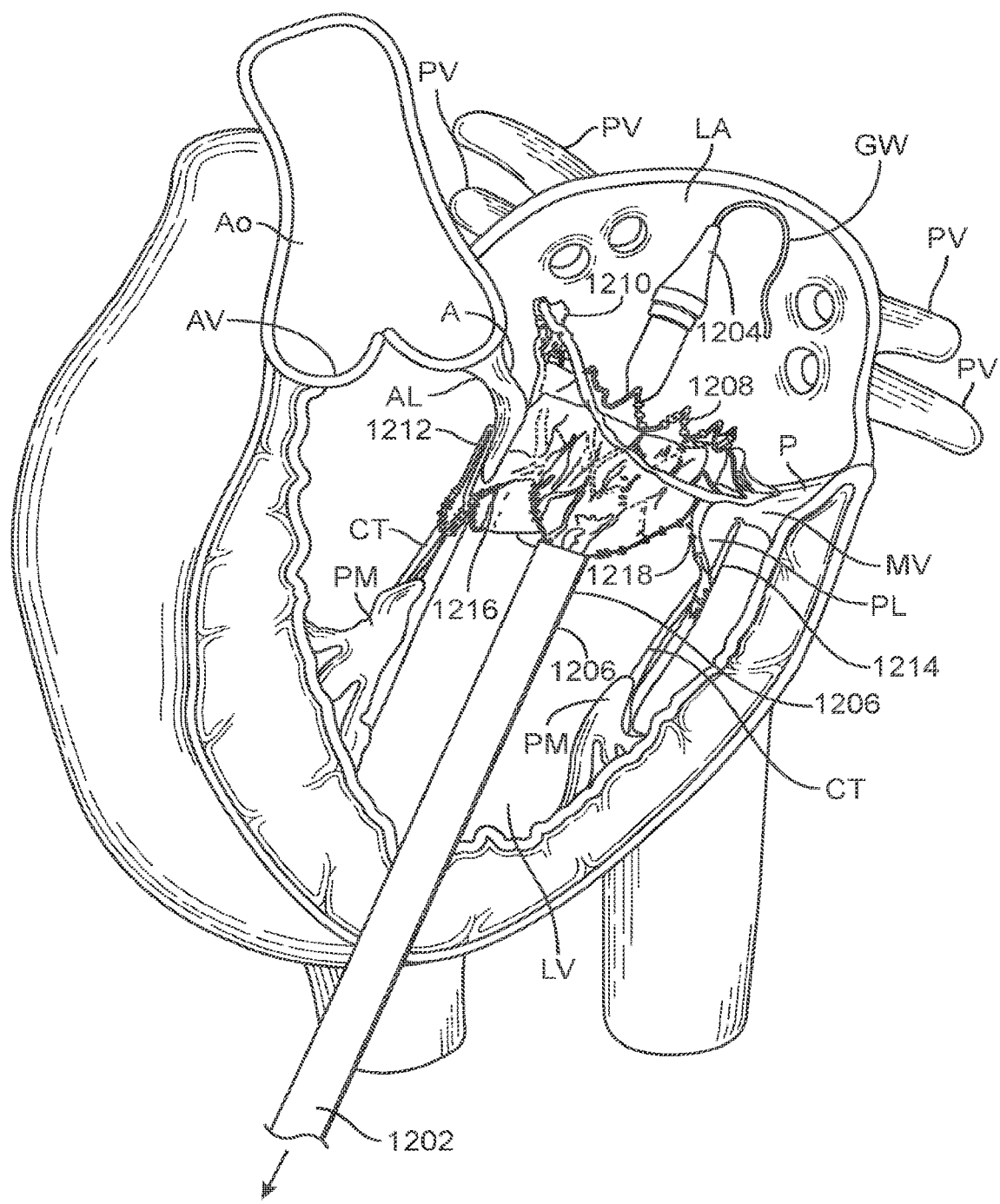
Figure 12H:
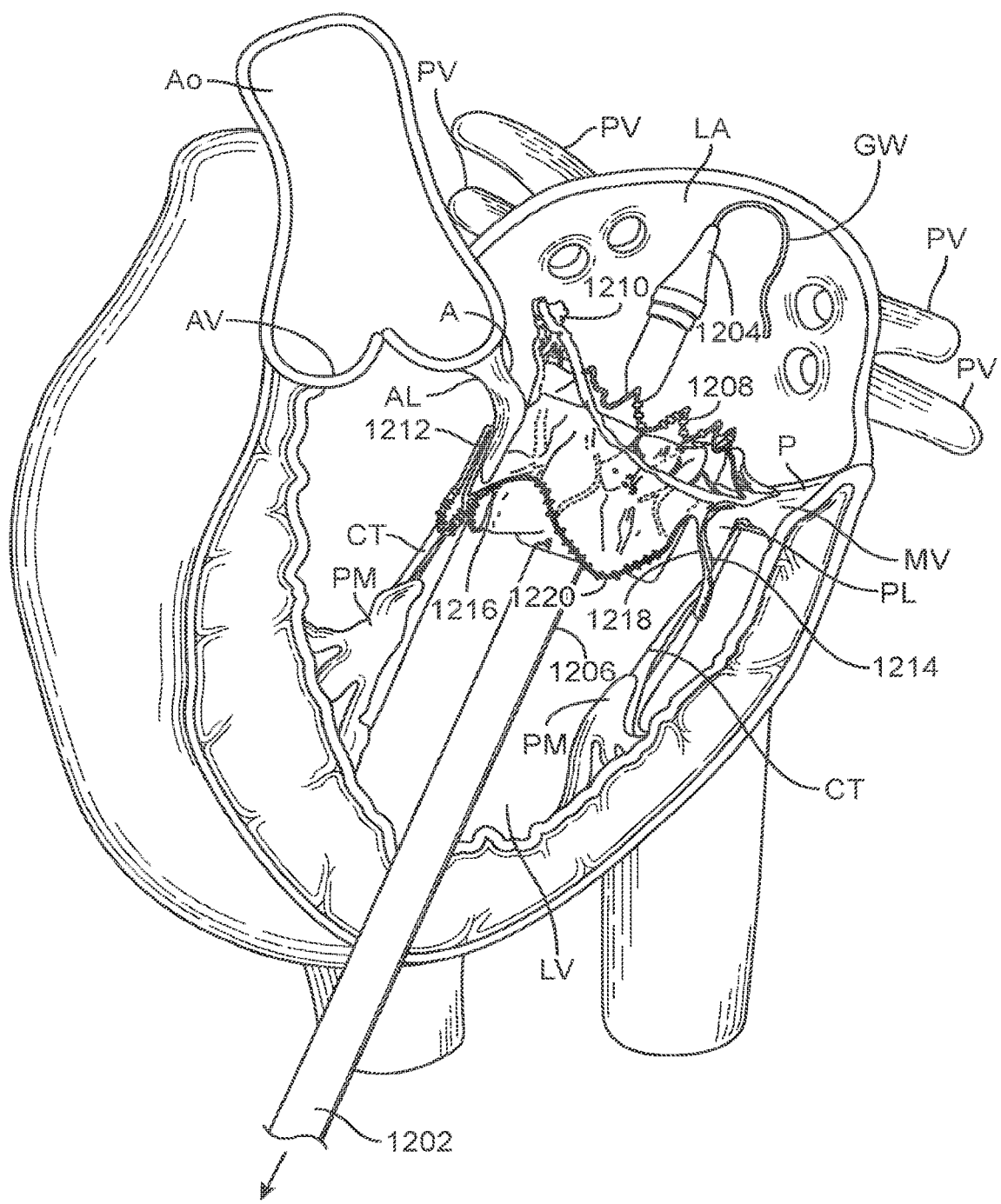

In FIG. 12G, further retraction of the outer sheath 1206 then releases the constraints from the posterior tab 1214 allowing it to complete its self-expansion, thereby capturing the posterior leaflet PL between an inner surface of the posterior tab 1214 and an outer surface of the ventricular skirt 1218. In FIG. 12H, the sheath is retracted further releasing the ventricular skirt 1220 and allowing the ventricular skirt 1220 to radially expand outward, further capturing the anterior and posterior leaflets between the outer surface of the ventricular skirt and their respective anterior or posterior tabs. Expansion of the ventricular skirt also pushes the anterior and posterior leaflets outward, thereby ensuring that the native leaflets do not interfere with any portion of the prosthetic valve or the prosthetic valve leaflets. The prosthetic valve is now anchored in position above the mitral valve, along the annulus, to the valve leaflets, and below the mitral valve, thereby securing it in position.

Figure 12I:
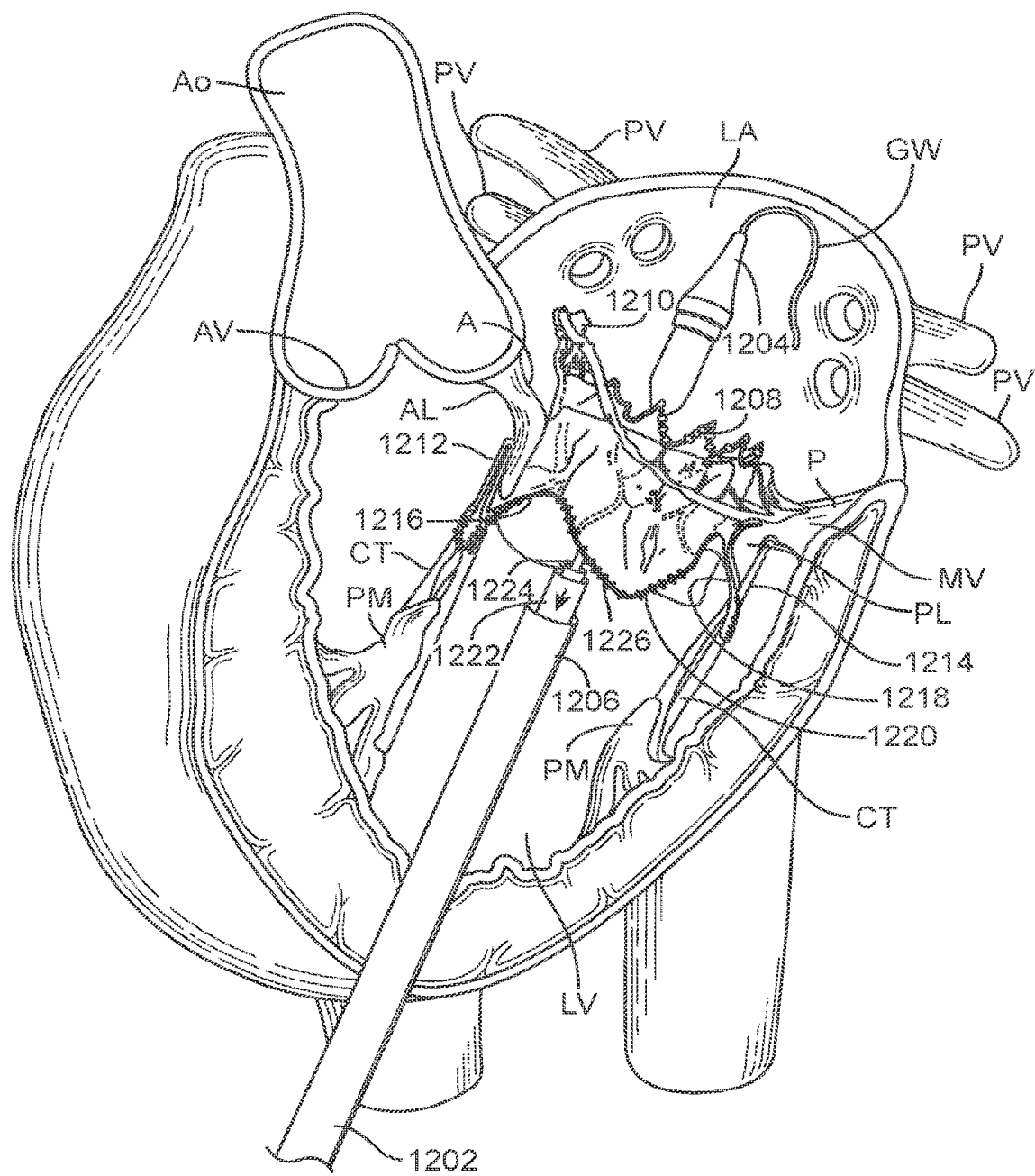
Figure 12J:
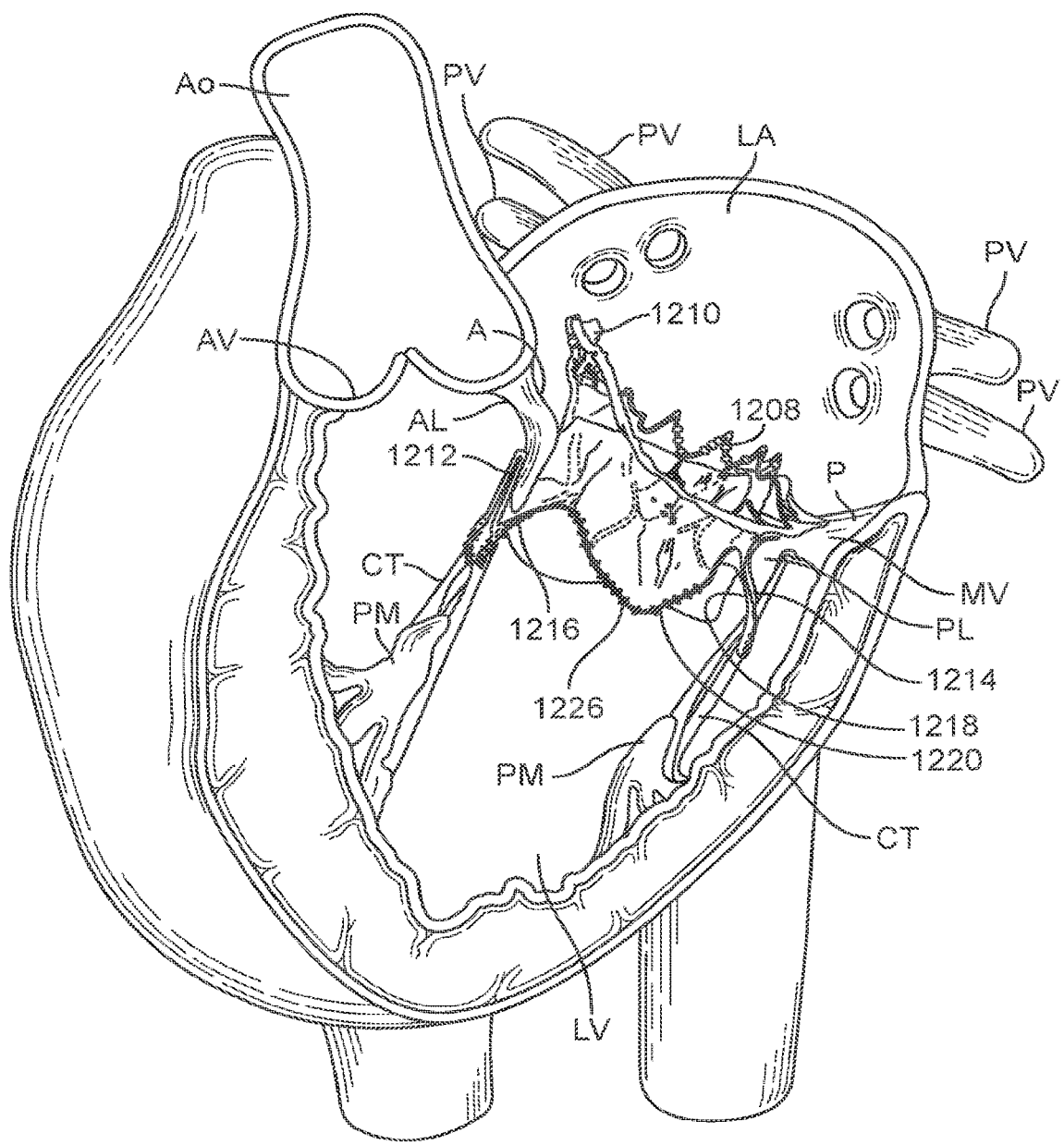

Further actuation of the delivery device now retracts the outer sheath 1206 and the bell catheter shaft 1222 so as to remove the constraint from the hub catheter 1224, as illustrated in FIG. 12I. This permits the prosthetic valve commissures 1226 to be released from the hub catheter, thus the commissures expand to their biased configuration. The delivery system 1202 and guidewire GW are then removed, leaving the prosthetic valve 1208 in position where it takes over for the native mitral valve, as seen in FIG. 12J.

Figure 12K:
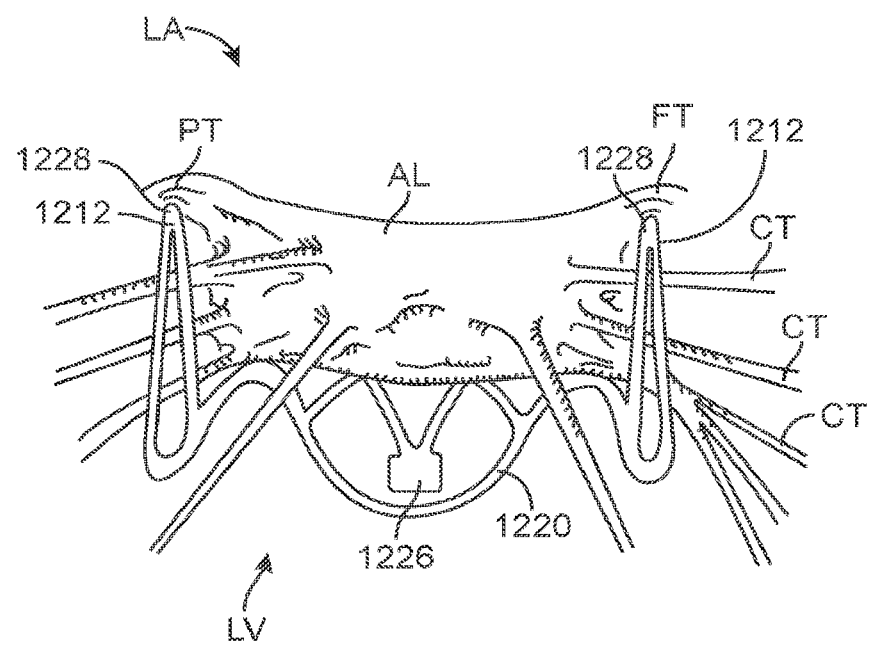
Figure 12L:
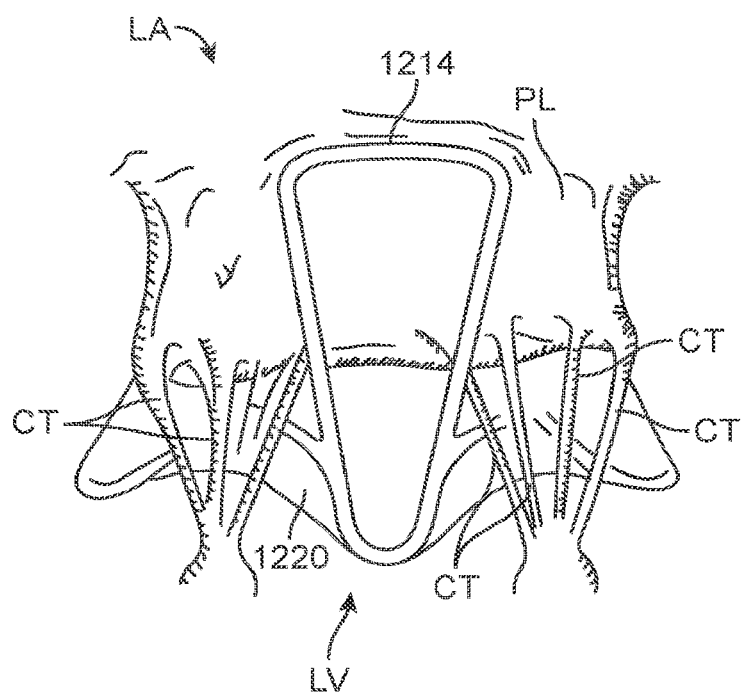

FIGS. 12K and 12L highlight engagement of the anterior and posterior tabs with the respective anterior and posterior leaflets. In FIG. 12K, after anterior tabs 1212 have been fully expanded, they capture the anterior leaflet AL and adjacent chordae tendineae between an inside surface of the anterior tab and an outer surface of the ventricular skirt 1220. Moreover, the tips 1228 of the anterior tabs 1212 are engaged with the fibrous trigones FT of the anterior side of the mitral valve. The fibrous trigones are fibrous regions of the valve thus the anterior tabs further anchor the prosthetic valve into the native mitral valve anatomy. One anterior tab anchors into the left fibrous trigone, and the other anterior tabs anchors into the right fibrous trigone. The trigones are on opposite sides of the anterior side of the leaflet. FIG. 12L illustrates engagement of the posterior tab 1214 with the posterior leaflet PL which is captured between an inner surface of the posterior tab and an outer surface of the ventricular skirt 1220. Additionally, adjacent chordae tendineae are also captured between the posterior tab and ventricular skirt.

FIGS. 13A-13L illustrate another exemplary embodiment of a delivery method. This embodiment is similar to that previously described, with the major difference being the order in which the prosthetic cardiac valve self-expands into engagement with the mitral valve. Any delivery device or any prosthetic cardiac valve disclosed herein may be used, however in preferred embodiments, the embodiment of FIG. 7 is used. Varying the order may allow better positioning of the implant, easier capturing of the valve leaflets, and better anchoring of the implant. This exemplary method also preferably uses a transapical route, although transseptal may also be used.

Figure 13A:
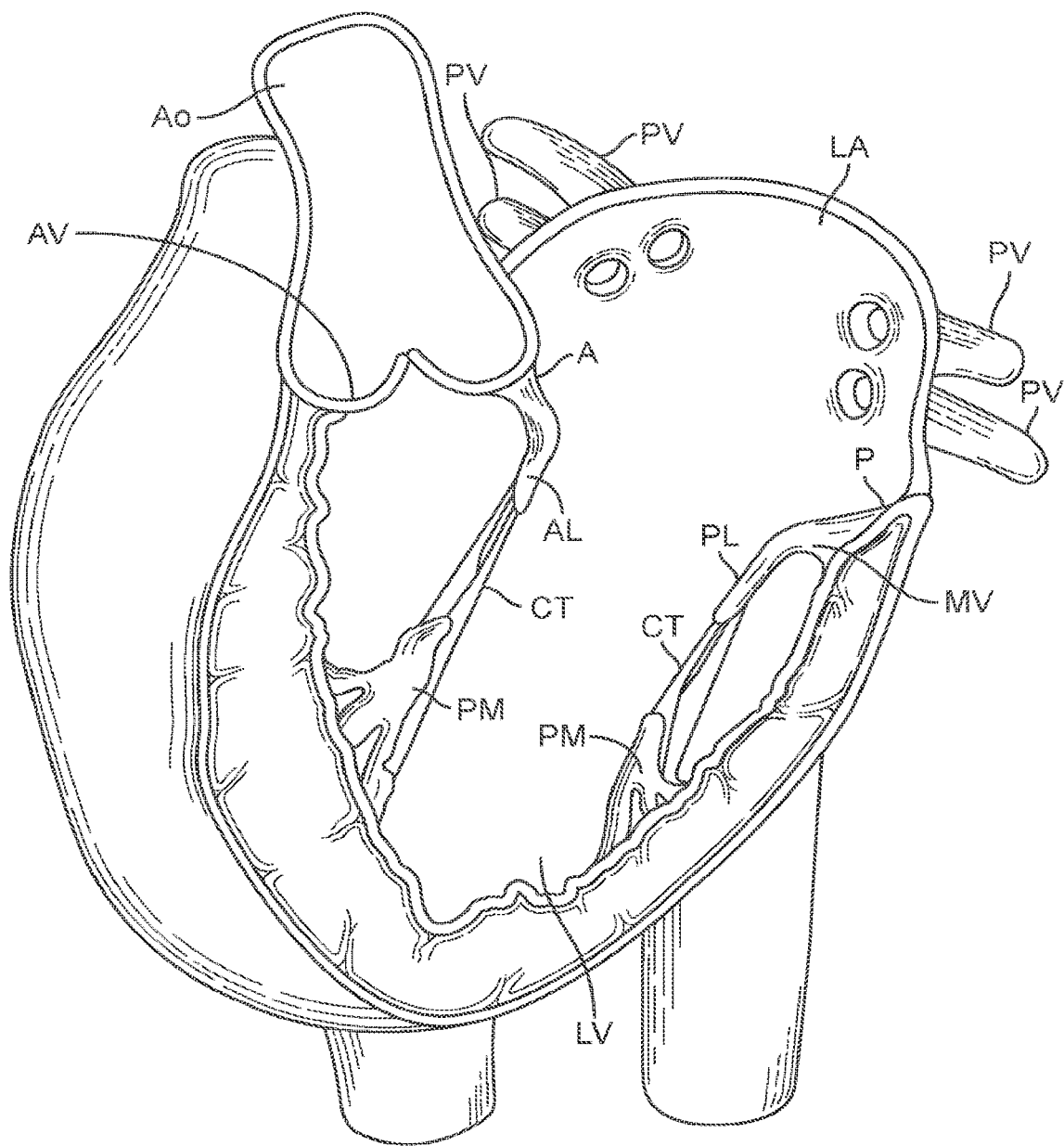
FIGS. 13A-13L illustrate another exemplary method of implanting a prosthetic cardiac valve.

FIG. 13A illustrates the basic anatomy of the left side of a patient's heart including the left atrium LA and left ventricle LV. Pulmonary veins PV return blood from the lungs to the left atrium and the blood is then pumped from the left atrium into the left ventricle across the mitral valve MV. The mitral valve includes an anterior leaflet AL on an anterior side A of the valve and a posterior leaflet PL on a posterior side P of the valve. The leaflets are attached to chordae tendineae CT which are subsequently secured to the heart walls with papillary muscles PM. The blood is then pumped out of the left ventricle into the aorta AO with the aortic valve AV preventing regurgitation.

Figure 13B:
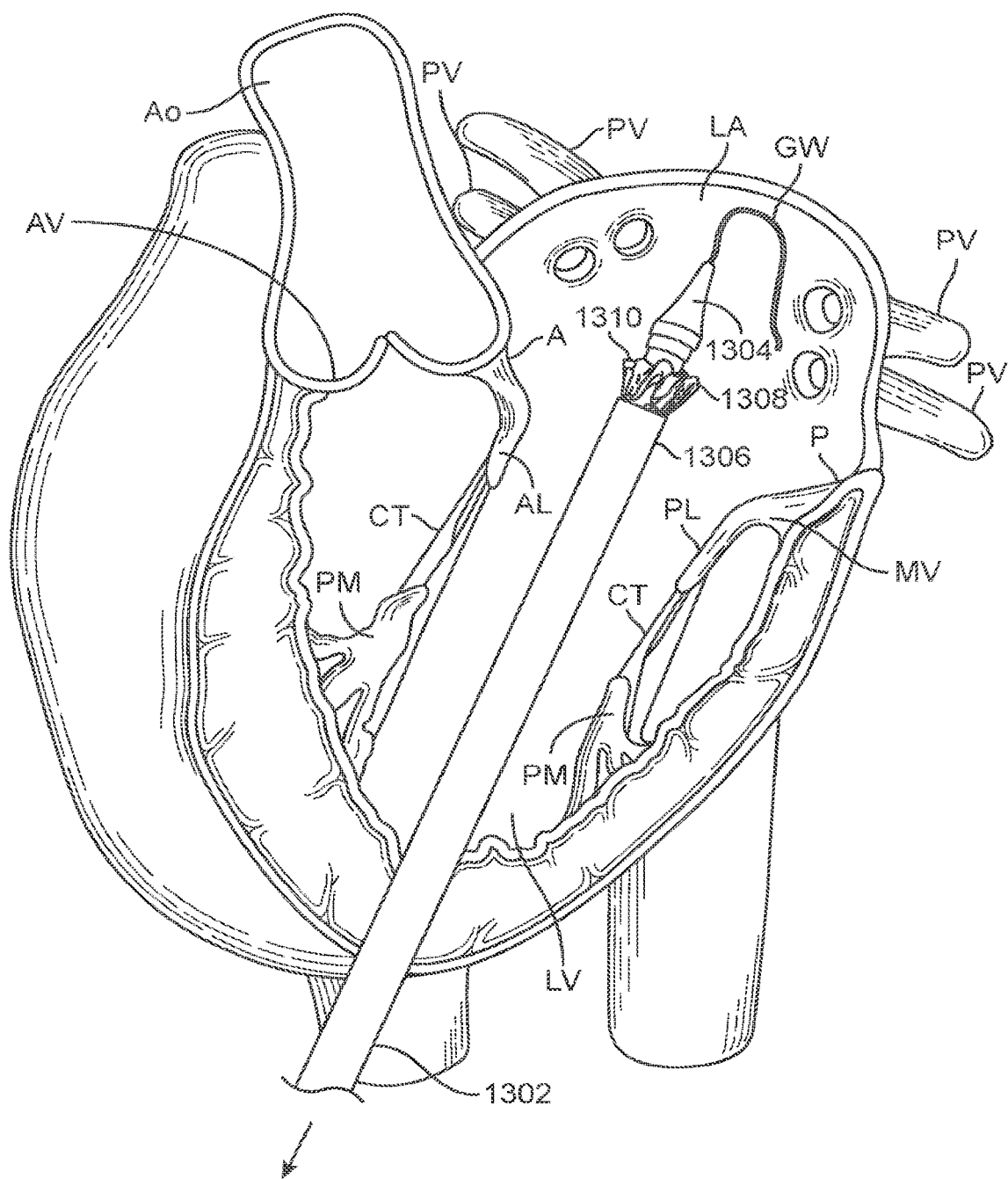
Figure 13C:
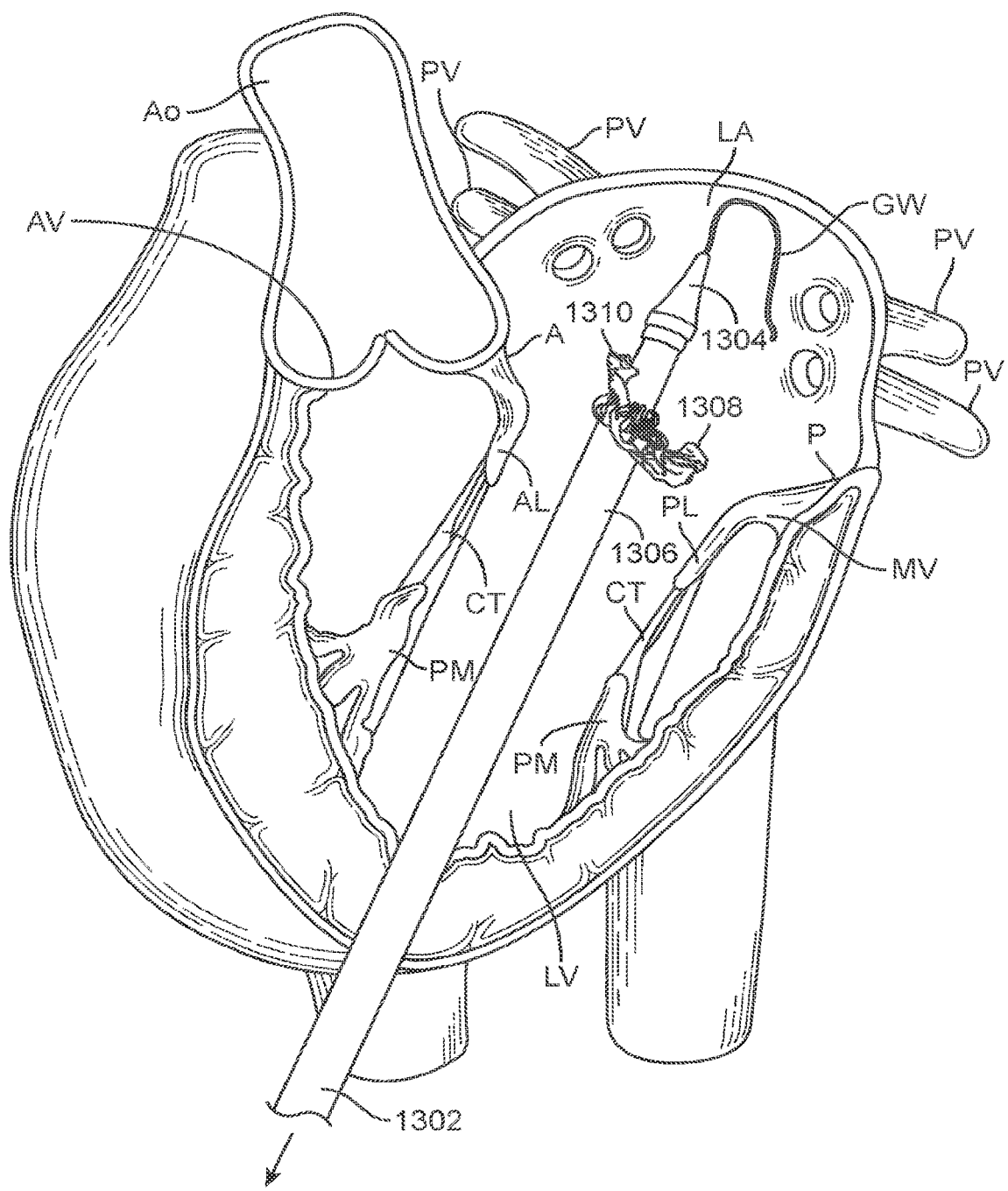
Figure 13D:
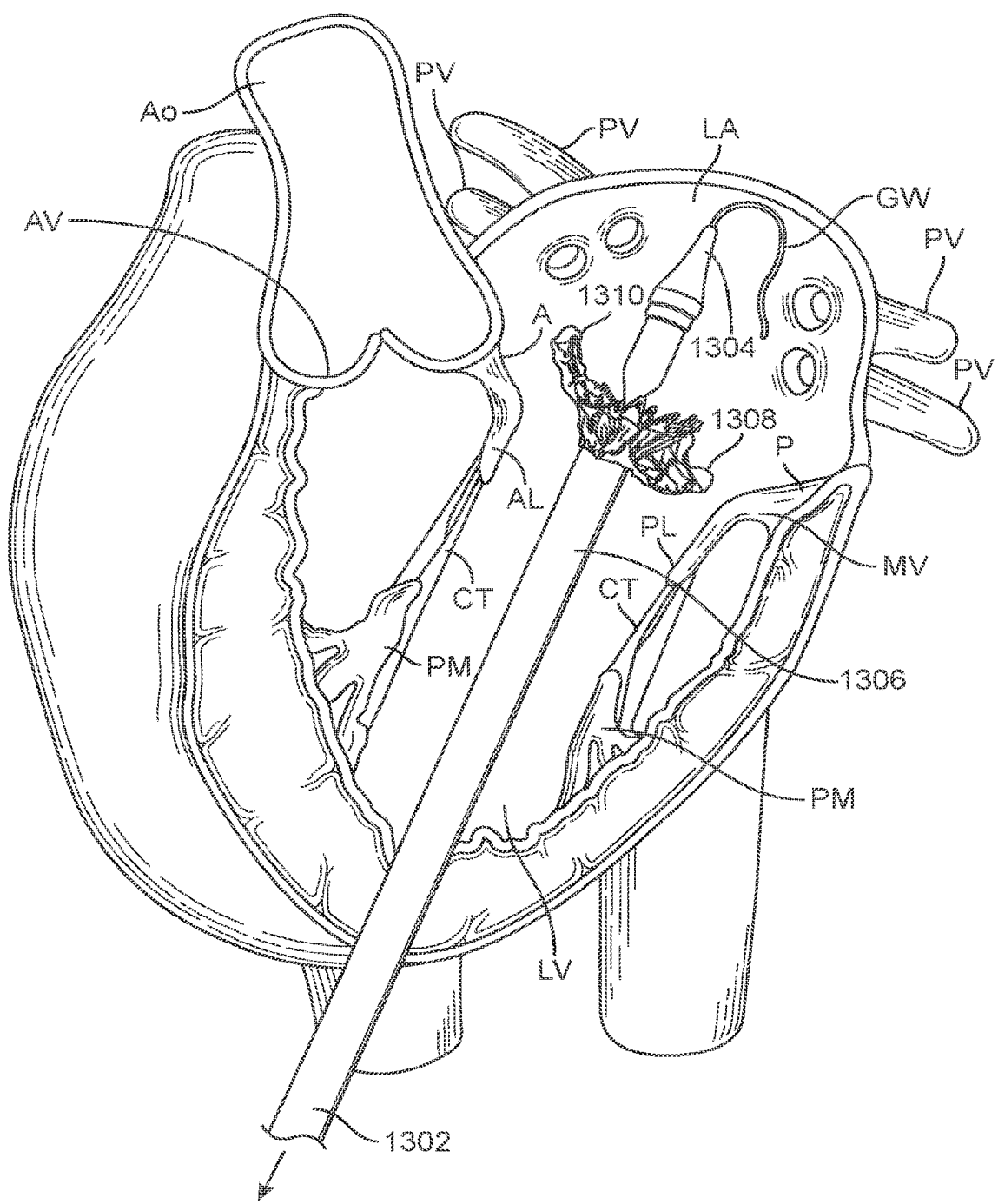

FIG. 13B illustrates transapical delivery of a delivery system 1302 through the apex of the heart into the left atrium LA. The delivery system 1302 may be advanced over a guidewire GW into the left atrium, and a tissue penetrating tip 1304 helps the delivery system pass through the apex of the heart by dilating the tissue and forming a larger channel for the remainder of the delivery system to pass through. The delivery catheter carries prosthetic cardiac valve 1308. Once the distal portion of the delivery system has been advanced into the left atrium, the outer sheath 1306 may be retracted proximally (e.g. toward the operator) thereby removing the constraint from the atrial portion of the prosthetic valve 1308. This allows the atrial skirt 1310 to self-expand radially outward. In FIG. 13C, as the outer sheath is further retracted, the atrial skirt continues to self-expand and peck out, until it fully deploys as seen in FIG. 13D. The atrial skirt may have a cylindrical shape or it may be D-shaped as discussed above with a flat anterior portion and a cylindrical posterior portion so as to avoid interfering with the aortic valve and other aspects of the left ventricular outflow tract. The prosthetic cardiac valve may be advanced upstream or downstream to properly position the atrial skirt. In preferred embodiments, the atrial skirt forms a flange that rests against a superior surface of the mitral valve and this anchors the prosthetic valve and prevents it from unwanted movement downstream into the left ventricle.

Figure 13E:
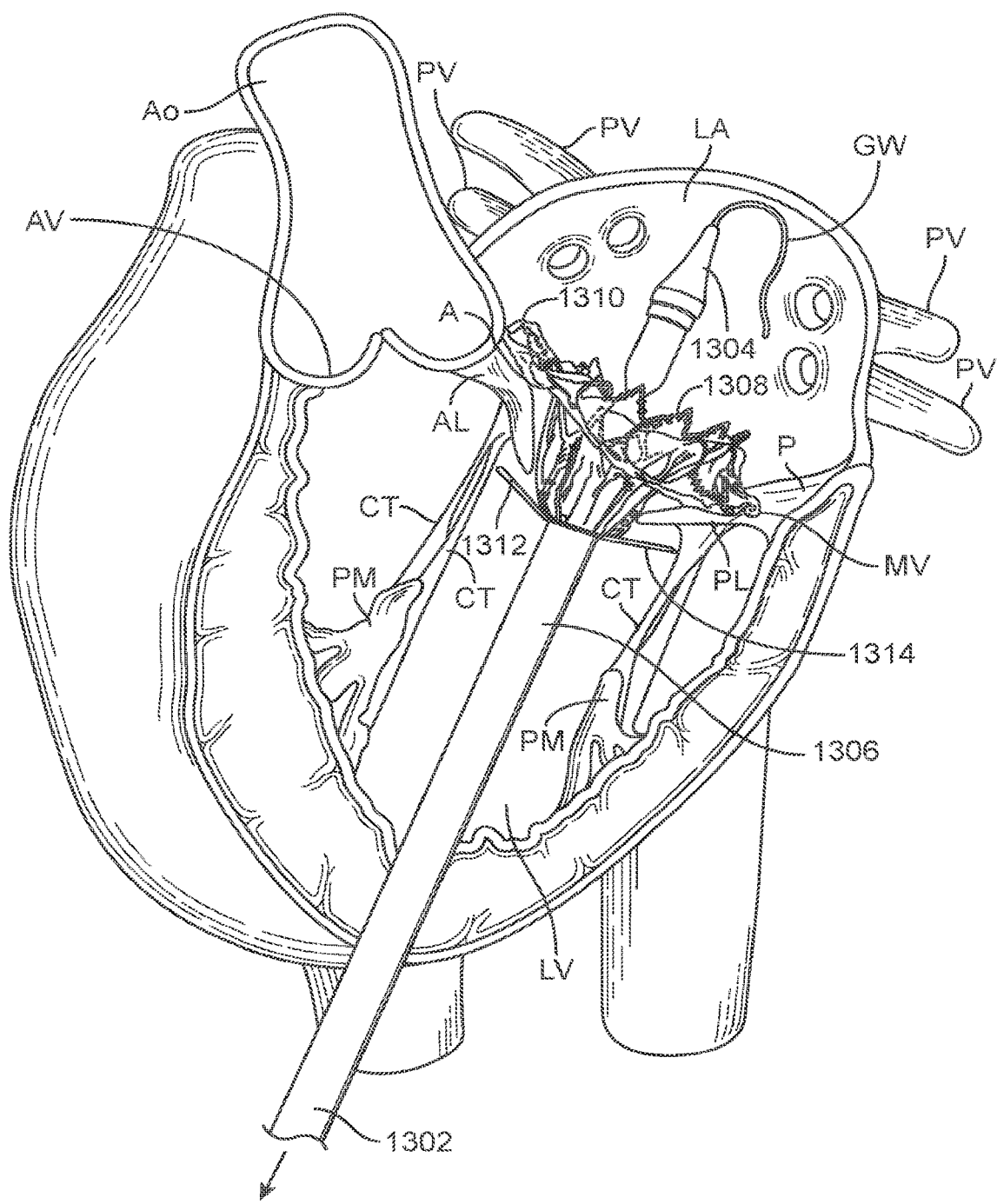
Figure 13F:
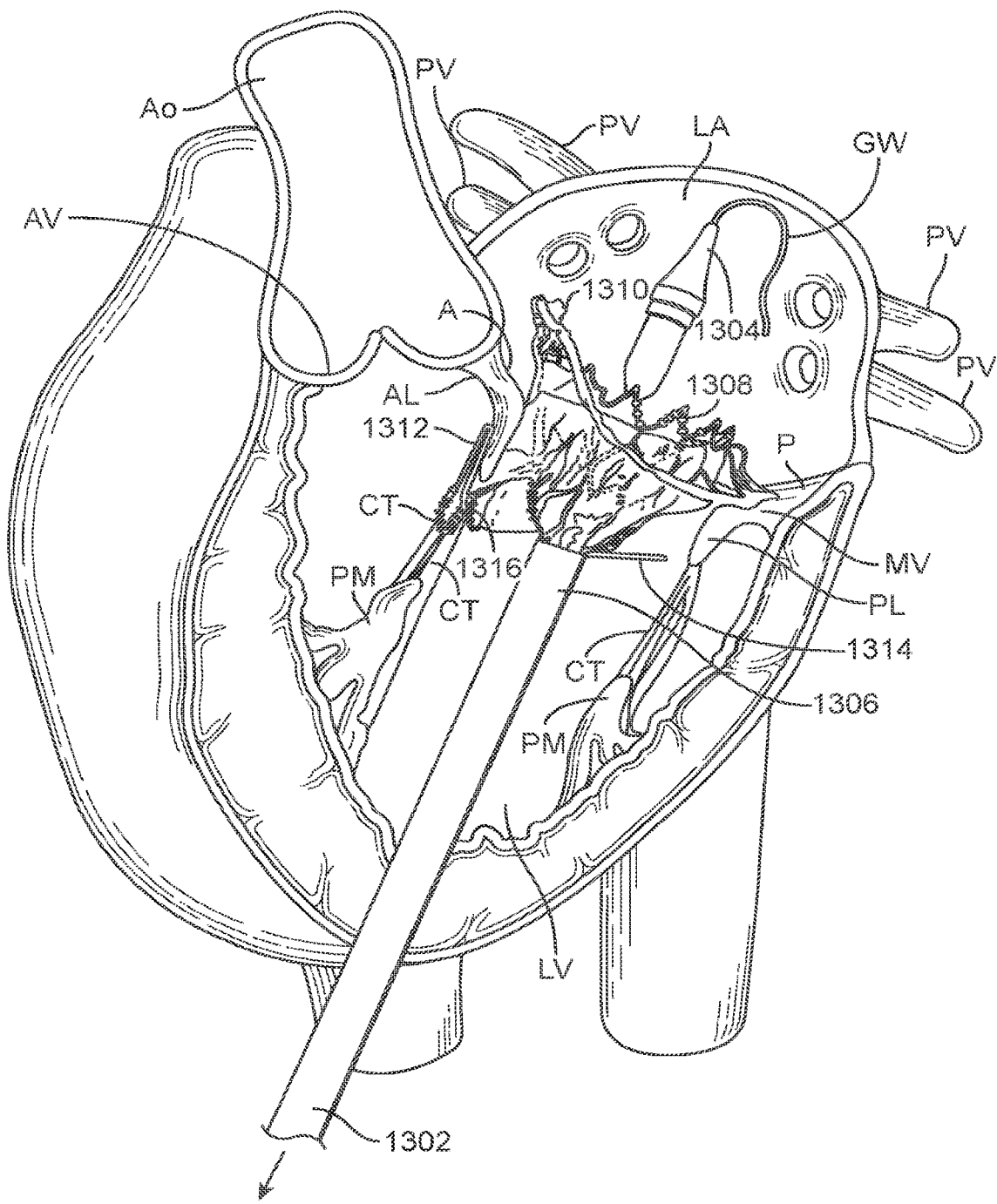

As the outer sheath 1306 continues to be proximally retracted, the annular region of the prosthetic cardiac valve self-expands next into engagement with the valve annulus. The annular region also preferably has the D-shaped geometry, although it may also be cylindrical or have other geometries to match the native anatomy. In FIG. 13E, retraction of sheath 1306 eventually allows both the anterior 1312 and posterior 1314 tabs to partially self-expand outward preferably without engaging the anterior or posterior leaflets or the chordae tendineae. In this embodiment, further retraction of the outer sheath 1306 then allows both the anterior tabs 1312 (only one visible in this view) to complete their self-expansion so that the anterior leaflet is captured between an inner surface of each of the anterior tabs and an outer surface of the ventricular skirt 1316, as illustrated in FIG. 13F. The posterior tab 1214 remains partially open, but has not completed its expansion yet. Additionally, the tips of the anterior tabs also anchor into the left and right fibrous trigones of the mitral valve, as will be illustrated in greater detail below.

Figure 13G:
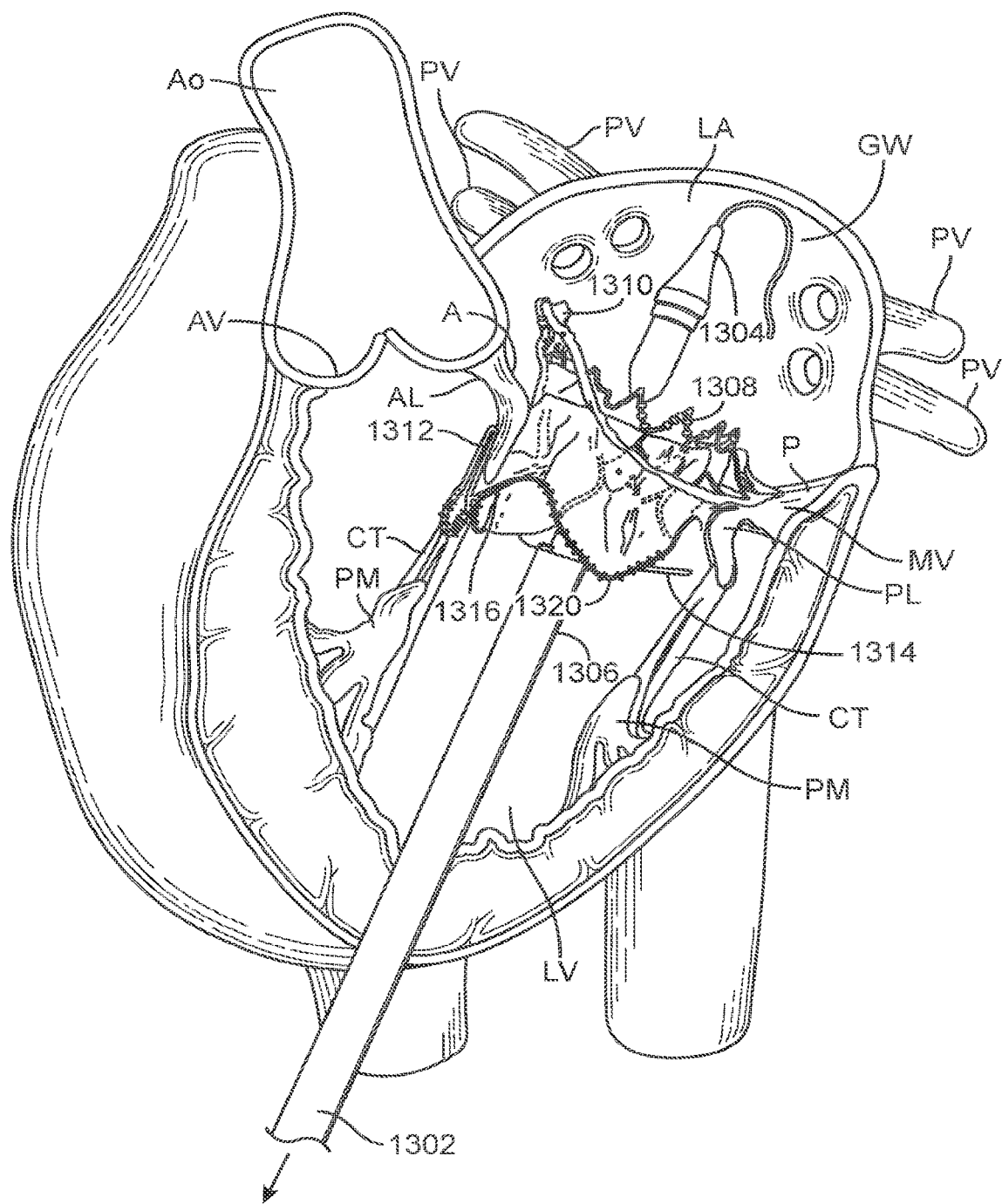
Figure 13H:
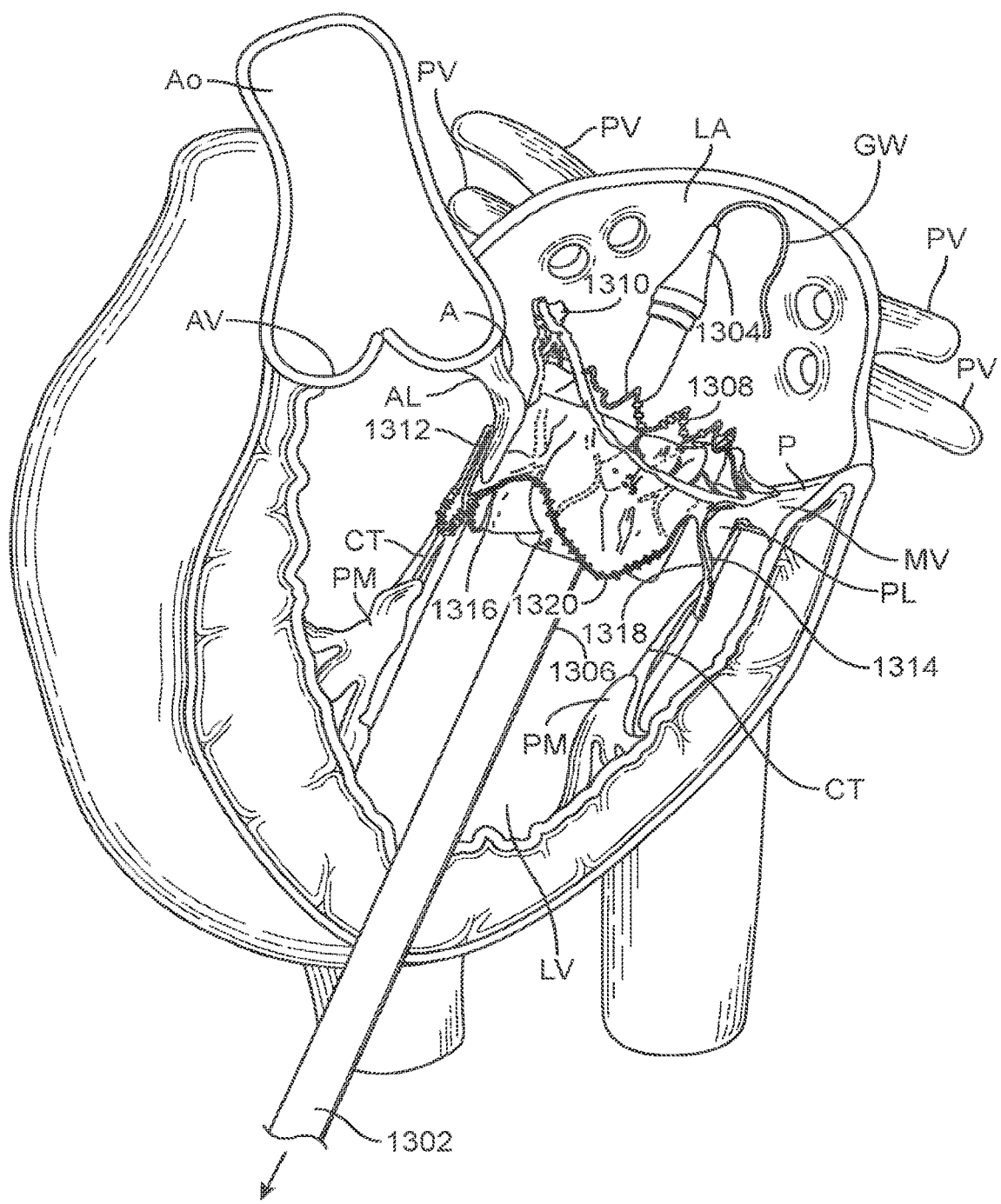

In FIG. 13G, further retraction of the outer sheath 1306 then releases the constraint from the ventricular skirt 1320 allowing the ventricular skirt to radially expand. This then further captures the anterior lealflets AL between the anterior tab 1312 and the ventricular skirt 1316. Expansion of the ventricular skirt also pushes the anterior and posterior leaflets outward, thereby ensuring that the native leaflets do not interfere with any portion of the prosthetic valve or the prosthetic valve leaflets. Further retraction of sheath 1306 as illustrated in FIG. 13H releases the constraint from the posterior tab 1314 allowing it to complete its self-expansion, thereby capturing the posterior leaflet PL between an inner surface of the posterior tab 1314 and an outer surface of the ventricular skirt 1318. The prosthetic valve is now anchored in position above the mitral valve, along the annulus, to the valve leaflets, and below the mitral valve, thereby securing it in position.

Figure 13I:
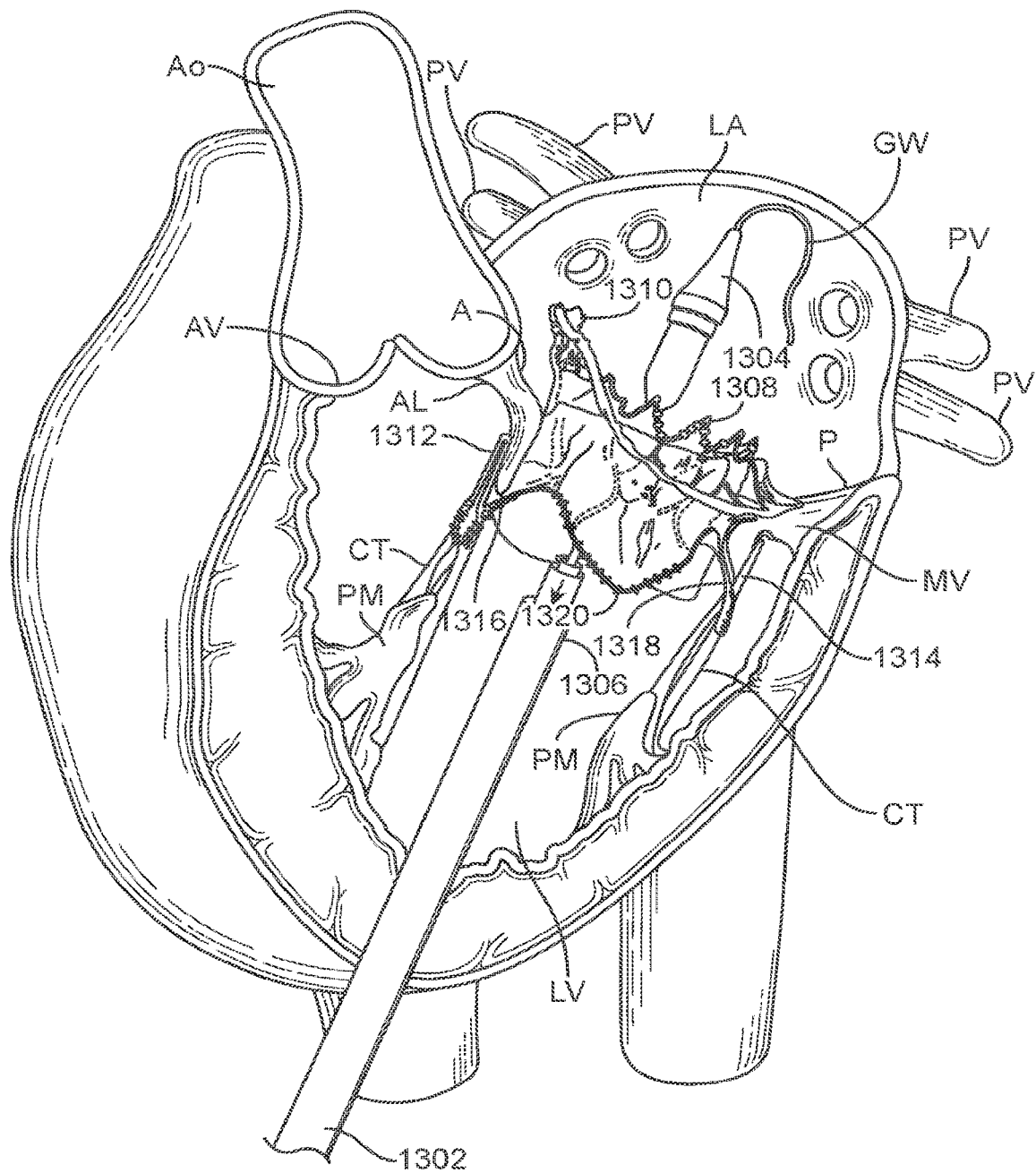
Figure 13J:
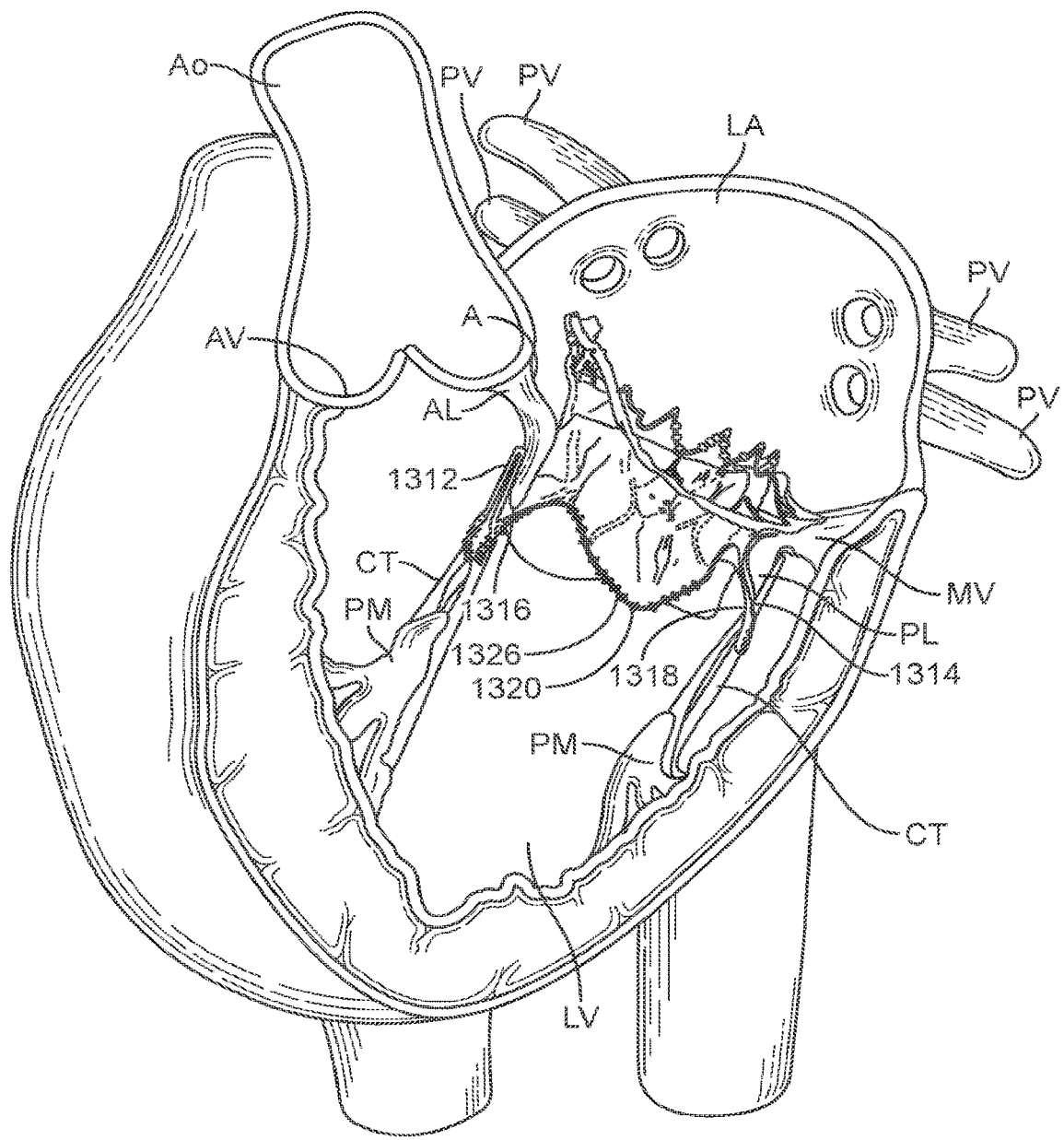

Further actuation of the delivery device now retracts the outer sheath 1306 and the bell catheter shaft 1322 so as to remove the constraint from the hub catheter 1324, as illustrated in FIG. 13I. This permits the prosthetic valve commissures 1326 to be released from the hub catheter, thus the commissures expand to their biased configuration. The delivery system 1302 and guidewire GW are then removed, leaving the prosthetic valve 1308 in position where it takes over for the native mitral valve, as seen in FIG. 13J.

Figure 13K:
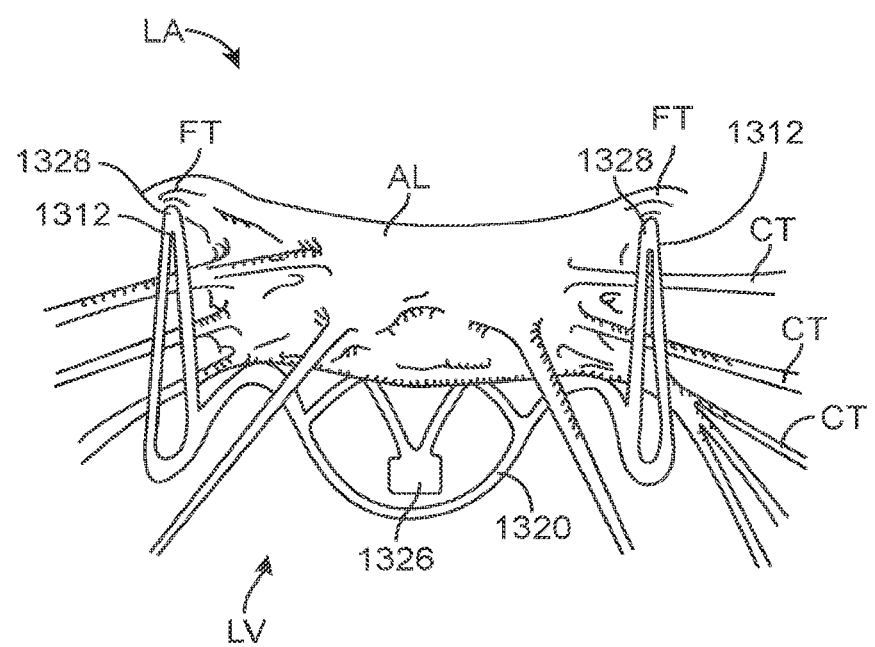
Figure 13L:
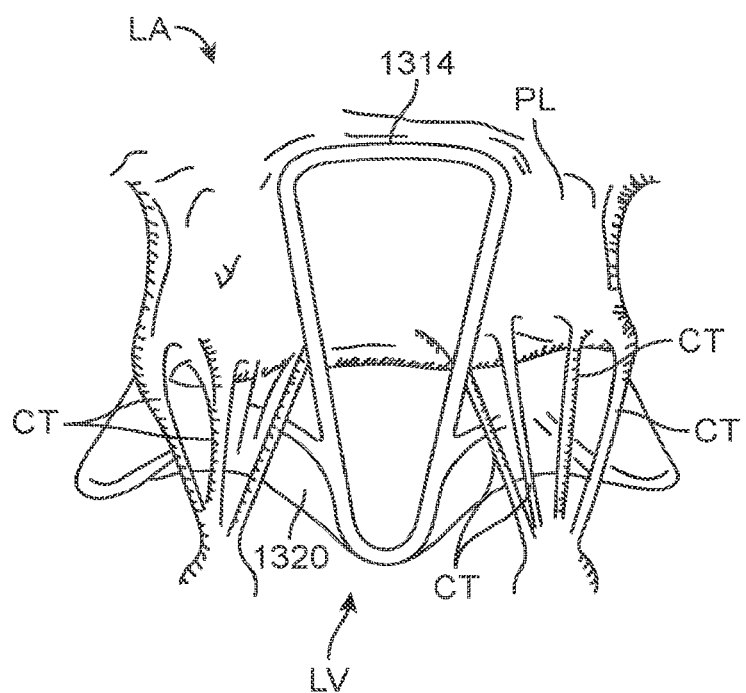

FIGS. 13K and 13L highlight engagement of the anterior and posterior tabs with the respective anterior and posterior leaflet. In FIG. 13K, after anterior tabs 1312 have been fully expanded, they capture the anterior leaflet AL and adjacent chordae tendineae between an inside surface of the anterior tab and an outer surface of the ventricular skirt 1320. Moreover, the tips 1328 of the anterior tabs 1312 are engaged with the fibrous trigones FT of the anterior side of the mitral valve. The fibrous trigones are fibrous regions of the valve thus the anterior tabs further anchor the prosthetic valve into the native mitral valve anatomy. One anterior tab anchors into the left fibrous trigone, and the other anterior tabs anchors into the right fibrous trigone. The trigones are on opposite sides of the anterior side of the leaflet. FIG. 13L illustrates engagement of the posterior tab 1314 with the posterior leaflet PL which is captured between an inner surface of the posterior tab and an outer surface of the ventricular skirt 1320. Additionally, adjacent chordae tendineae are also captured between the posterior tab and ventricular skirt.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A device for loading a prosthesis onto a delivery system, said device comprising:
    an inlet;
    an outlet;
    a central bore extending between the inlet and the outlet;
    one or more actuators disposed adjacent the outlet and configured to actuate radially inward and outward, wherein:
        the one or more actuators are configured to be actuated radially inward to selectively deflect a plurality of engagement tabs of the prosthesis radially inward to mate the engagement tabs with the delivery system; and
        the one or more actuators are configured to deflect the engagement tabs radially inward to a first diameter while the prosthesis is at least partially compressed in the central bore to a second diameter; and
        the first diameter is less than the second diameter.

2. The device of claim 1, wherein the central bore comprises a constant diameter region.

3. The device of claim 1, wherein the central bore comprises a tapered region adapted to radially collapse the prosthesis from an initial diameter to a smaller diameter when the prosthesis is passed therethrough.

4. The device of claim 1, wherein the one or more actuators comprise three actuators circumferentially disposed around the housing about every 120 degrees.

5. The device of claim 1, wherein the one or more actuators are operably coupled together such that the one or more actuators are actuated simultaneously.

6. The device of claim 1, further comprising a collar threadably engaged with the housing and wherein rotating the collar actuates the one or more actuators.

7. The device of claim 1, wherein the one or more actuators comprise spring loaded actuators biased to return to a position disposed radially outward from the central bore.

8. The device of claim 1, wherein the prosthesis comprises a prosthetic heart valve.

9. The device of claim 1, wherein the prosthesis comprises the plurality of engagement tabs, and wherein actuation of the one or more actuators is adapted to move the plurality of engagement tabs radially inward.

10. The device of claim 9, wherein the plurality of engagement tabs are adapted to be releasably engaged with retaining features on the delivery catheter.

11. The device of claim 9, wherein the prosthesis comprises a prosthetic heart valve and the plurality of engagement tabs comprise commissure posts of the prosthetic heart valve.

* * * * *